US009246107B2

(12) United States Patent
Lee et al.

(10) Patent No.: US 9,246,107 B2
(45) Date of Patent: Jan. 26, 2016

(54) COMPOUND FOR ORGANIC OPTOELECTRONIC DEVICE, ORGANIC LIGHT EMITTING DIODE INCLUDING THE SAME AND DISPLAY DEVICE INCLUDING THE ORGANIC LIGHT EMITTING DIODE

(75) Inventors: Kyoung-Mi Lee, Uiwang-si (KR); Sung-Hyun Jung, Uiwang-si (KR); Dong-Wan Ryu, Uiwang-si (KR); Seung-Min Lee, Uiwang-si (KR); Hyon-Gyu Lee, Uiwang-si (KR); Mi-Young Chae, Uiwang-si (KR); Dal-Ho Huh, Uiwang-si (KR); Jin-Seok Hong, Uiwang-si (KR)

(73) Assignee: CHEIL INDUSTRIES, INC., Gumi-si, Kyeongsangbuk-do (KR)

( * ) Notice: Subject to any disclaimer, the term of this patent is extended or adjusted under 35 U.S.C. 154(b) by 345 days.

(21) Appl. No.: 13/288,352

(22) Filed: Nov. 3, 2011

(65) Prior Publication Data

US 2012/0112174 A1 May 10, 2012

(30) Foreign Application Priority Data

Nov. 4, 2010 (KR) ........................ 10-2010-0109425

(51) Int. Cl.

| | |
|---|---|
| ***H01L 51/54*** | (2006.01) |
| ***C07D 307/91*** | (2006.01) |
| ***C07D 405/12*** | (2006.01) |
| ***C07D 409/12*** | (2006.01) |
| ***C07D 495/02*** | (2006.01) |
| ***C07D 405/14*** | (2006.01) |
| ***C07D 409/14*** | (2006.01) |
| ***C07D 407/14*** | (2006.01) |
| ***C07D 491/02*** | (2006.01) |
| ***C07D 333/76*** | (2006.01) |
| ***C07D 407/12*** | (2006.01) |
| ***H01L 51/00*** | (2006.01) |
| ***C07D 307/93*** | (2006.01) |
| ***C07D 333/50*** | (2006.01) |
| ***C07D 491/04*** | (2006.01) |
| ***C07D 495/04*** | (2006.01) |
| ***H01L 51/50*** | (2006.01) |
| ***C09K 11/06*** | (2006.01) |
| ***C09B 57/00*** | (2006.01) |
| ***H05B 33/22*** | (2006.01) |

(52) U.S. Cl.

CPC .......... *H01L 51/0071* (2013.01); *C07D 307/93* (2013.01); *C07D 333/50* (2013.01); *C07D405/12* (2013.01); *C07D 409/12* (2013.01); *C07D 409/14* (2013.01); *C07D 491/04* (2013.01); *C07D 495/04* (2013.01); *C09B 57/00* (2013.01); *C09B 57/008* (2013.01); *C09K 11/06* (2013.01); *H01L 51/006* (2013.01); *H01L 51/0061* (2013.01); *H01L 51/0074* (2013.01); *H01L 51/5056* (2013.01); *H05B 33/22* (2013.01); *C09K 2211/1029* (2013.01); *C09K 2211/1088* (2013.01); *C09K 2211/1092* (2013.01); *H01L 51/0073* (2013.01); *Y02E 10/549* (2013.01)

(58) Field of Classification Search

None

See application file for complete search history.

(56) References Cited

U.S. PATENT DOCUMENTS

| | | | | |
|---|---|---|---|---|
| 2007/0190356 | A1 | 8/2007 | Arakane et al. | |
| 2008/0102312 | A1 | 5/2008 | Parham et al. | |
| 2008/0124572 | A1 | 5/2008 | Mizuki et al. | |
| 2008/0145708 | A1* | 6/2008 | Heil et al. ..................... | 428/704 |
| 2008/0220285 | A1 | 9/2008 | Vestweber et al. | |
| 2009/0159874 | A1 | 6/2009 | Vestweber et al. | |
| 2009/0184313 | A1 | 7/2009 | Buesing et al. | |
| 2009/0261717 | A1 | 10/2009 | Buesing et al. | |
| 2010/0187977 | A1 | 7/2010 | Kai et al. | |
| 2010/0187978 | A1 | 7/2010 | Yu et al. | |
| 2011/0272684 | A1* | 11/2011 | Parham et al. .................. | 257/40 |

100

FOREIGN PATENT DOCUMENTS

| | | | | | |
|---|---|---|---|---|---|
| CN | 101228250 | A | 7/2008 | | |
| CN | 101460434 | A | 6/2009 | | |
| DE | 10 2006 025846 | A1 | 12/2007 | | |
| DE | 10 2006 031990 | A1 | 1/2008 | | |
| DE | 10 2009 005289 | A1 | 7/2010 | | |
| JP | 2010-045281 | A | 2/2010 | | |
| KR | 10-2008-0015865 | A | 2/2008 | | |
| KR | 10-2008-0104997 | A | 12/2008 | | |
| KR | 10-2009-0024756 | A | 3/2009 | | |
| KR | 10-2010-0017154 | A | 2/2010 | | |
| WO | WO 2008/056746 | A1 | 5/2008 | | |
| WO | WO 2010/083872 | A2 * | 7/2010 | ........... | C07D 209/94 |

OTHER PUBLICATIONS

European Search Report in EP 11179192.7-1555, dated Mar. 13, 2013 (Lee, et al.).
Chinese Search Report which was attached to Office Action dated Jan. 13, 2014.

* cited by examiner

*Primary Examiner* — J. L. Yang
(74) *Attorney, Agent, or Firm* — Lee & Morse, P.C.

(57) ABSTRACT

A compound for an organic optoelectronic device, an organic light emitting diode, and a display device, the compound including moieties represented by the following Chemical Formula 1; Chemical Formula 4; and one of Chemical Formulae 2 and 3;

[Chemical Formula 1]

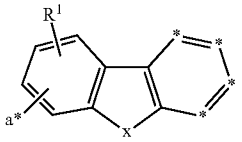

[Chemical Formula 2]

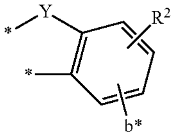

[Chemical Formula 3]

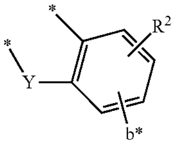

[Chemical Formula 4]

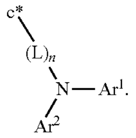

21 Claims, 5 Drawing Sheets

COMPOUND FOR ORGANIC OPTOELECTRONIC DEVICE, ORGANIC LIGHT EMITTING DIODE INCLUDING THE SAME AND DISPLAY DEVICE INCLUDING THE ORGANIC LIGHT EMITTING DIODE

BACKGROUND

1. Field

Embodiments relate to a compound for an organic optoelectronic device, an organic light emitting diode including the same, and a display including the organic light emitting diode.

2. Description of the Related Art

An organic optoelectronic device is, in a broad sense, a device for transforming photo-energy to electrical energy or, conversely, a device for transforming electrical energy to photo-energy.

An organic optoelectronic device may be classified as follows in accordance with its driving principles. One type of organic optoelectronic device is an electronic device driven as follows: excitons are generated in an organic material layer by photons introduced from an external light source to a device; the excitons are separated into electrons and holes; and the electrons and holes are respectively transferred to different electrodes and used as a current source (a voltage source).

Another type of organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

For example, the organic optoelectronic device may include an organic light emitting diode (OLED), an organic solar cell, an organic photo-conductor drum, an organic transistor, an organic memory device, and the like. and may include a hole injecting or transporting material, an electron injecting or transporting material, or a light emitting material.

The organic light emitting diode (OLED) has recently drawn attention due to an increase in demand for a flat panel display. In general, organic light emission refers to transformation of electrical energy to photo-energy.

SUMMARY

Embodiments are directed to a compound for an organic optoelectronic device, an organic light emitting diode including the same, and a display including the organic light emitting diode.

The embodiments may be realized by providing a compound for an organic optoelectronic device, the compound including moieties represented by the following Chemical Formula 1; Chemical Formula 4; and one of Chemical Formulae 2 and 3;

[Chemical Formula 1]

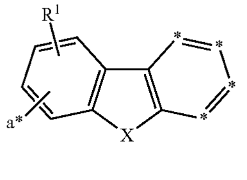

-continued

[Chemical Formula 2]

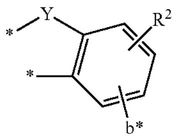

[Chemical Formula 3]

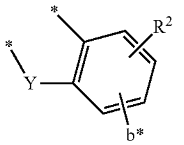

[Chemical Formula 4]

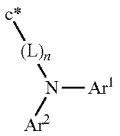

wherein, in Chemical Formulae 1 to 4, X is O, S, (O=S=O), (P=O), or (C=O), Y is CR'R" or NR', R', R", $R^1$, and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof, $Ar^1$ and $Ar^2$ are each independently a substituted or unsubstituted C6 to C30 aryl group or a substituted or unsubstituted C2 to C30 heteroaryl group, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof, n is 0 or 1, two adjacent *s of Chemical Formula 1 are linked to respective *s of Chemical Formula 2 or 3 to provide a fused ring, and one of a* of Chemical Formula 1 an b* of Chemical Formula 2 or 3 are linked to c* of Chemical Formula 4 through a sigma bond, and the other of a* and b*, not linked to c*, is hydrogen.

The compound may include a moiety represented by the following Chemical Formula 5:

[Chemical Formula 5]

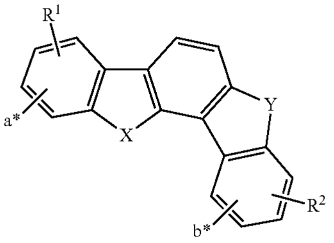

wherein in Chemical Formula 5, X is O, S, (O═S═O), (P═O), or (C═O), Y is CR'R" or NR', R', R", $R^1$, and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and one of a* and b* of the above Chemical Formula 5 forms a sigma bond with the c* of the above Chemical Formula 4, and the other of a* and b*, not linked to c *, is hydrogen.

The compound may be represented by the following Chemical Formula 6:

[Chemical Formula 6]

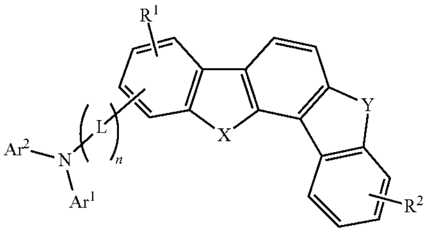

wherein, in Chemical Formula 6, X is O, S, (O═S═O), (P═O), or (C═O), Y is CR'R" or NR', R', R", $R^1$ and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof, $Ar^1$ and $Ar^2$ are each independently a substituted or unsubstituted C6 to C30 aryl group or a substituted or unsubstituted C2 to C30 heteroaryl group, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof, and n is 0 or 1.

Y may be CR'R", and R' and R" may each independently be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

Y may be NR', and R' may be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

The compound may be represented by the following Chemical Formula 7:

[Chemical Formula 7]

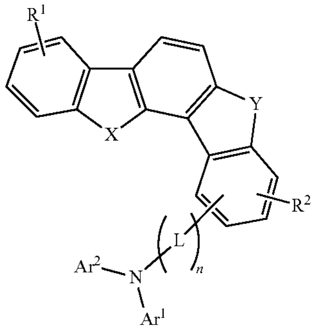

wherein, in Chemical Formula 7, X is O, S, $SO_2$ (O═S═O), PO(P═O), or CO(C═O), Y is CR'R" or NR', R', R", $R^1$, and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof, $Ar^1$ and $Ar^2$ are each independently a substituted or unsubstituted C6 to C30 aryl group or a substituted or unsubstituted C2 to C30 heteroaryl group, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof, and n is 0 or 1.

Y may be CR'R", and R' and R" may each independently be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

Y may be NR', and R' may be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

The compound may be represented by one of the following Chemical Formulae A-1 to A-7 and A-9 to A-51:

[A-1]

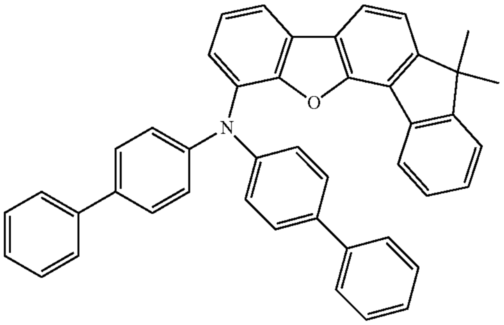

[A-2]

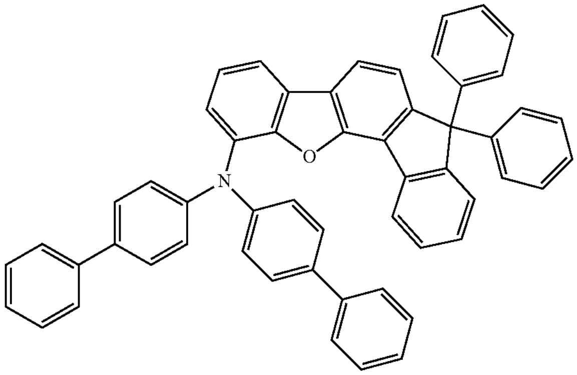

-continued
[A-3]
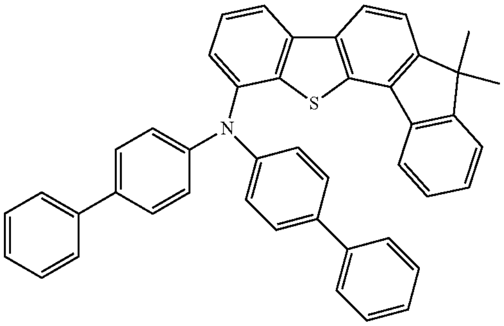
[A-4]
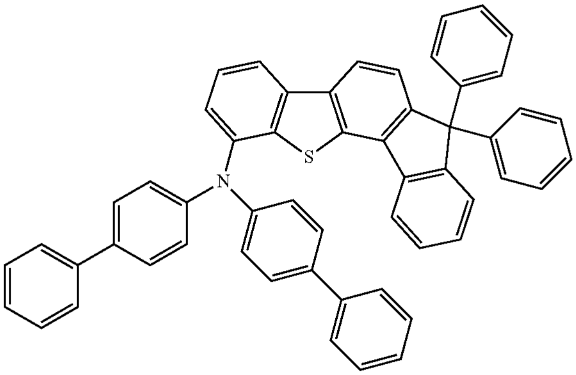
[A-5]
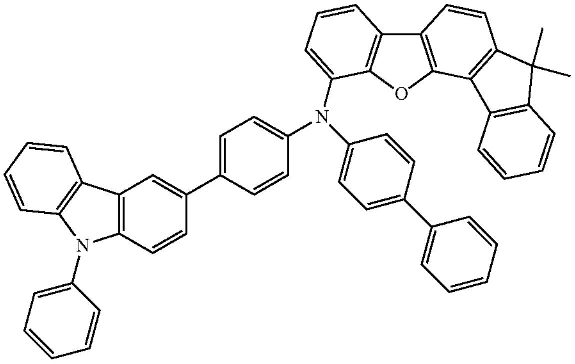
[A-6]
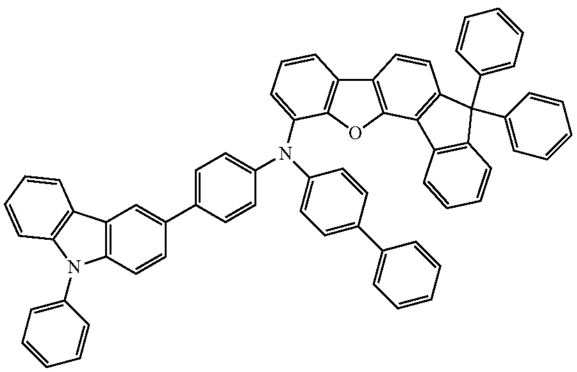
-continued
[A-7]
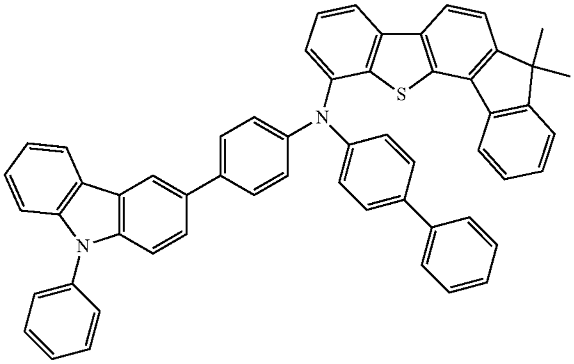
[A-9]
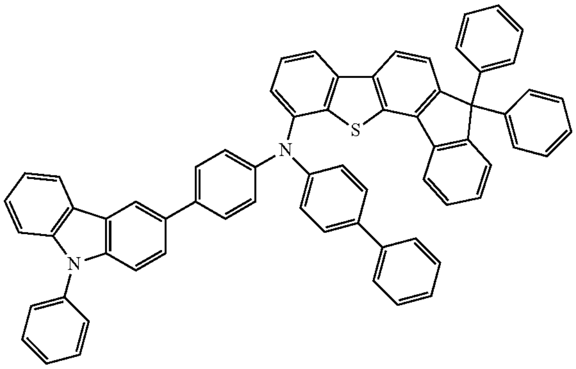
[A-10]
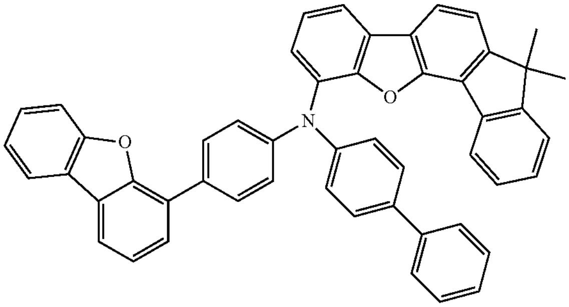
[A-11]
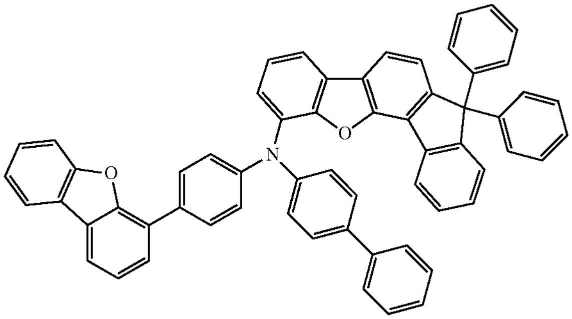

-continued
[A-12]
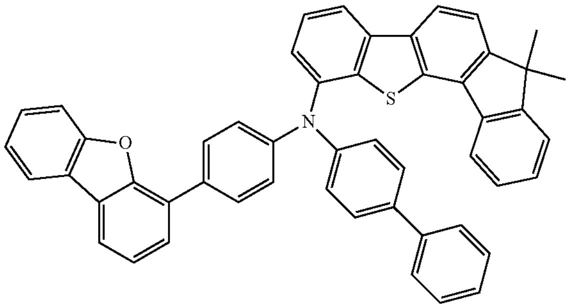
[A-13]
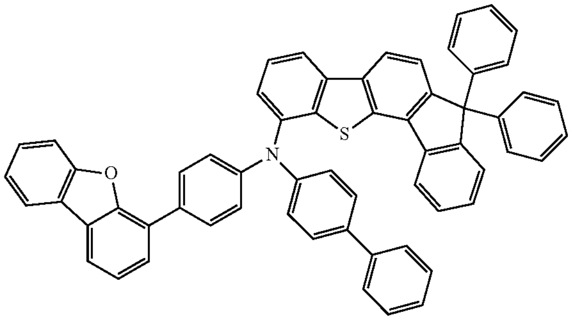
[A-14]
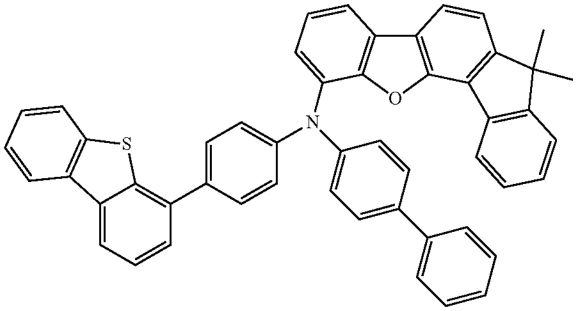
[A-15]
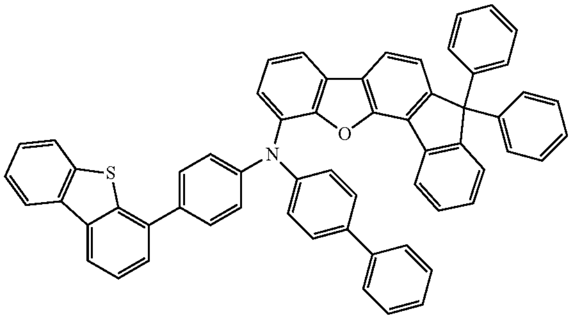
-continued
[A-16]
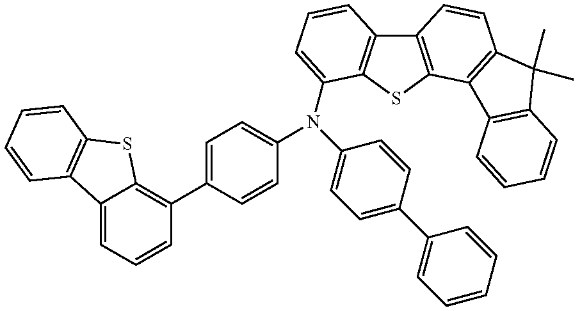
[A-17]
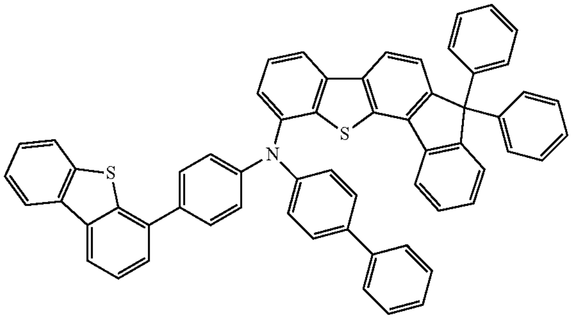
[A-18]
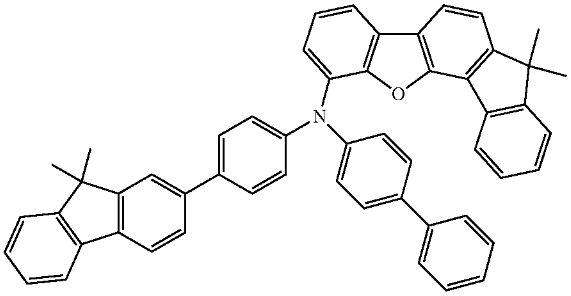
[A-19]
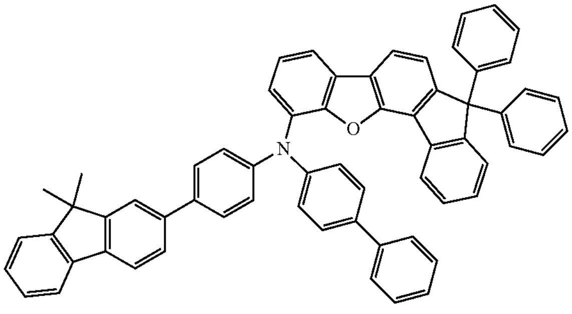

-continued
[A-20]
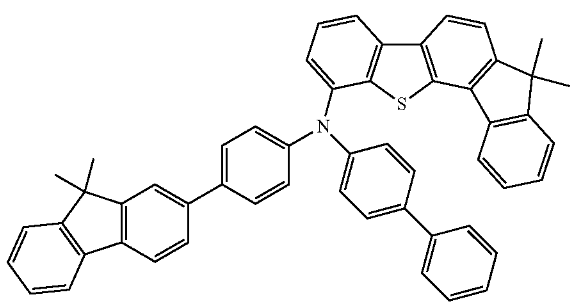
[A-21]
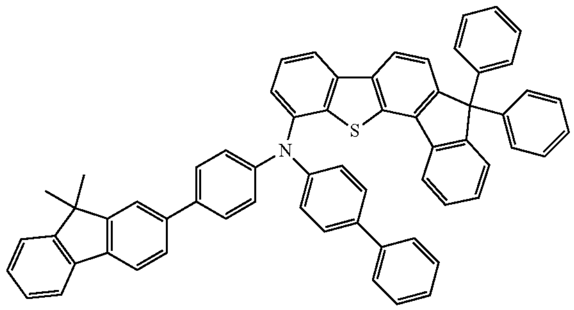
[A-22]
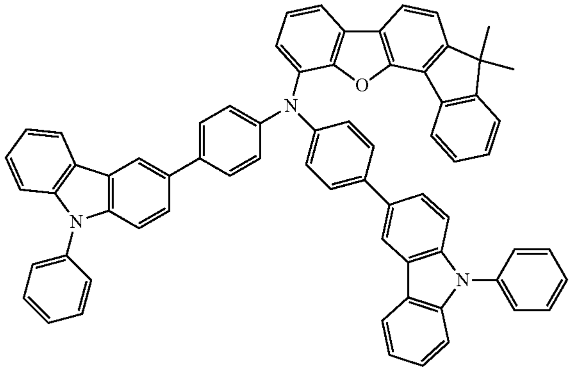
[A-23]
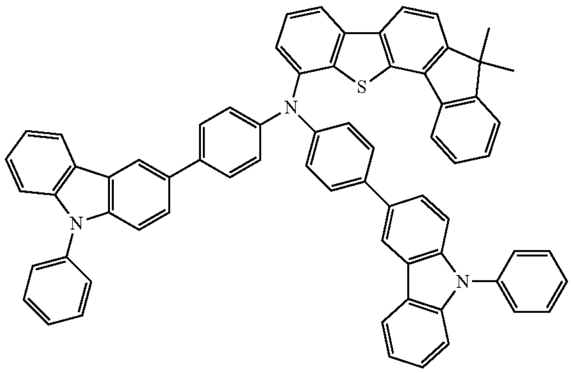
-continued
[A-24]
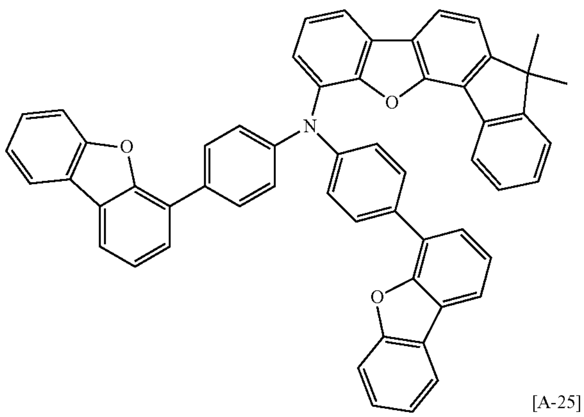
[A-25]
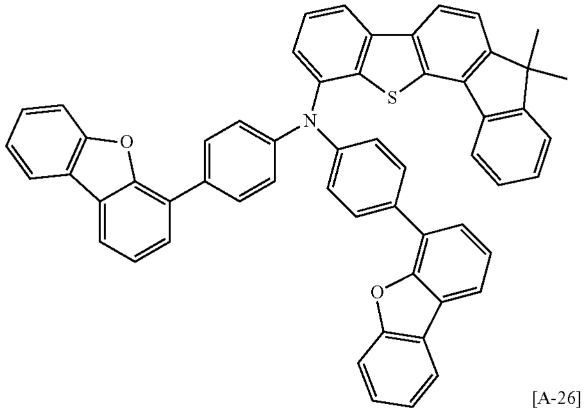
[A-26]
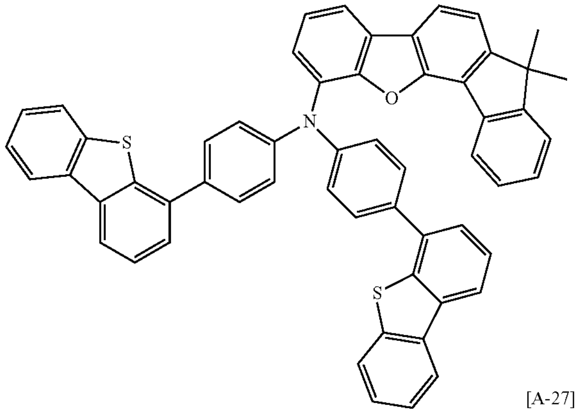
[A-27]
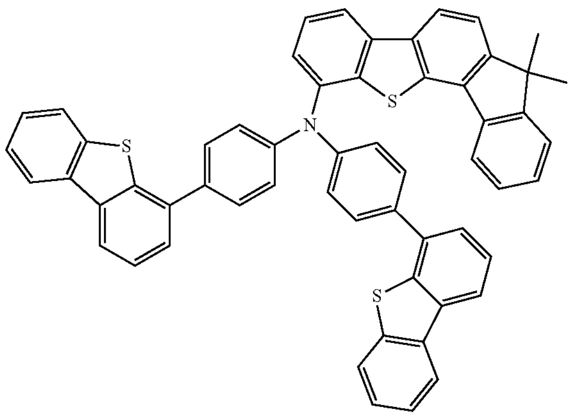

-continued
[A-28]
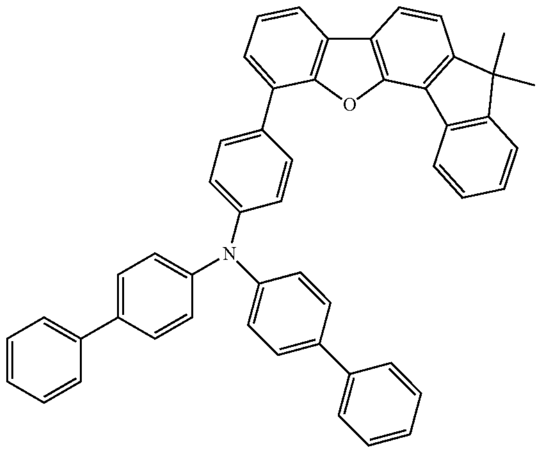
[A-29]
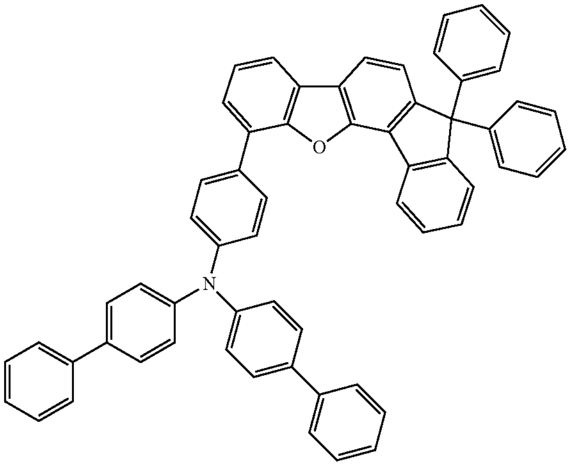
[A-30]
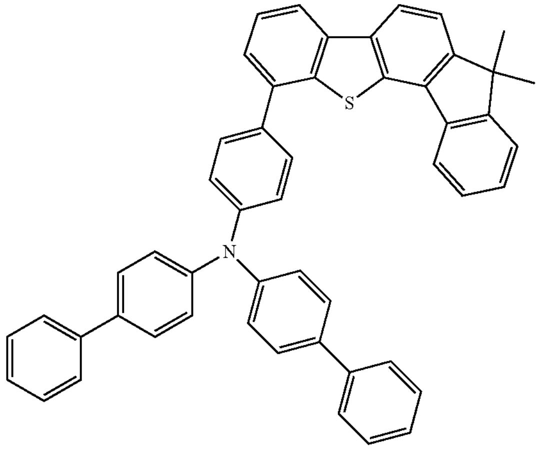
-continued
[A-31]
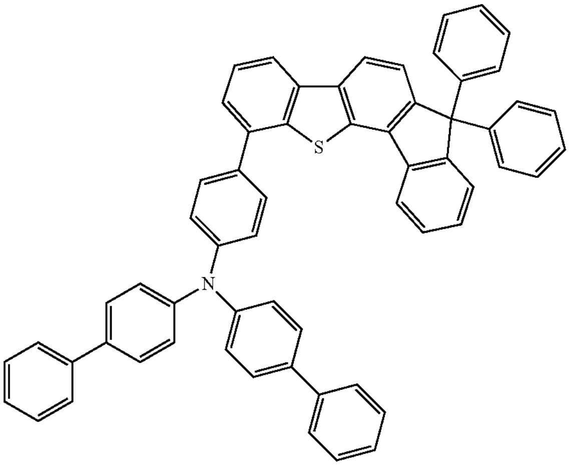
[A-32]
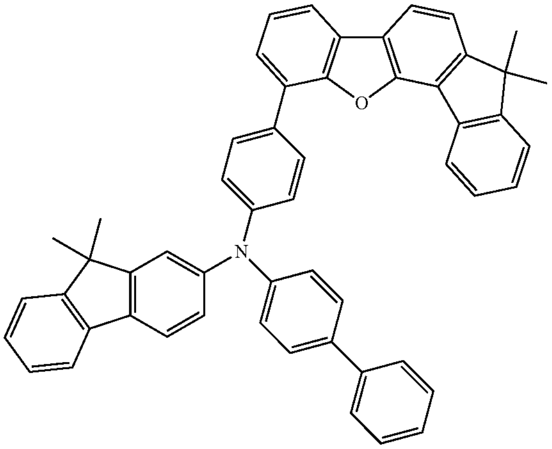
[A-33]
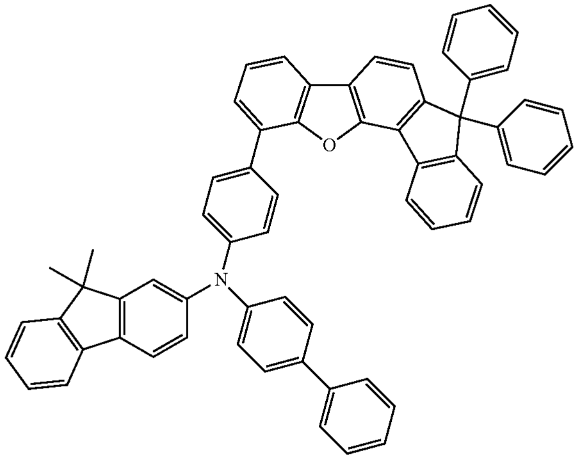

-continued
[A-34]
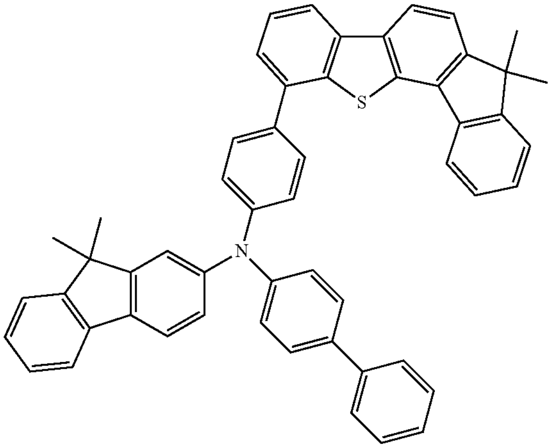
[A-35]
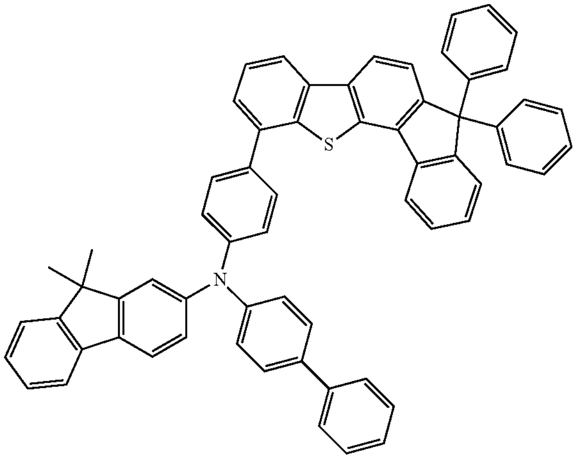
[A-36]
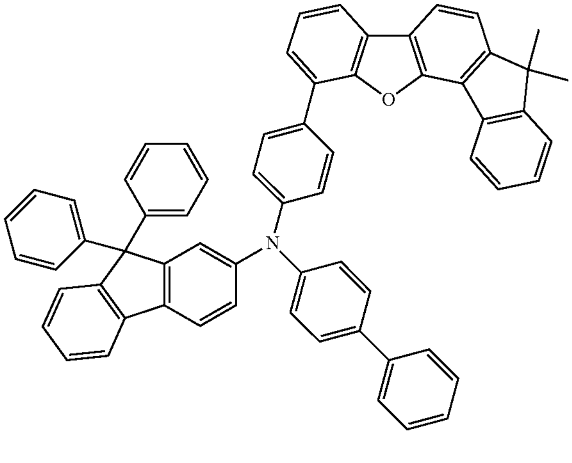
-continued
[A-37]
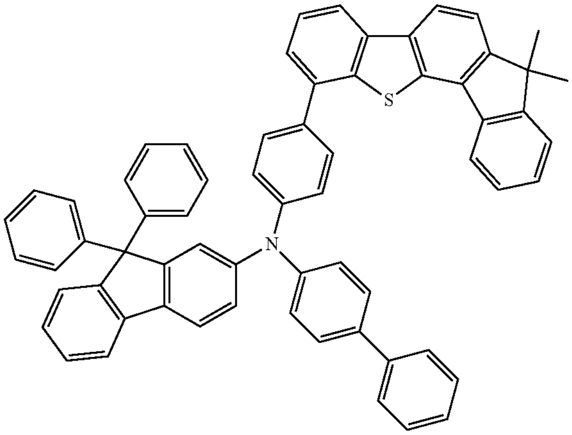
[A-38]
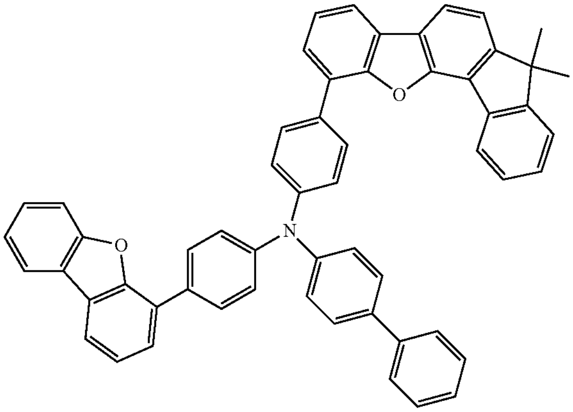
[A-39]
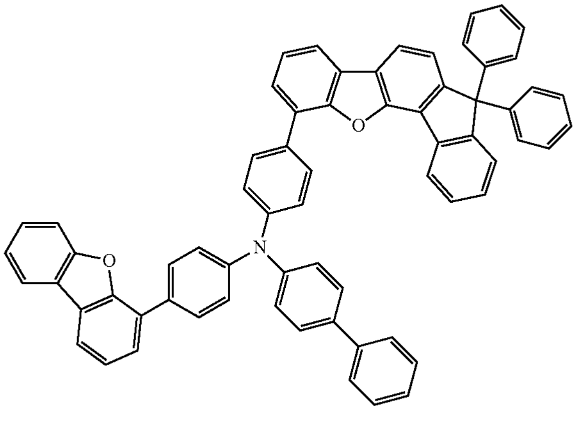

-continued
[A-40]
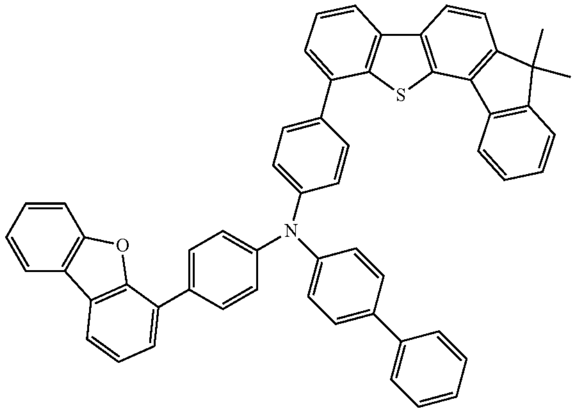
[A-41]
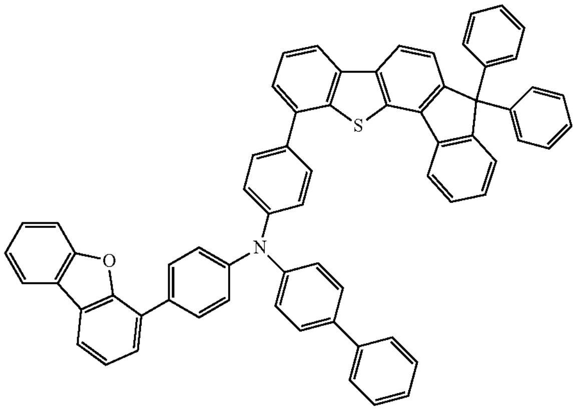
[A-42]
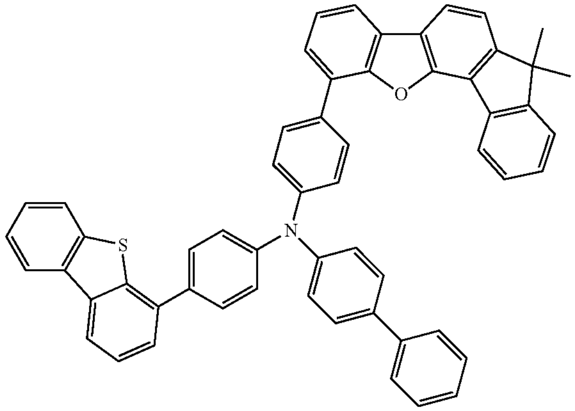
-continued
[A-43]
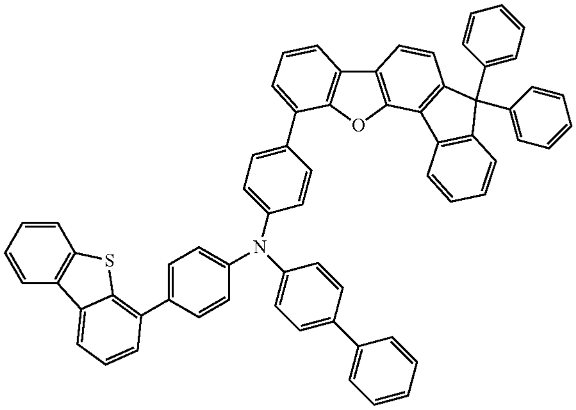
[A-44]
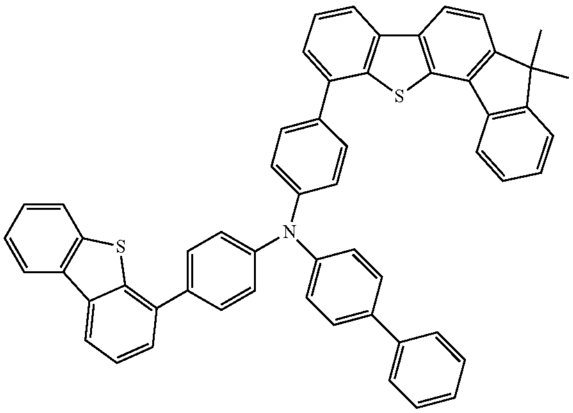
[A-45]
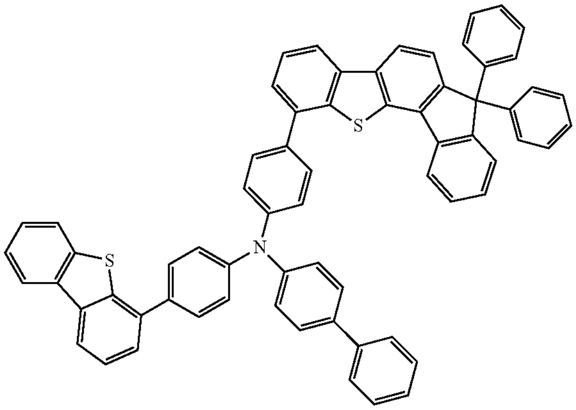

-continued
[A-46]
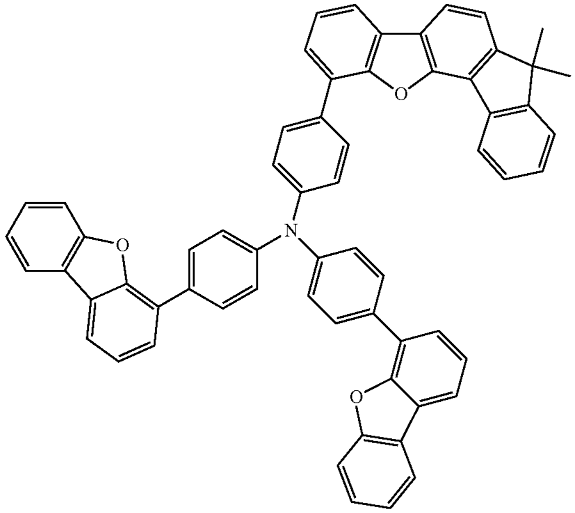
[A-47]
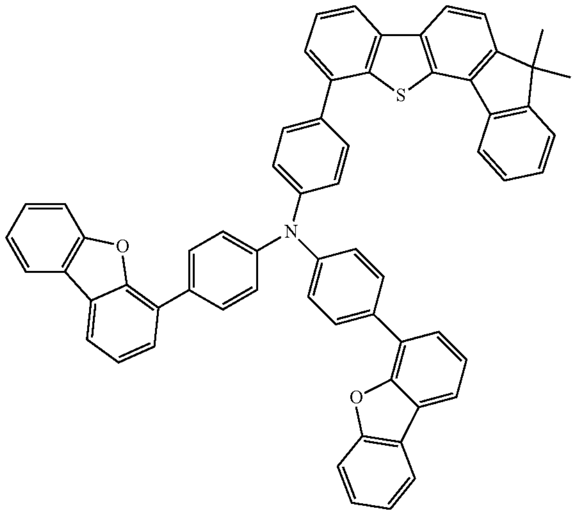
[A-48]
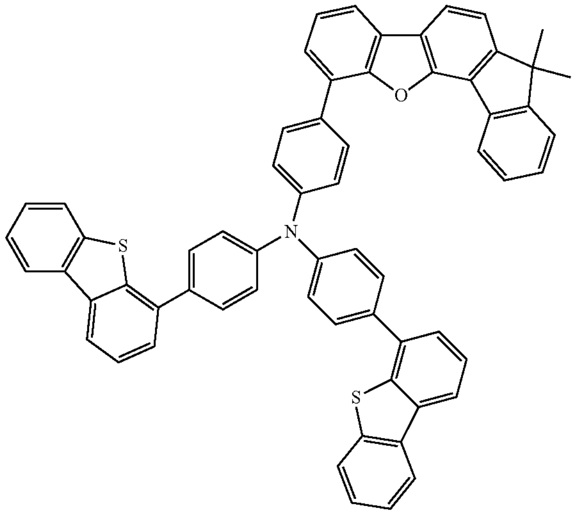
-continued
[A-49]
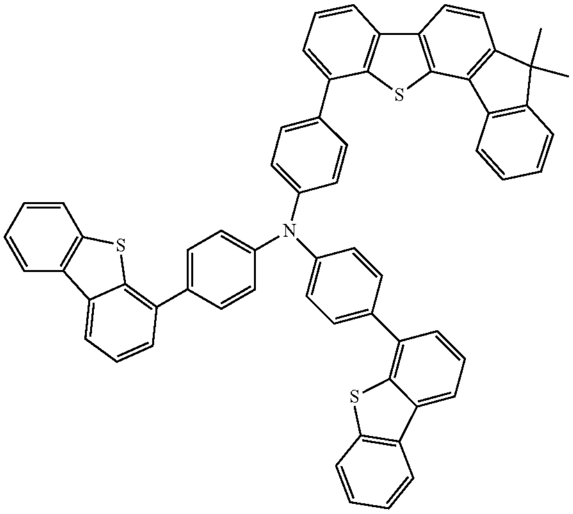
[A-50]
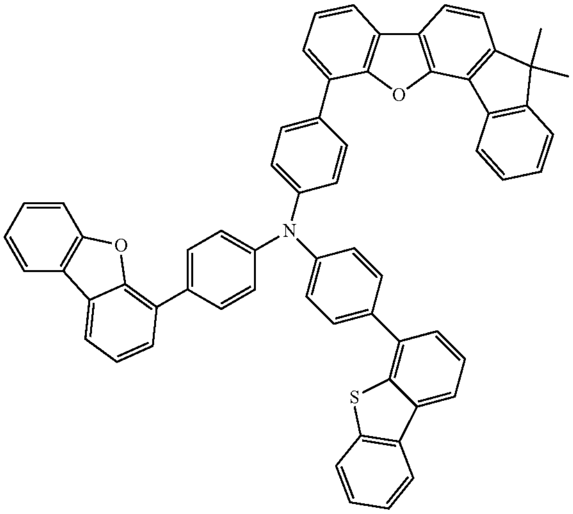
[A-51]
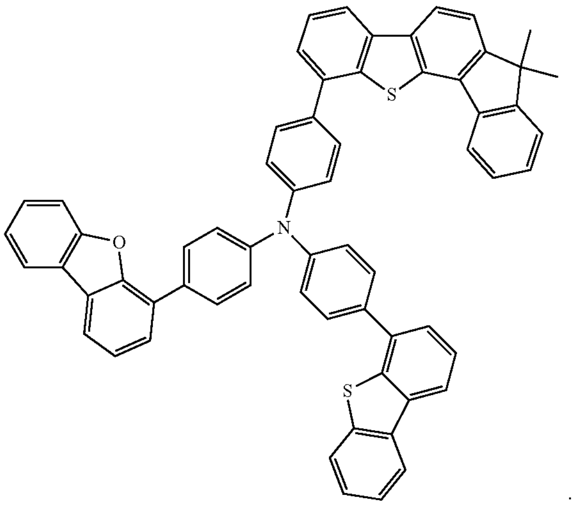
The compound may be represented by one of the following Chemical Formulae B-1 to B-32:

-continued
[B-1]
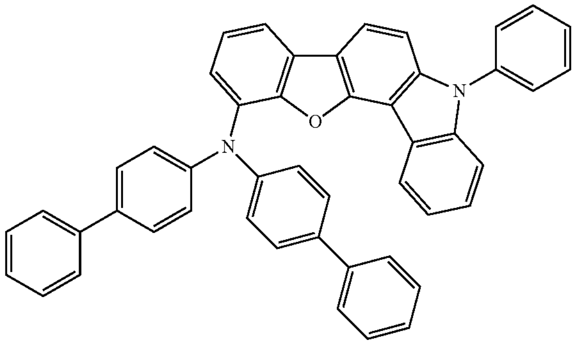
[B-2]
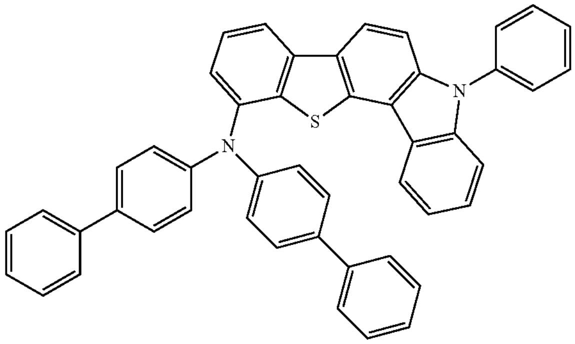
[B-3]
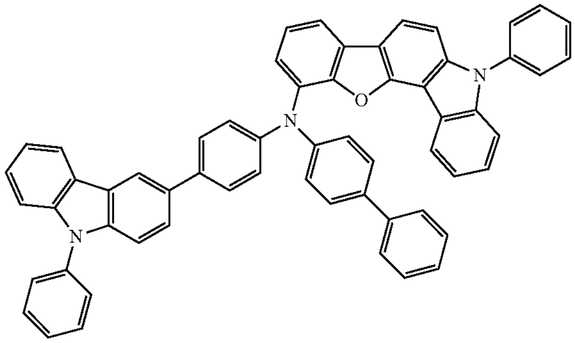
[B-4]
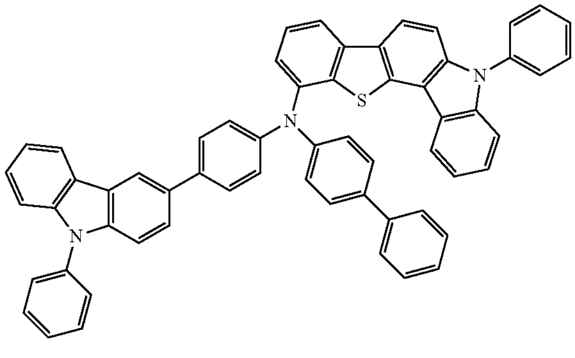
[B-5]
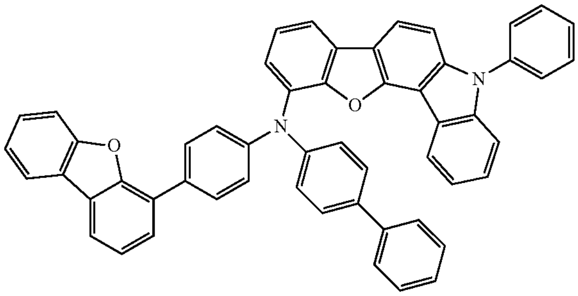
[B-6]
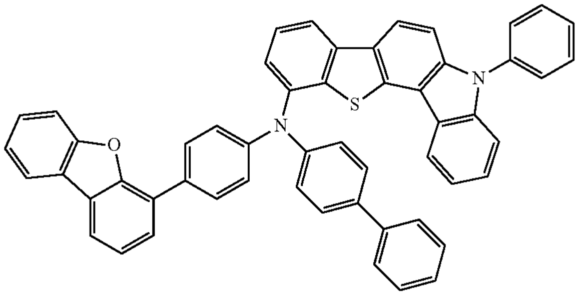
[B-7]
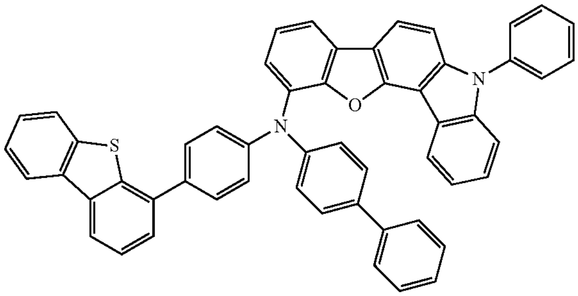
[B-8]
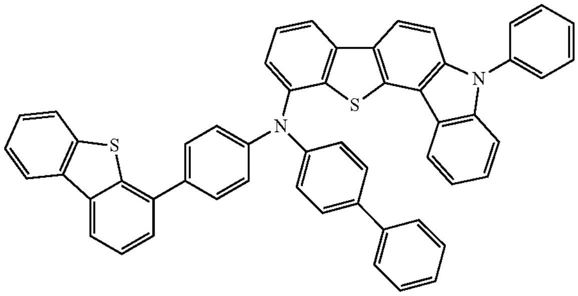
[B-9]
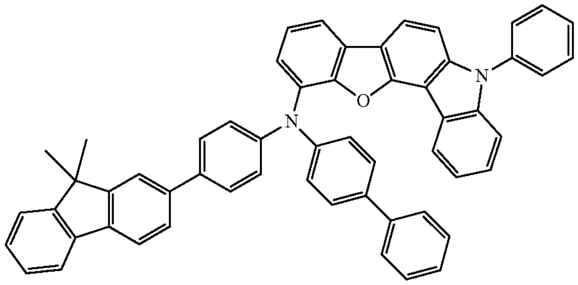

-continued
[B-10]
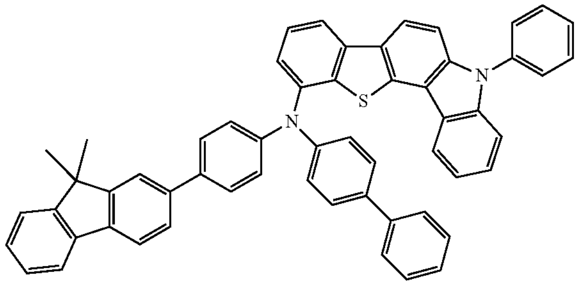
[B-11]
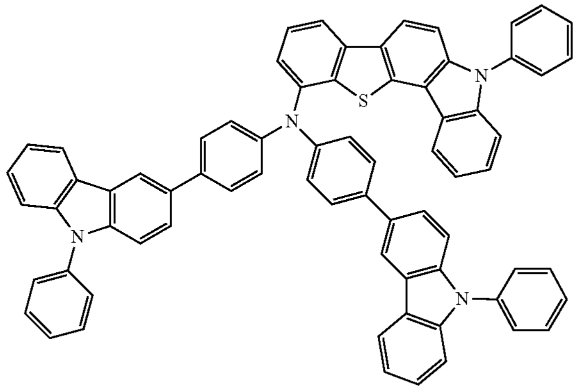
[B-12]
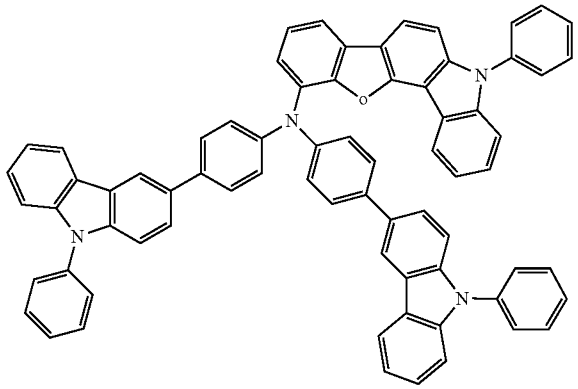
[B-13]
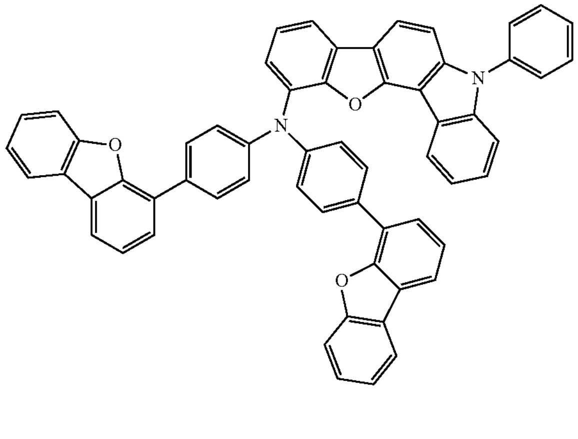
-continued
[B-14]
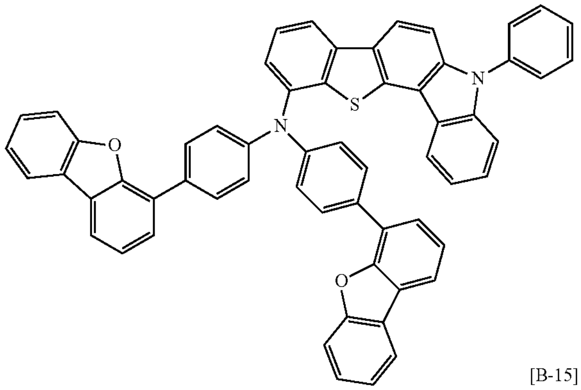
[B-15]
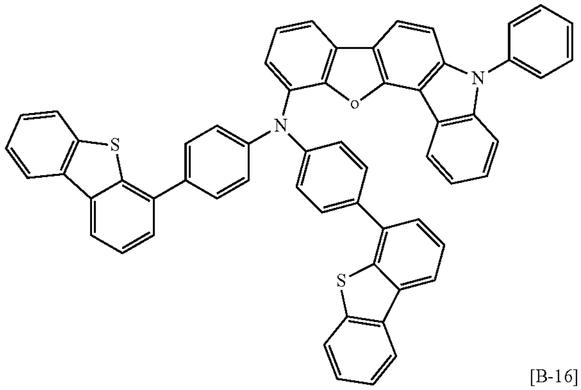
[B-16]
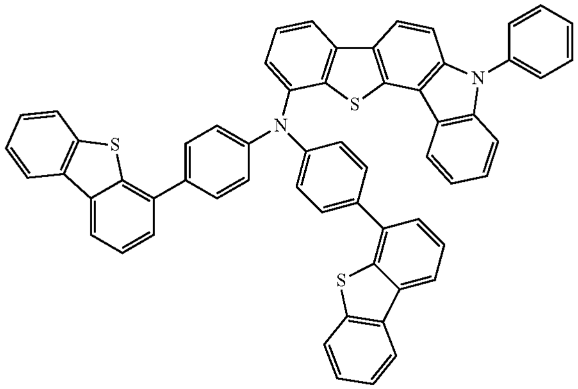
[B-17]
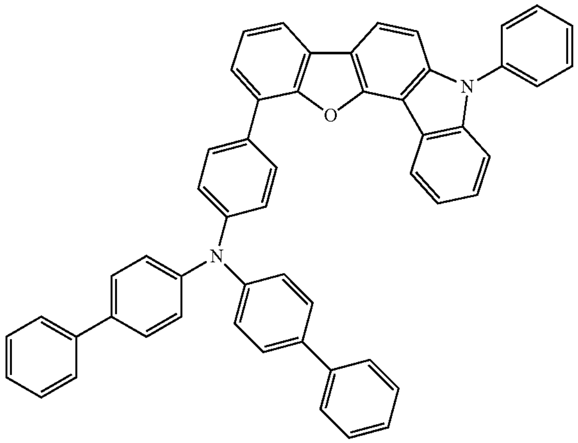

-continued
[B-18]
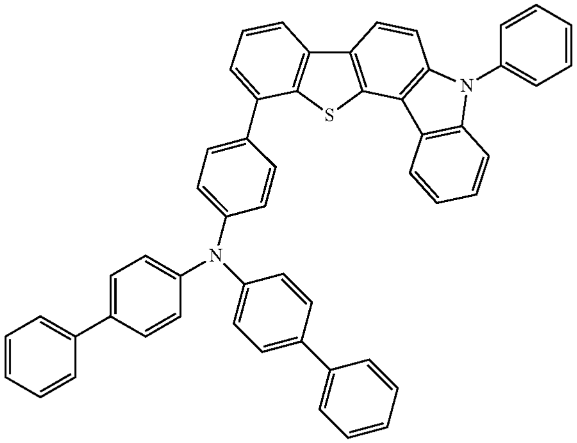
[B-19]
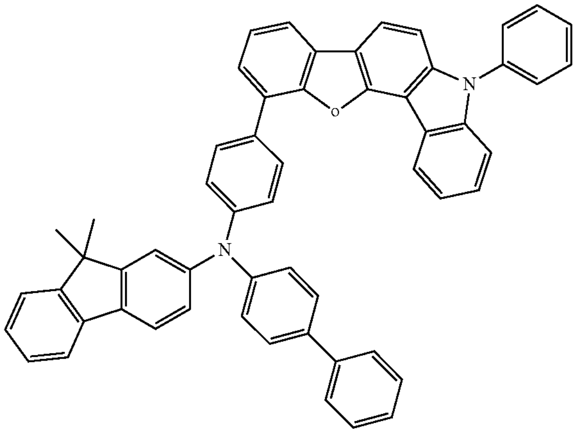
[B-20]
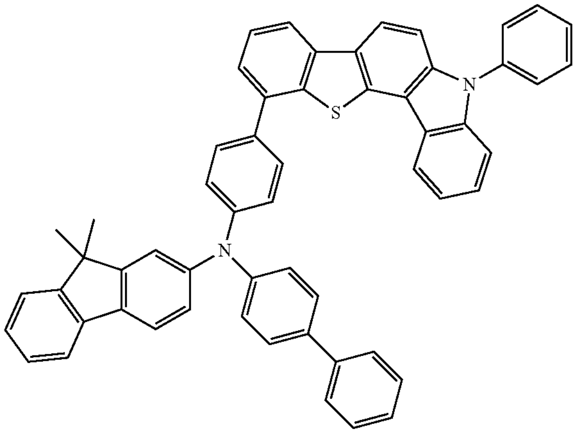
-continued
[B-21]
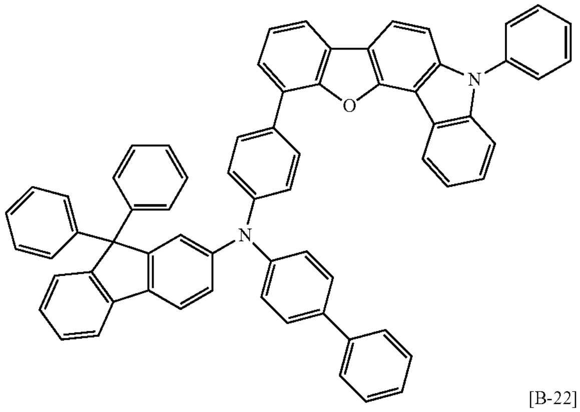
[B-22]
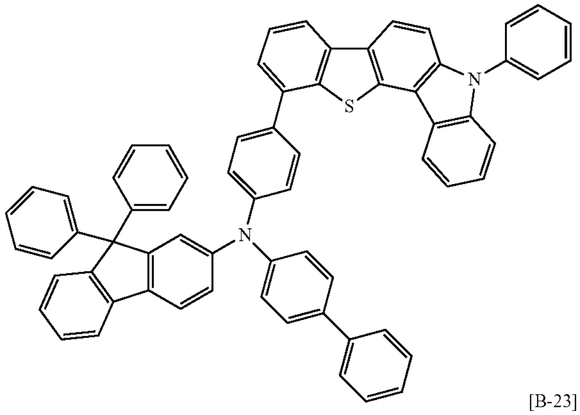
[B-23]
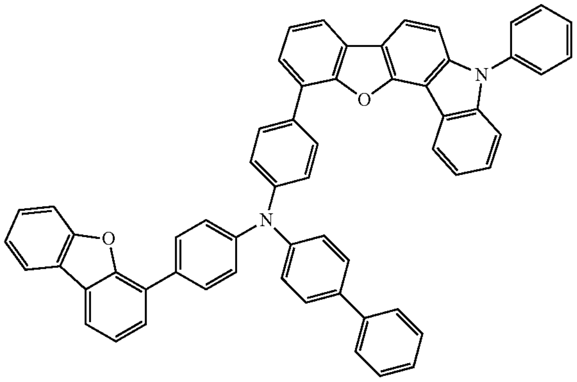
[B-24]
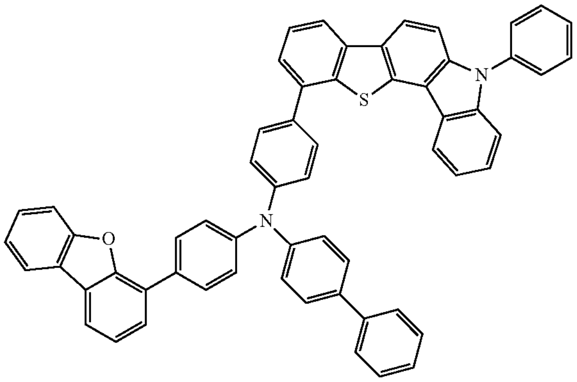

-continued
[B-25]
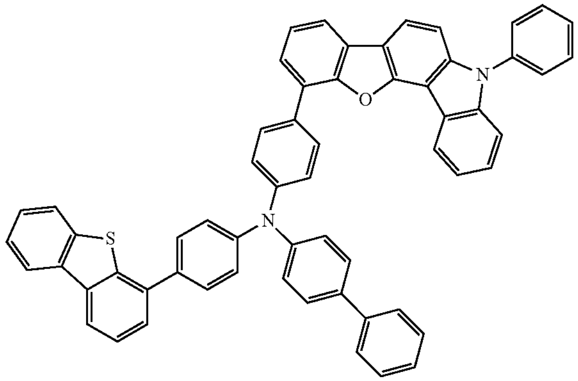
[B-26]
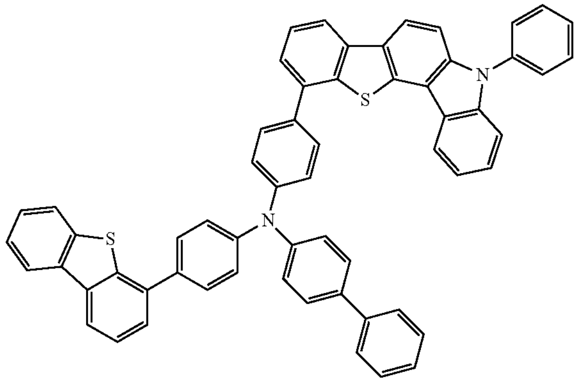
[B-27]
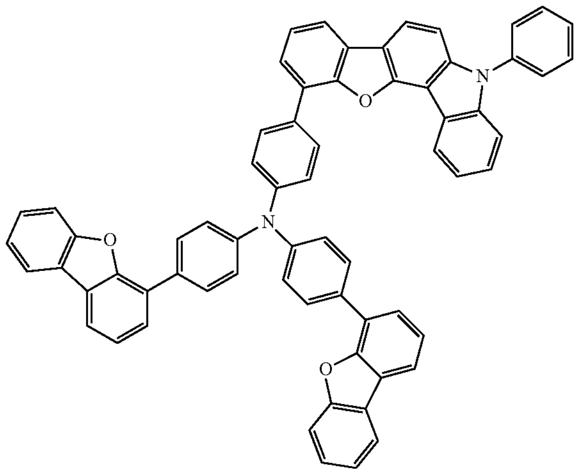
-continued
[B-28]
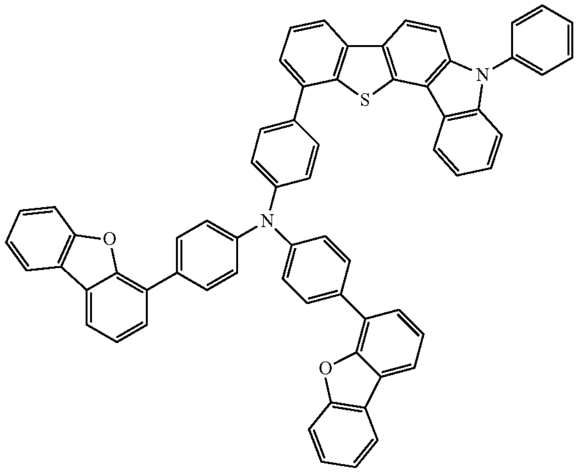
[B-29]
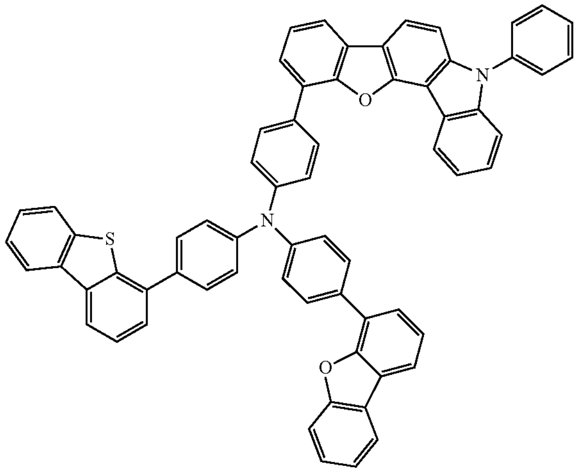
[B-30]
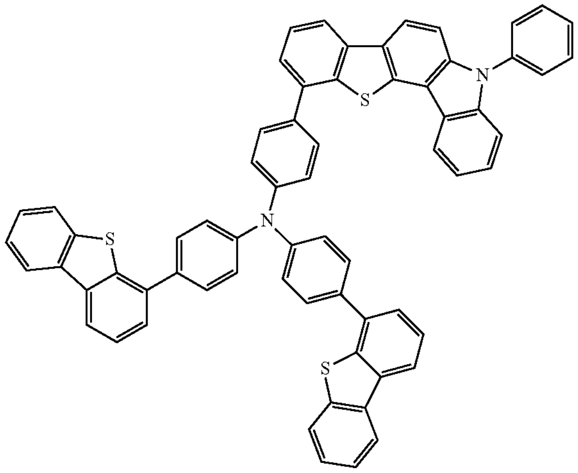

-continued
[B-31]
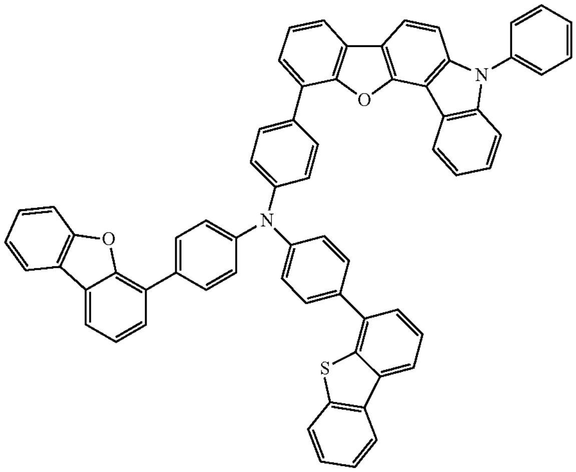
[B-32]
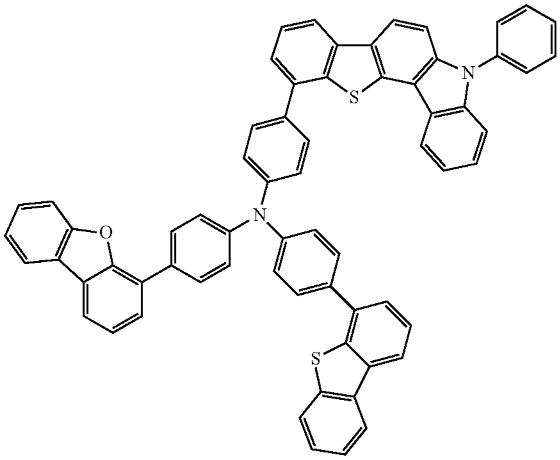
The compound may be represented by one of the following Chemical Formulae C-1 to C-41:
[C-1]
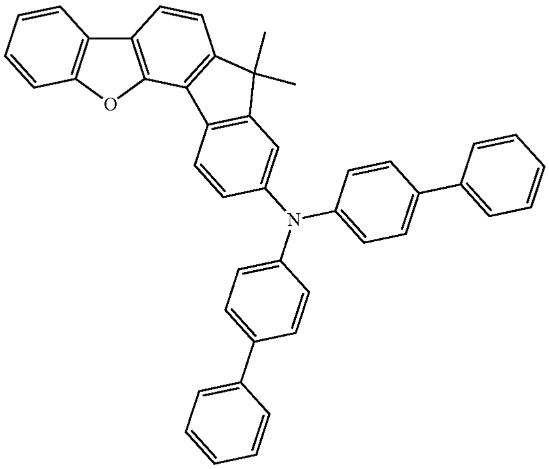
-continued
[C-2]
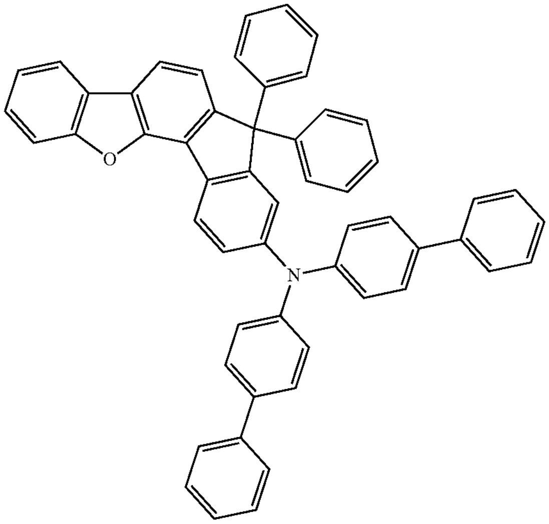
[C-3]
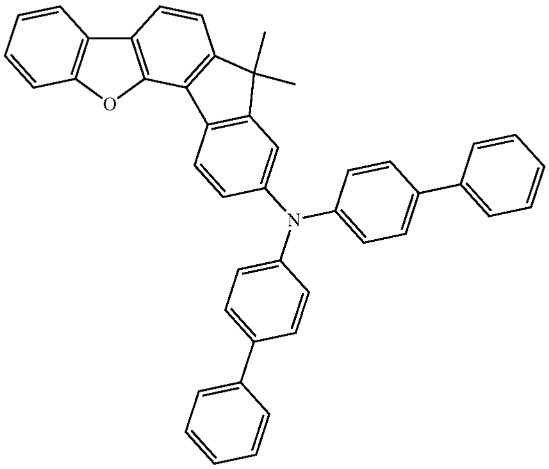
[C-4]
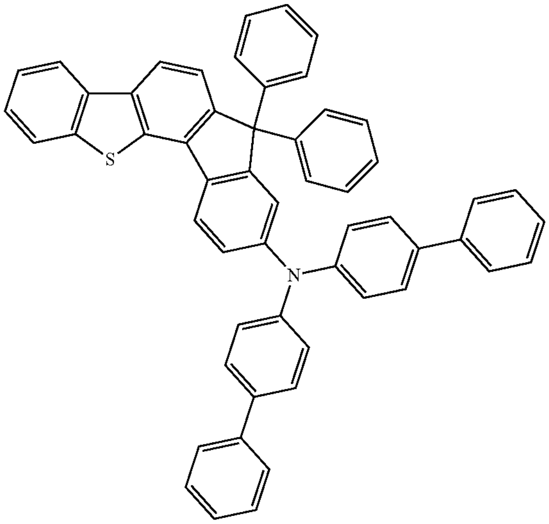

-continued
[C-5]
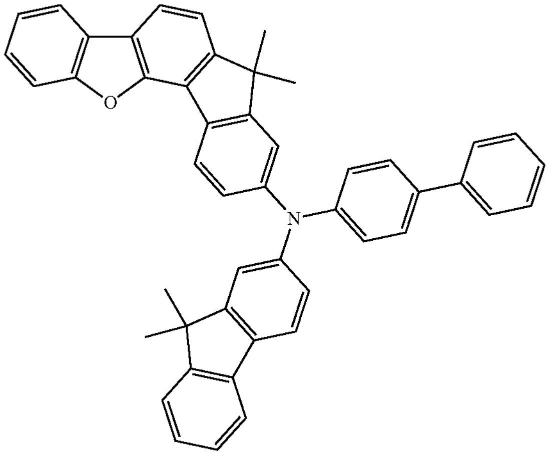
[C-6]
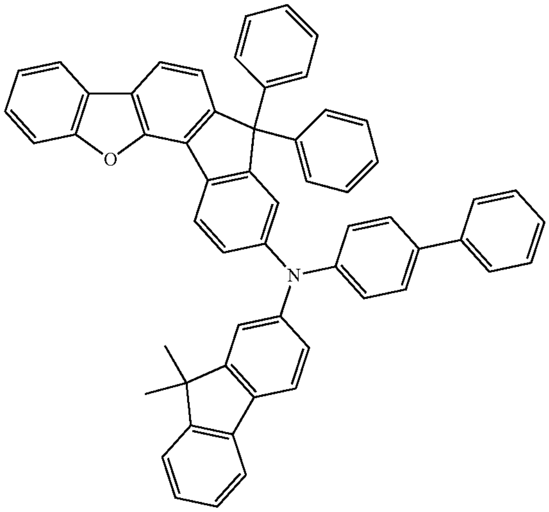
[C-7]
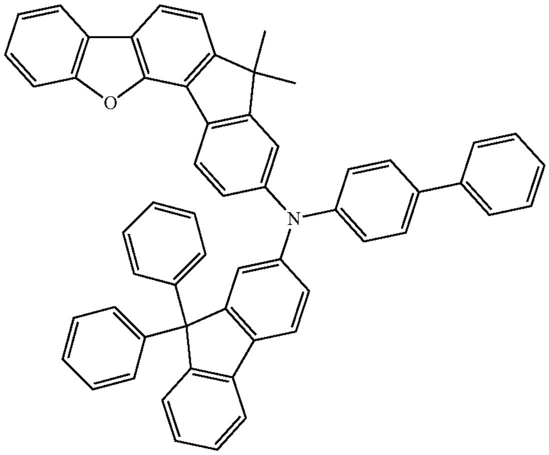
-continued
[C-8]
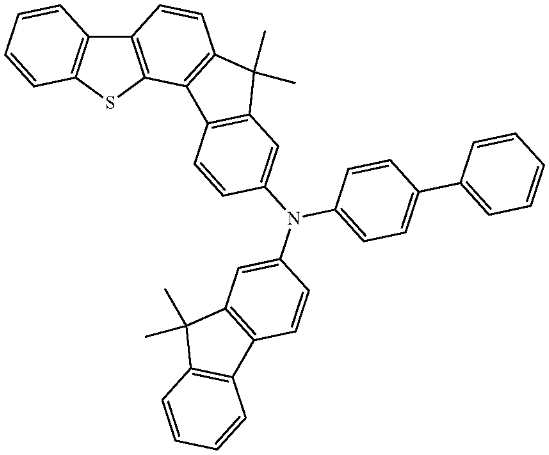
[C-9]
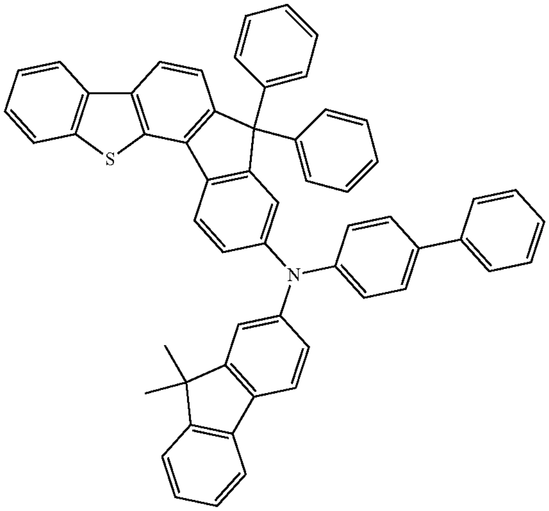
[C-10]
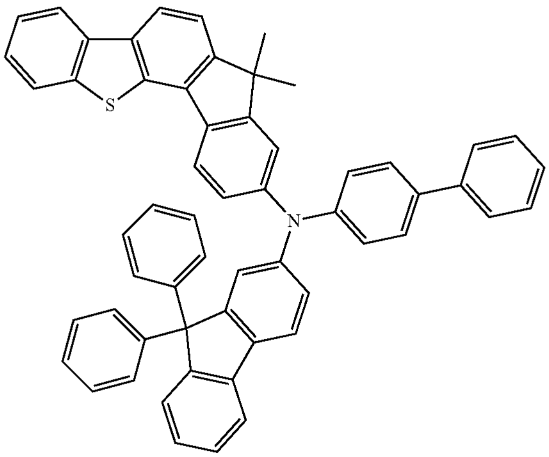

-continued
[C-11]
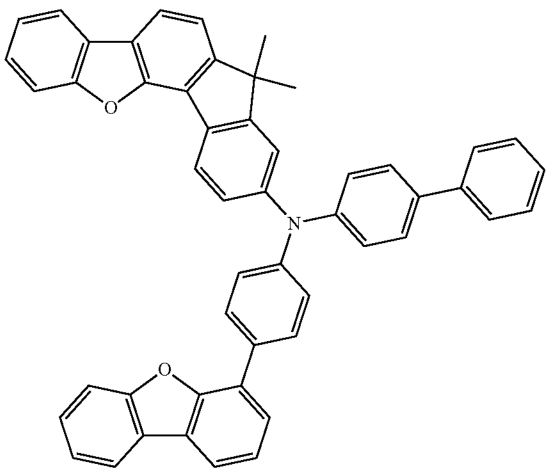
[C-12]
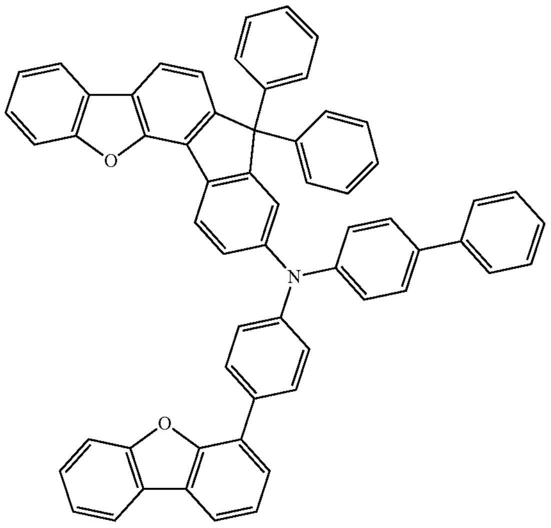
[C-13]
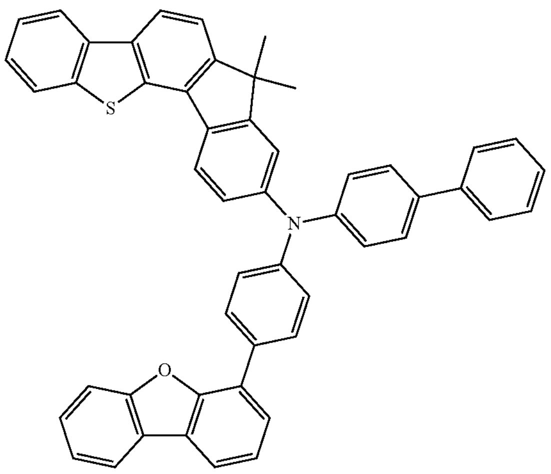
-continued
[C-14]
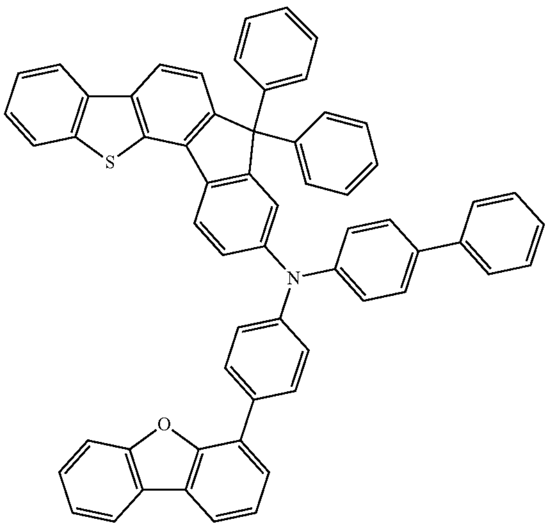
[C-15]
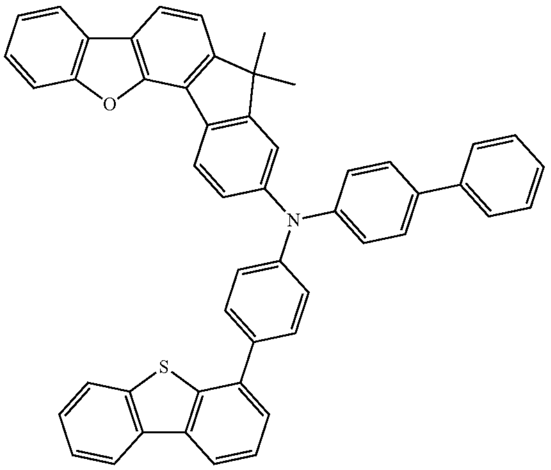
[C-16]
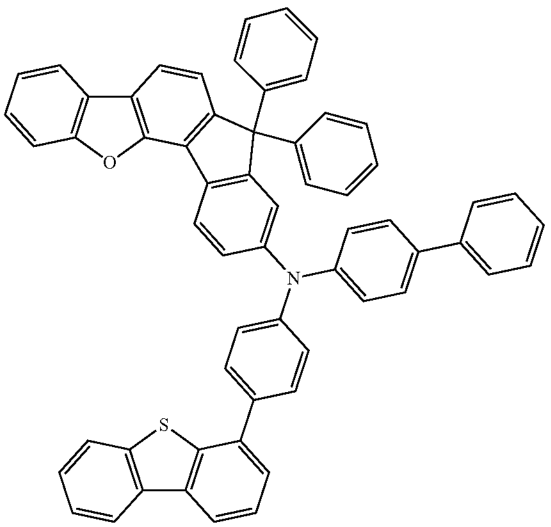

-continued
[C-17]
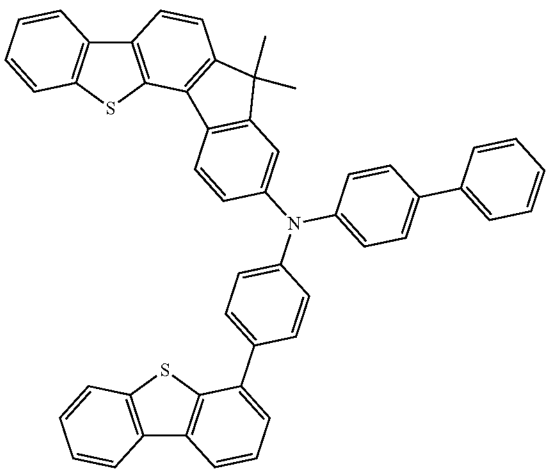
[C-18]
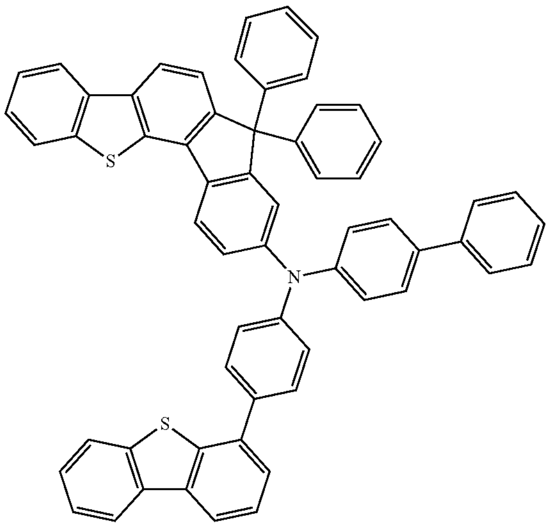
[C-19]
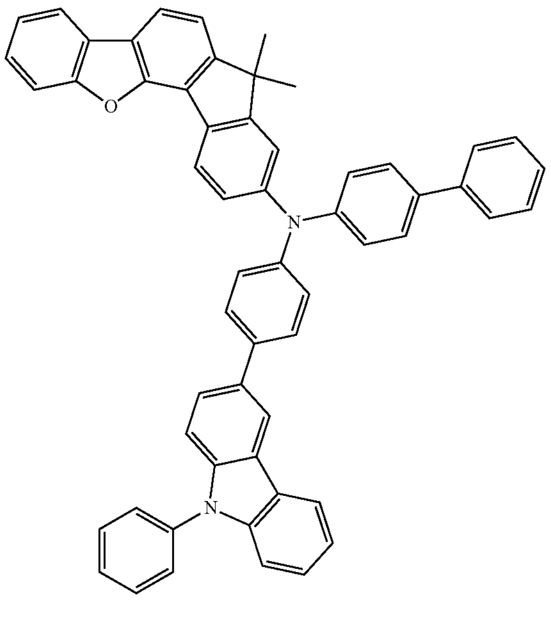
-continued
[C-20]
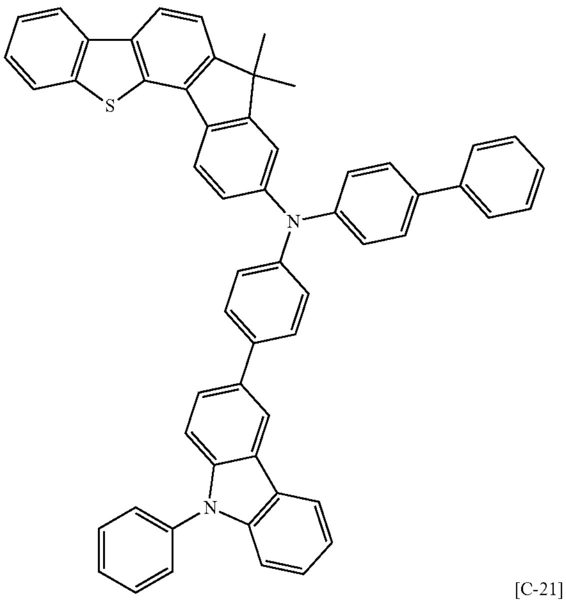
[C-21]
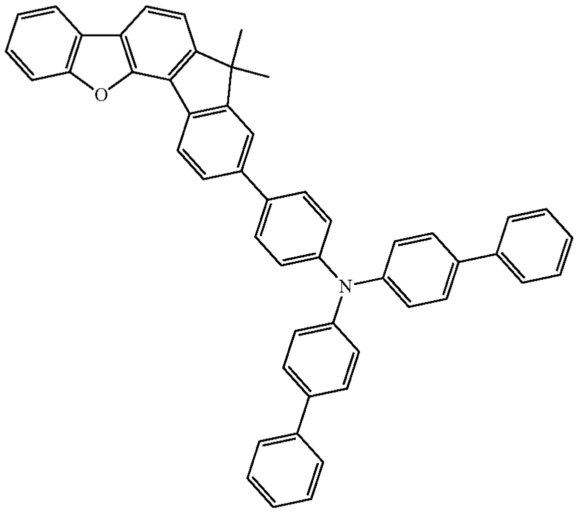
[C-22]
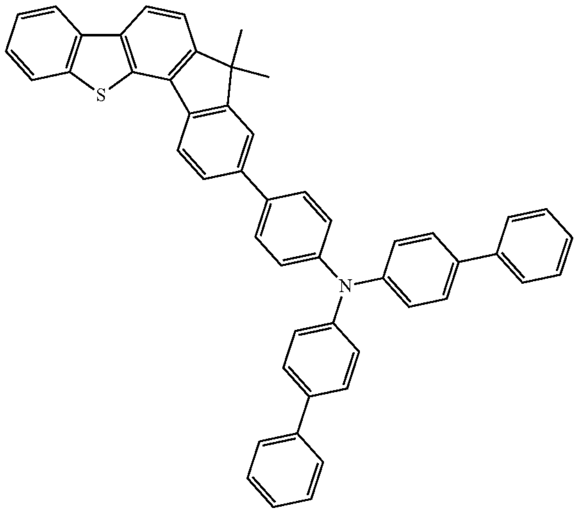

-continued
[C-23]
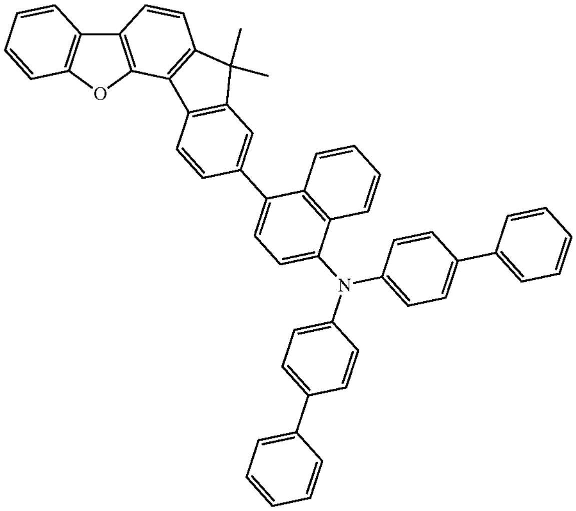
[C-24]
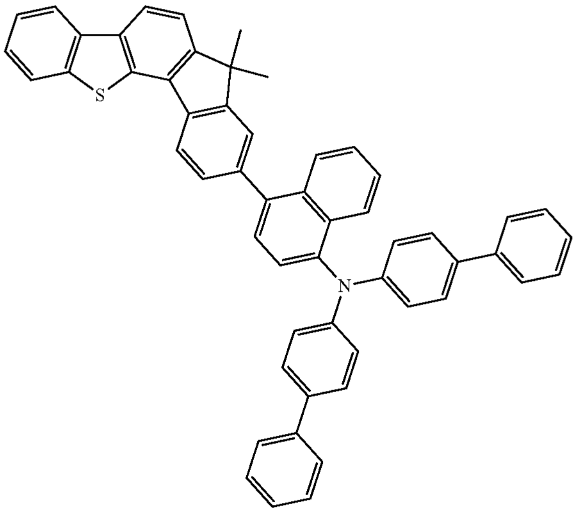
[C-25]
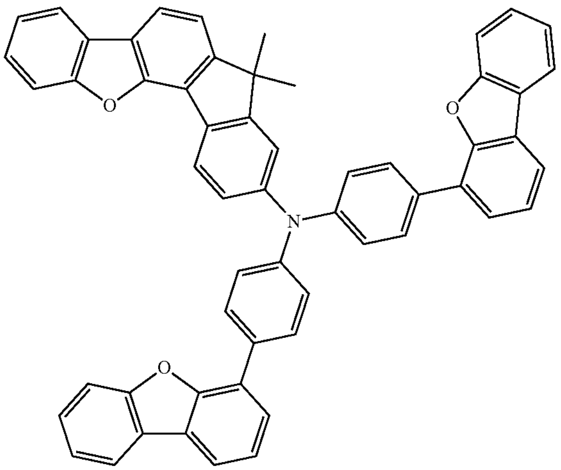
-continued
[C-26]
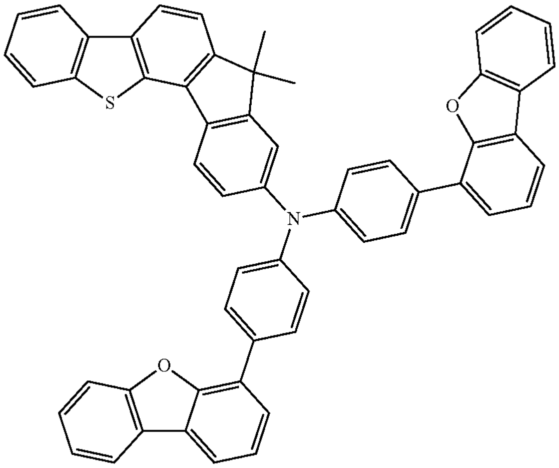
[C-27]
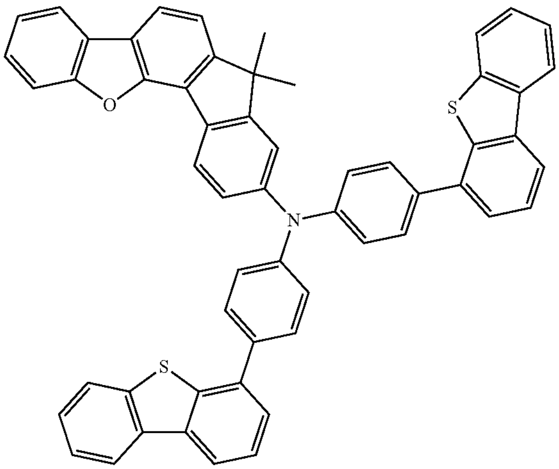
[C-28]
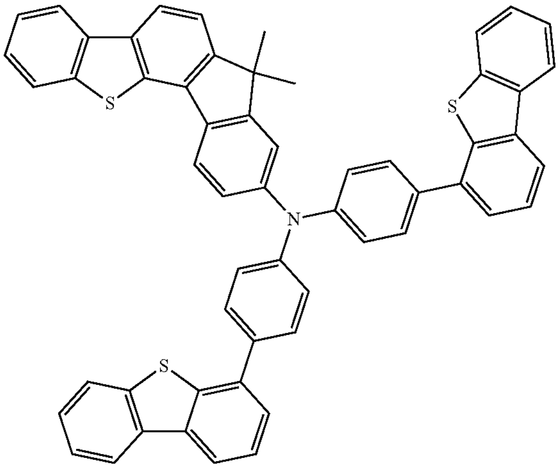

-continued
[C-29]
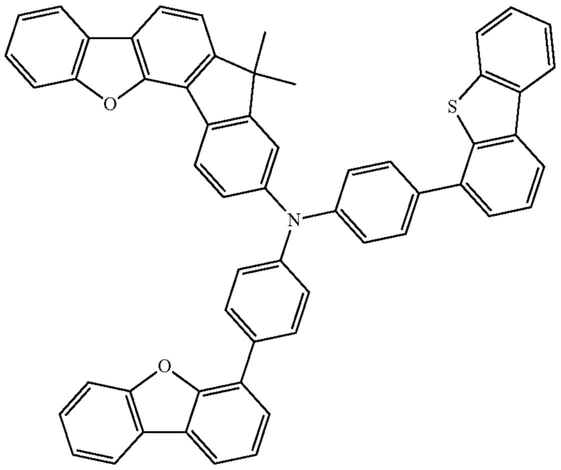
[C-30]
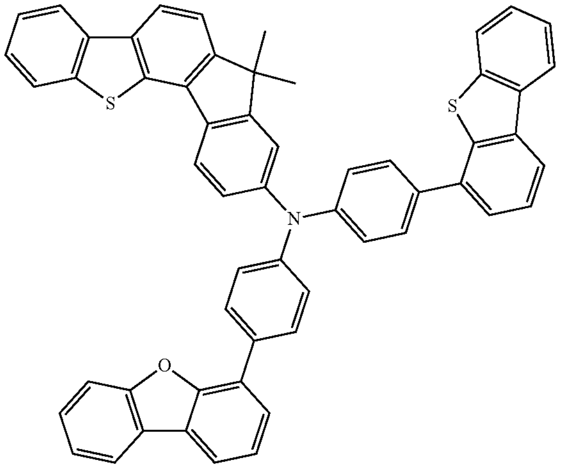
[C-31]
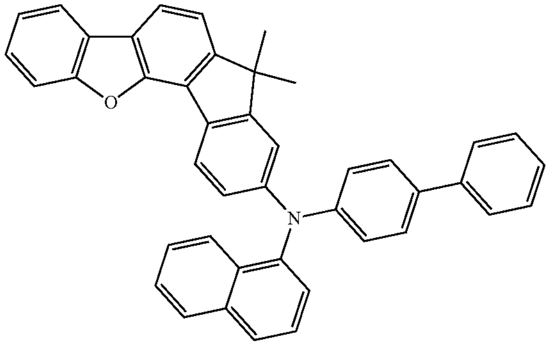
-continued
[C-32]
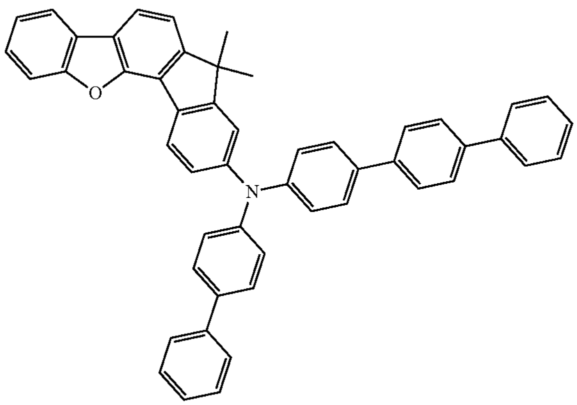
[C-33]
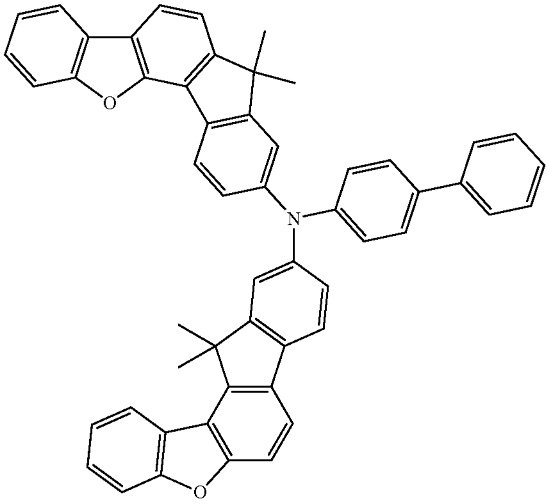
[C-34]
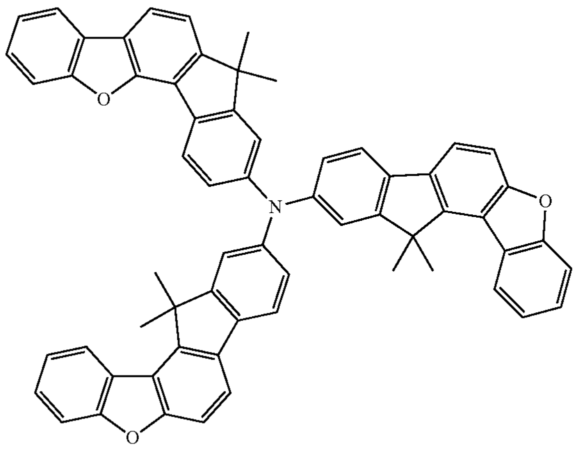

-continued
[C-35]
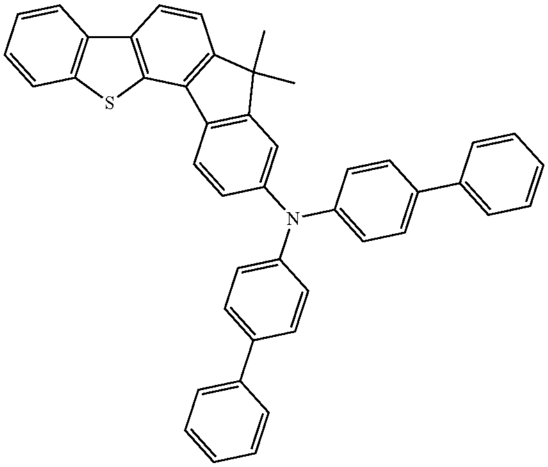
[C-36]
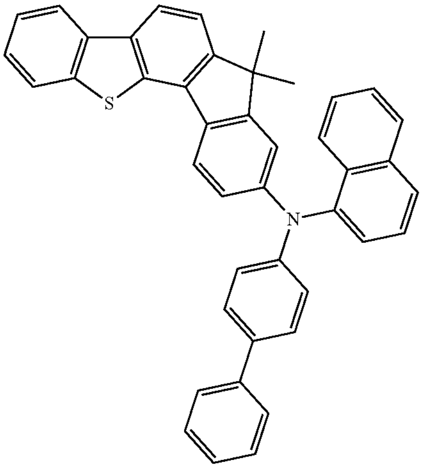
[C-37]
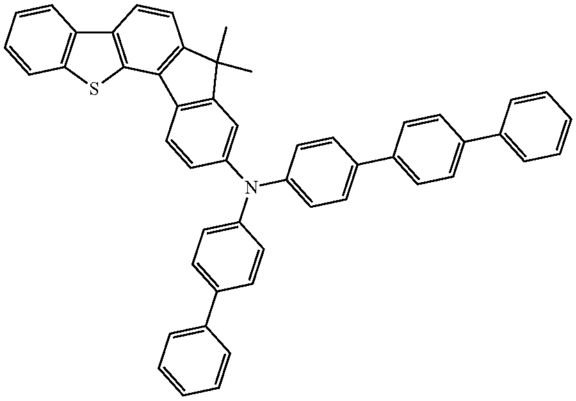
-continued
[C-38]
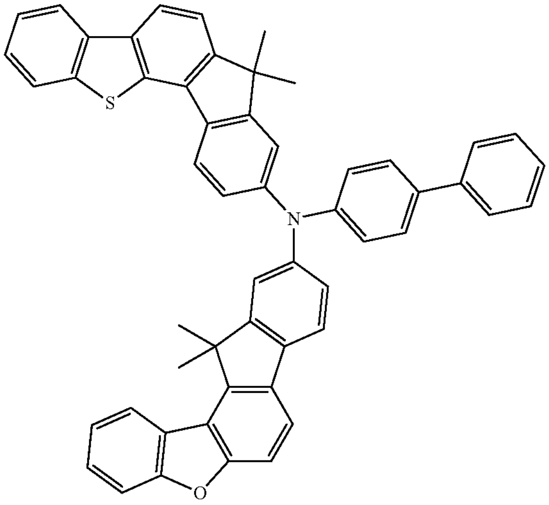
[C-39]
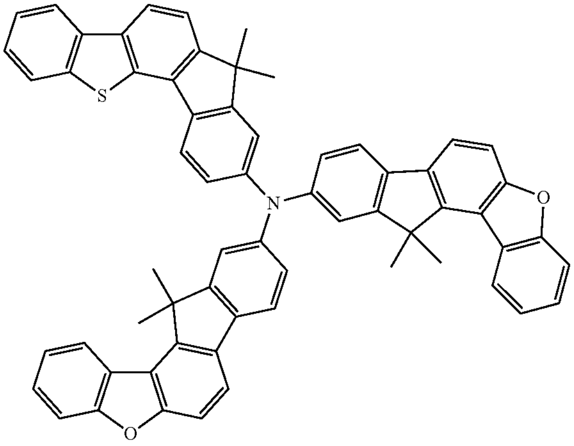
[C-40]
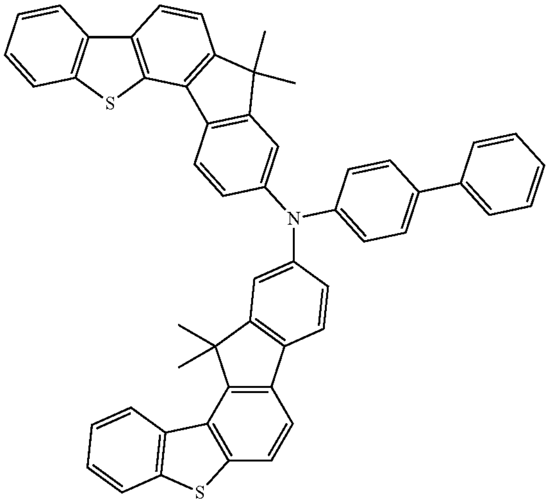

-continued
[C-41]
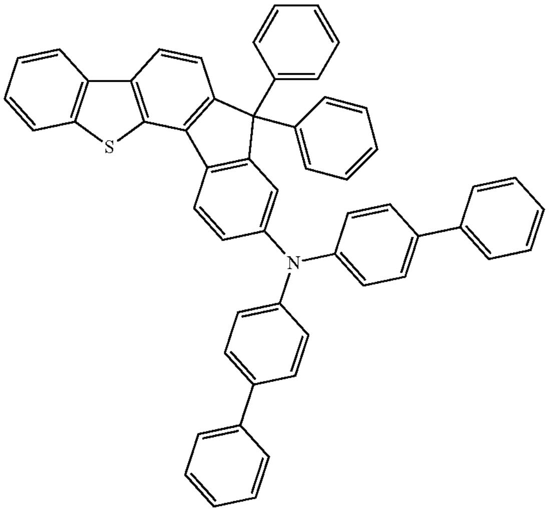
The compound may be represented by one of the following Chemical Formulae D-1 to D-20:
[D-1]
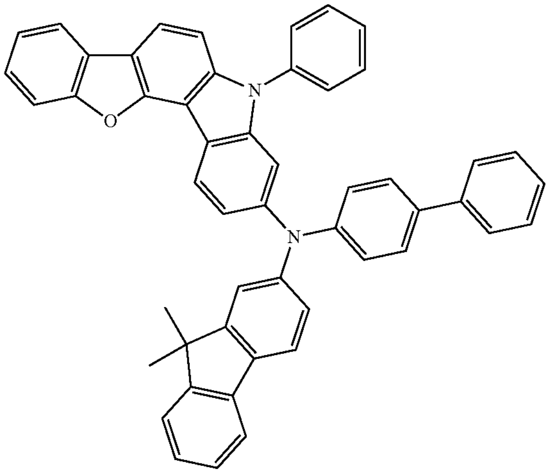
[D-2]
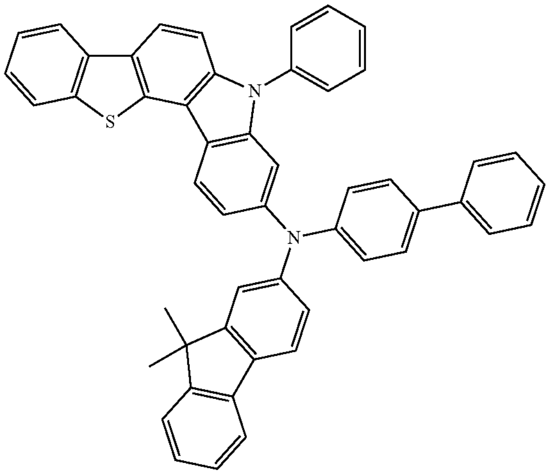
-continued
[D-3]
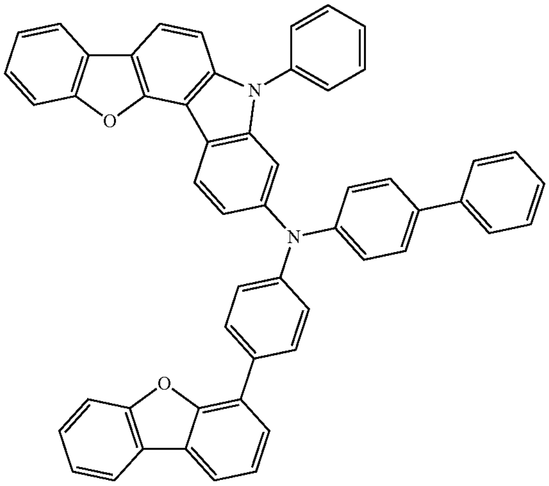
[D-4]
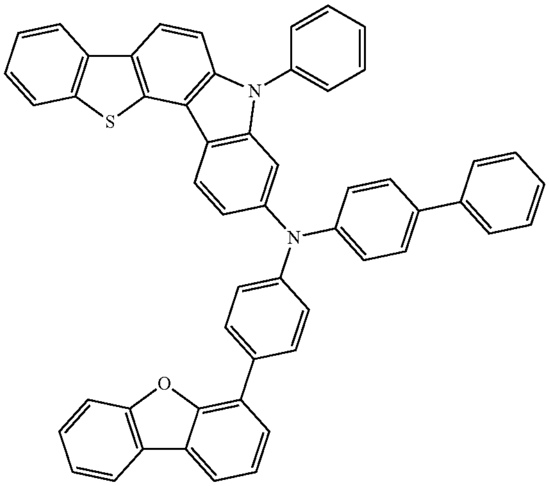
[D-5]
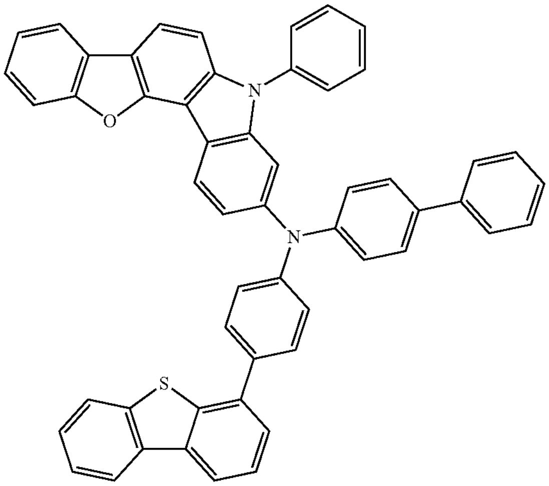

-continued
[D-6]
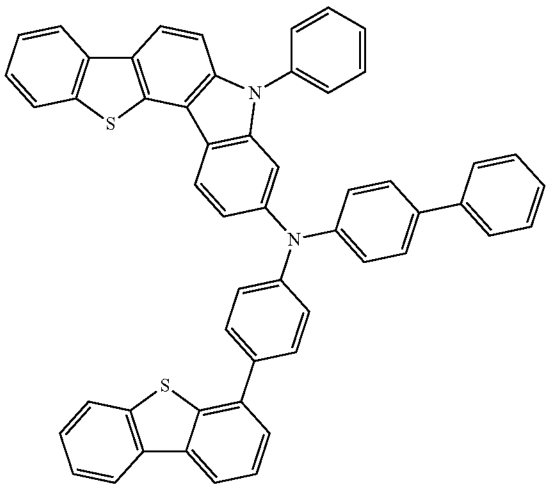
[D-7]
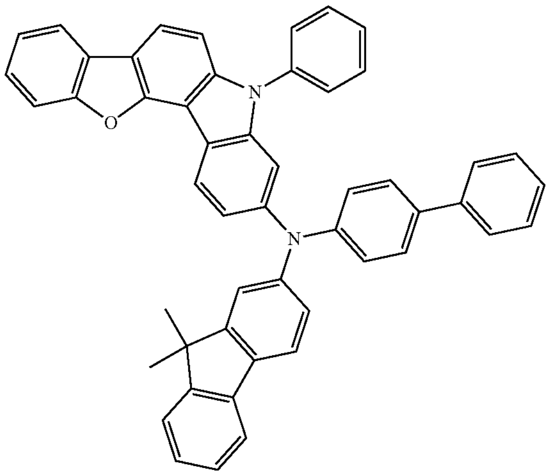
[D-8]
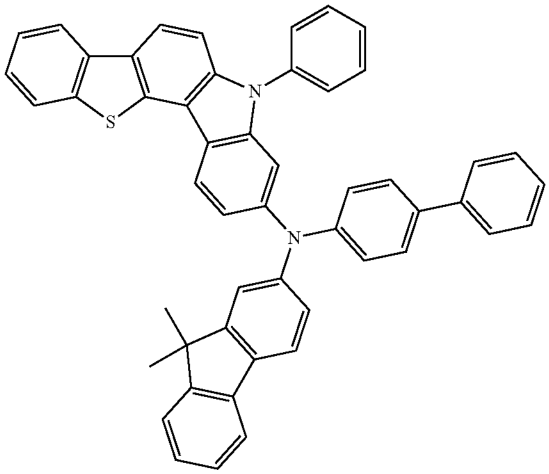
-continued
[D-9]
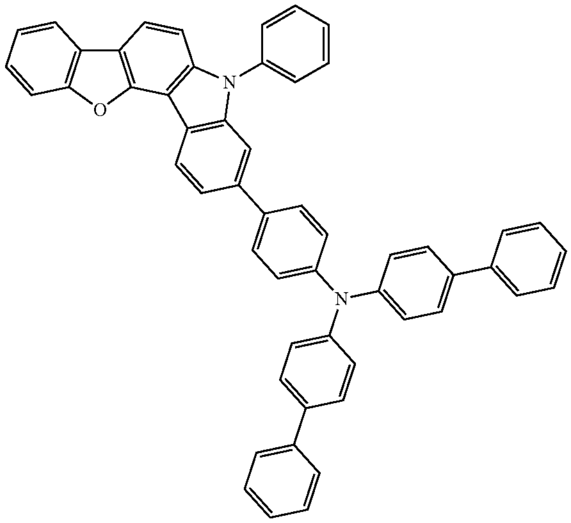
[D-10]
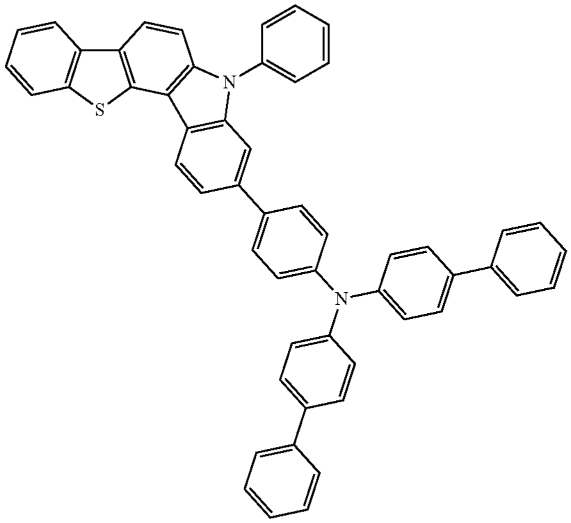
[D-11]
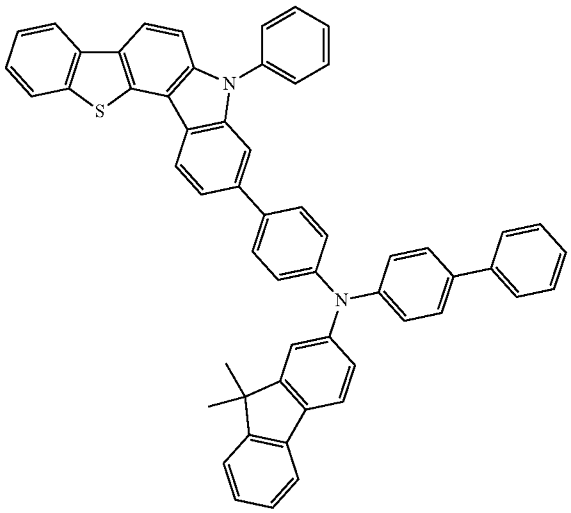

-continued
[D-12]
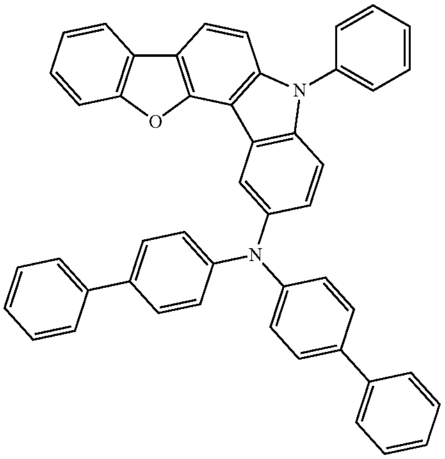
[D-13]
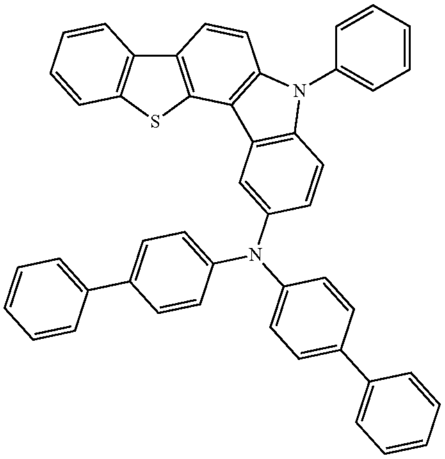
[D-14]
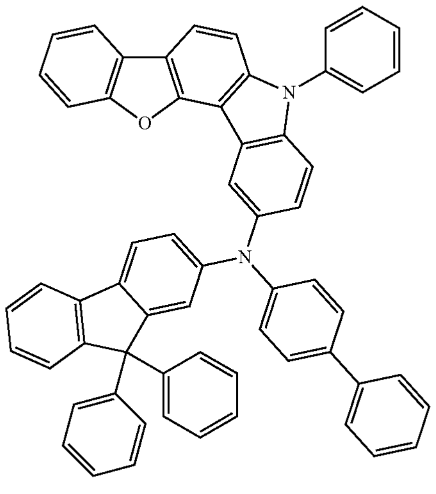
-continued
[D-15]
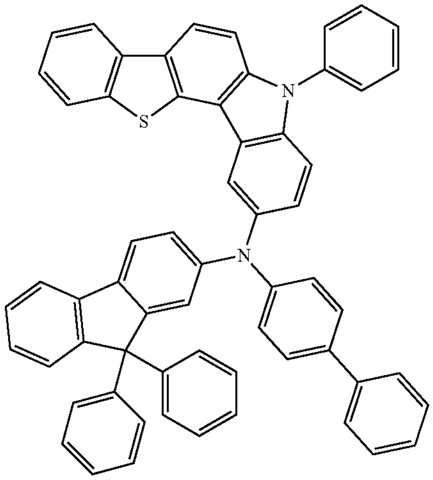
[D-16]
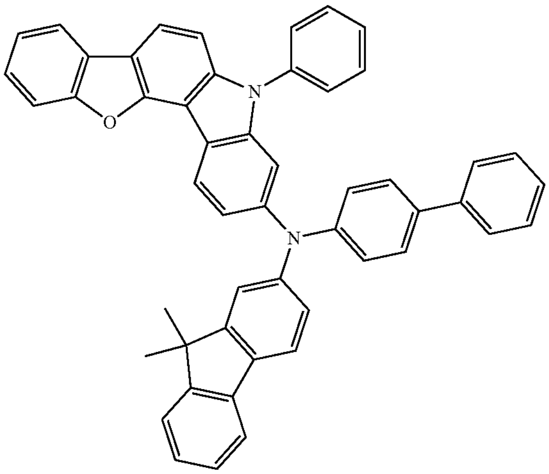
[D-17]
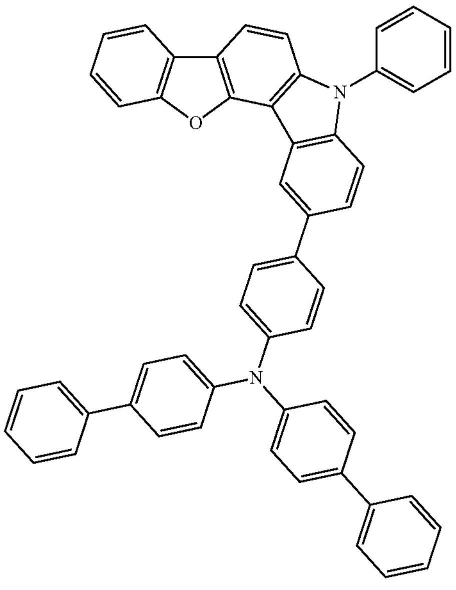

-continued

[D-18]

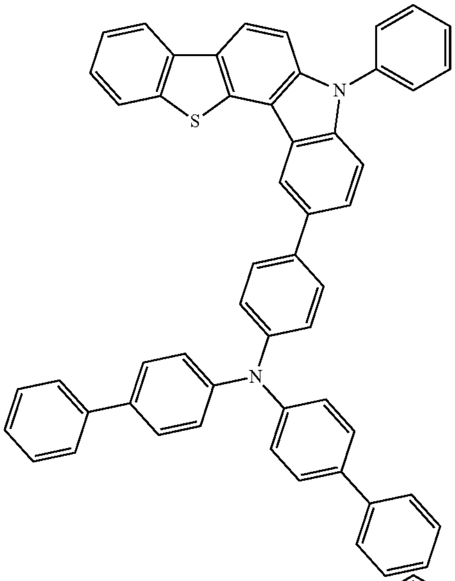

[D-19]

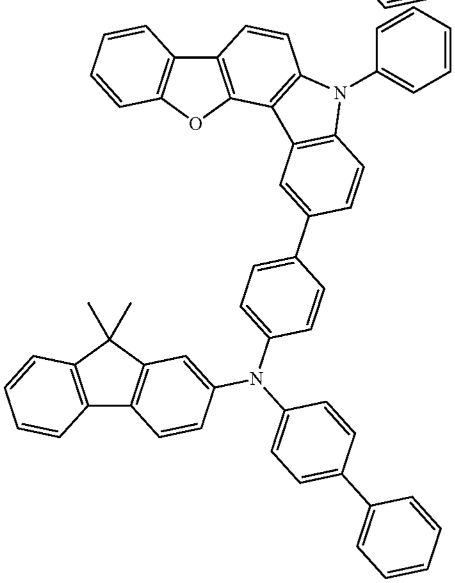

[D-20]

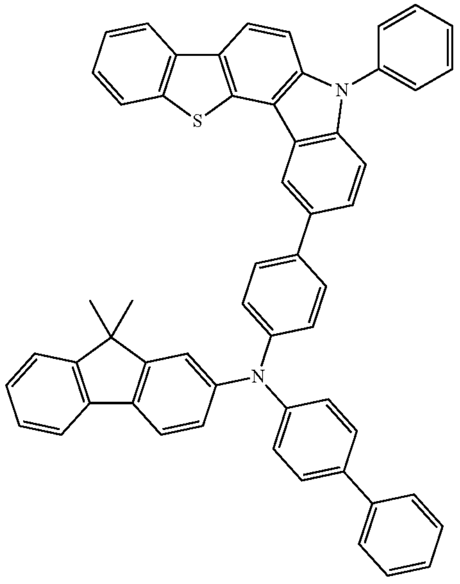

The compound may be a hole transport material or a hole injection material for an organic light emitting diode.

The compound may have a triplet excitation energy (T1) of about 2.0 eV or greater.

The organic optoelectronic device may be selected from the group of an organic photoelectronic device, an organic light emitting diode, an organic solar cell, an organic transistor, an organic photoconductor drum, and an organic memory device.

The embodiments may also be realized by providing an organic light emitting diode including an anode; a cathode; and at least one organic thin layer between the anode and the cathode, wherein the at least one organic thin layer includes the compound for an organic optoelectronic device according to an embodiment.

The at least one organic thin layer may be selected from the group of an emission layer, a hole transport layer (HTL), a hole injection layer (HIL), an electron transport layer (ETL), an electron injection layer (EIL), a hole blocking film, and a combination thereof.

The at least one organic thin layer may include a hole transport layer (HTL) or a hole injection layer (HIL), and the compound for an organic optoelectronic device is included in the hole transport layer (HTL) or the hole injection layer (HIL).

The at least one organic thin layer may include an emission layer, and the compound for an organic optoelectronic device is included in the emission layer.

The at least one organic thin layer may include an emission layer, and the compound for an organic optoelectronic device is a phosphorescent host material or fluorescent host material in the emission layer.

The embodiments may also be realized by providing a display device including the organic light emitting diode according to an embodiment.

DETAILED DESCRIPTION

Figure 1:
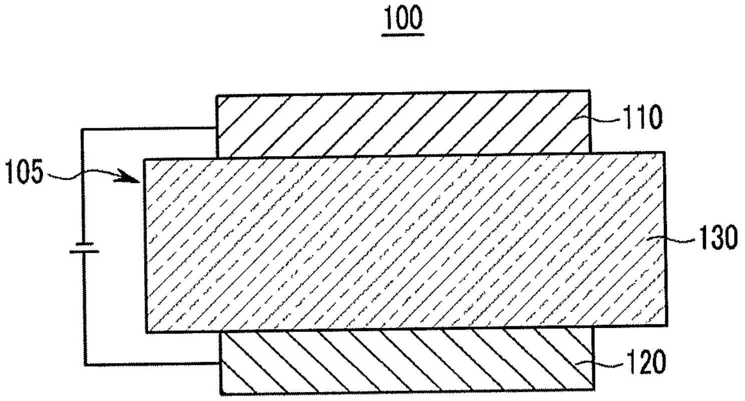
FIGS. 1 to 5 illustrate cross-sectional views of organic light emitting diodes including compounds according to various embodiments.

Korean Patent Application No. 10-2010-0109425, filed Nov. 4, 2010, in the Korean Intellectual Property Office on, and entitled: "Compound for Organic Optoelectronic Device, Organic Light Emmiting Diode Including the Same and Display Including the Organic Light Emmiting Diode," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, the term "substituted" may refer to one substituted with deuterium, a halogen, a hydroxy group, an amino group, a substituted or unsubstituted C1 to C20 amine group, nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group, or a cyano group, instead of at least hydrogen of substituents or compounds.

As used herein, when specific definition is not otherwise provided, the prefix "hetero" may refer to one including 1 to 3 of N, O, S, or P, and remaining carbons in one ring.

As used herein, when a definition is not otherwise provided, the term "combination thereof" may refer to at least two substituents bound to each other by a linker, or at least two substituents condensed to each other.

As used herein, when a definition is not otherwise provided, the term "alkyl group" may refer to an aliphatic hydrocarbon group. The alkyl group may be a saturated alkyl group that does not include any alkene group or alkyne group. The alkyl may be an unsaturated alkyl group that includes at least one alkene group or alkyne group. The term "alkene" group may refer to a group in which at least two carbon atoms are bound in at least one carbon-carbon double bond, and the term "alkyne" group may refer to a group in which at least two carbon atoms are bound in at least one carbon-carbon triple bond. Regardless of being saturated or unsaturated, the alkyl may be branched, linear, or cyclic.

The alkyl group may have 1 to 20 carbon atoms. The alkyl group may be a medium-sized alkyl having 1 to 10 carbon atoms. The alkyl group may be a lower alkyl having 1 to 6 carbon atoms.

For example, a C1-C4 alkyl may have 1 to 4 carbon atoms and may be selected from the group of methyl, ethyl, propyl, iso-propyl, n-butyl, iso-butyl, sec-butyl, and t-butyl.

Examples of an alkyl group may be selected from a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, which may be individually and independently substituted.

The "aromatic group" may refer to a cyclic functional group where all elements have conjugated p-orbital. Examples of the aromatic group include an aryl group and a heteroaryl group.

The term "aryl" group may refer to an aryl group including a carbocyclic aryl (e.g., phenyl) having at least one ring having a covalent pi electron system.

The term "heteroaryl group" may refer to an aryl group where 1 to 3 heteroatoms selected from N, O, S, and P, and remaining carbon. When the heteroaryl group is a fused ring, each ring may include 1 to 3 heteroatoms.

In the specification, a carbazole-based derivative may refer to a substituted or unsubstituted carbazolyl group in which nitrogen is substituted with a hetero atom.

According to an embodiment, a compound for an organic optoelectronic device may have a core structure in which an aryl amine group is linked to a fused ring structure including at least one hetero atom.

The core structure may include a hetero fused ring and an amine group having excellent hole properties and, thus, may be used as a hole injection material or a hole transport material for an organic light emitting diode.

In addition, the fused ring may decrease symmetry inside a molecule and, thus, may reduce crystallinity of a compound and suppress recrystallization thereof in a device.

At least one substituent linked to the core may have excellent electron properties. Accordingly, the compound may be reinforced with electron properties (in addition to excellent hole properties) and thus, may be desirable for use in an emission layer. For example, the compound may be used as a host material for an emission layer.

Furthermore, the compound for an organic optoelectronic device may have a core part and various substituents on a substituent of the core and thus, may have various energy bandgaps.

When the compound (having an appropriate energy level depending on a substituent) is used for an organic photoelectric device, it may help strengthen hole or electron transport capabilities and may help achieve excellent efficiency, driving voltage, and electrochemical and thermal stability, resultantly improving life-span characteristics of the organic photoelectric device.

According to an embodiment, the compound for an organic optoelectronic device may include a moiety represented by the following Chemical Formula 1; a moiety represented by the following Chemical Formula 4; and a moiety represented by one of Chemical Formulae 2 and 3.

[Chemical Formula 1]

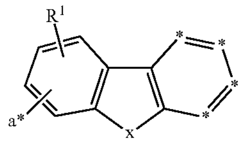

[Chemical Formula 2]

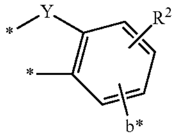

[Chemical Formula 3]

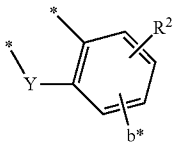

[Chemical Formula 4]

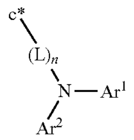

In Chemical Formulae 1 to 4, X may be O, S, $SO_2$ (O=S=O), PO(P=O), or CO(C=O). Y may be CR'R" or NR'. R', R", $R^1$, and $R^2$ may each independently be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof. $Ar^1$ and $Ar^2$ may each independently be a substituted or unsubstituted C6 to C30 aryl group, or a substituted or unsubstituted C2 to C30 heteroaryl group. L may be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof. n may be 0 or 1. Two adjacent *s of Chemical Formula 1 may be linked to respective or adjacent *s of Chemical Formula 2 or 3 to provide a fused ring. In an implementation, two adjacent *s of Chemical Formula 1 may be directly linked to the *s of Chemical Formula 2 or 3. One of a* of Chemical Formula 1 and b* of Chemical Formula 2 or 3 may be linked to c* of Chemical Formula 4 through a sigma bond; and the other of a* or b* (not linked to c*) may be hydrogen.

When the moieties represented by the above Chemical Formulae are combined as set forth herein, the resultant compound for an organic optoelectronic device may have excellent hole or electron properties, film stability, and thermal stability as well as a high triplet excitation energy (T1).

The compound for an organic photoelectric device may include a moiety represented by the following Chemical Formula 5.

[Chemical Formula 5]

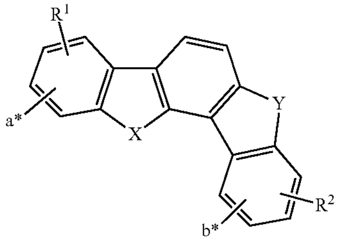

In Chemical Formula 5, X may be O, S, $SO_2$ (O═S═O), PO(P═O), or CO(C═O). Y may be CR'R" or NR'. R', R", $R^1$, and $R^2$ may each independently be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof. One of a* and b* of Chemical Formula 5 may be linked to c* of Chemical Formula 4 through a sigma bond, and the other of a* and b* (not linked to c*) may be hydrogen.

The substituents may be appropriately combined or selected to prepare a compound with excellent thermal stability and/or resistance against oxidation.

When either of $R^1$ and $R^2$ is not hydrogen (but rather one of the other aforementioned substituents), the compound may be subtly regulated regarding electro-optical characteristics and thin film characteristics to optimize performance of an organic photoelectric device as well as to maintain basic characteristic of a compound with no substituent.

In addition, the compound including a moiety represented by the above Chemical Formula 5 may have an advantage in terms of synthesis and high triplet energy when a substituent is linked to a main chain at a meta position.

The compound for an organic optoelectronic device may be a compound represented by the following Chemical Formula 6 or 7, below.

[Chemical Formula 6]

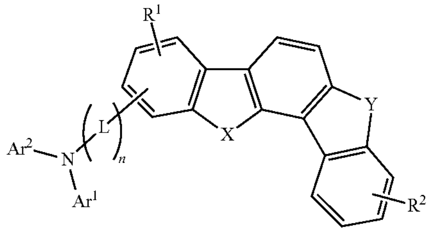

[Chemical Formula 7]

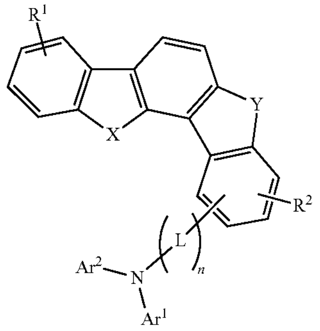

In Chemical Formulae 6 and 7, X may be O, S, $SO_2$ (O═S═O), PO(P═O), or CO(C═O). Y may be CR'R" or NR'. R', R", $R^1$, and $R^2$ may each independently be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof. $Ar^1$ and $Ar^2$ may each independently be a substituted or unsubstituted C6 to C30 aryl group, or a substituted or unsubstituted C2 to C30 heteroaryl group. L may be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof. n may be 0 or 1.

When the aryl amine group is included in the compound as shown in the above Chemical Formula 6, the compound may exhibit characteristics of a material including the X, e.g., carbazole-type materials. When the aryl amine group is included in the compound as shown in the above Chemical Formula 7, the compound may exhibit characteristics of a material including the Y, e.g., fluorene-type materials.

The substituents may be appropriately combined or selected to prepare a compound with an asymmetrical bipolar structure. The asymmetrical bipolar structure may improve hole and electron transport capabilities and thus, may help improve luminous efficiency and performance of a device.

In addition, the substituents may be regulated to prepare a compound with a bulky structure and thus, may help to lower crystallinity. The compound with lower crystallinity may help improve life-span of a device.

As noted above, Y may be CR'R", and R', R" may each independently be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

When Y includes carbon (e.g., when Y is CR'R"), the compound may exhibit fluorene characteristics.

As noted above, Y may be NR', and R' may be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

When Y includes nitrogen (e.g., when Y is NR'), the compound may exhibit carbazole characteristics.

Examples of $Ar^1$ and $Ar^2$ may include a substituted or unsubstituted phenyl group, a substituted or unsubstituted carbazolyl group, a substituted or unsubstituted dibenzofuranyl, a substituted or unsubstituted dibenzothiophenyl group, a substituted or unsubstituted fluorenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triperylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quninolinyl group, a substituted or unsubstituted isoquninolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, and the like.

$Ar^1$ and $Ar^2$ may be selected in consideration of length to thereby help regulate an entire π-conjugation length and thus, a triplet energy bandgap of the compound. Accordingly, the compound may be used as a phosphorescent host and thus may be usefully applied to the emission layer of an organic photoelectric device. In addition, when a heteroaryl group is introduced into the compound, the compound may have bipolar characteristic in its molecule structure. When the compound is used as a phosphorescent host, high efficiency of a device may be achieved.

When $Ar^1$ and $Ar^2$ is a substituted or unsubstituted carbazolyl group, a substituted or unsubstituted dibenzofuranyl, and/or a substituted or unsubstituted dibenzothiophenyl group, the compound may not be easily recrystallized (due to asymmetry of entire molecules) and may also exhibit excellent hole transport properties of a carbazolyl-based derivative. Accordingly, when the compound is applied to a hole injection and/or a hole transport layer (HTL) for an organic light emitting diode, a device including the organic light emitting diode may have a long life-span and high efficiency.

In addition, including a substituted or unsubstituted fluorenyl group in the compound may increase planarity of molecules and thus may help increase mobility of holes. Accordingly, when the compound is applied to a hole injection layer and/or a hole transport layer (HTL) for an organic light emitting diode, the organic light emitting diode may have long life-span and high efficiency.

The compound for an organic optoelectronic device may be a compound represented by one of the following Chemical Formulae A-1 to A-7 and A-9 to A-51. In the compounds represented by the following Chemical Formulae A-1 to A-7 and A-9 to A-51, dibenzofuran or dibenzothiophene is combined with fluorene in one molecule. Thus, the compound may have main or primary characteristics of dibenzofuran or dibenzothiophene and auxiliary or secondary characteristics of fluorene.

[A-1]

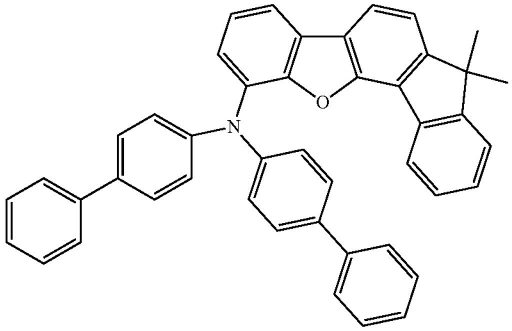

[A-2]

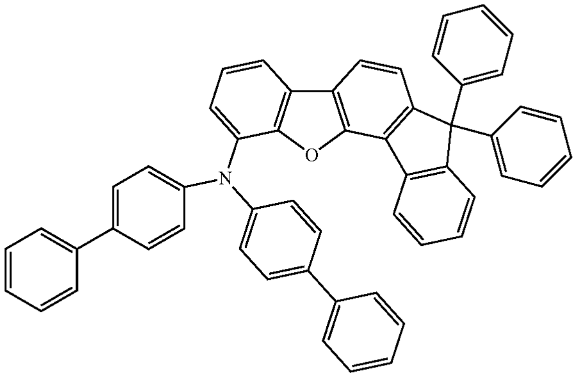

-continued

[A-3]

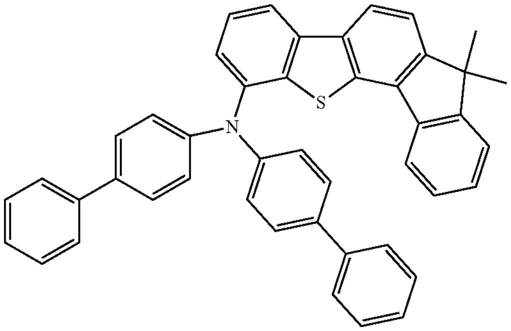

[A-4]

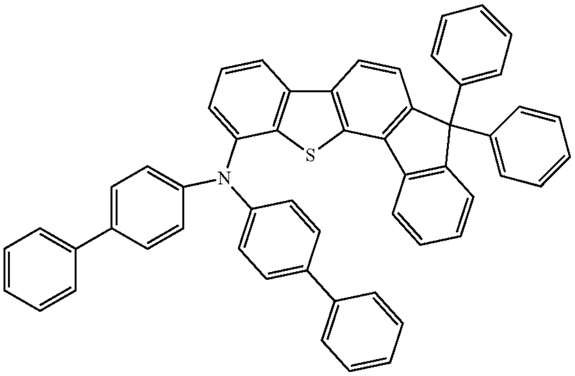

[A-5]

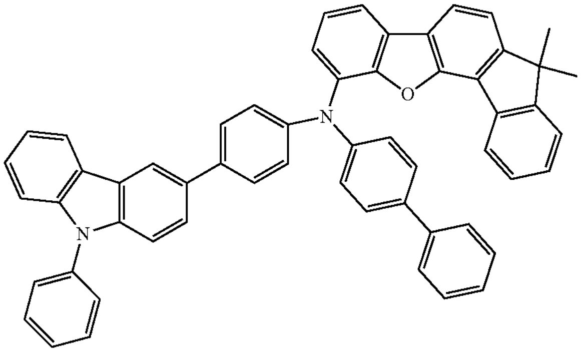

[A-6]

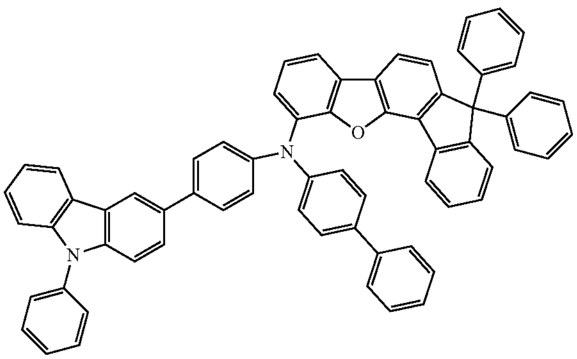

-continued
[A-7]
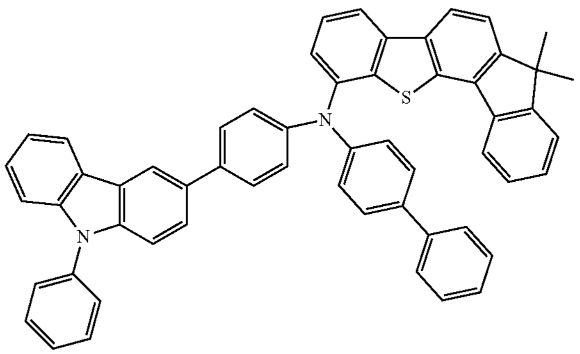
[A-9]
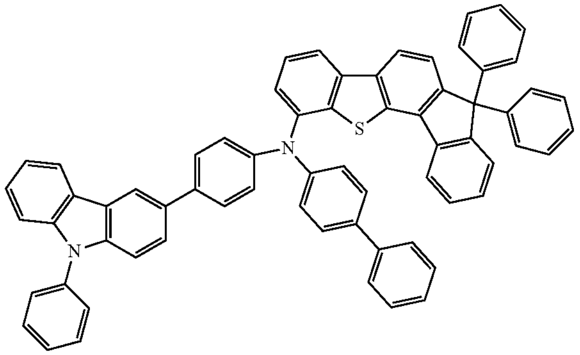
[A-10]
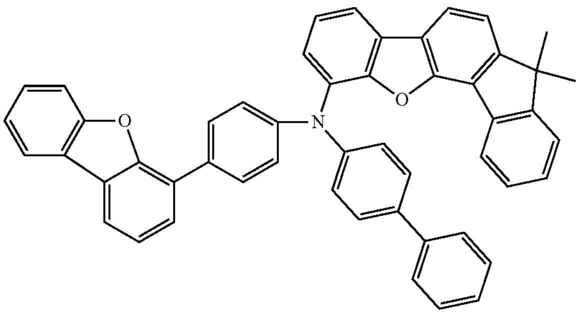
[A-11]
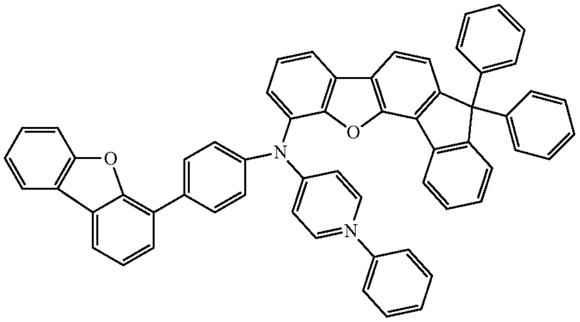
-continued
[A-12]
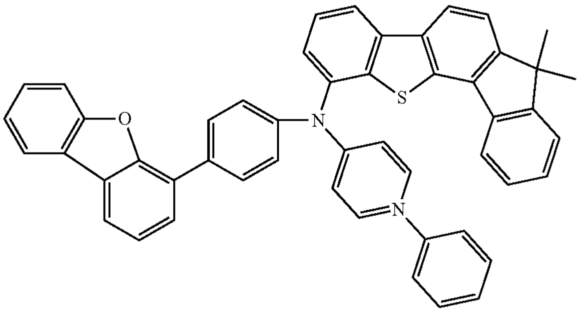
[A-13]
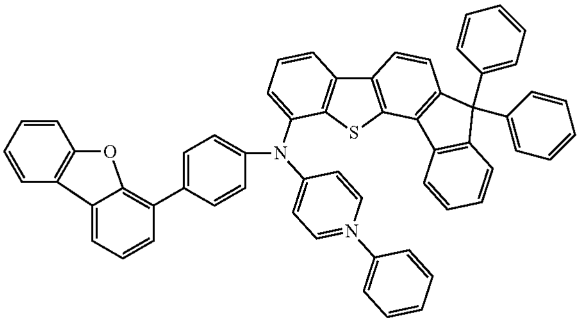
[A-14]
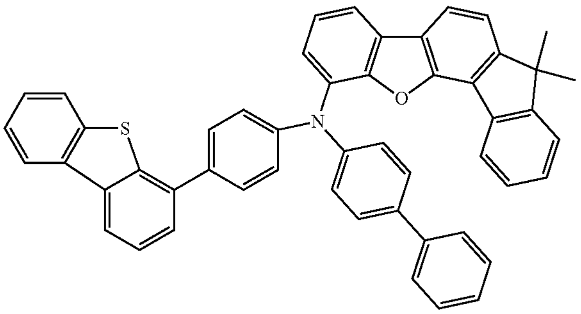
[A-15]
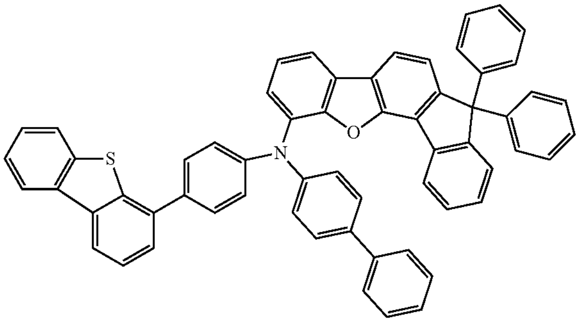

-continued
[A-16]
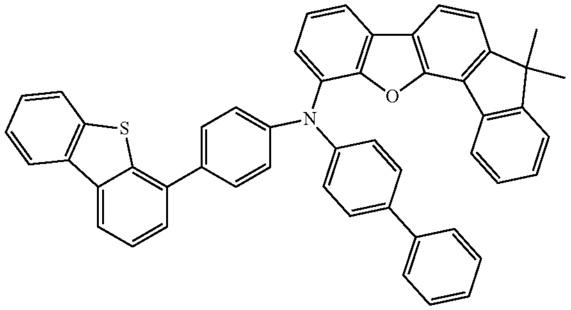
[A-17]
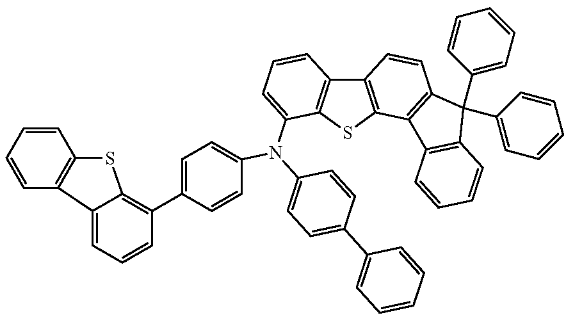
[A-18]
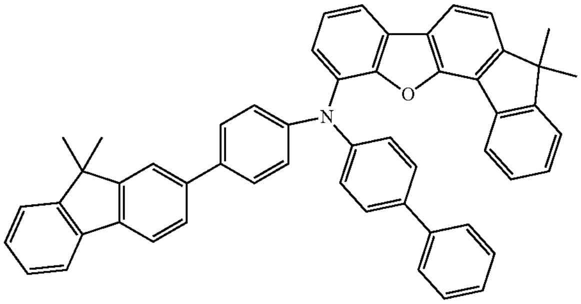
[A-19]
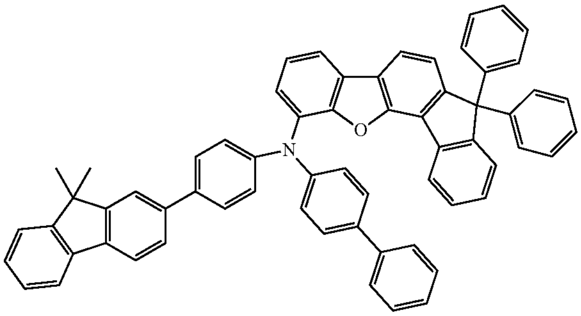
-continued
[A-20]
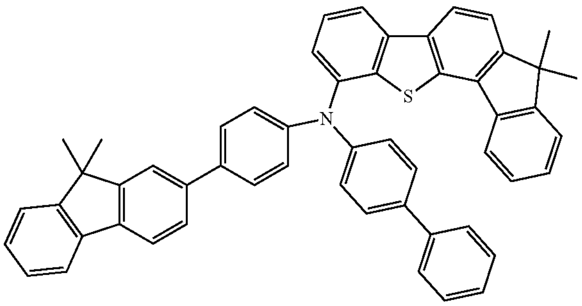
[A-21]
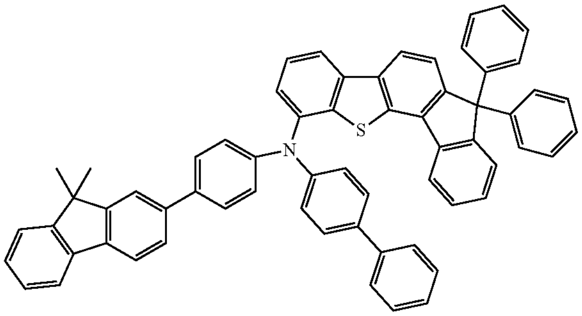
[A-22]
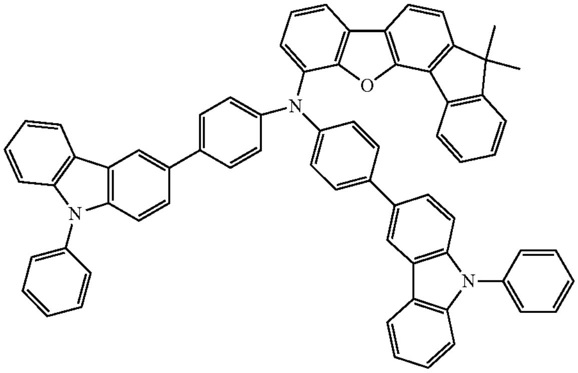
[A-23]
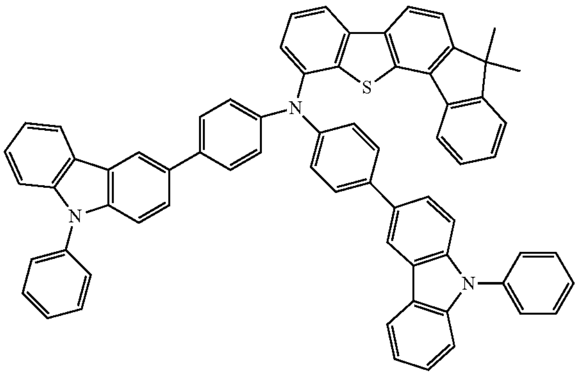

-continued
[A-24]
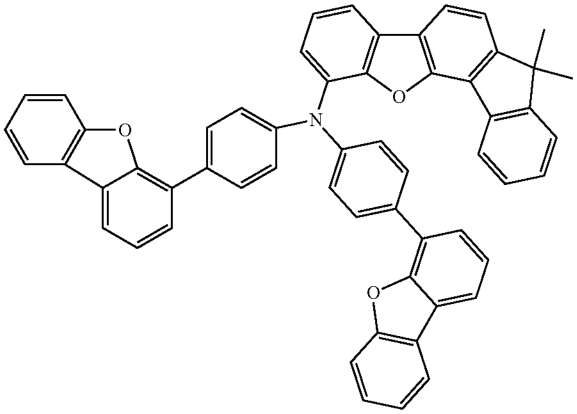
[A-25]
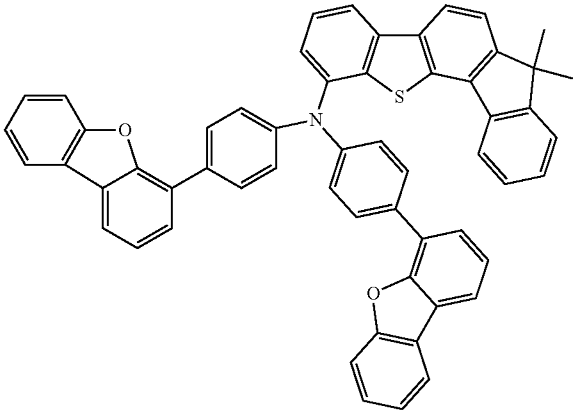
[A-26]
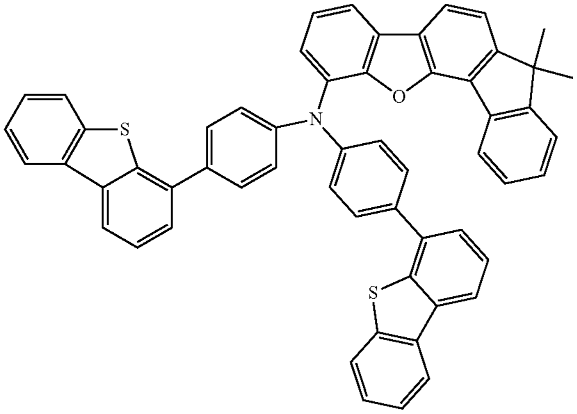
-continued
[A-27]
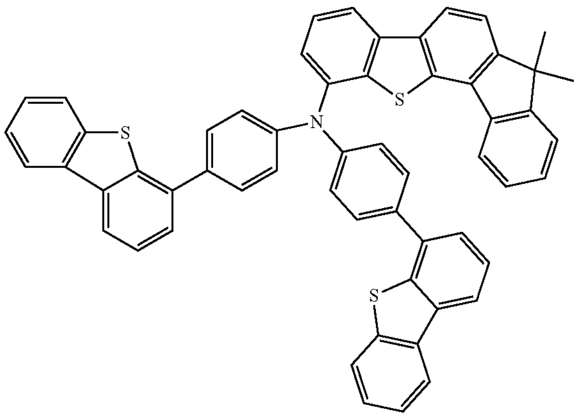
[A-28]
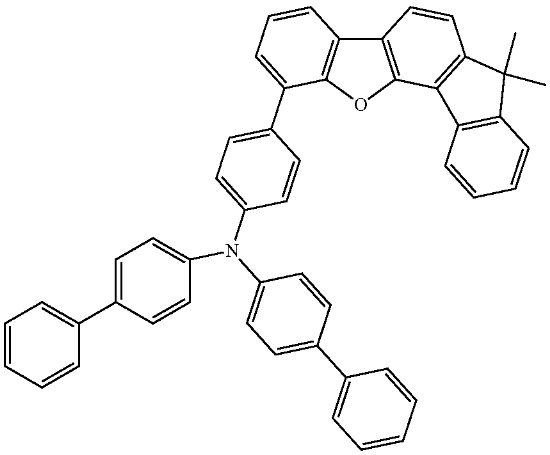
[A-29]
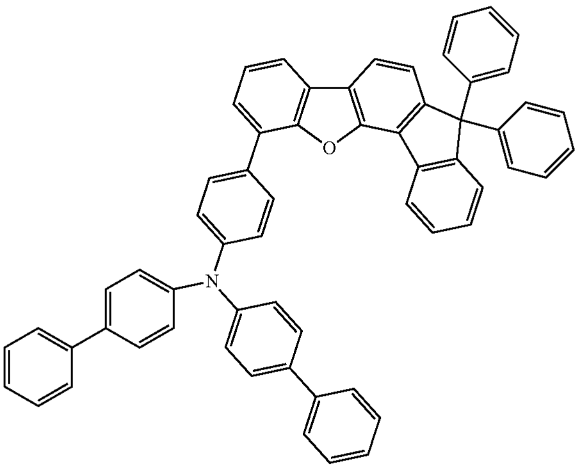

-continued
[A-30]
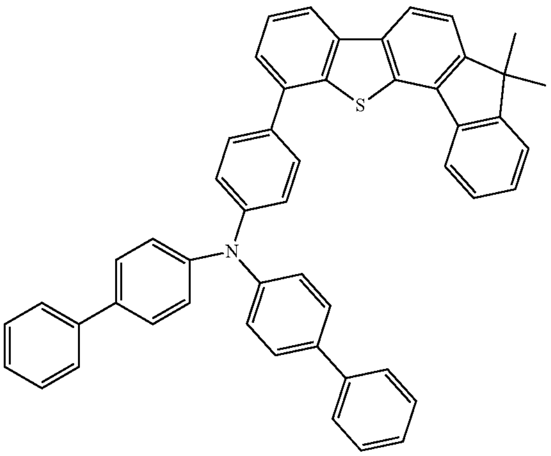
[A-31]
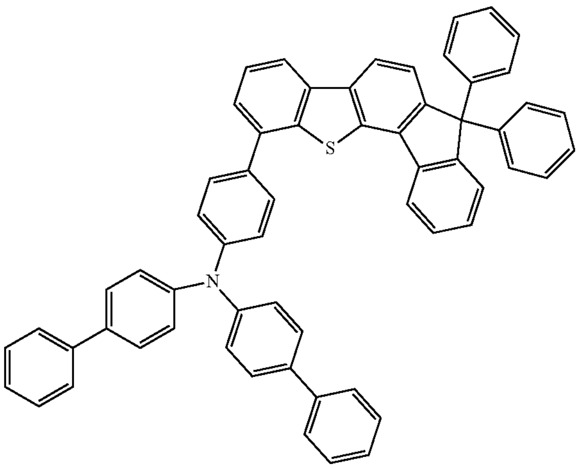
[A-32]
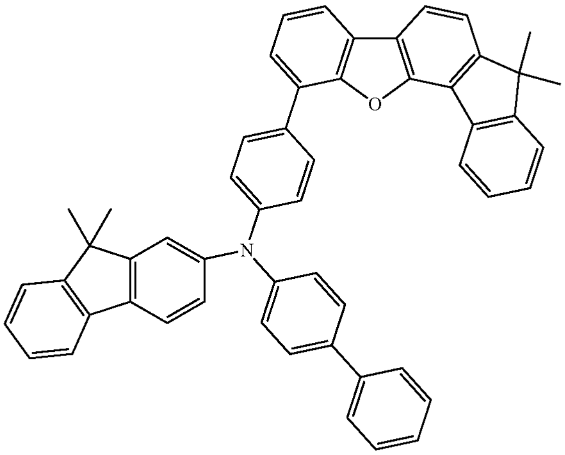
-continued
[A-33]
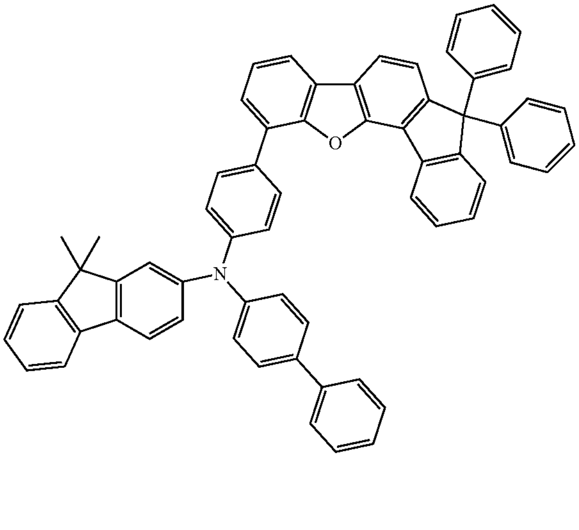
[A-34]
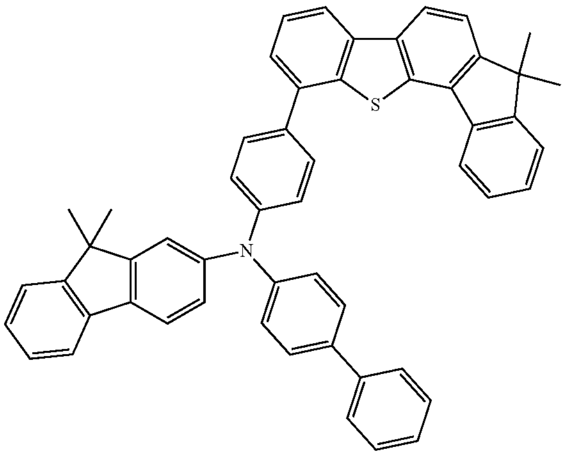
[A-35]
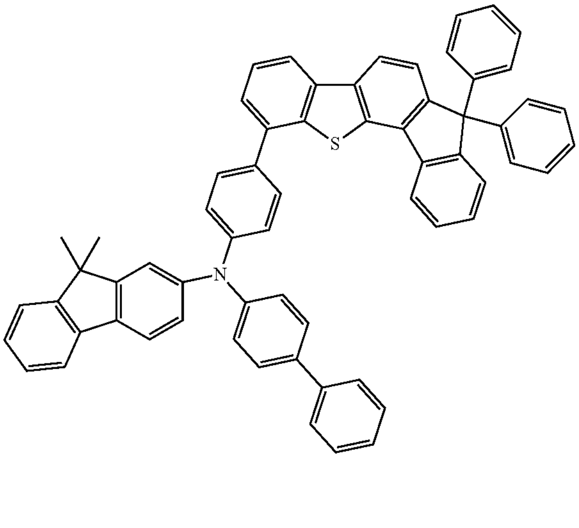

-continued
[A-36]
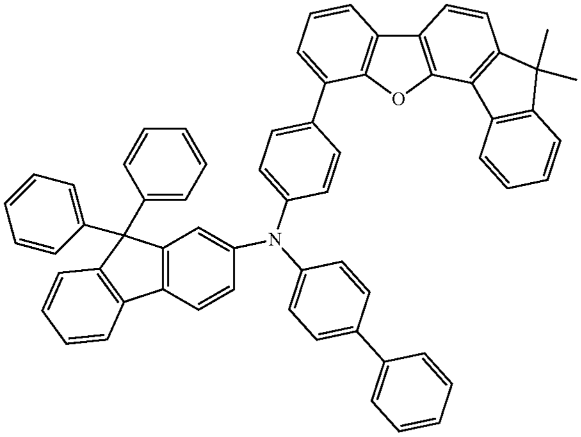
[A-37]
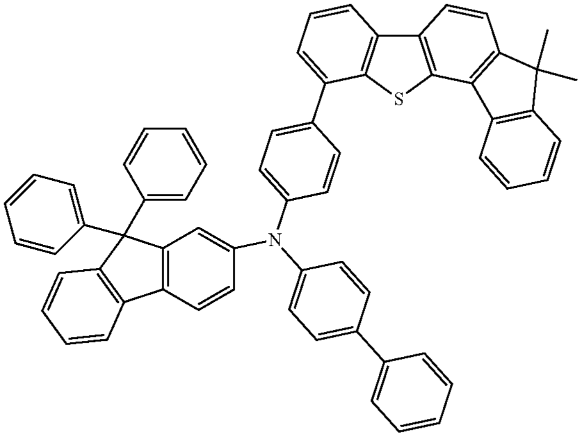
[A-38]
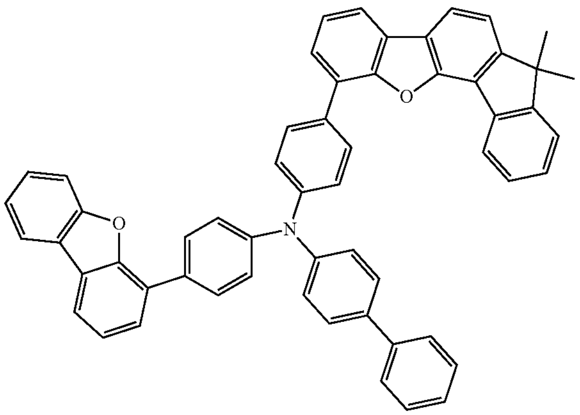
-continued
[A-39]
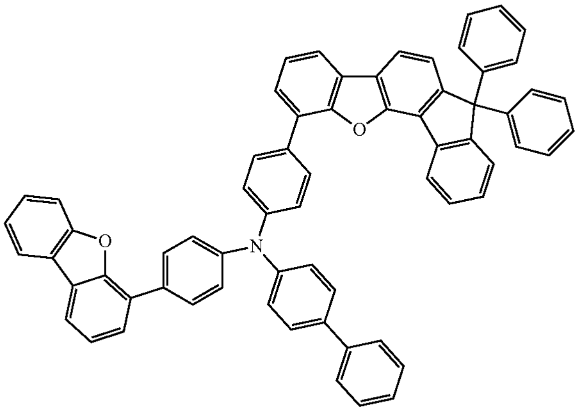
[A-40]
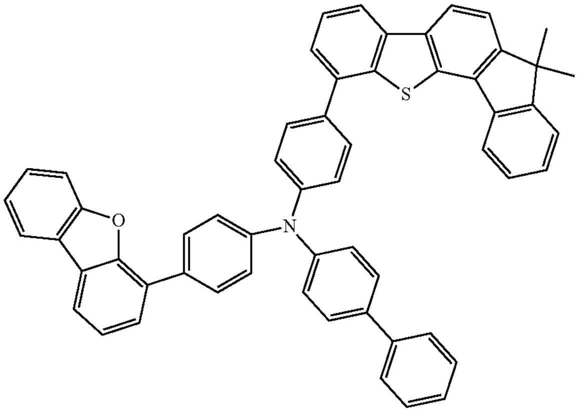
[A-41]
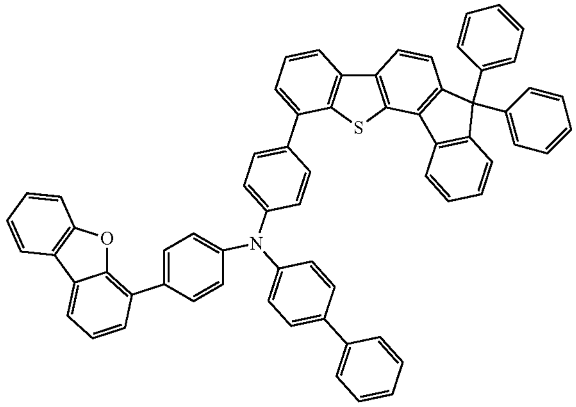

[A-42]
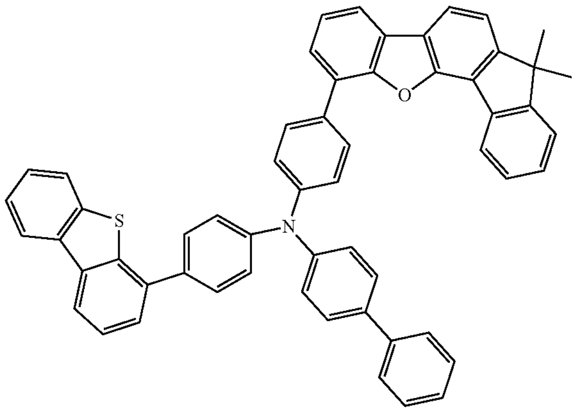
[A-43]
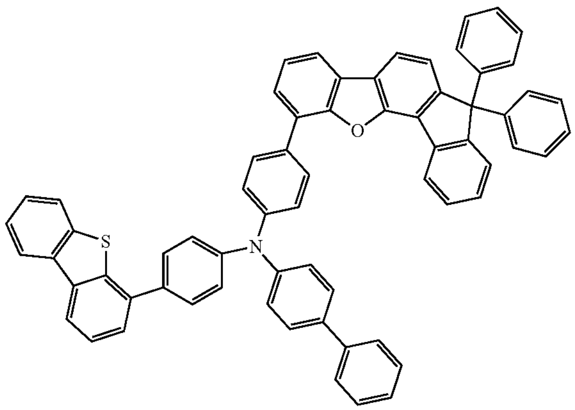
[A-44]
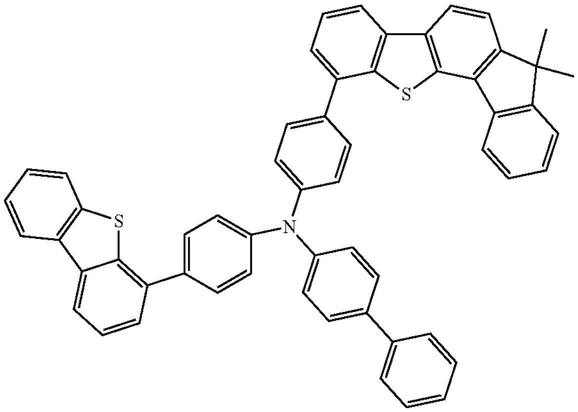
[A-45]
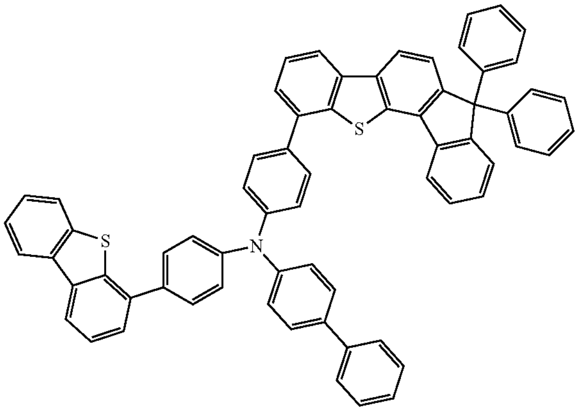
[A-46]
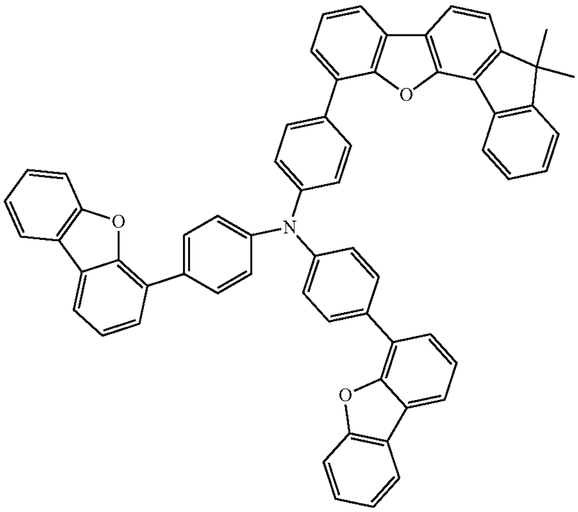
[A-47]
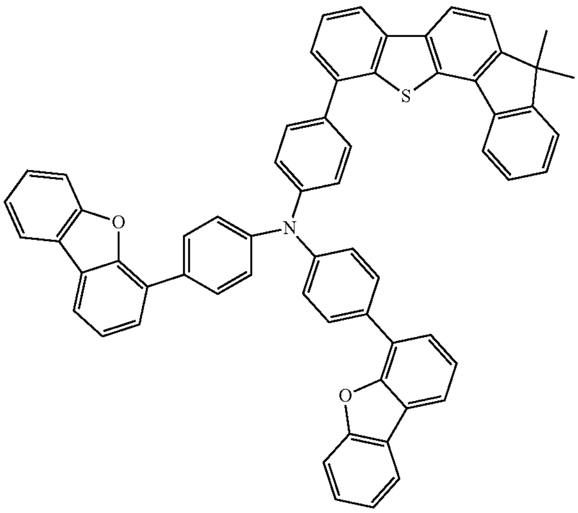

-continued

[A-48]

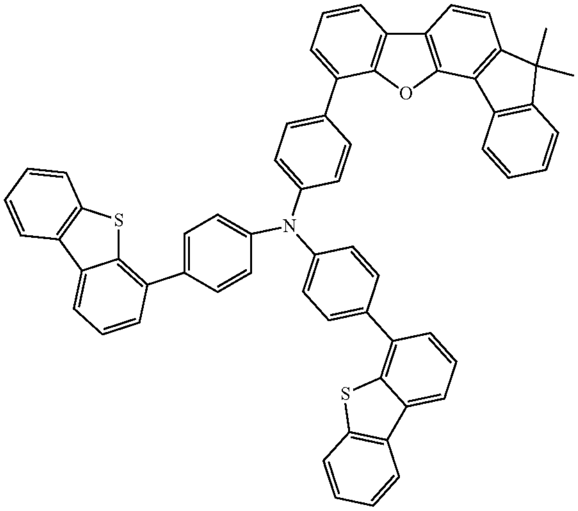

[A-49]

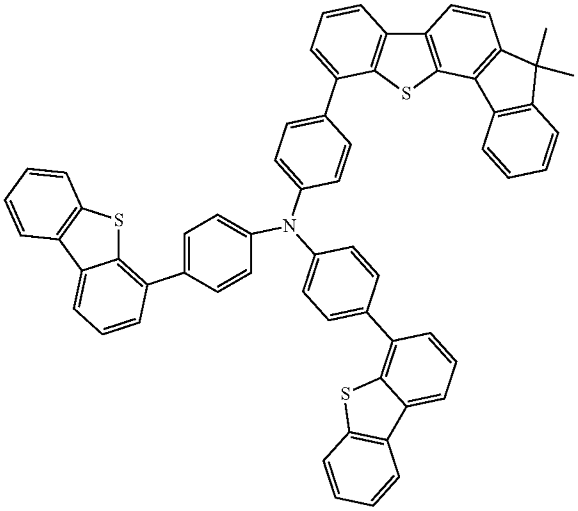

[A-50]

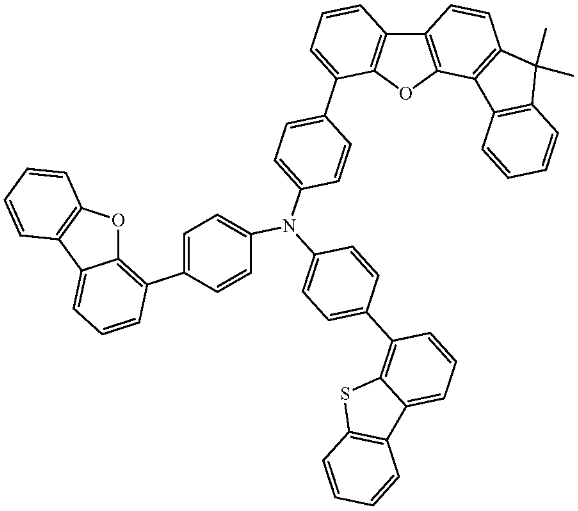

-continued

[A-51]

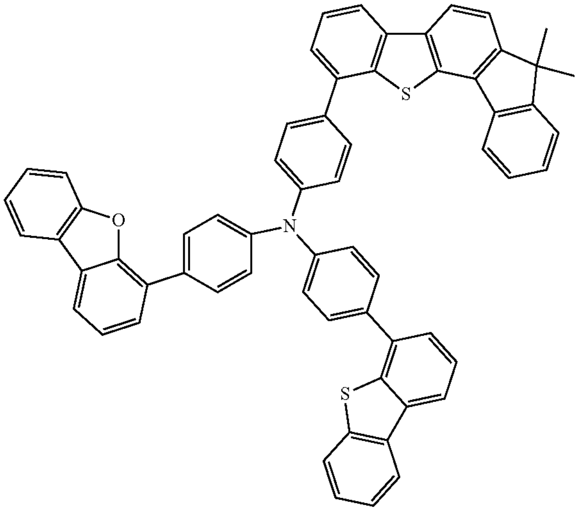

The compound for an organic optoelectronic device may be a compound represented by one of the following Chemical Formulae B-1 to B-32. In the compounds represented by the following Chemical Formulae B-1 to B-32, dibenzofuran or dibenzothiophene is combined with carbazole in one molecule. Thus, the compound may have main or primary characteristics of dibenzofuran or dibenzothiophene and auxiliary or secondary characteristics of carbazole.

[B-1]

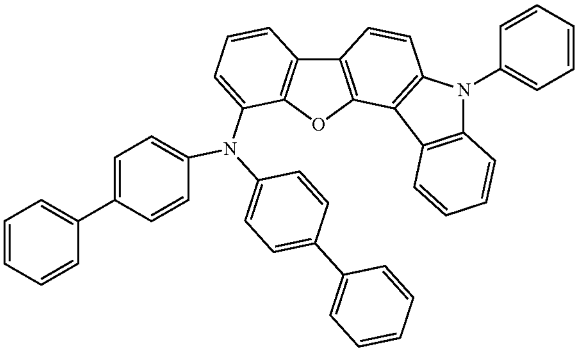

[B-2]

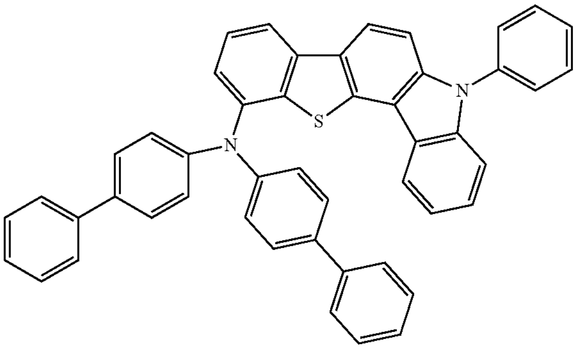

-continued
[B-3]
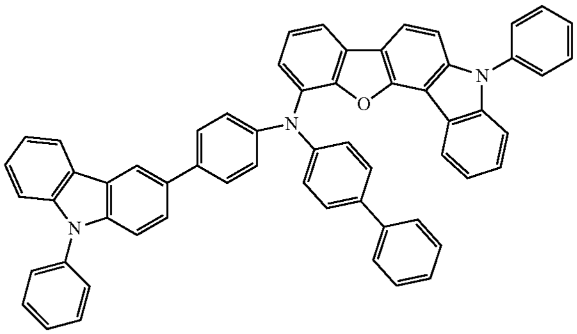
[B-4]
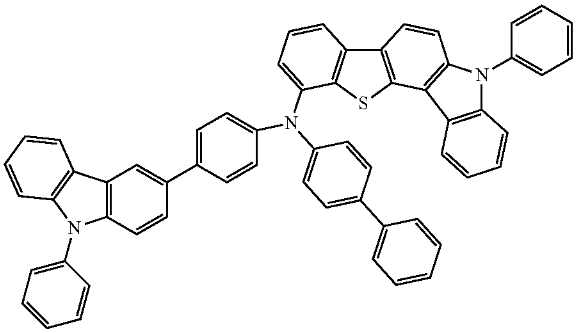
[B-5]
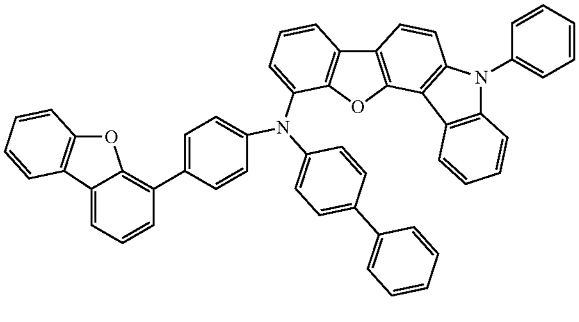
[B-6]
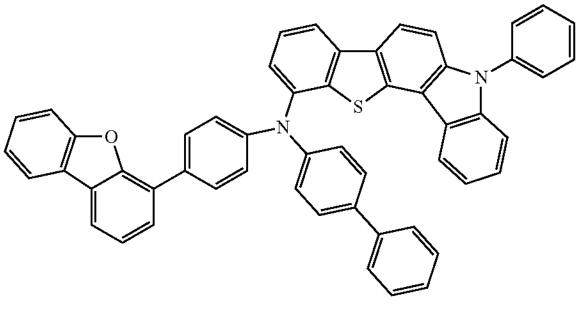
-continued
[B-7]
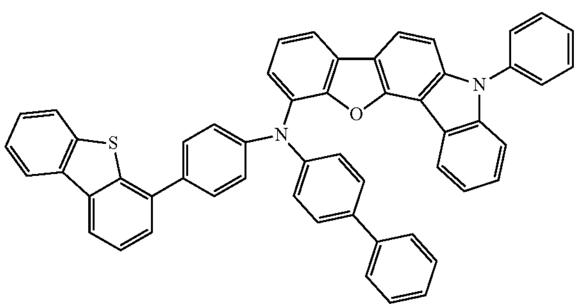
[B-8]
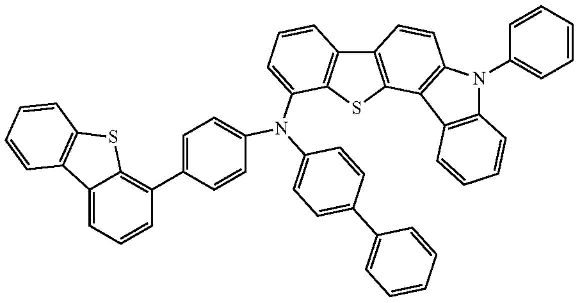
[B-9]
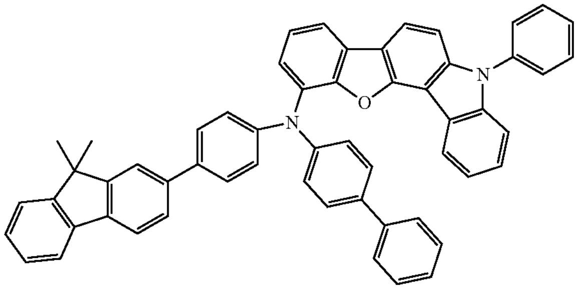
[B-10]
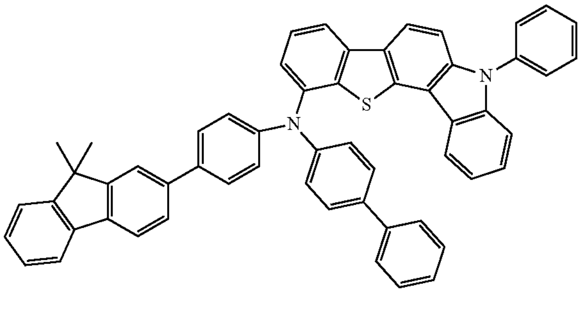

-continued
[B-11]
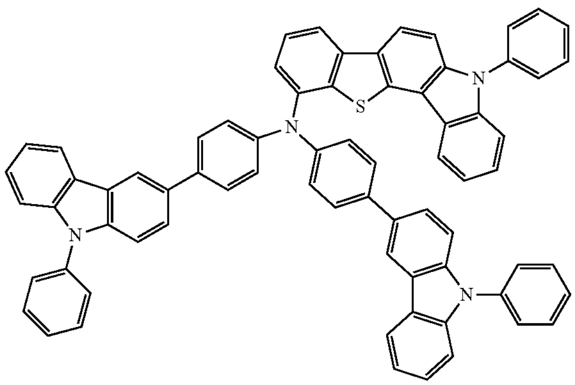
[B-12]
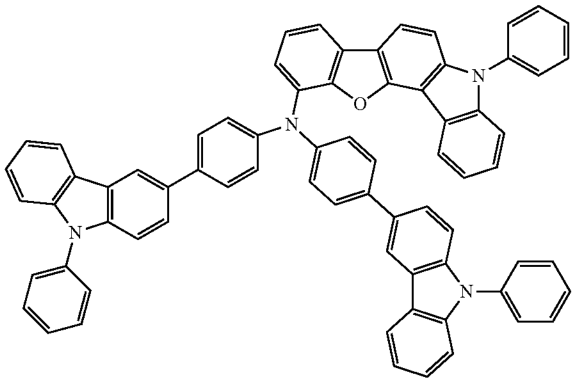
[B-13]
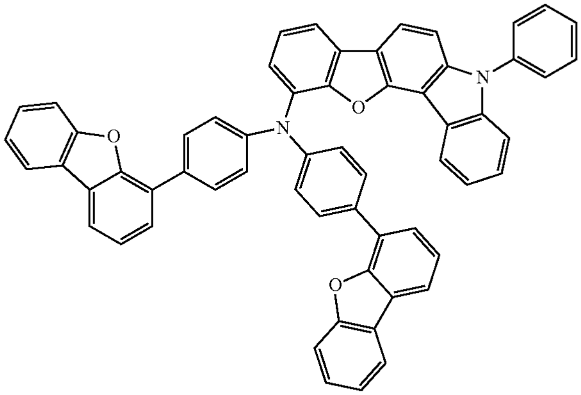
[B-14]
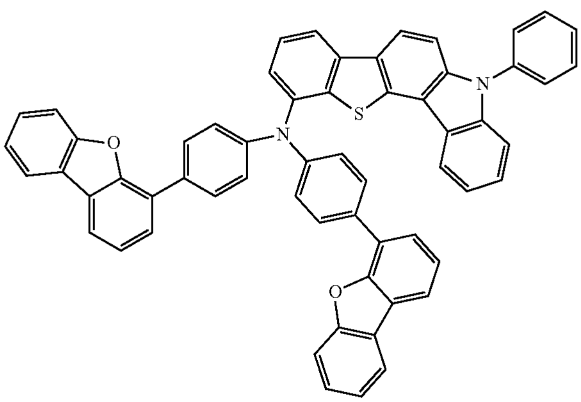
-continued
[B-15]
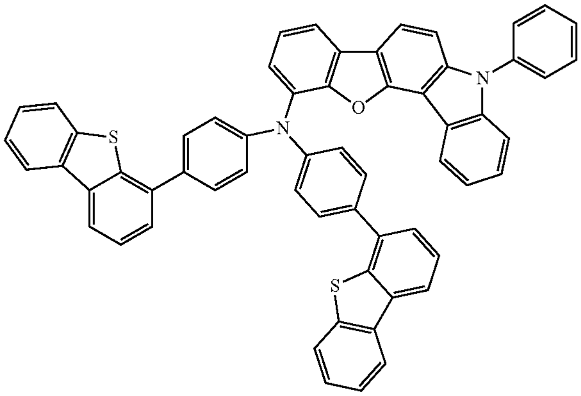
[B-16]
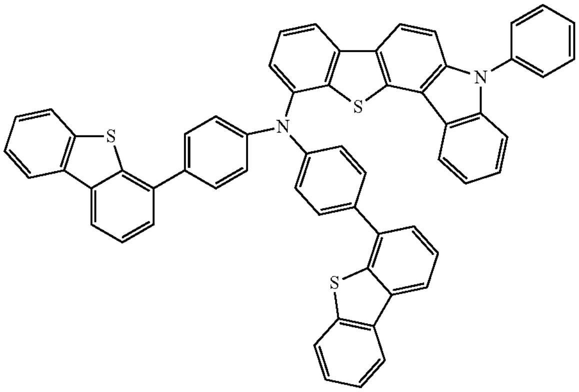
[B-17]
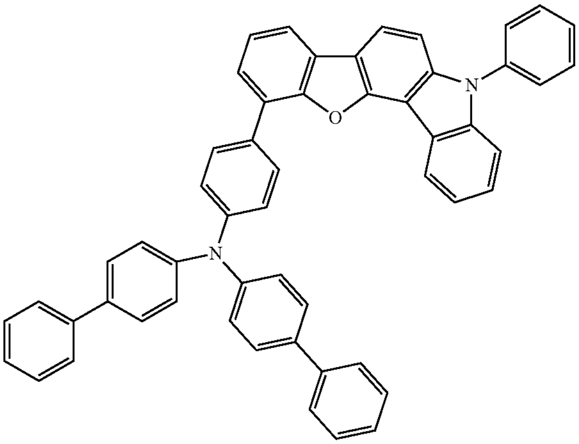

-continued
[B-18]
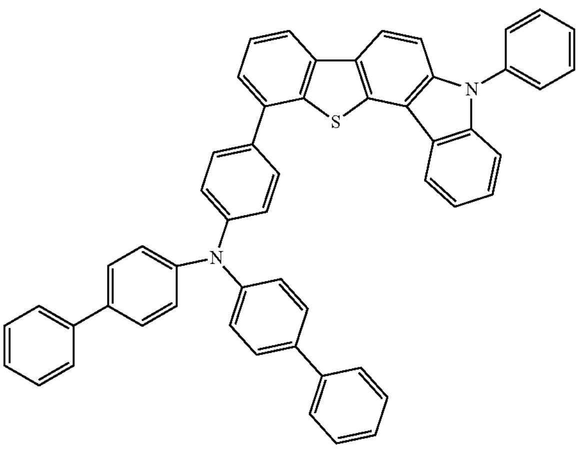
[B-19]
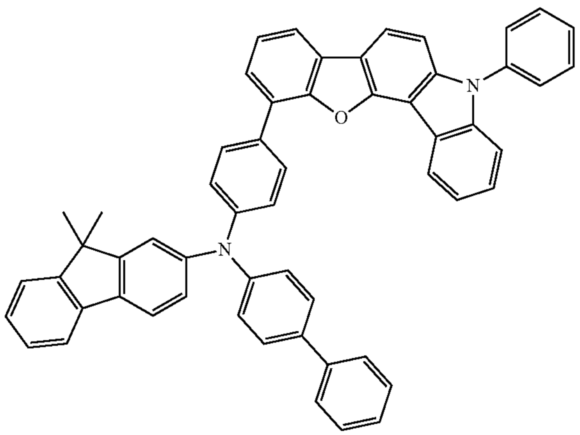
[B-20]
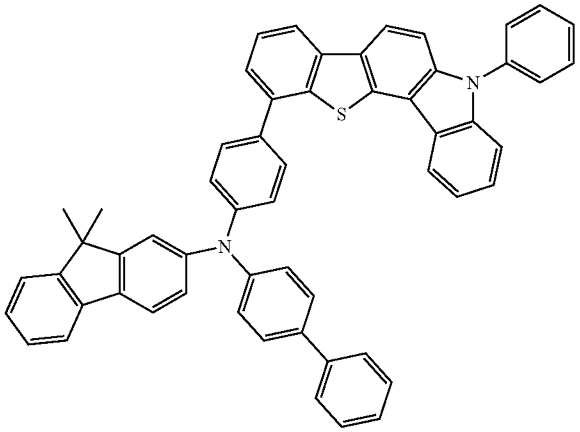
-continued
[B-21]
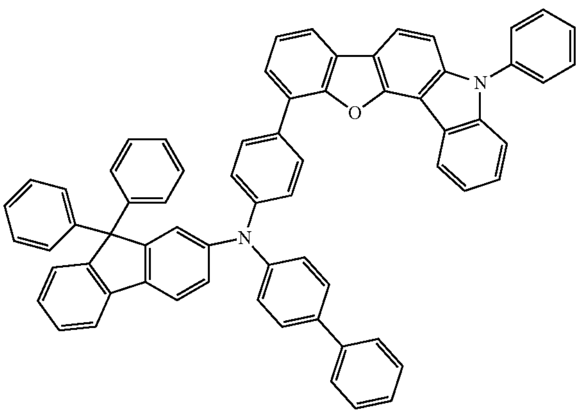
[B-22]
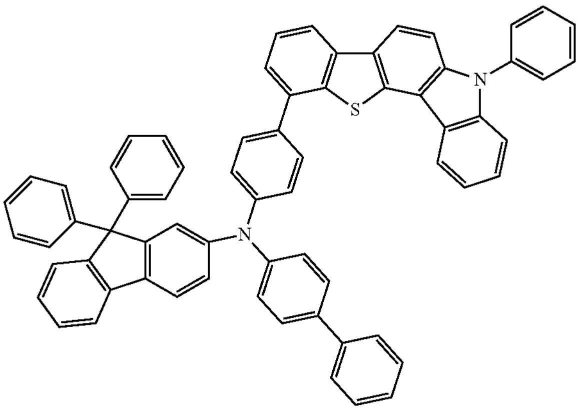
[B-23]
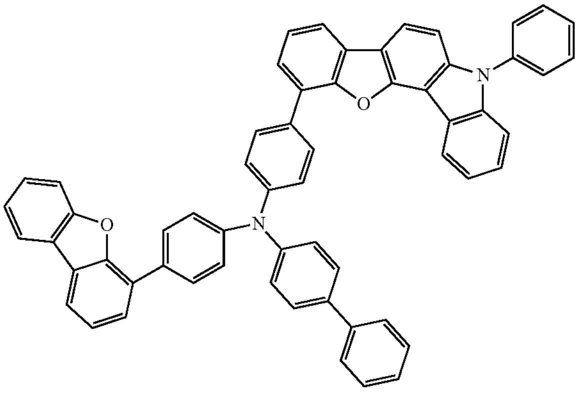

-continued
[B-24]
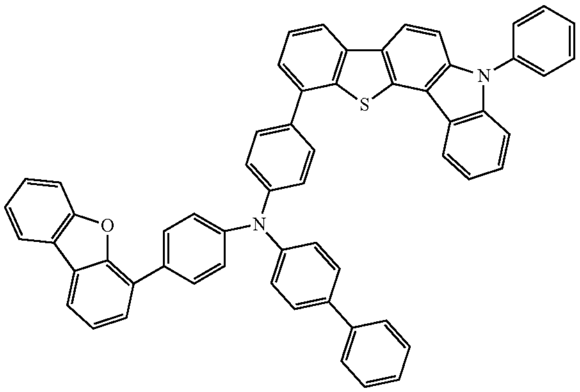
[B-25]
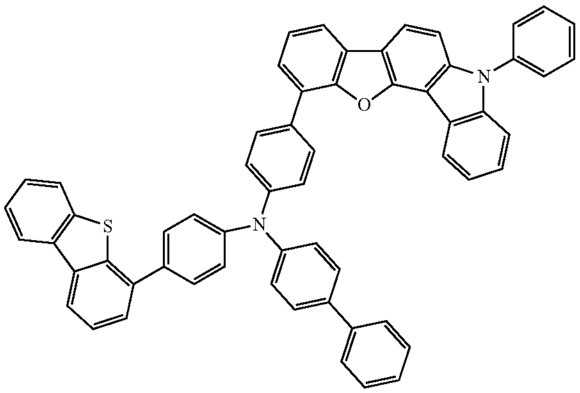
[B-26]
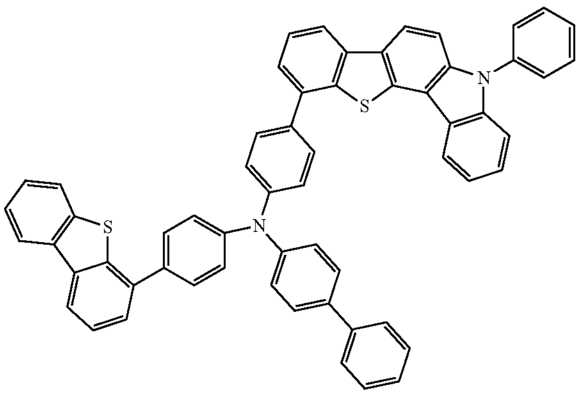
-continued
[B-27]
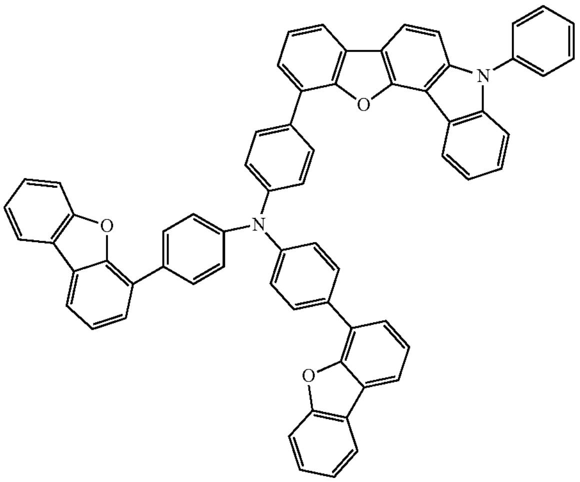
[B-28]
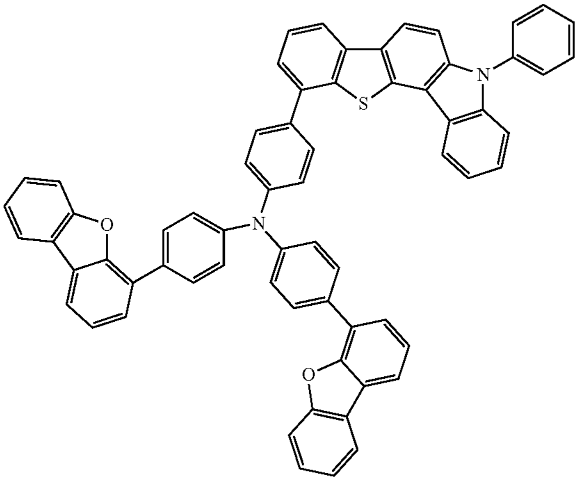
[B-29]
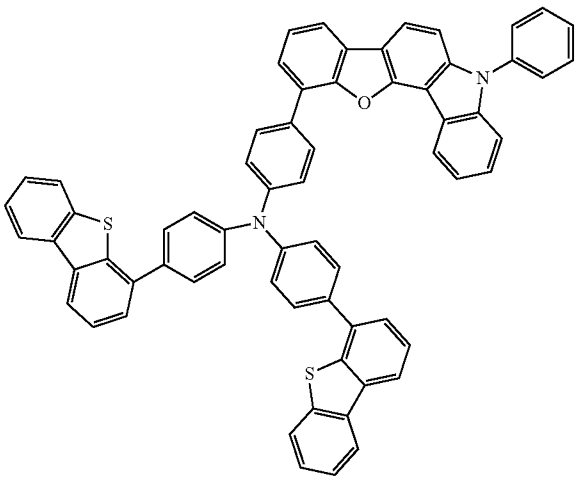

-continued

[B-30]

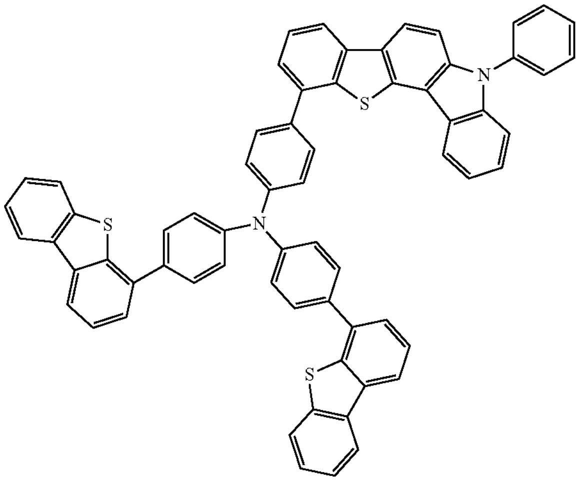

[B-31]

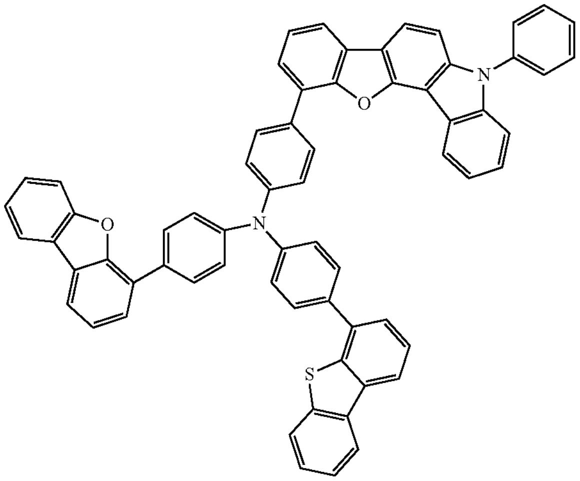

[B-32]

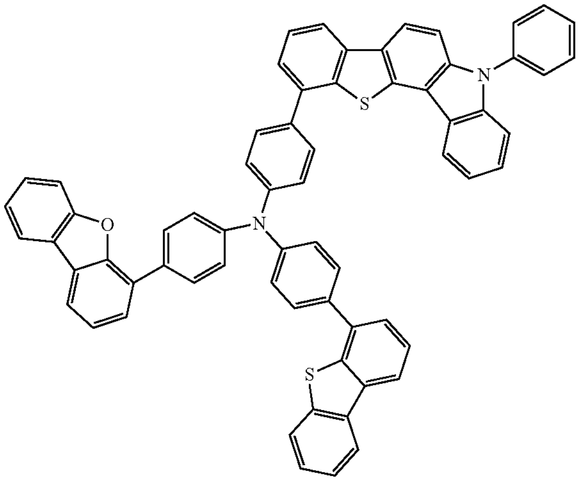

The compound for an organic optoelectronic device may be a compound represented by one of the following Chemical Formulae C-1 to C-41. In the compounds represented by one of the following Chemical Formulae C-1 to C-41, dibenzofuran or dibenzothiophene is combined with fluorene in one molecule. Thus, the compound may have main or primary characteristics of dibenzofuran or dibenzothiophene and auxiliary or secondary characteristics of fluorene.

[C-1]

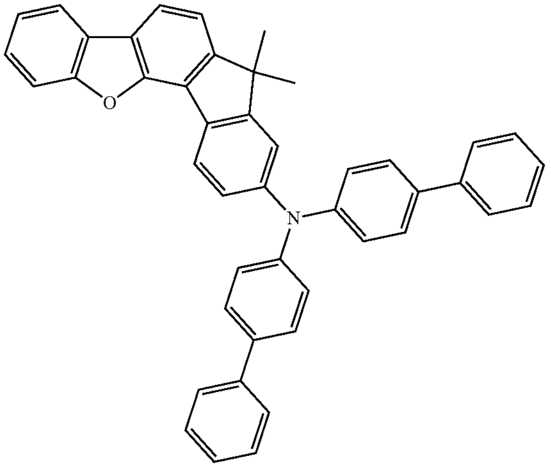

[C-2]

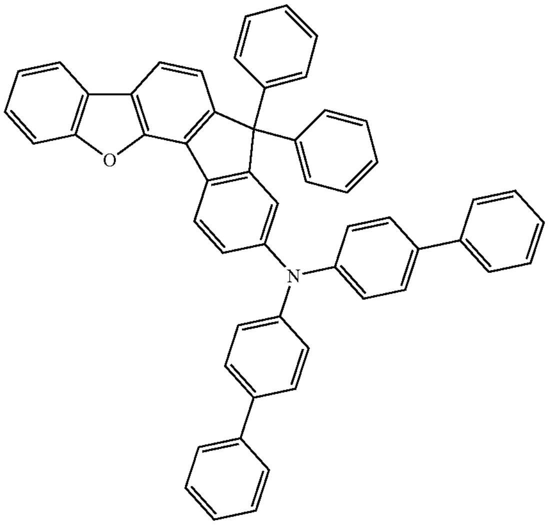

[C-3]

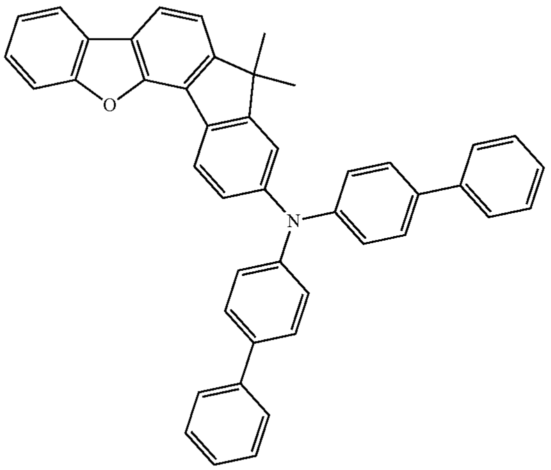

-continued
[C-4]
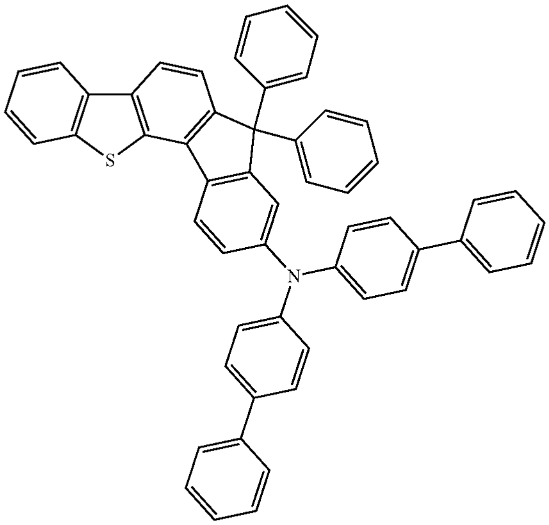
[C-5]
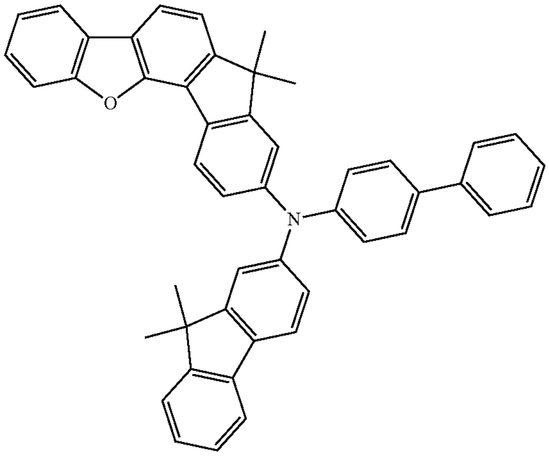
[C-6]
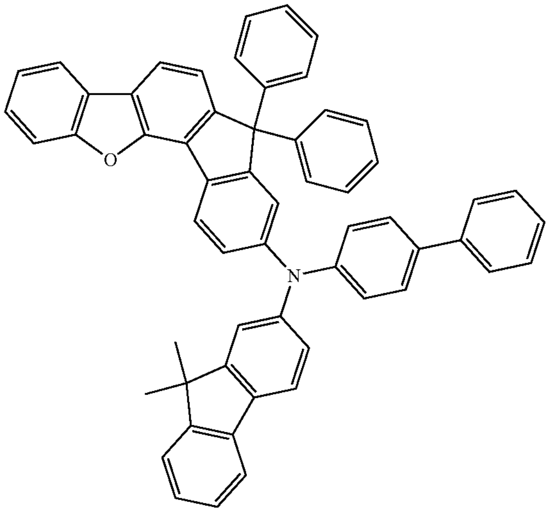
-continued
[C-7]
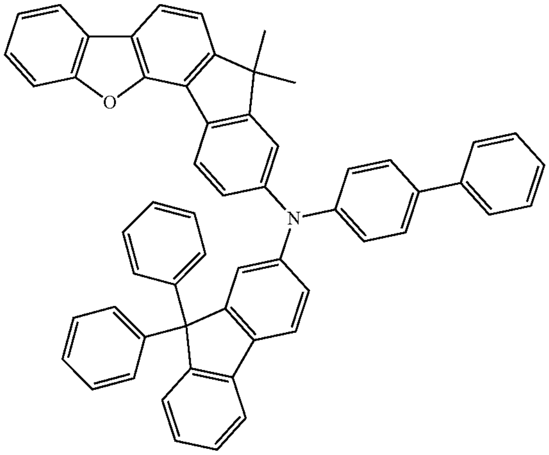
[C-8]
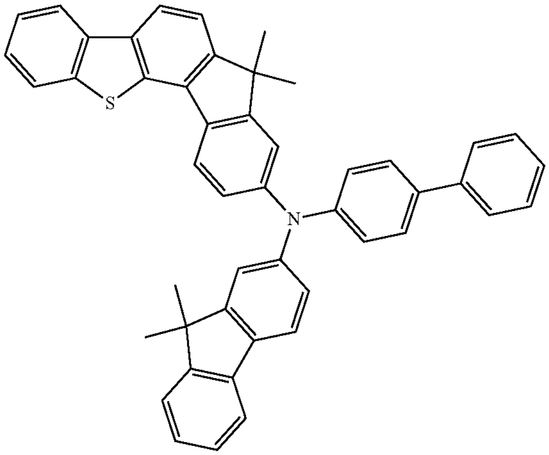
[C-9]
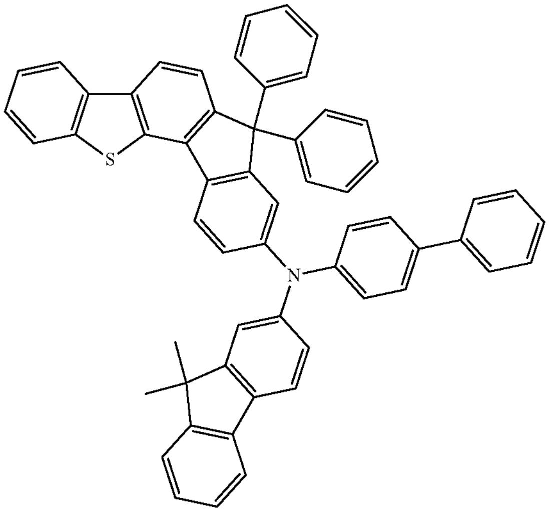

-continued
[C-10]
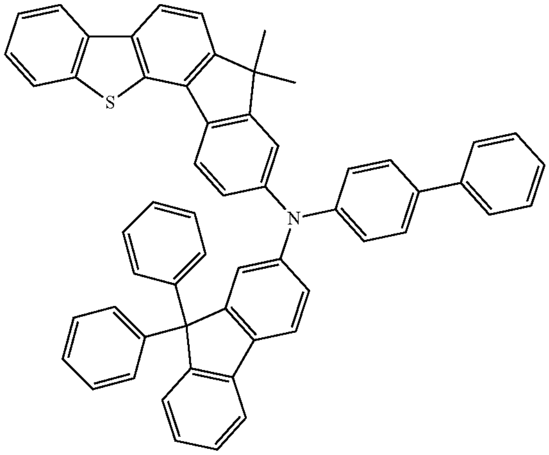
[C-11]
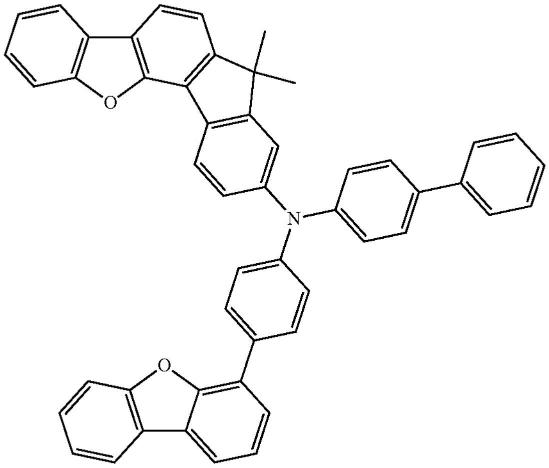
[C-12]
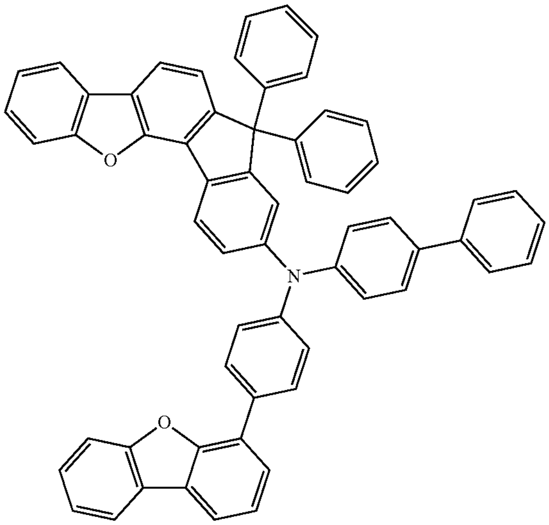
-continued
[C-13]
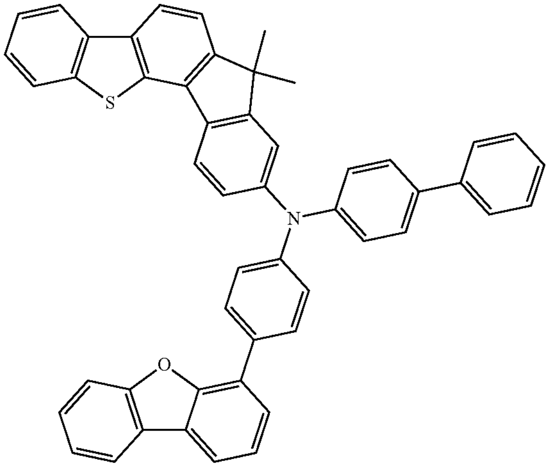
[C-14]
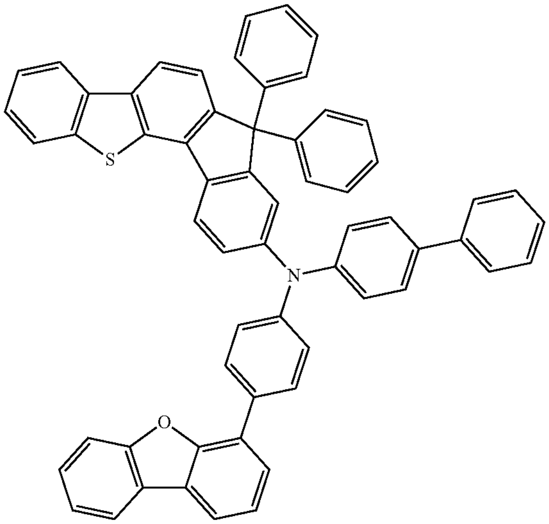
[C-15]
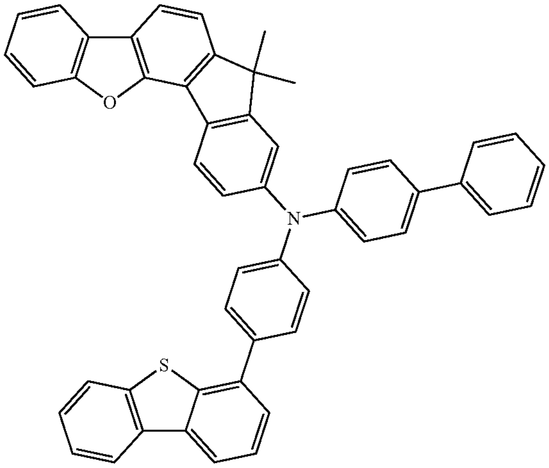

-continued
[C-16]
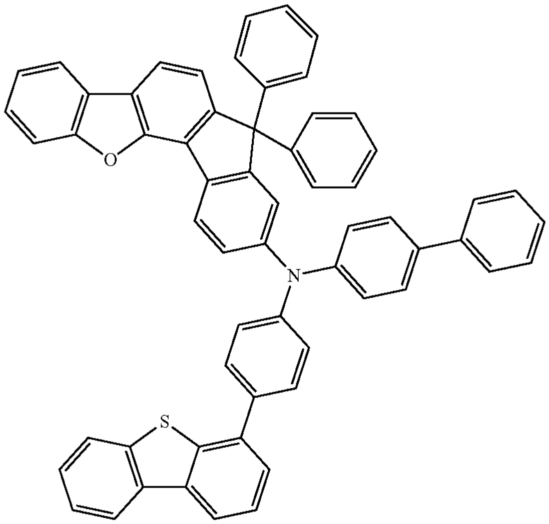
[C-17]
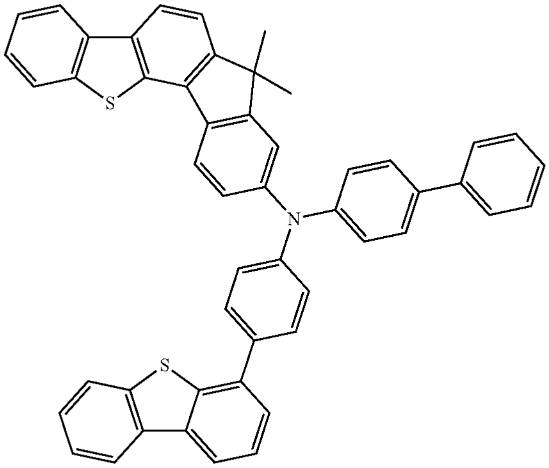
[C-18]
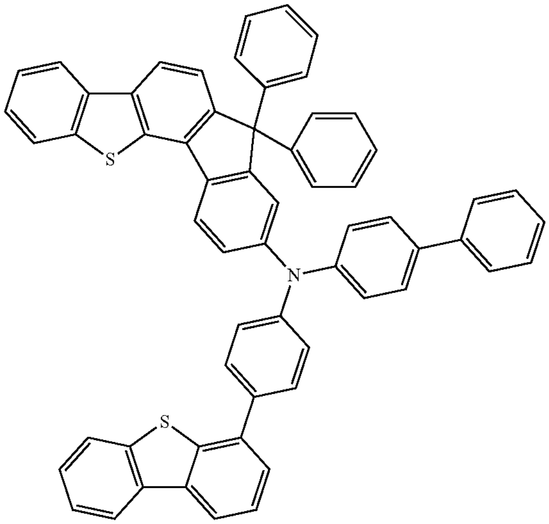
-continued
[C-19]
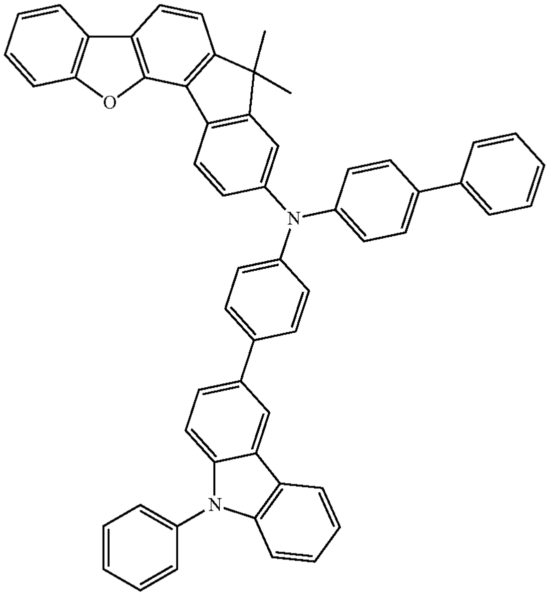
[C-20]
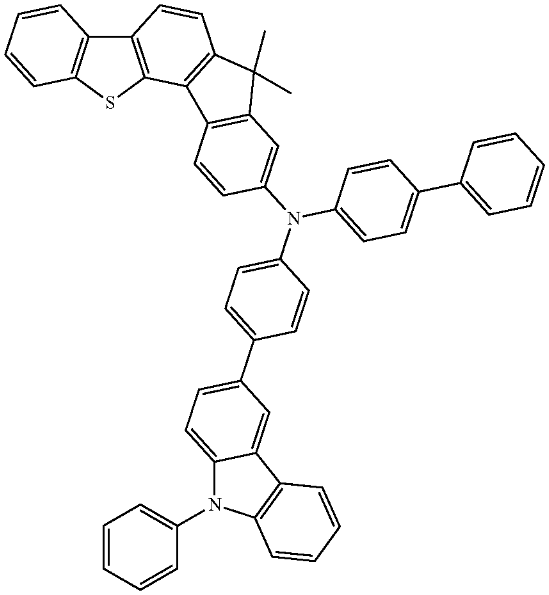

-continued
[C-21]
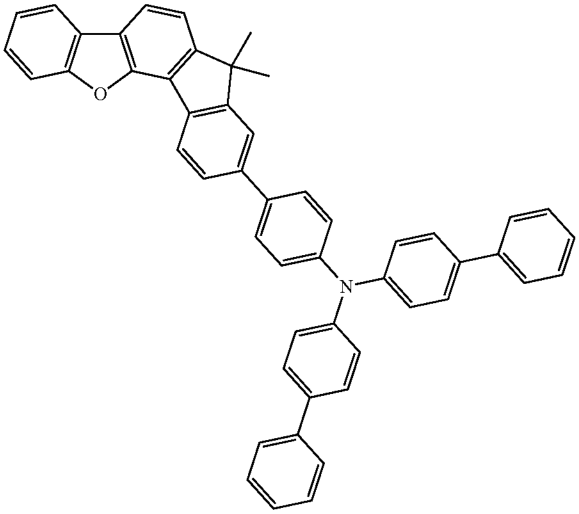
[C-22]
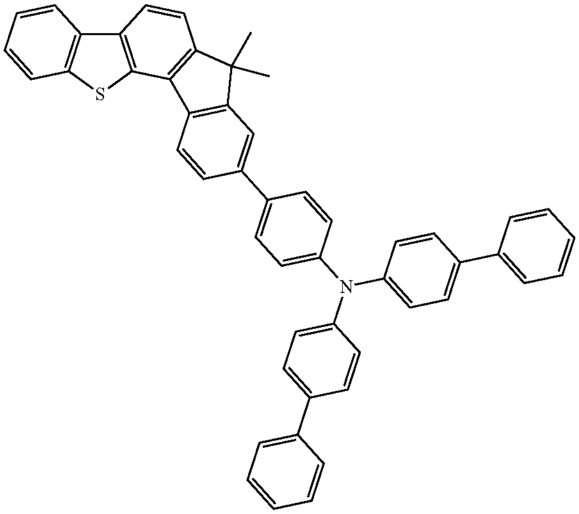
[C-23]
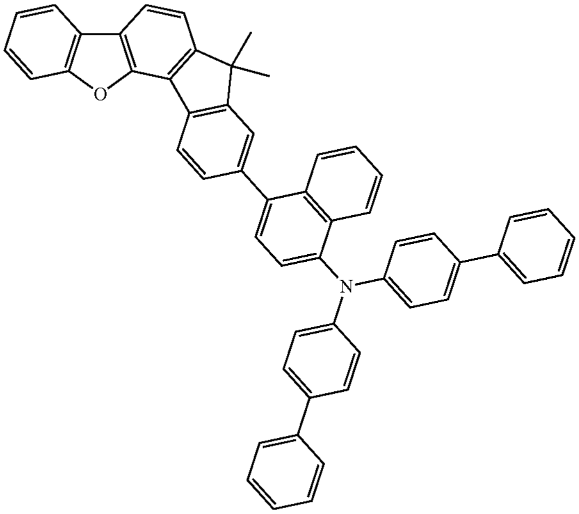
-continued
[C-24]
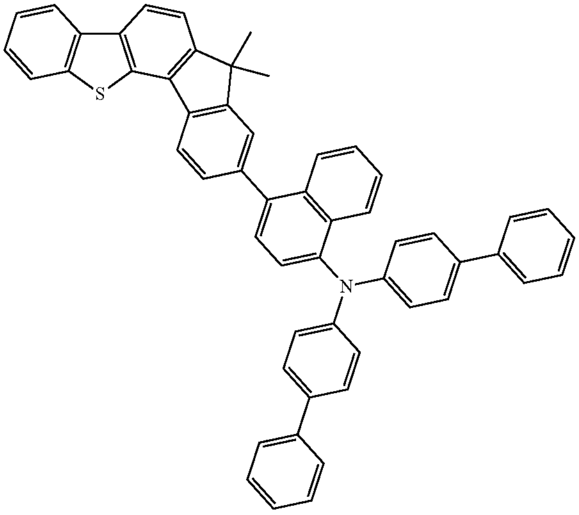
[C-25]
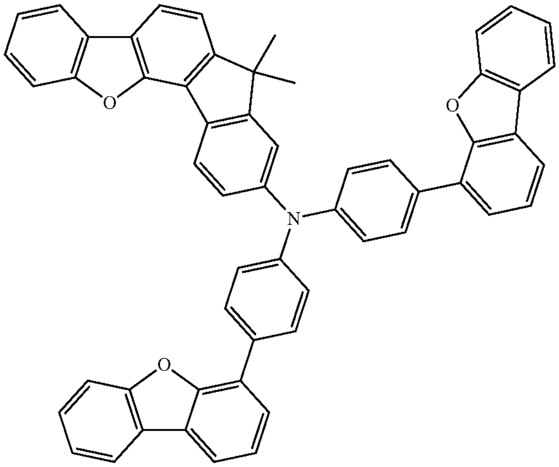
[C-26]
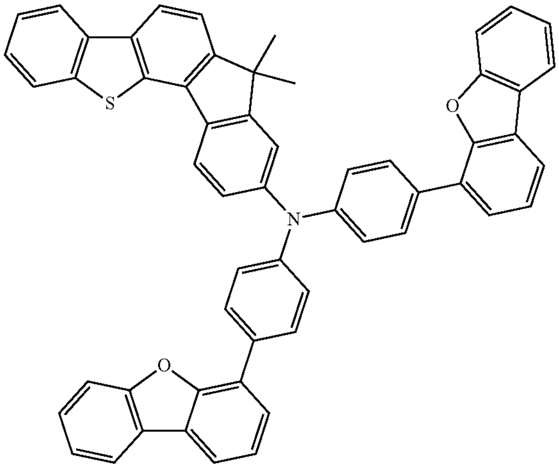

-continued
[C-27]
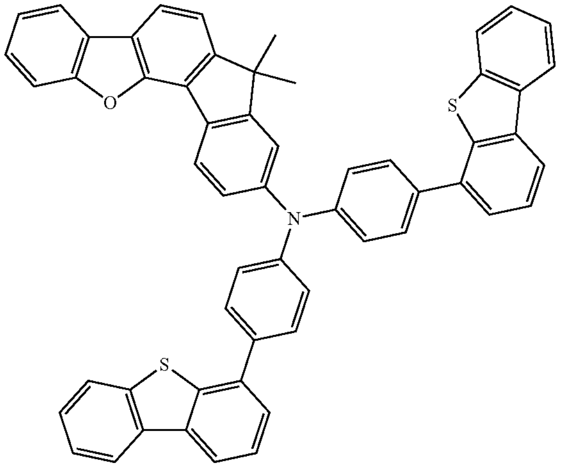
[C-28]
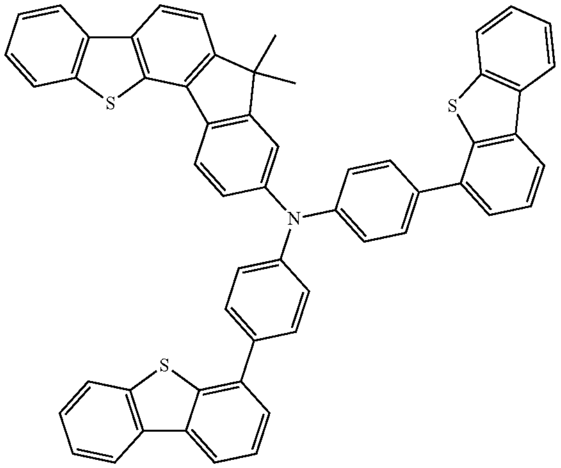
[C-29]
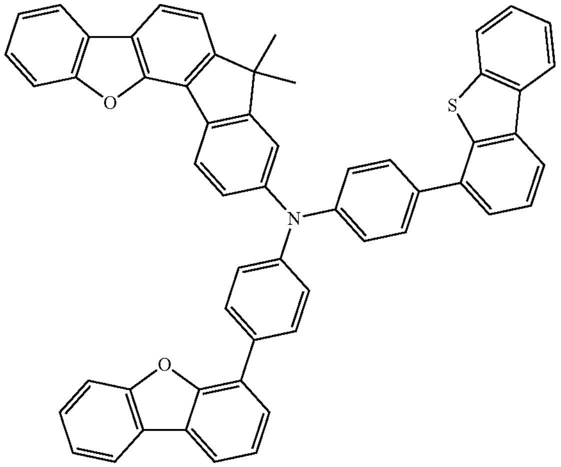
-continued
[C-30]
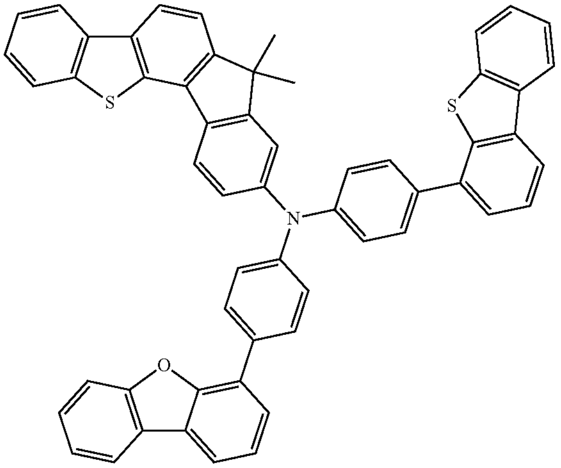
[C-31]
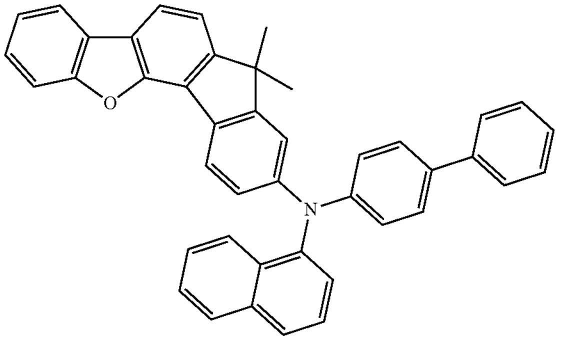
[C-32]
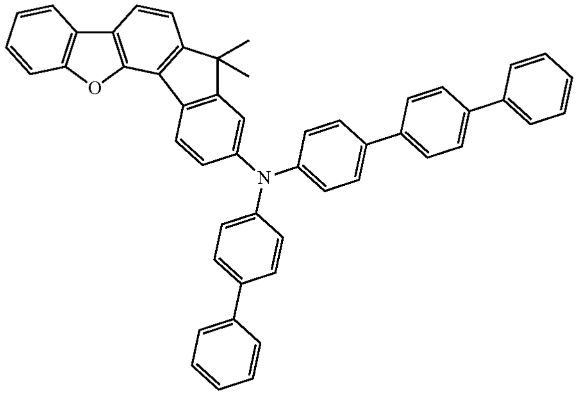

-continued
[C-33]
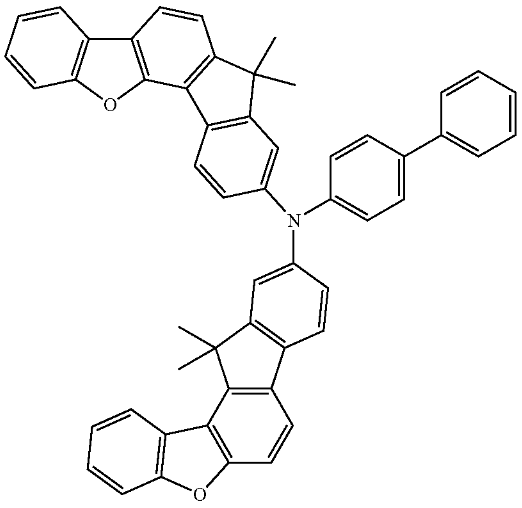
[C-34]
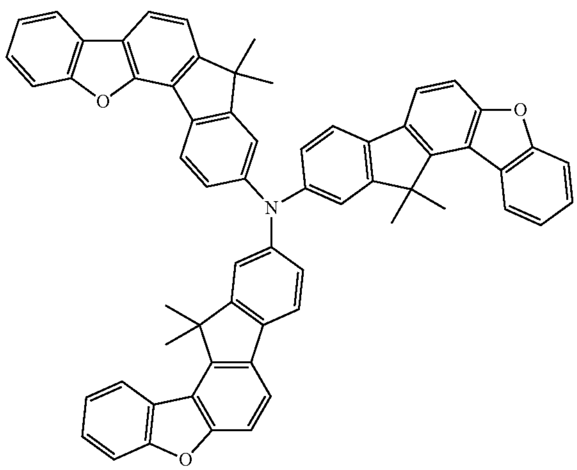
[C-35]
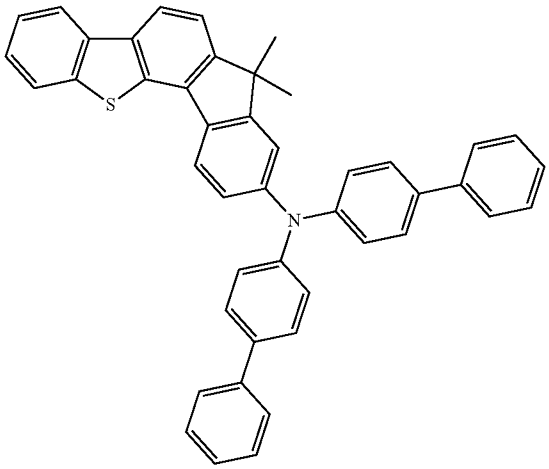
-continued
[C-36]
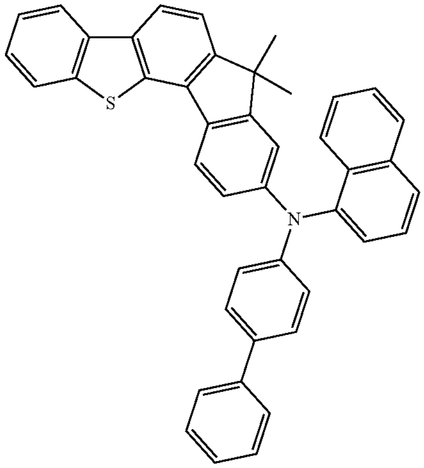
[C-37]
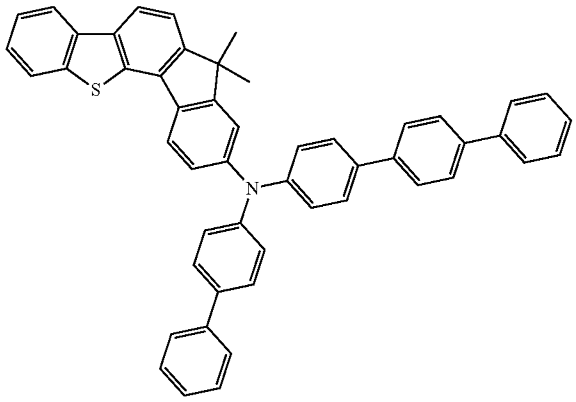
[C-38]
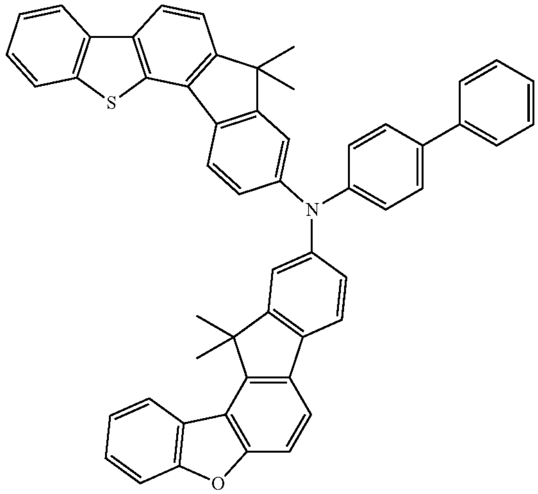

-continued

[C-39]

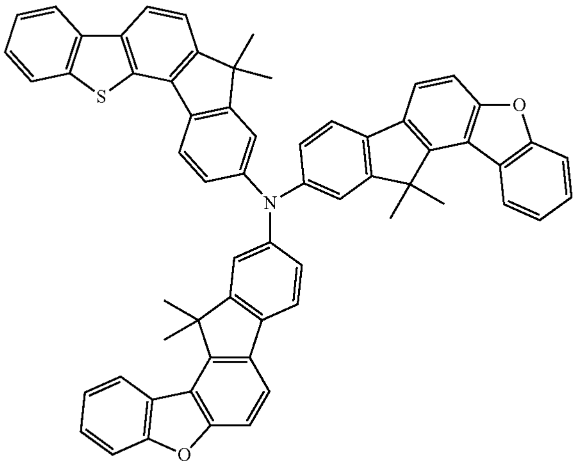

[C-40]

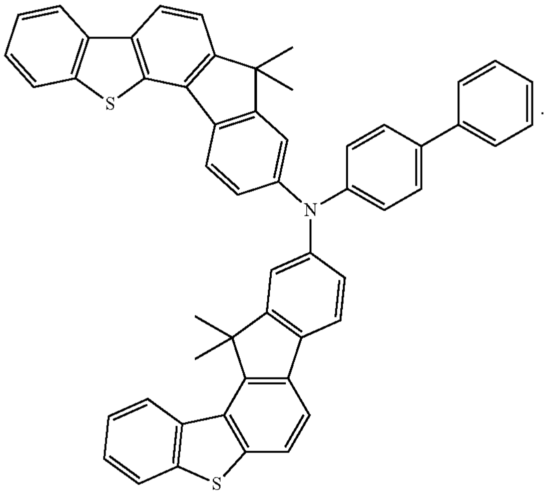

The compound for an organic optoelectronic device may be a compound represented by one of the following Chemical Formulae D-1 to D-20. In the compounds represented by the following Chemical Formulae D-1 to D-20, dibenzofuran or dibenzothiophene is combined with carbazole in one molecule. Thus, the compound may have main or primary characteristics of carbazole and auxiliary or secondary characteristics of dibenzofuran or dibenzothiophene.

[D-1]

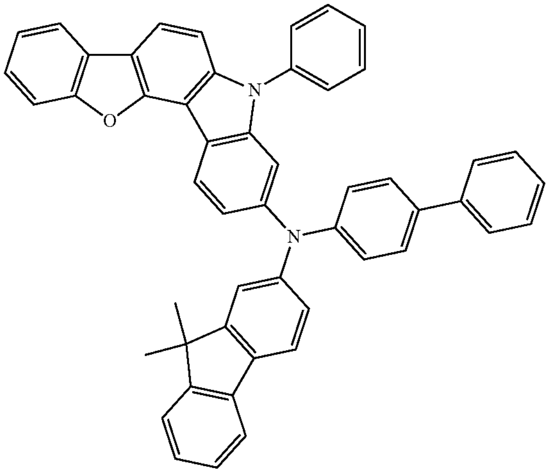

[D-2]

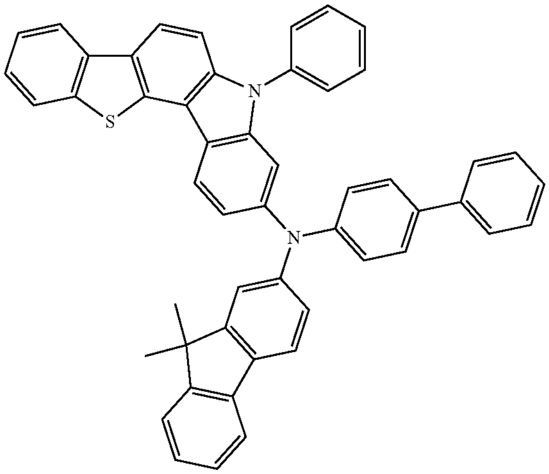

[D-3]

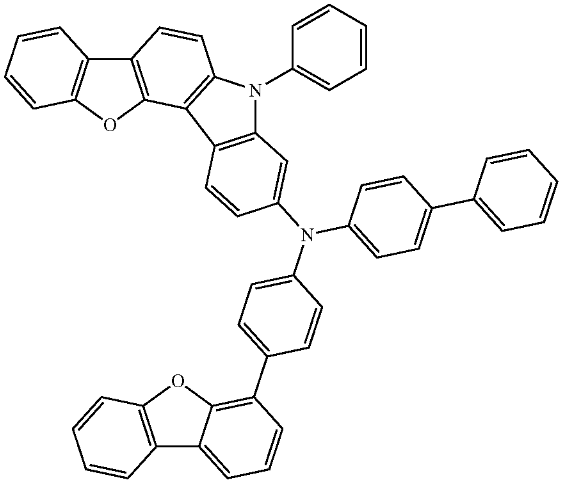

-continued
[D-4]
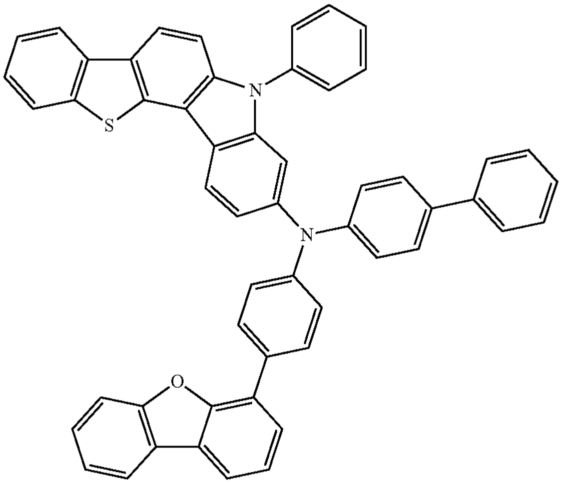
[D-5]
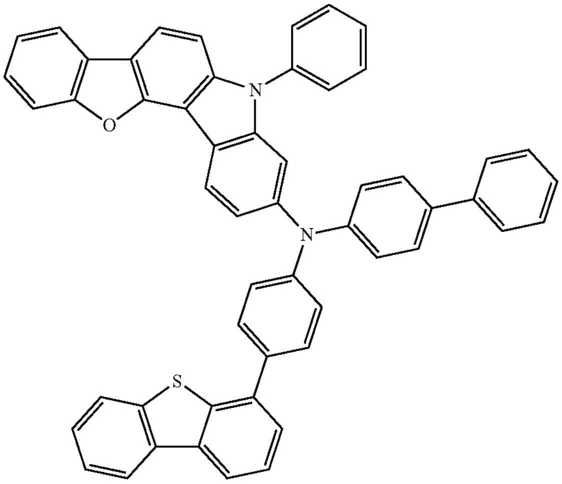
[D-6]
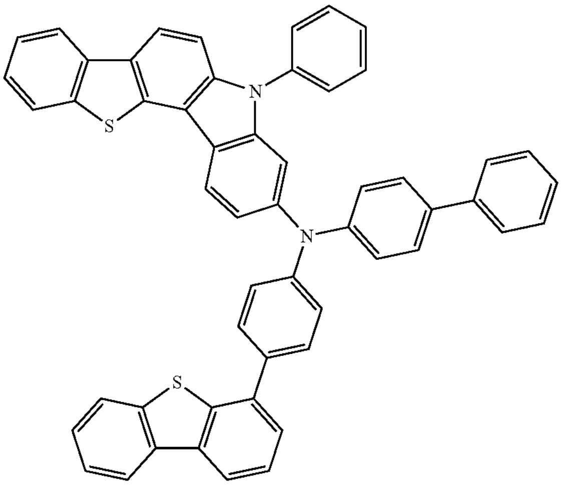
-continued
[D-7]
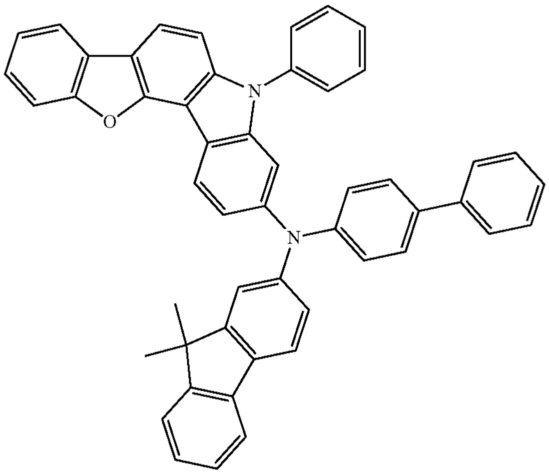
[D-8]
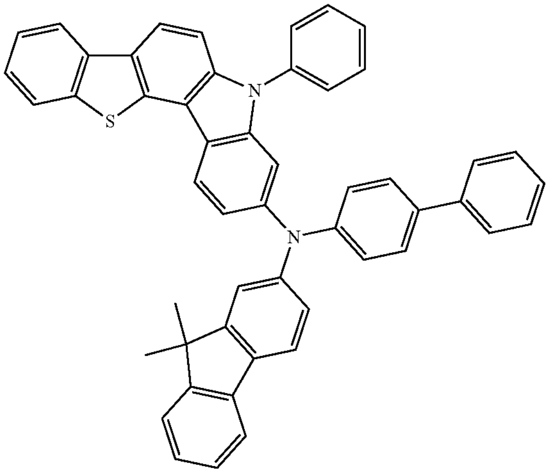
[D-9]
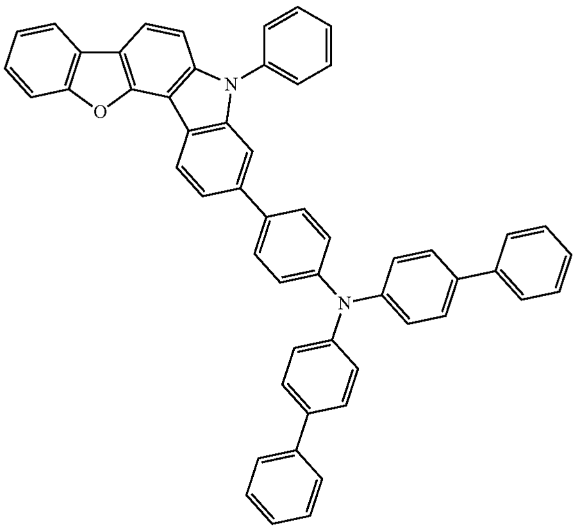

[D-10]
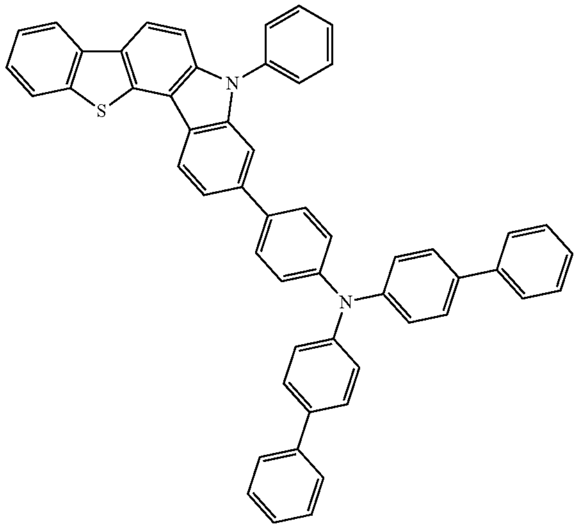
[D-11]
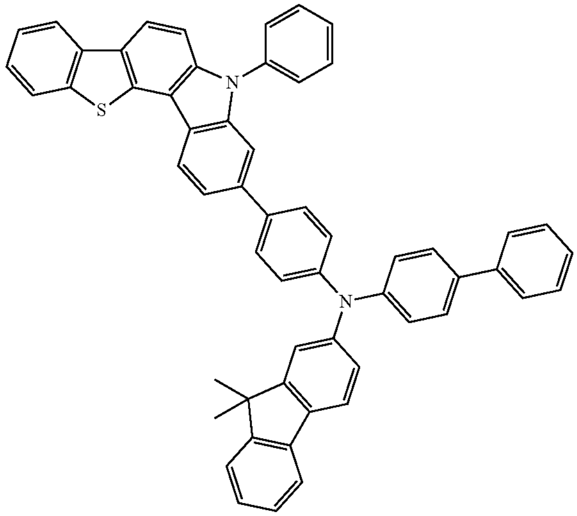
[D-12]
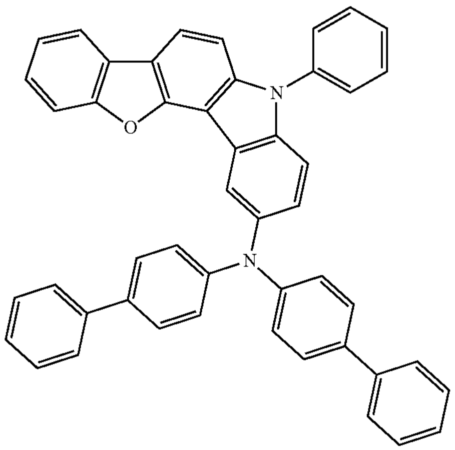
[D-13]
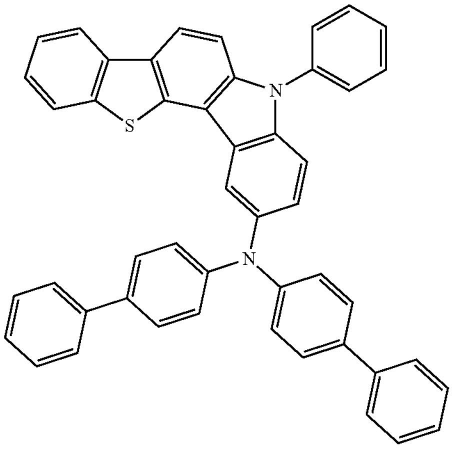
[D-14]
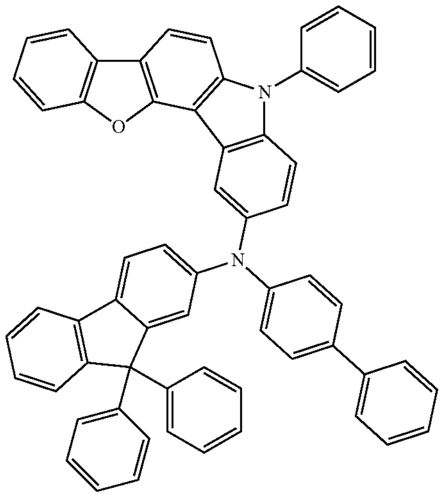
[D-15]
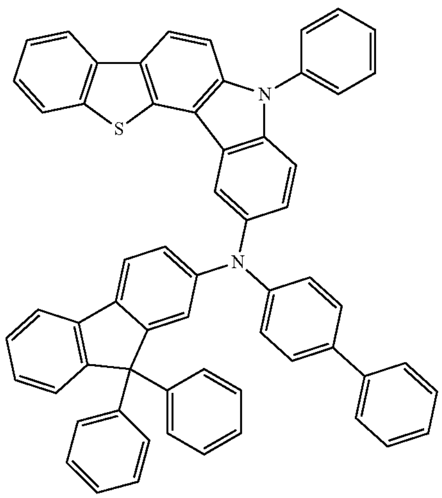

-continued

[D-16]

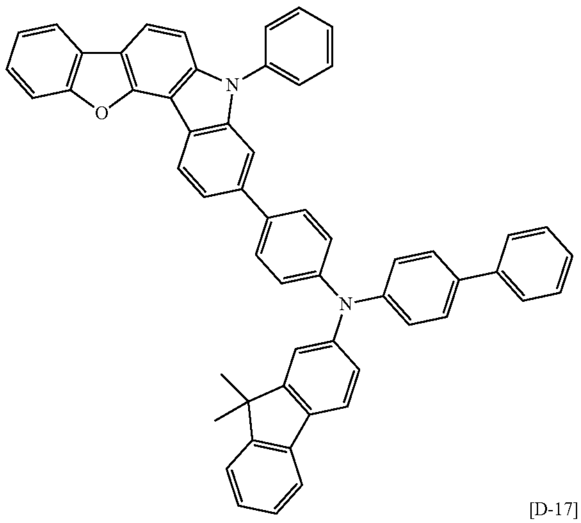

[D-17]

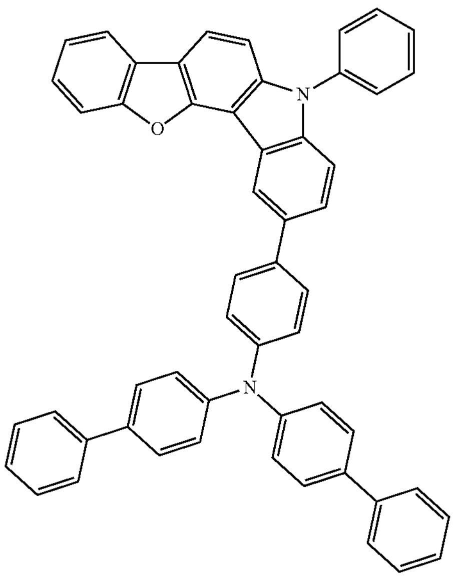

[D-18]

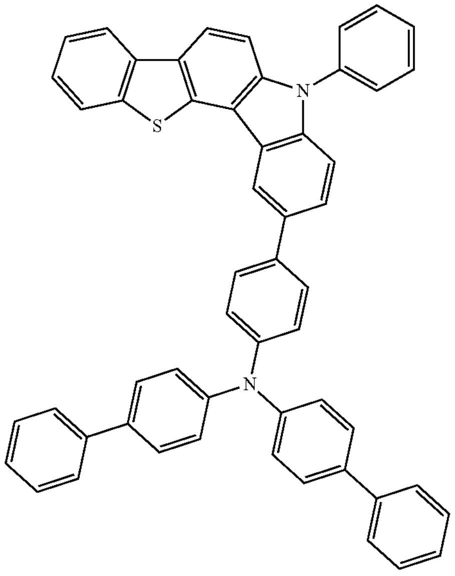

-continued

[D-19]

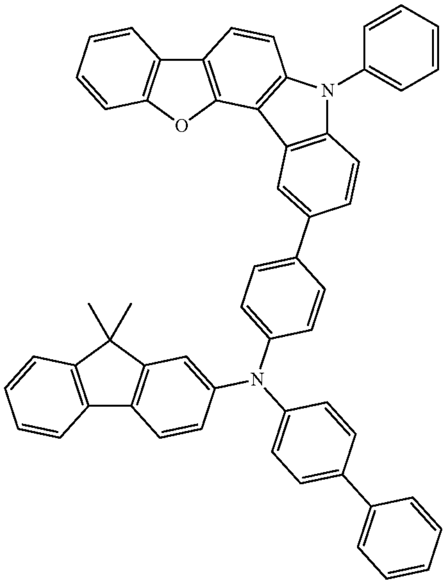

[D-20]

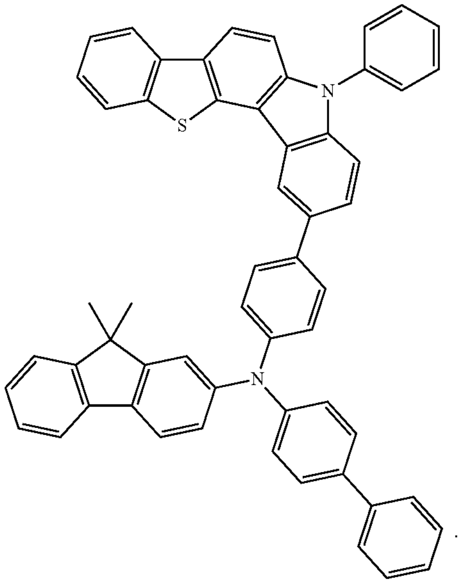

When the compound for an organic optoelectronic device according to an embodiment is used to prepare an electron blocking layer (or a hole transport layer (HTL)), if a functional group with electron properties is included therein, electron blocking properties may be deteriorated. Accordingly, the compound may not include a functional group with electron properties when used for an electron blocking layer. Examples of the functional group with electron properties may include benzoimidazole, pyridine, pyrazine, pyrimidine, triazine, quinoline, isoquinoline, and the like. However, such a condition may only be applicable when the compound is applied to an electron-blocking film or a hole transport layer (HTL) (or a hole injection layer (HIL)).

When it is desired that the compound according to an embodiment exhibit both electron properties and hole properties, the functional group with electron properties may be included in the compound, thereby improving life-span of an organic optoelectronic device, (e.g., an organic light emitting diode) and decreasing a driving voltage thereof.

According an embodiment, the compound for an organic optoelectronic device may have maximum light emitting wavelength of about 320 nm to about 500 nm and a triplet excitation energy (T1) of about 2.0 eV or more, e.g., from about 2.0 to about 4.0 eV. Accordingly, the compound may be used as a host material or a charge transport material because charges of the host material with high triplet excitation energy may be well transported to a dopant and may increase luminous efficiency of the dopant; and HOMO and LUMO energy levels of the host material may be freely adjusted.

In addition, the compound for an organic optoelectronic device may have photoactive and electric activity. Thus, the compound may be used as an optic material, electrode material, discoloring material, photo switch, sensor, module, wave guide, organic transistor, laser, light-absorbing agent, dielectric material, membrane, and the like.

The compound for an organic optoelectronic device may have a glass transition temperature of about 90° C. or higher, and a thermal decomposition temperature of about 400° C. or higher and thus, may exhibit excellent thermal stability. Accordingly, the compound may provide an organic optoelectronic device with high efficiency.

The compound for an organic optoelectronic device (including the compounds described above) may play a role in emitting light or injecting and/or transporting electrons. In an implementation, the compound may act as a light emitting host together with a suitable dopant. For example, the compound for an organic optoelectronic device may be used as a phosphorescent or fluorescent host material, a blue light emitting dopant material, or an electron transporting material.

The compound for an organic optoelectronic device according to an embodiment may be used for an organic thin layer. Thus, it may help improve the life span characteristic, efficiency characteristic, electrochemical stability, and thermal stability of an organic photoelectric device, and may help decrease the driving voltage thereof.

Another embodiment provides an organic optoelectronic device that includes the compound for an organic optoelectronic device. The organic photoelectric device may include, e.g., an organic light emitting diode, an organic solar cell, an organic transistor, an organic photosensitive drum, an organic memory device, or the like. For example, the compound for an organic optoelectronic device according to an embodiment may be included in an electrode or an electrode buffer layer in the organic solar cell (to help improve quantum efficiency) and it may be used as an electrode material for a gate, a source-drain electrode, or the like in the organic transistor.

Hereinafter, a detailed description relating to the organic light emitting diode will be provided.

The organic thin layer may include the compound for an organic optoelectronic device. The organic thin layer may include at least one layer selected from the group of an emission layer, a hole transport layer (HTL), a hole injection layer (HIL), an electron transport layer (ETL), an electron injection layer (EIL), a hole blocking film, and a combination thereof. The at least one layer may include the compound for an organic optoelectronic device according to an embodiment.

For example, the electron transport layer (ETL) or the electron injection layer (EIL) may include the compound for an organic optoelectronic device according to an embodiment. In addition, when the compound for an organic optoelectronic device is included in the emission layer, the compound may be included as a phosphorescent or fluorescent host, or as a fluorescent blue dopant material.

FIGS. 1 to 5 illustrate cross-sectional views of an organic light emitting diode including the compound for an organic optoelectronic device according to an embodiment.

Referring to FIGS. 1 to 5, organic light emitting diode 100, 200, 300, 400, and 500 according to an embodiment may include at least one organic thin layer 105 interposed between an anode 120 and a cathode 110.

The anode 120 may include an anode material laving a large work function to facilitate hole injection into an organic thin layer. The anode material may include, e.g., a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, but is not limited thereto. In an implementation, a transparent electrode including indium tin oxide (ITO) may be used as the anode.

The cathode 110 may include a cathode material having a small work function to facilitate electron injection into an organic thin layer. The cathode material may include, e.g., a metal such as magnesium, calcium, sodium, potassium, titanium, indium, yttrium, lithium, gadolinium, aluminum, silver, tin, lead, cesium, barium, and the like, or alloys thereof; or a multi-layered material such as LiF/Al, $LiO_2$/Al, LiF/Ca, LiF/Al, and $BaF_2$/Ca, but is not limited thereto. In an implementation, a metal electrode including aluminum may be used as the cathode.

Referring to FIG. 1, the organic light emitting diode 100 may include an organic thin layer 105 including only an emission layer 130.

Figure 2:
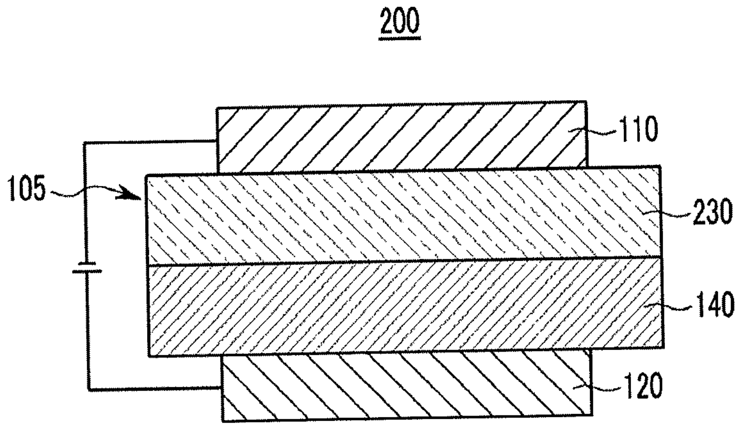

Referring to FIG. 2, the emission layer 230 may also function as an electron transport layer (ETL); and the hole transport layer (HTL) 140 layer may have an excellent binding property with a transparent electrode such as ITO or an excellent hole transporting property.

Figure 3:
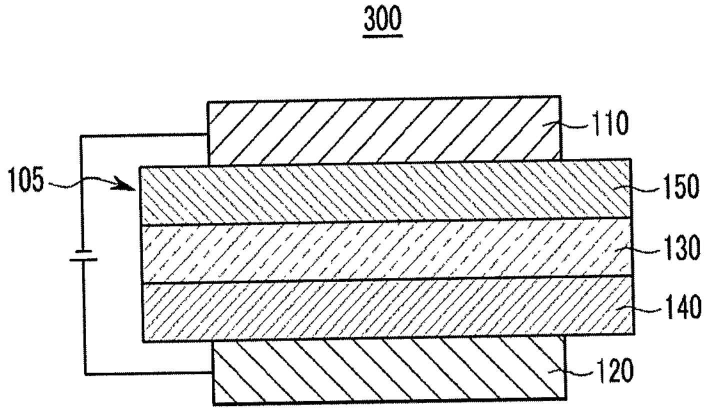

Referring to FIG. 3, a three-layered organic light emitting diode 300 may include an organic thin layer 105 including an electron transport layer (ETL) 150, an emission layer 130, and a hole transport layer (HTL) 140. The emission layer 130 may be independently installed; and layers having an excellent electron transporting property or an excellent hole transporting property may be separately stacked.

Figure 4:
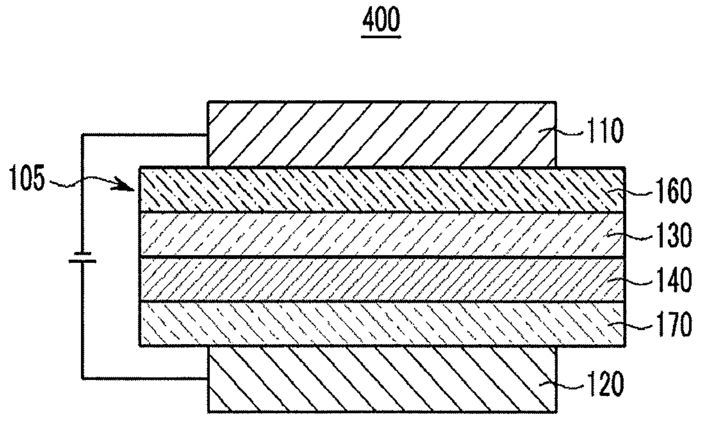

Referring to FIG. 4, a four-layered organic light emitting diode 400 may include an organic thin layer 105 including an electron injection layer (EIL) 160, an emission layer 130, a hole transport layer (HTL) 140, and a hole injection layer (HIL) 170 for binding with the anode 120 of ITO.

Figure 5:
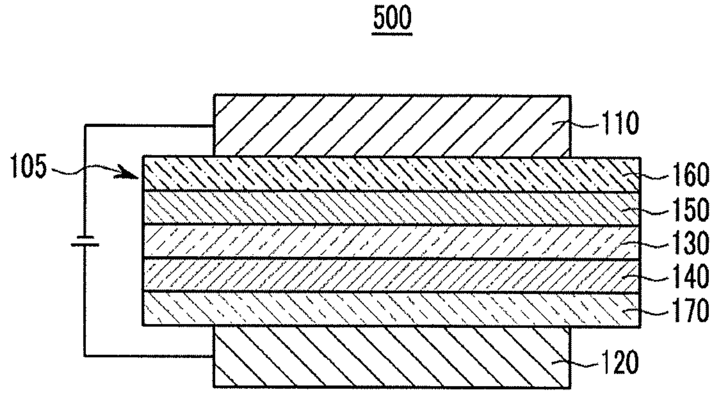

Referring to FIG. 5, a five-layered organic light emitting diode 500 may include an organic thin layer 105 including an electron transport layer (ETL) 150, an emission layer 130, a hole transport layer (HTL) 140, and a hole injection layer (HIL) 170, and may further include an electron injection layer (EIL) 160 to achieve a low voltage.

In FIG. 1 to FIG. 5, the organic thin layer 105 (including at least one selected from the group of an electron transport layer (ETL) 150, an electron injection layer (EIL) 160, an emission layer 130 and 230, a hole transport layer (HTL) 140, a hole injection layer (HIL) 170, and combinations thereof) may include the compound for an organic optoelectronic device according to an embodiment. In an implementation, the compound for the organic optoelectronic device may be used for the electron transport layer (ETL) 150 or electron injection layer (EIL) 160. When the compound is used for the electron transport layer (ETL), it is possible to provide an organic light emitting diode having a simpler structure because an additional hole blocking layer (not shown) may be omitted.

Furthermore, when the compound for an organic optoelectronic device is included in the emission layer 130 and 230, the compound may be included as a phosphorescent or fluorescent host, or a fluorescent blue dopant.

The organic light emitting diode may be fabricated by, e.g., forming an anode on a substrate; forming an organic thin layer in accordance with a dry coating method such as evaporation, sputtering, plasma plating, and ion plating, or a wet coating method such as spin coating, dipping, and flow coating; and providing a cathode thereon.

Another embodiment provides a display device including the organic light emitting diode according to the above embodiment.

The following Examples and Comparative Examples are provided in order to set forth particular details of one or more embodiments. However, it will be understood that the embodiments are not limited to the particular details described. Further, the Comparative Examples are set forth to highlight certain characteristics of certain embodiments, and are not to be construed as either limiting the scope of the invention as exemplified in the Examples or as necessarily being outside the scope of the invention in every respect.

(Preparation of Compound for Organic Optoelectronic Device)

Synthesis of Intermediate

Synthesis of Intermediate M-1

[Reaction Scheme 1]

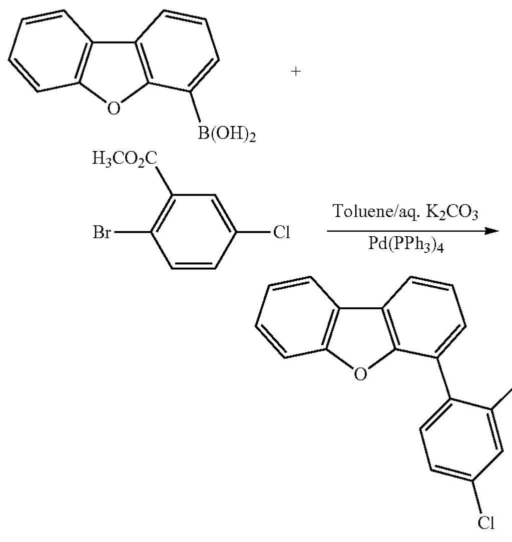

M-1

30 g (141.5 mmol) of (4-dibenzofuranyl)boronic acid, 37.1 g (148.6 mmol) of methyl-2-bromo-5-chlorobenzoate, and 8.2 g (7.1 mmol) of tetrakis(triphenylphosphine)palladium were put in a flask and dissolved in 550 ml of toluene under a nitrogen atmosphere. Then, 353.8 ml of an aqueous solution in which 104.2 g (707.51 mmol) of potassium carbonate was dissolved was added thereto. The mixture was agitated for 12 hours. When the reaction was complete, the resulting product was extracted with ethyl acetate. The extraction solution was dried with magnesium sulfate, filtered, and then concentrated under a reduced pressure. The concentrated product was purified through silica gel column chromatography by using n-hexane/dichloromethane mixed in a volume ratio of 7:3, obtaining a desired compound, an intermediate M-1 as 38.2 g of a white solid (yield: 80%).

LC-MS (theoretical value: 336.06 g/mol, measured value: M+1=336 g/mol)

Synthesis of Intermediate M-2

[Reaction Scheme 2]

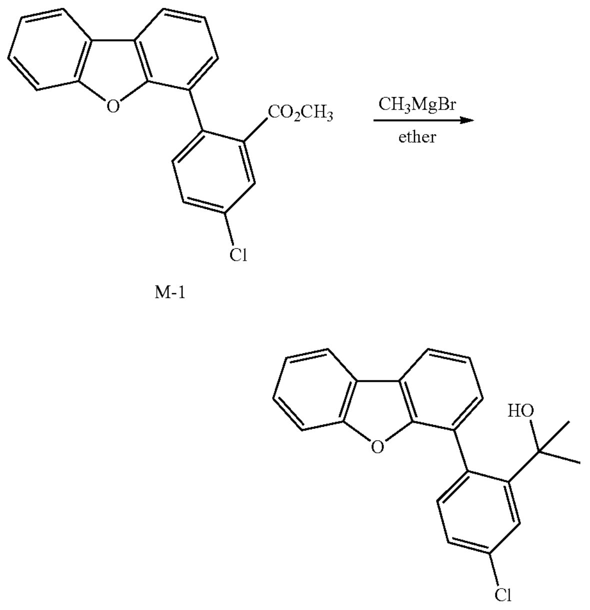

M-1

M-2

38.18 g (113.37 mmol) of the intermediate M-1 was put in a flask and dissolved in 500 ml of anhydrous ether under a nitrogen atmosphere. The solution was cooled down to 0° C. and agitated. Then, 110 mL of 3M methyl magnesium bromide (in 340.1 mmol of diethyl ether) was slowly added to the agitated solution. The mixture was agitated at room temperature under a nitrogen atmosphere for 5 hours. When the reaction was complete, the resulting solution was concentrated under a reduced pressure to remove the solvent and then extracted with distilled water and dichloromethane. The extracted solution was dried with anhydrous magnesium sulfate, filtered, and then concentrated under a reduced pressure, obtaining a desired compound, an intermediate M-2 as a liquid with high viscosity.

Synthesis of Intermediate M-3

[Reaction Scheme 3]

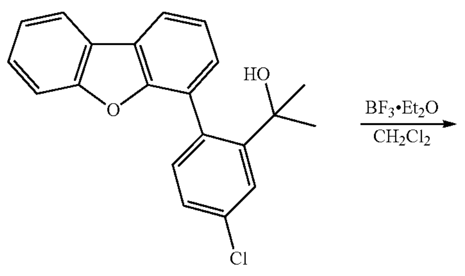

M-2

-continued

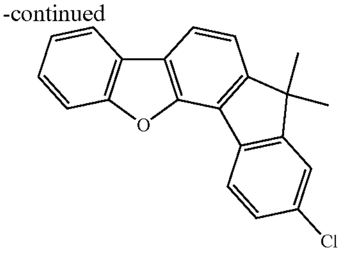

M-3

The intermediate M-3 was dissolved in 250 ml of dichloromethane. The solution was cooled down to 0° C. and then agitated. Then, a solution prepared by dissolving boron trifluoride in 20 mL of dichloromethane and 15.18 g (56.7 mmol) of diethyl ether complex were slowly added to the above agitated solution. The mixture was agitated for 5 hours. When the reaction was complete, the resulting product was extracted with ethyl acetate. The extracted solution was dried with magnesium sulfate, filtered, and then concentrated under a reduced pressure. The product was purified through silica gel column chromatography by using n-hexane, obtaining a desired compound, an intermediate M-3 as 29 g of a white solid (yield: 80%).

GC-MS (theoretical value: 318.8 g/mol, measured value: M+1=318 g/mol)

Synthesis of Intermediate M-4

[Reaction Scheme 4]

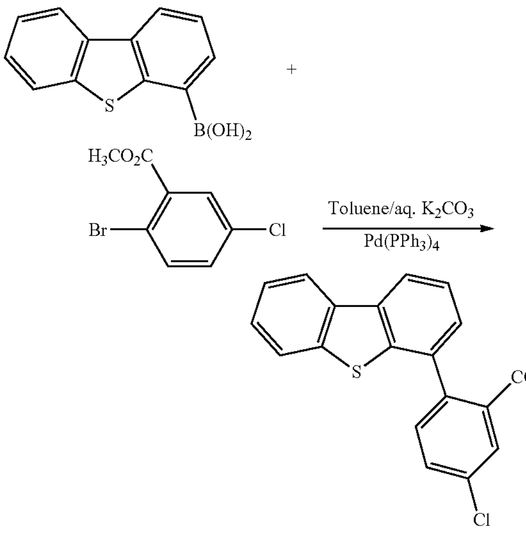

M-4

30 g (141.5 mmol) of (4-dibenzofuranyl)boronic acid as an intermediate, 37.1 g (148.6 mmol) of methyl-2-bromo-5-chlorobenzoate, and 8.2 g (7.1 mmol) of tetrakis(triphenylphosphine)palladium were put in a flask and dissolved in 550 ml of toluene under a nitrogen atmosphere. The, 353.8 ml of an aqueous solution in which 104.2 g (707.51 mmol) of potassium carbonate was dissolved was added thereto. The mixture was refluxed and agitated for 12 hours. When the reaction was complete, the agitated product was extracted with ethyl acetate. The extracted solution was dried with magnesium sulfate, filtered, and then concentrated under a reduced pressure. The concentrated product was purified through a silica gel column using n-hexane/dichloromethane mixed in a volume ratio of 7:3, obtaining a desired compound, an intermediate M-1 as 38.2 g of a white solid (yield: 80%).

LC-MS (theoretical value: 336.06 g/mol, measured value: M+1=336 g/mol)

Synthesis of Intermediate M-5

[Reaction Scheme 5]

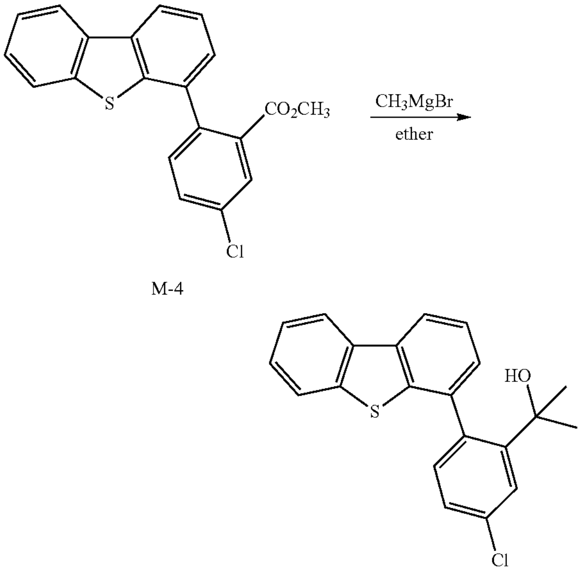

M-4

M-5

38.2 g (113.37 mmol) of the intermediate M-4 was put in a flask and dissolved in 500 ml of anhydrous ether under a nitrogen atmosphere. The resulting reactant was cooled down to 0° C. and agitated. Then, 110 mL of 3M methyl magnesium bromide (in 324.63 mmol of diethyl ether) was slowly added to the resulting product. The mixture was cooled down to a room temperature and agitated under a nitrogen atmosphere for 5 hours. When the reaction was complete, the reactant was concentrated under a reduced pressure to remove the solvent, extracted with distilled water and dichloromethane, dried with magnesium sulfate, filtered, and concentrated under a reduced pressure, obtaining a desired compound, an intermediate M-2, as a liquid with high viscosity.

Synthesis of Intermediate M-6

[Reaction Scheme 6]

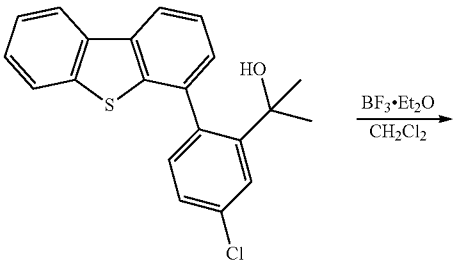

M-5

-continued

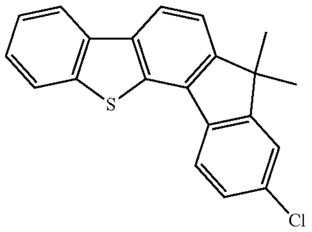

M-6

The intermediate M-5 was dissolved in 250 ml of dichloromethane and then cooled down to 0° C. and agitated. Then, boronitrilefluoride dissolved in 20 mL of boron trifluoride and 14.5 g (54.1 mmol) of diethyl ether complex were slowly added to the agitated product. The mixture was agitated at room temperature for 5 hours. When the reaction was complete, the resulting product was extracted with ethyl acetate. The extracted solution was dried with magnesium sulfate, filtered, and then concentrated under a reduced pressure. The concentrated product was purified through silica gel column chromatography by using n-hexane, obtaining a desired compound, an intermediate M-6, as 31 g of a white solid (yield: 85.5%).

GC-MS (theoretical value: 334.86 g/mol, measured value: 335 g/mol)

Synthesis of Intermediate M-7

[Reaction Scheme 7]

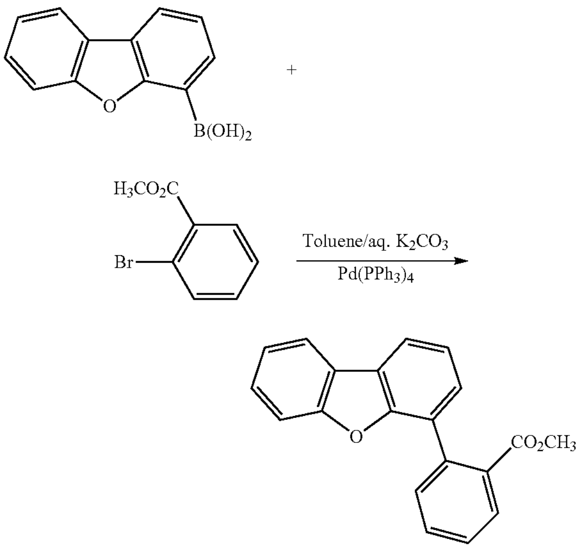

M-7

23 g (108.5 mmol) of (4-dibenzofuranyl)boronic acid as an intermediate, 24.5 g (113.9 mmol) of methyl-2-bromo-benzoate, and 6.3 g (5.47 mmol) of tetrakis(triphenylphosphine) palladium were put in a flask and dissolved in 500 ml of toluene under a nitrogen atmosphere. Then, 271.2 ml of an aqueous solution prepared by dissolving 79.9 g (542.4 mmol) of potassium carbonate was added thereto. The mixture was refluxed and agitated for 12 hours. When the reaction was complete, the agitated solution was extracted with ethyl acetate. The extracted solution was dried with magnesium sulfate, filtered, and then concentrated under a reduced pressure. The concentrated product was purified through silica gel column chromatography by using n-hexane/dichloromethane mixed in a volume ratio of 7:3, obtaining a desired compound, an intermediate M-7, as 31 g of a white solid (yield: 94.5%).

LC-MS (theoretical value: 302.32 g/mol, measured value: M+1=303 g/mol)

Synthesis of Intermediate M-8

[Reaction Scheme 8]

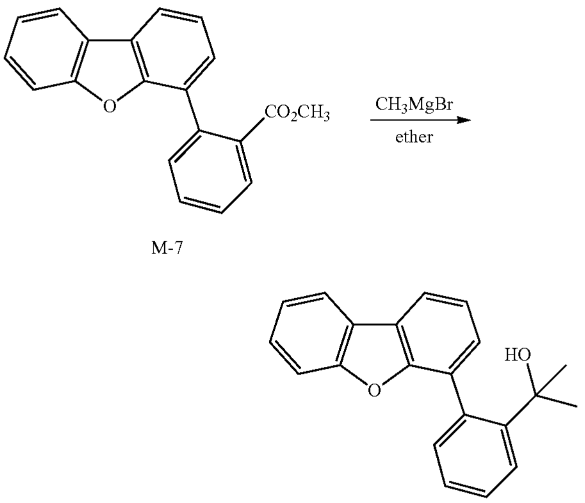

M-7

M-8

29 g (95.92 mmol) of the intermediate M-7 was put in a flask and dissolved in 400 ml of anhydrous tetrahydrofuran (THF) under a nitrogen atmosphere. The solution was cooled down to 0° C. and agitated. Then, 95.9 mL of 3M methyl magnesium bromide (in 287.8 mmol of diethyl ether) was slowly added to the agitated solution. The mixture was agitated at room temperature under a nitrogen atmosphere for 5 hours. When the reaction was complete, the agitated solution was concentrated under a reduced pressure to remove the solvent. The resulting product was extracted with distilled water and dichloromethane. The extracted solution was dried with magnesium sulfate, filtered, and then concentrated under a reduced pressure, obtaining a desired compound, an intermediate M-8, as a liquid with high viscosity.

Synthesis of Intermediate M-9

[Reaction Scheme 9]

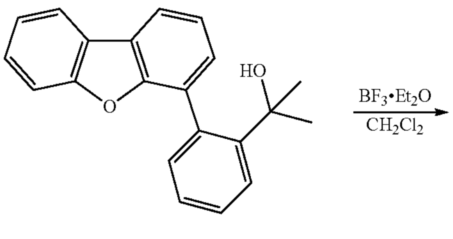

M-8

-continued

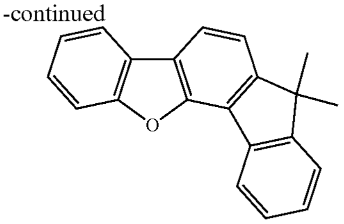

M-9

The intermediate M-8 was dissolved in 250 ml of dichloromethane and cooled down to 0° C. and then, agitated. Next, 12.84 g (47.5 mmol) of boronitrilefluoride and diethyl ether complex dissolved in 20 mL of dichloromethane were slowly added to the agitated product. The mixture was agitated at room temperature for 5 hours. When the reaction was complete, the agitated solution was extracted with ethyl acetate. The extracted solution was dried with magnesium sulfate, filtered, and then concentrated under a reduced pressure. The resulting product was purified through silica gel column chromatography using n-hexane, obtaining a desired compound, an intermediate M-9, as 22 g of a white solid (yield: 71.9%).

LC-MS (theoretical value: 284.35 g/mol, measured value: M+1=284 g/mol)

Synthesis of Intermediate M-10

[Reaction Scheme 10]

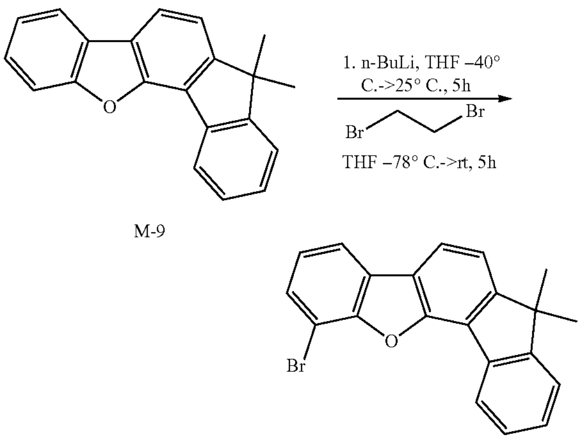

M-9

M-10

10 g (59.5 mmol) of the intermediate M-9 was put under a nitrogen atmosphere in a 2-necked round-bottomed flask heated and dried under vacuum; and 119 mL of anhydrous tetrahydrofuran was added thereto. The mixture was cooled down to 40° C. and agitated. Next, 26 mL of 1.6M n-butyllithium (in 65.5 mmol of hexane) was slowly added to the agitated solution. The mixture was agitated at room temperature under a nitrogen atmosphere for 5 hours. The resulting product was cooled down to −78° C., and 22.4 g (119 mmol) of 1,2-dibromoethane dissolved in 10 mL of anhydrous tetrahydrofuran was slowly added thereto. The mixture was agitated at room temperature for 5 hours. When the reaction was complete, the agitated solution was concentrated under a reduced pressure to remove the solvent. The concentrated solution was extracted with distilled water and dichloromethane. The extracted solution was dried with magnesium sulfate, filtered, and then concentrated under a reduced pressure. The concentrated product was recrystallized with n-hexane, obtaining a desired compound, an intermediate M-10, as 11 g of a white solid (yield: 75%).

GC-MS (theoretical value: 245.97 g/mol, measured value: 246 g/mol)

Synthesis of Intermediate M-11

[Reaction Scheme 11]

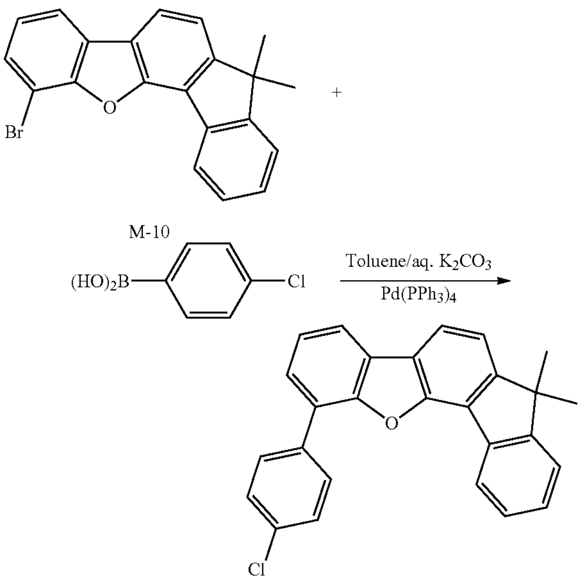

M-10

M-11

11 g (30.28 mmol) of the intermediate M-10, 5.0 g (31.8 mmol) of 4-chlorophenylboronic acid, and 1.8 g (1.5 mmol) of tetrakis(triphenylphosphine)palladium were put in a flask and dissolved in 120 ml of toluene under a nitrogen atmosphere, and 75.7 ml of an aqueous solution prepared by dissolving 22.3 g (151.4 mmol) of potassium carbonate. The mixture was refluxed and agitated for 12 hours. When the reaction was complete, the agitated solution was extracted with ethyl acetate. The extracted solution was dried with magnesium sulfate, filtered, and then concentrated under a reduced pressure. The concentrated product is purified through a silica gel column using n-hexane/dichloromethane mixed in a volume ratio of 7:3, obtaining a desired compound, an intermediate M-11, as 8.0 g of a white solid (yield: 66.7%).

GC-MS (theoretical value: 394.89 g/mol, measured value: 395 g/mol)

Synthesis of Intermediate M-12

[Reaction Scheme 12]

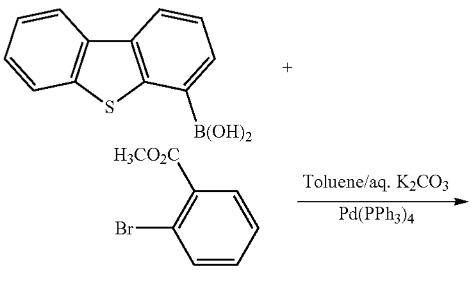

-continued

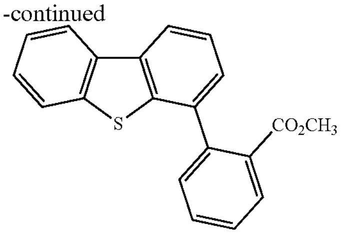

M-12

25 g (109.62 mmol) of (4-dibenzothiophenyl)boronic acid as an intermediate, 24.8 g (115.1 mmol) of methyl-2-bromobenzoate, and 6.3 g (5.48 mmol) of tetrakis(triphenylphosphine)palladium were put in a flask and dissolved in 500 ml of toluene under a nitrogen atmosphere, and 274 ml of an aqueous solution in which 80.7 g (548.1 mmol) of potassium carbonate was dissolved was added thereto. The mixture was refluxed and agitated for 12 hours. When the reaction was complete, the agitated solution was extracted with ethyl acetate. The extracted solution was dried with magnesium sulfate, filtered, and then concentrated under a reduced pressure. The concentrated product was purified through silica gel column chromatography using n-hexane/dichloromethane mixed in a volume ratio of 7:3, obtaining a desired compound, an intermediate M-12, as 31 g of a white solid (yield: 88.8%).

GC-MS (theoretical value: 318.39 g/mol, measured value: M+1=318 g/mol)

Synthesis of Intermediate M-13

[Reaction Scheme 13]

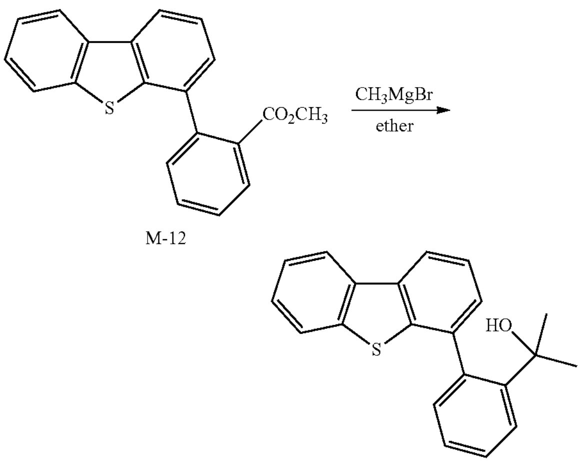

M-12

M-13

15.4 g (47.1 mmol) of the intermediate M-12 was put in a flask and dissolved in 400 ml of anhydrous tetrahydrofuran under a nitrogen atmosphere. The mixture was cooled down to 0° C. and agitated. Next, 50 mL of 3M methyl magnesium bromide (in 141.34 mmol of diethyl ether) was slowly added to the agitated mixture. The resulting mixture was agitated at room temperature under a nitrogen atmosphere for 5 hours. When the reaction was complete, the agitated solution was concentrated under a reduced pressure to remove the solvent and extracted with water and dichloromethane. The extracted solution was dried with magnesium sulfate, filtered, and then concentrated under a reduced pressure, obtaining a desired compound, an intermediate M-13, as a liquid with high viscosity.

Synthesis of Intermediate M-14

[Reaction Scheme 14]

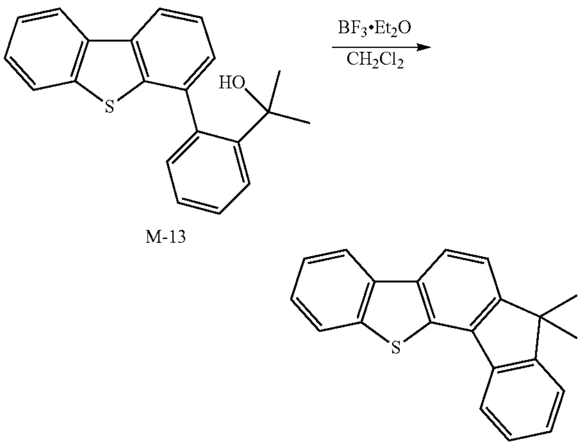

M-13

M-14

The intermediate M-13 was dissolved in 250 ml of dichloromethane. The solution was cooled down to 0° C. and agitated. Next, 12.6 g (47.1 mmol) of boronitrilefluoride and diethyl ether complex dissolved in 20 mL of dichloromethane were slowly added to the agitated solution. The mixture was agitated at room temperature for 5 hours. When the reaction was complete, the agitated mixture was extracted with ethyl acetate. The extracted solution was dried with magnesium sulfate, filtered, and then concentrated under a reduced pressure. The concentrated product was purified through silica gel column chromatography by using n-hexane, obtaining a desired compound, an intermediate M-14, as 10.5 g of a white solid of (yield: 74.3%).

LC-MS (theoretical value: 300.42 g/mol, measured value: M+1=300 g/mol)

Synthesis of Intermediate M-15

[Reaction Scheme 15]

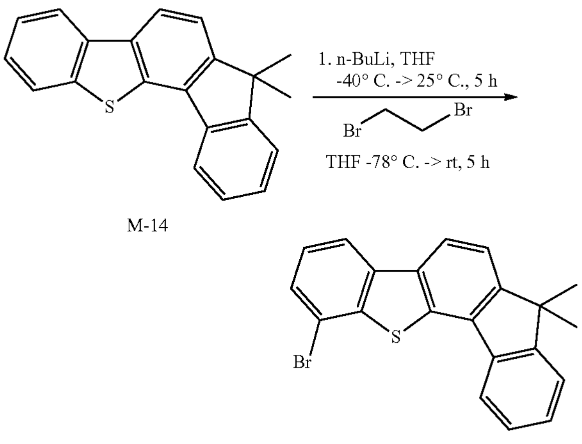

M-14

M-15

9.6 g (31.79 mmol) of the intermediate M-14 was put under a nitrogen atmosphere in a 2-necked round-bottomed flask heated and dried under vacuum, and 100 mL of anhydrous tetrahydrofuran was added thereto. The mixture was cooled down to −40° C. and agitated. Next, 20.7 mL of 1.6M n-butyllithium (in 63.6 mmol of hexane) was slowly added to the agitated mixture. The resulting mixture was agitated at room temperature under a nitrogen atmosphere for 5 hours. The resulting reactant was cooled down to −78° C., and 11.9 g (63.58 mmol) of 1,2-dibromoethane dissolved in 10 mL of anhydrous tetrahydrofuran was slowly added thereto. The mixture was agitated at room temperature for 5 hours. When the reaction was complete, the agitated product was concentrated under a reduced pressure to remove the solvent and then, extracted with distilled water and dichloromethane. The extracted solution was dried with magnesium sulfate, filtered, and then concentrated under a reduced pressure. The concentrated reactant was recrystallized with n-hexane, obtaining a desired compound, an intermediate M-15, as 9.5 g of a white solid (yield: 78.8%).

GC-MS (theoretical value: 379.31 g/mol, measured value: 380 g/mol)

Synthesis of Intermediate M-16

[Reaction Scheme 16]

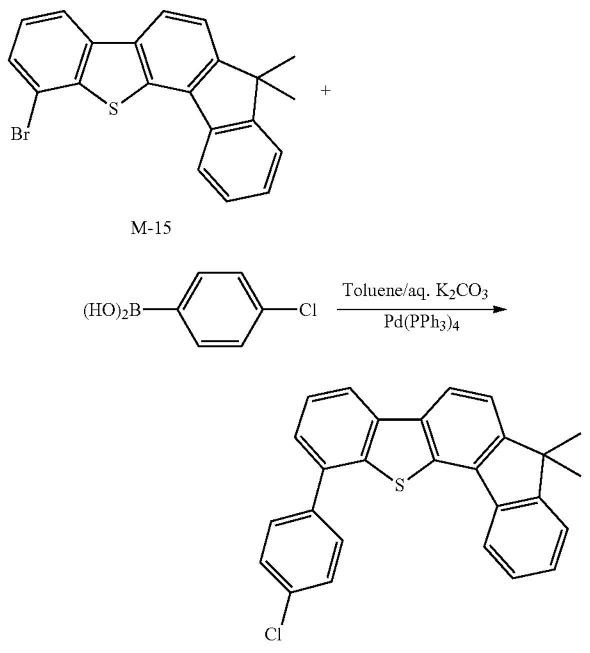

M-15

M-16

9.5 g (26.4 mmol) of the intermediate M-15, 4.3 g (27.7 mmol) of 4-chlorophenylboronic acid, and 1.5 g (1.3 mmol) of tetrakis(triphenylphosphine)palladium were put in a flask and dissolved in 150 ml of toluene under a nitrogen atmosphere, and 64.9 ml of an aqueous solution in which 19.4 g (130.9 mmol) of potassium carbonate was dissolved was added thereto. The mixture was refluxed and agitated for 12 hours. When the reaction was complete, the agitated product was extracted with ethyl acetate. The extracted solution was dried with magnesium sulfate and then concentrated under a reduced pressure. The concentrated product was purified through a silica gel column using n-hexane/dichloromethane in a volume ratio of 7:3, obtaining a desired compound, an intermediate M-16, as 5.3 g of a white solid (yield: 48.5%).

GC-MS (theoretical value: 394.89 g/mol, measured value: 395 g/mol)

Synthesis of Intermediate M-17

[Reaction Scheme 17]

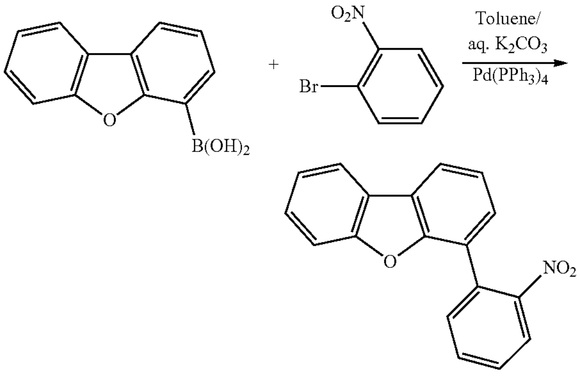

M-17

15.0 g (70.7 mmol) of dibenzofuran boronic acid, 19.38 g (77.83 mmol) of 1-bromo-2-nitro benzene, and 2.46 g (2.12 mmol) of tetrakis(triphenylphosphine)palladium were put in a 500 mL round-bottomed flask under a nitrogen atmosphere and dissolved in 200 mL of toluene, and 19.56 g (141 mmol) of potassium acetate and 70 mL of water were added thereto. The mixture was agitated at 90° C. for 24 hours. When the reaction was complete, the reactant was cooled down to room temperature and extracted with toluene and water. The extracted reactant was dried with anhydrous magnesium sulfate and filtered. Then, the solvent was removed from the reactant. The resulting product was purified through a silica gel column using methylene chloride/hexane mixed in a ratio of 1:1, obtaining an intermediate M-17 of 15 g (yield: 73.3%).

Synthesis of Intermediate M-18

[Reaction Scheme 18]

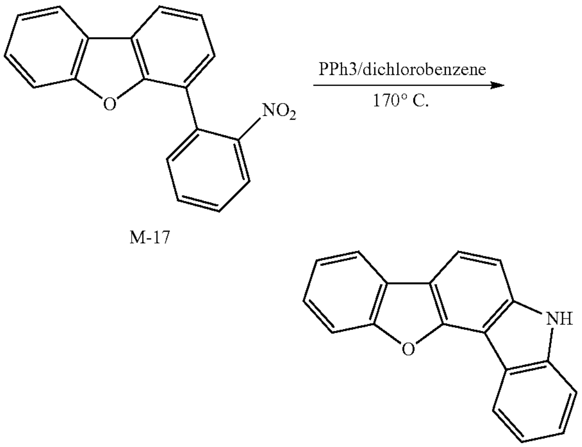

M-17

M-18

15.0 g (51.8 mmol) of the intermediate M-17 and 36 g (137.5 mmol) of triphenylphosphine were put in a 500 mL round-bottomed flask under a nitrogen atmosphere and dissolved in dichlorobenzene. The solution was agitated at 160° C. for 24 hours. When the reaction was complete, the reactant was cooled down to room temperature, and dichlorobenzene was removed therefrom under a reduced pressure. The resulting product was purified through a silica gel column using a solvent of methylene chloride/hexane mixed in a ratio of 1:1, obtaining an intermediate M-18 of 9.1 g (yield: 68.2%).

Synthesis of Intermediate M-19

[Reaction Scheme 19]

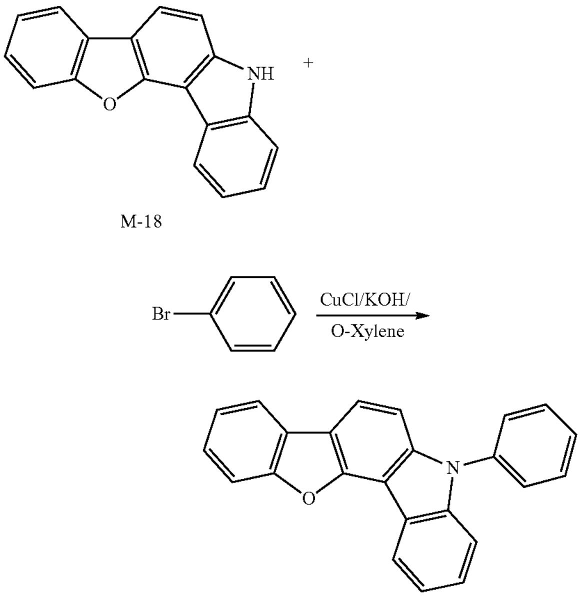

M-18

M-19

9 g (34.9 mmol) of the intermediate M-18, 10.9 g (69.9 mmol) of bromobenzene, 1.6 g (17.4 mmol) of copper chloride, 20 g (356.4 mmol) of potassium hydroxide were dissolved in 100 mL of xylene in a 250 mL round-bottomed flask under a nitrogen atmosphere. The solution was agitated at 150° C. for 48 hours and cooled down to room temperature, and xylene therein was removed under a reduced pressure. The remaining solid was dissolved in methylene chloride, washed several times with water and then treated with anhydrous magnesium sulfate to remove moisture and filtered. Then, the solvent was removed from the filtered solution. The resulting product was purified through a silica gel column using a solvent of hexane/methylene chloride mixed in a ratio of 1:2, obtaining 10 g of a desired compound M-19 (yield: 86%)

Synthesis of Intermediate M-20

[Reaction Scheme 20]

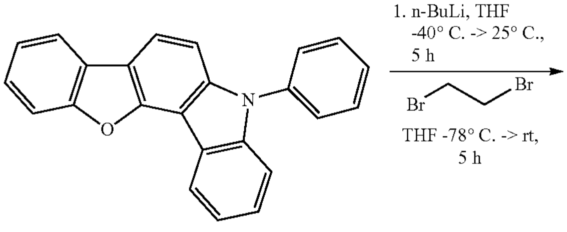

M-19

-continued

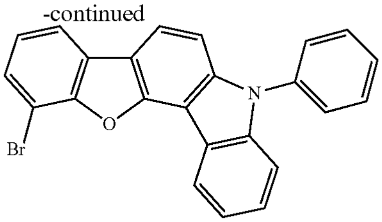

M-20

10.0 g (30.0 mmol) of the intermediate M-19 was put under a nitrogen atmosphere in a two-necked round-bottomed flask heated and dried under vacuum, and 100 mL of anhydrous tetrahydrofuran was added thereto. The mixture was cooled down to −40° C. and agitated. Then, 10.4 mL of 1.6M n-butyllithium (in 31.20 mmol of hexane) was slowly added to the agitated mixture. The resulting mixture was agitated at room temperature under a nitrogen atmosphere for 5 hours. The reactant solution was cooled down to −78° C., and 11.3 g (60.0 mmol) of 1,2-dibromoethane dissolved in 10 mL of anhydrous tetrahydrofuran was slowly added thereto. The mixture was agitated at room temperature for 5 hours. When the reaction was complete, the agitated reactant was concentrated under a reduced pressure concentrate to remove the solvent and then, extracted with distilled water and dichloromethane. The extracted solution was dried with magnesium sulfate, filtered, and then concentrated under a reduced pressure. The reactant was recrystallized with n-hexane, obtaining a desired compound, an intermediate M-20, as 9.7 g of a white solid (yield: 78.4%).

GC-MS (theoretical value: 412.28 g/mol, measured value: 412 g/mol)

Synthesis of Intermediate M-21

[Reaction Scheme 21]

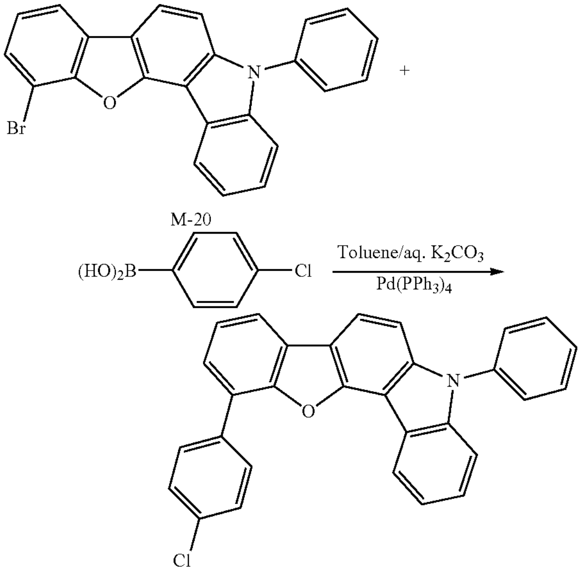

M-20

M-21

9.7 g (23.5 mmol) of the intermediate M-20, 3.9 g (24.7 mmol) of 4-chlorophenyl boronic acid, and 1.4 g (1.2 mmol) of tetrakis(triphenylphosphine)palladium were put in a flask and dissolved in 100 ml of toluene under a nitrogen atmosphere, and 58.8 ml of an aqueous solution in which 17.3 g (117.6 mmol) of potassium carbonate was dissolved was added thereto. The mixture was refluxed and agitated for 12 hours. When the reaction was complete, the agitated reactant was extracted with ethyl acetate. The extracted solution was dried with anhydrous magnesium sulfate, filtered, and then concentrated under a reduced pressure. The concentrated product was purified through silica gel column chromatography using n-hexane/methylene chloride mixed in a volume ratio of 7:3, obtaining a desired compound, an intermediate M-21, as 7.0 g of a white solid (yield: 67.0%).

GC-MS (theoretical value: 443.92 g/mol, measured value: 444 g/mol)

Synthesis of Intermediate M-22

[Reaction Scheme 22]

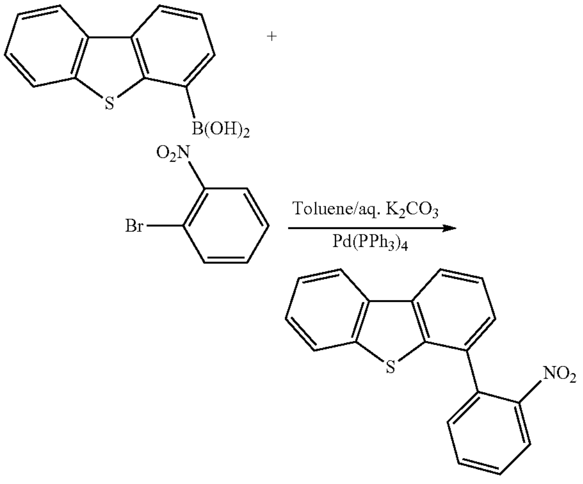

M-22

15.0 g (65.7 mmol) of dibenzofuran boronic acid, 18.0 g (72.3 mmol) of 1-bromo-2-nitro benzene, and 2.3 g (1.97 mmol) of tetrakis(triphenylphosphine)palladium were put in a 500 mL round-bottomed flask and dissolved in 200 mL of toluene under a nitrogen atmosphere, and 18.2 g (131.5 mmol) of potassium acetate and 70 mL of water were added thereto. The mixture was agitated at 90° C. for 24 hours. When the reaction was complete, the reactant was cooled down to room temperature and extracted with toluene and water, and then treated with anhydrous magnesium sulfate to remove moisture. The resulting product was filtered, and the solvent therein was removed. The resulting product was purified through a silica gel column using a mixed solvent of methylene chloride/hexane mixed in a ratio of 1:1, obtaining an intermediate M-22 of 14 g (yield: 69.7%).

Synthesis of Intermediate M-23

[Reaction Scheme 23]

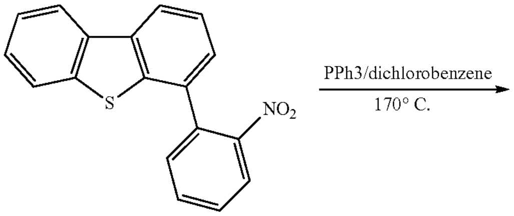

M-22

-continued

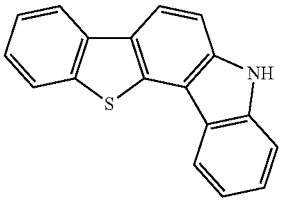

M-23

14.0 g (45.8 mmol) of the intermediate M-22 and 36 g (137.5 mmol) of triphenylphosphine were dissolved in dichlorobenzene in a 500 mL round-bottomed flask under a nitrogen atmosphere. The solution was agitated at 160° C. for 24 hours. When the reaction was complete, the reactant was cooled down to room temperature, and the dichlorobenzene therein was removed under a reduced pressure. The resulting reactant was purified through a silica gel column using methylene chloride/hexane mixed in a ratio of 1:1, obtaining an intermediate M-23 of 9.7 g (yield: 77.6%).

Synthesis of Intermediate M-24

[Reaction Scheme 24]

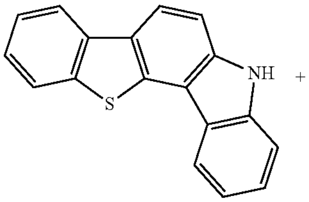

M-23

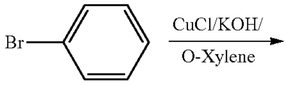

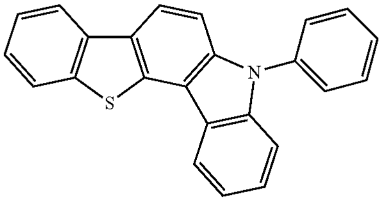

M-24

9.7 g (35.4 mmol) of the intermediate M-23, 11.1 g (70.9 mmol) of bromobenzene, 1.6 g (17.4 mmol) of copper chloride, and 20 g (356.4 mmol) of potassium hydroxide were dissolved in 100 mL of xylene in a 250 mL round-bottomed flask under a nitrogen atmosphere. The solution was agitated at 150° C. for 48 hours and cooled down to room temperature, and the xylene was removed under a reduced pressure. The remaining solid was dissolved in methylene chloride and several times washed with water and then, treated with anhydrous magnesium sulfate to remove moisture. Then, the reactant was filtered, and the solvent was removed therefrom. The resulting product was purified through a silica gel column using a solvent of hexane/methylene chloride mixed in a ratio of 1:2, obtaining a desired compound M-24 of 11 g (yield: 89%).

Synthesis of Intermediate M-25

[Reaction Scheme 25]

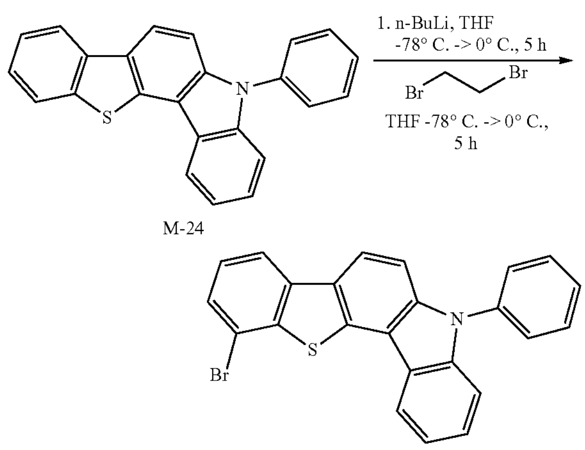

M-24

M-25

10.0 g (28.6 mmol) of the intermediate M-24 was put under a nitrogen atmosphere in a 2-necked round-bottomed flask heated and dried under vacuum, and 100 mL of anhydrous tetrahydrofuran was added thereto for dissolution. The solution was cooled down to −40° C. and agitated. Then, 9.92 mL of 1.6M n-butyllithium (in 29.76 mmol of hexane) was slowly added to the agitated solution. The mixture was agitated at room temperature under a nitrogen atmosphere for 5 hours. The agitated reactant was cooled down to −78° C., and 10.8 g (57.2 mmol) of 1,2-dibromoethane dissolved in 10 mL of anhydrous tetrahydrofuran was slowly added thereto. The mixture was agitated at room temperature for 5 hours. When the reaction was complete, the resulting product was concentrated under a reduced pressure to remove the solvent and extracted with distilled water and dichloromethane. The extracted solution was dried with magnesium sulfate, filtered, and then concentrated under a reduced pressure. The reactant was recrystallized with n-hexane, obtaining a desired compound, an intermediate M-25, as 9.8 g of a white solid (yield: 79.9%).

GC-MS (theoretical value: 428.34 g/mol, measured value: 428 g/mol)

Synthesis of Intermediate M-26

[Reaction Scheme 26]

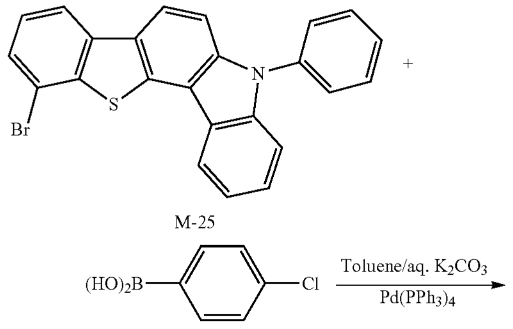

M-25

-continued

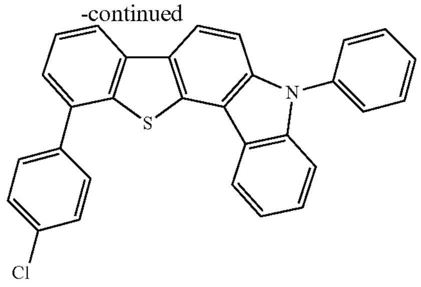

M-26

9.8 g (22.9 mmol) of the intermediate M-25, 3.8 g (24.0 mmol) of 4-chlorophenylboronic acid, and 1.3 g (1.1 mmol) of tetrakis(triphenylphosphine)palladium were put in a flask and dissolved in 100 ml of toluene under a nitrogen atmosphere, and 57.2 ml of an aqueous solution in which 16.8 g (114.4 mmol) of potassium carbonate was dissolved was added thereto. The mixture was refluxed and agitated for 12 hours. When the reaction was complete, the reactant was extracted with ethyl acetate. The extracted solution was dried with magnesium sulfate, filtered, and then concentrated under a reduced pressure. The resulting product was purified through silica gel column chromatography using n-hexane/dichloromethane mixed in a volume ratio 7:3, obtaining a desired compound, an intermediate M-26, as 6.0 g of a white solid (yield; 57.0%).

GC-MS (theoretical value: 459.99 g/mol, measured value: 460 g/mol)

Synthesis of Intermediate M-27

[Reaction Scheme 27]

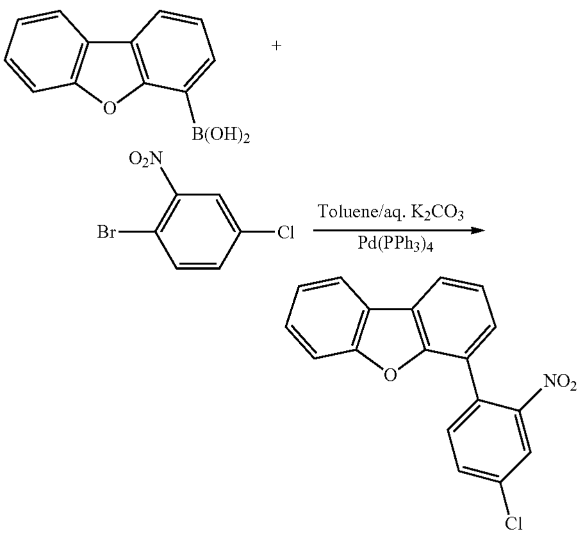

M-27

20.0 g (94.3 mmol) of dibenzofuran boronic acid, 24.5 g (103.7 mmol) of 2-bromo-5-chloronitrobenzene, and 3.28 g (2.83 mmol) of tetrakis(triphenylphosphine)palladium were put in a 1 L round-bottomed flask and dissolved in toluene of 300 mL under a nitrogen atmosphere, and 26 g (188.6 mmol) of potassium acetate and 100 mL of water were added thereto. The mixture was agitated at 90° C. for 24 hours. When the reaction was complete, the reactant was cooled down to room temperature and extracted with toluene and water. The extracted reactant was treated with anhydrous magnesium sulfate to remove moisture and treated, and the solvent was removed. Then, the resulting product was purified through a silica gel column using methylene chloride/hexane mixed in a ratio of 1:1, obtaining an intermediate M-27 of 20 g (yield: 65.49%).

Synthesis of Intermediate M-28

[Reaction Scheme 28]

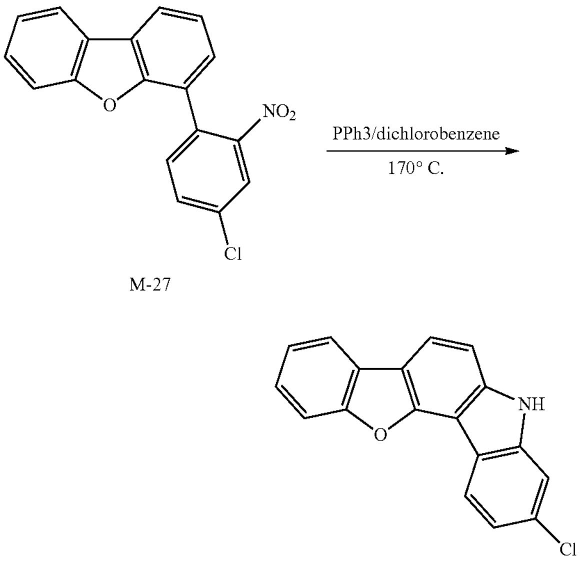

M-27

M-28

20.0 g (61.7 mmol) of the intermediate M-27 and 48.6 g (185.3 mmol) of triphenylphosphine were dissolved in 500 mL of dichlorobenzene in a round-bottomed flask under a nitrogen atmosphere. The solution was agitated at 160° C. for 24 hours. When the reaction was complete, the reactant was cooled down to room temperature, and the dichlorobenzene was removed under a reduced pressure. The resulting product was purified through a silica gel column using methylene chloride/hexane mixed in a ratio of 1:1, obtaining an intermediate M-28 of 14.5 g (yield: 81%).

Synthesis of Intermediate M-29

[Reaction Scheme 29]

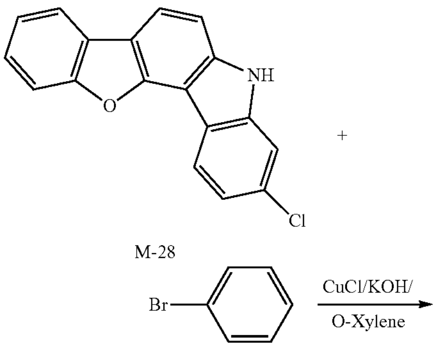

M-28

-continued

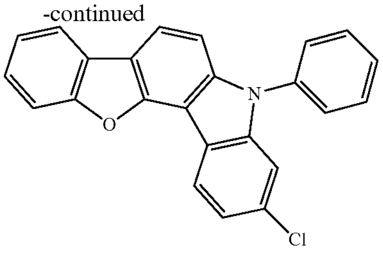

M-29

14 g (47.9 mmol) of the intermediate M-28, 15 g (95.9 mmol) of bromobenzene, 3.2 g (34.8 mmol) of copper chloride, and 30 g (535.7 mmol) of potassium hydroxide were dissolved in 200 mL xylene in a 250 mL round-bottomed flask under a nitrogen atmosphere. The solution was agitated at 150° C. for 48 hours and cooled down to a room temperature, and the xylene was removed under a reduced pressure. The remaining solid was dissolved in methylene chloride, washed several times with water, and treated with anhydrous magnesium sulfate to remove moisture, and then, the solvent was removed. The resulting product was purified through a silica gel column using hexane/methylene chloride mixed in a ratio of 1:2, obtaining a desired compound M-29 of 14 g (yield: 79.5%).

Synthesis of Intermediate M-30

[Reaction Scheme 30]

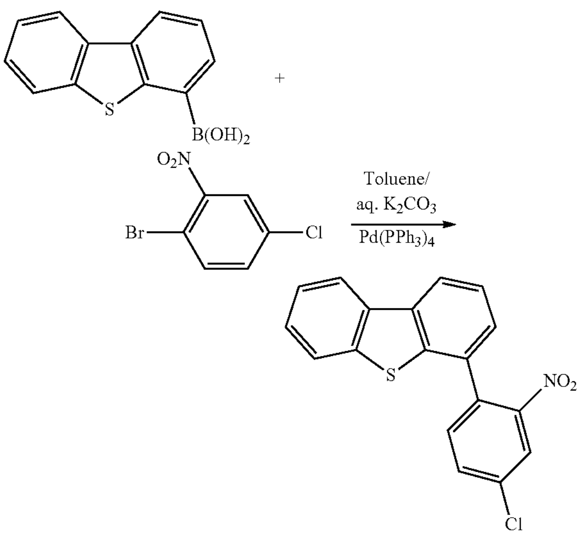

M-30

20.0 g (87.6 mmol) of dibenzothiophene boronic acid, 22.8 g (96.4 mmol) of 2-bromo-5-chloronitrobenzene, and 3 g (2.63 mmol) of tetrakis(triphenylphosphine)palladium was dissolved in 300 mL of toluene in a 1 L round-bottomed flask under a nitrogen atmosphere, and 24.2 g (175.3 mmol) of potassium acetate and 100 mL of water were added thereto. The mixture was agitated at 90° C. for 24 hours. When the reaction was complete, the reactant was cooled down to room temperature, extracted with toluene and water, treated with anhydrous magnesium sulfate to remove moisture, and filtered, and then the solvent was removed therefrom. The resulting product was purified through a silica gel column using methylene chloride/hexane mixed in a ratio of 1:1, obtaining an intermediate M-27 of 23 g (yield: 77.2%).

Synthesis of Intermediate M-31

[Reaction Scheme 31]

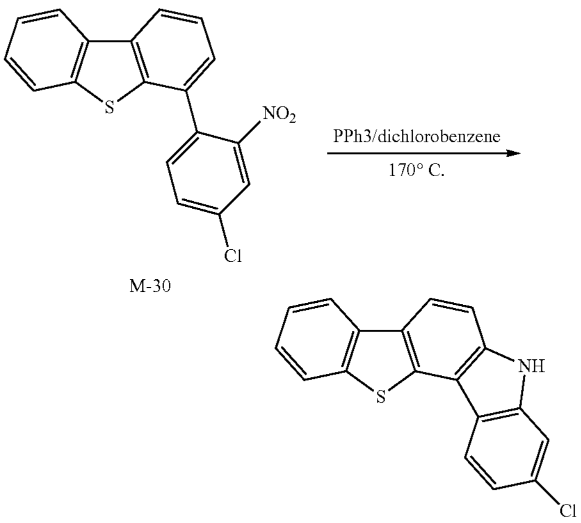

M-30

M-31

20.0 g (58.8 mmol) of the intermediate M-30 and 48.6 g (185.3 mmol) of triphenylphosphine were dissolved in dichlorobenzene in a 500 mL round-bottomed flask under a nitrogen atmosphere. The solution was agitated at 160° C. for 24 hours. When the reaction was complete, the reactant was cooled down to room temperature, and the dichlorobenzene was removed under a reduced pressure. The resulting reactant was purified through a silica gel column using methylene chloride/hexane mixed in ratio of 1:1, obtaining an intermediate M-31 of 14 g (yield: 77.3%).

Synthesis of Intermediate M-32

[Reaction Scheme 32]

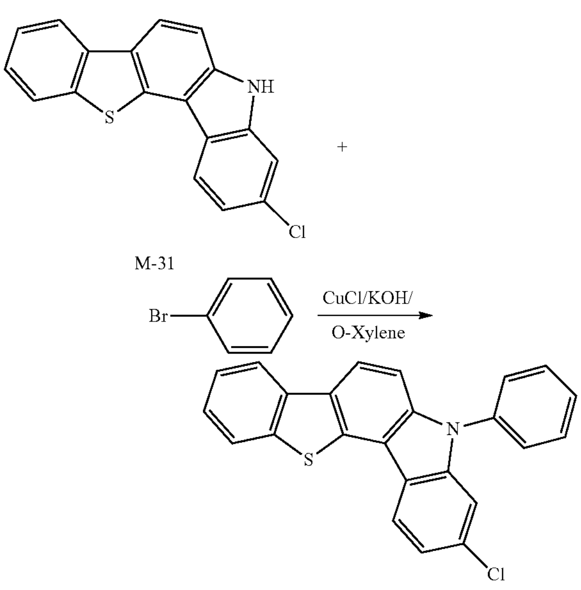

M-31

M-32

14 g (45.4 mmol) of the M-31, 14.2 g (90.9 mmol) of bromobenzene, 3.2 g (34.8 mmol) of copper chloride, and 30 g (535.7 mmol) of potassium hydroxide were dissolved in 200 mL of xylene in a 250 mL round-bottomed flask under a nitrogen atmosphere. The solution was agitated at 150° C. for 48 hours and cooled down to room temperature, and the xylene was removed under a reduced pressure. The remaining solid was dissolved in methylene chloride, washed several times with water, treated with anhydrous magnesium sulfate to remove moisture, filtered, and then the solvent was removed. The resulting product was purified through a silica gel column using hexane/methylene chloride mixed in a ratio of 1:2, obtaining a compound M-32 of 13 g (74.6%).

Synthesis of Intermediate M-33

[Reaction Scheme 33]

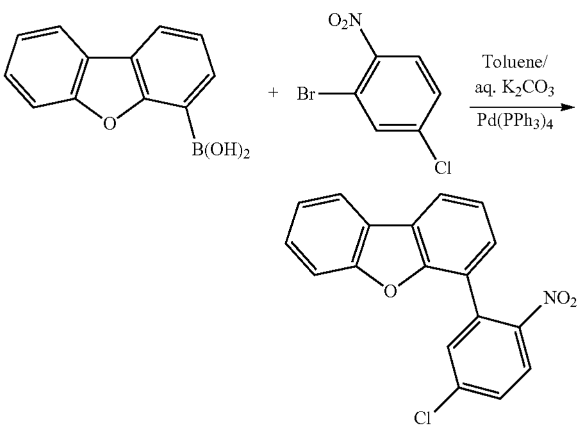

M-33

20.0 g (94.3 mmol) of dibenzofuran boronic acid, 24.5 g (103.7 mmol) 2-bromo-5-chloronitrobenzene, and 3.28 g (2.83 mmol) of tetrakis(triphenylphosphine)palladium were dissolved in 300 mL of toluene in a 1 L round-bottomed flask under a nitrogen atmosphere, and 26 g (188.6 mmol) of potassium acetate and 100 mL of water were added thereto. The mixture was agitated at 90° C. for 24 hours. When the reaction was complete, the reactant was cooled down to room temperature, extracted with toluene and water, and treated with anhydrous magnesium sulfate to remove moisture, filtered, and then the solvent was removed therefrom. The resulting reactant was purified through a silica gel column using methylene chloride/hexane mixed in a ratio of 1:1, obtaining an intermediate M-33 of 21 g (yield: 68.7%).

Synthesis of Intermediate M-34

[Reaction Scheme 34]

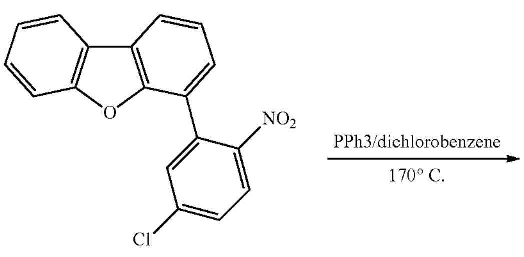

M-33

-continued

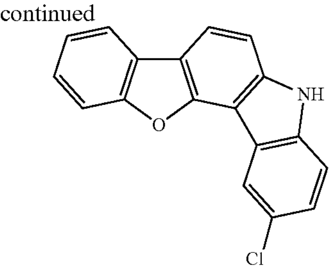

M-34

20.0 g (61.7 mmol) of the intermediate M-33 and 48.6 g (185.3 mmol) of triphenylphosphine were dissolved in dichlorobenzene in a 500 mL round-bottomed flask under a nitrogen atmosphere and then, agitated at 160° C. for 24 hours. When the reaction was complete, the reactant was cooled down to room temperature, and the dichlorobenzene was removed under a reduced pressure. The resulting reactant was purified through a silica gel column using methylene chloride/hexane mixed in a ratio of 1:1, obtaining an intermediate M-34 of 14 g (yield: 77.7%).

Synthesis of Intermediate M-35

[Reaction Scheme 35]

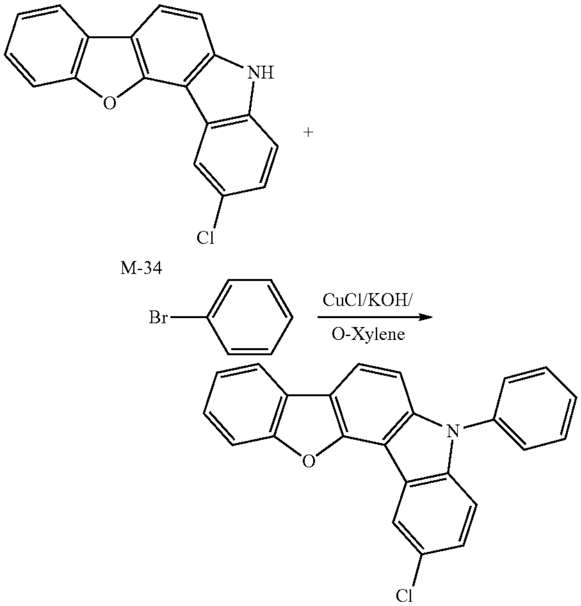

M-34

M-35

14 g (47.9 mmol) of M-34, 15 g (95.9 mmol) of bromobenzene, 3.2 g (34.8 mmol) of copper chloride, and 30 g (535.7 mmol) of potassium hydroxide were dissolved in 200 mL of xylene in a 250 mL round-bottomed flask under a nitrogen atmosphere. The solution was agitated at 150° C. for 48 hours and cooled down to room temperature, and xylene was removed under a reduced pressure. The remaining solid was dissolved in methylene chloride, washed several times with water, treated with anhydrous magnesium sulfate to moisture, filtered, and the solvent was removed therefrom. The resulting product was purified through a silica gel column using hexane/methylene chloride mixed in a ratio of 1:2, obtaining a desired compound M-5 of 14.5 g (yield: 82.3%).

Synthesis of Intermediate M-36

[Reaction Scheme 36]

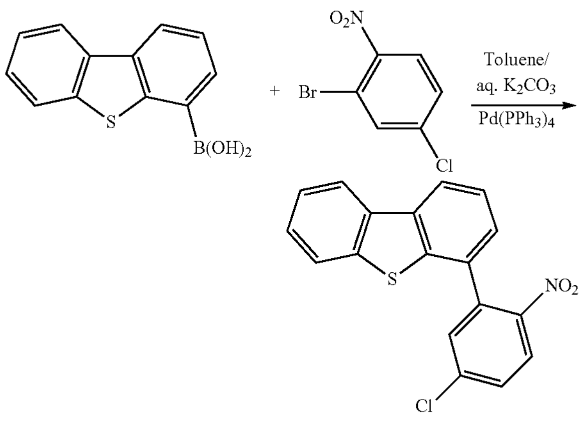

M-36

20.0 g (87.6 mmol) of dibenzothiophene boronic acid, 22.8 g (96.4 mmol) of 2-bromo-5-chloronitrobenzene, and 3 g (2.63 mmol) of tetrakis(triphenylphosphine)palladium were dissolved in 300 mL of toluene in a 1 L round-bottomed flask under a nitrogen atmosphere, and 24.2 g (175.3 mmol) of potassium acetate and 100 mL of water were added thereto. The mixture was agitated at 90° C. for 24 hours. When the reaction was complete, the reactant was cooled down to room temperature, extracted with toluene and water, and treated with anhydrous magnesium sulfate to remove moisture, and the solvent was removed therefrom. Then, the reactant was purified through a silica gel column using methylene chloride/hexane mixed in a ratio of 1:1, obtaining an intermediate M-36 of 22 g (yield: 73.8%).

Synthesis of Intermediate M-37

[Reaction Scheme 37]

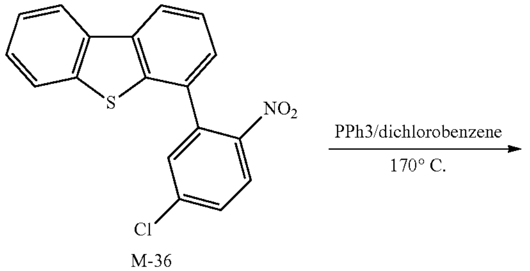

M-36

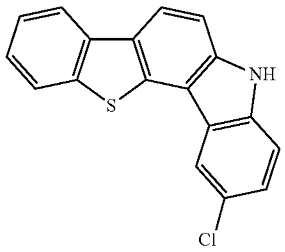

M-37

20.0 g (58.8 mmol) of the intermediate M-36 and 48.6 g (185.3 mmol)triphenylphosphine were dissolved in dichlorobenzene in a 500 mL round-bottomed flask under a nitrogen atmosphere and agitated at 160° C. for 24 hours. When the reaction was complete, the reactant was cooled down to room temperature, and the dichlorobenzene was removed under a reduced pressure. The resulting reactant was purified through a silica gel column using methylene chloride/hexane mixed in a ratio of 1:1, obtaining an intermediate M-37 of 14.5 g (yield: 80.5%).

Synthesis of Intermediate M-38

[Reaction Scheme 38]

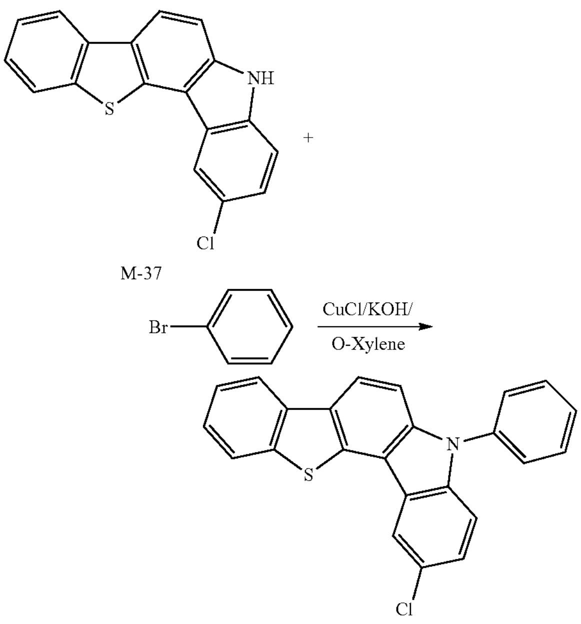

M-37

M-38

14 g (45.4 mmol) of M-37, 14.2 g (90.9 mmol) of bromobenzene, 3.2 g (34.8 mmol) of copper chloride, and 30 g (535.7 mmol) of potassium hydroxide were dissolved in 200 mL of xylene in a 250 mL round-bottomed flask under a nitrogen atmosphere. The solution was agitated at 150° C. for 48 hours and cooled down to room temperature, and the xylene was removed under a reduced pressure. The remaining solid was dissolved in methylene chloride, washed several times with water, treated with anhydrous magnesium sulfate to remove moisture, and the solvent was removed. Then, the reactant was purified through a silica gel column using hexane/methylene chloride mixed in a ratio of 1:2, obtaining a compound M-38 of 13.5 g (yield: 77.5%).

Synthesis of intermediate M-39

[Reaction Scheme 39]

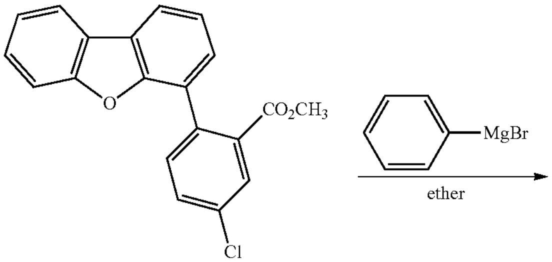

M-1

-continued

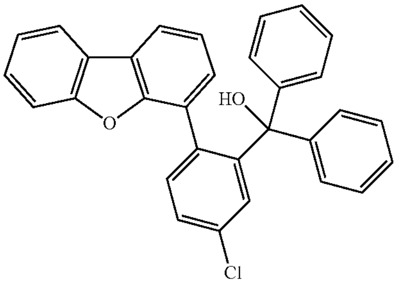

M-39

A compound M-39 was synthesized according to the same method as the method of preparing the intermediate M-2 except for using phenylmagnesium bromide instead of methylmagnesium bromide.

Synthesis of Intermediate M-40

[Reaction Scheme 40]

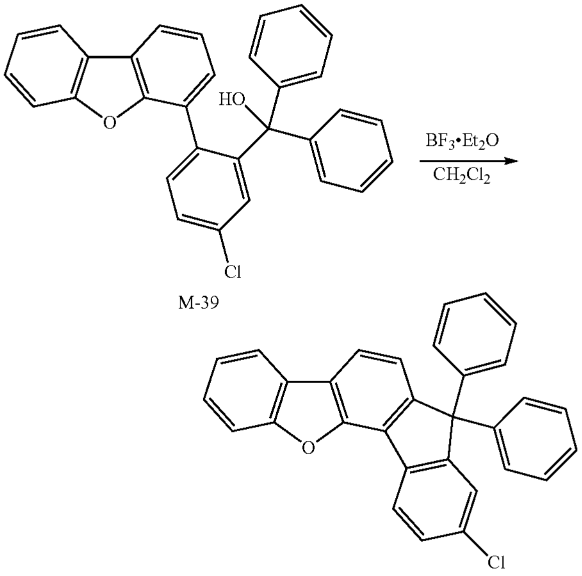

M-39

M-40

20 g of a compound M-40 (yield: 82%) was synthesized according to the same method as the method of preparing the intermediate M-3, except for using the intermediate M-39.

Synthesis of Intermediate M-41

[Reaction Scheme 41]

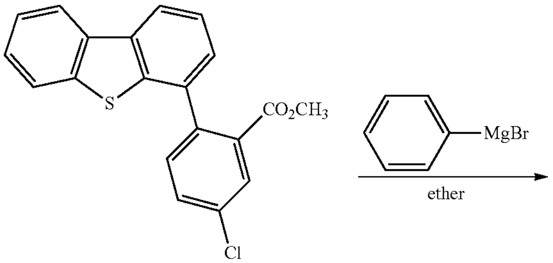

M-4

-continued

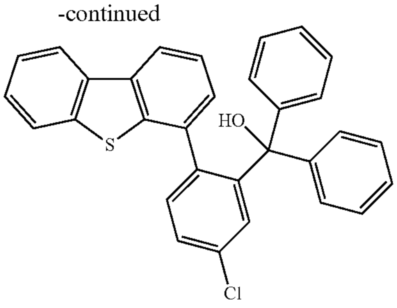

M-41

A compound M-41 was synthesized according to the same method as the method of preparing the intermediate M-5 except for using phenylmagnesiumbromide instead of methylmagnesium bromide.

Synthesis of Intermediate M-42

[Reaction Scheme 42]

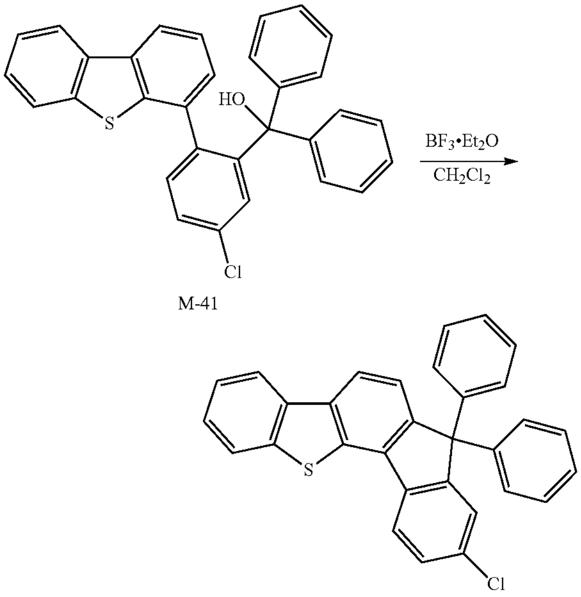

M-41

M-42

22 g of a compound M-42 (yield: 81%) was synthesized according to the same method as the method of preparing the intermediate M-6, except for using the intermediate M-41.

Example 1

Preparation of Compound C-1

[Reaction Scheme 43]

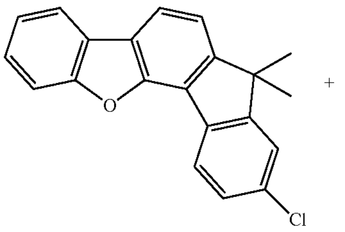

M-3

-continued

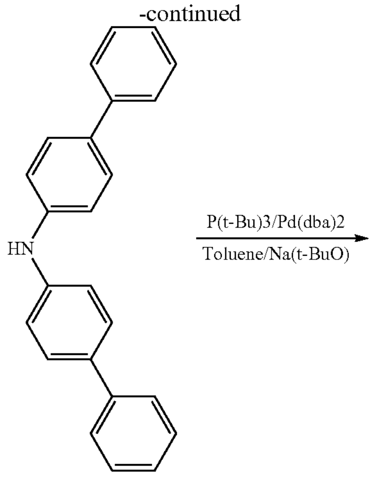

A

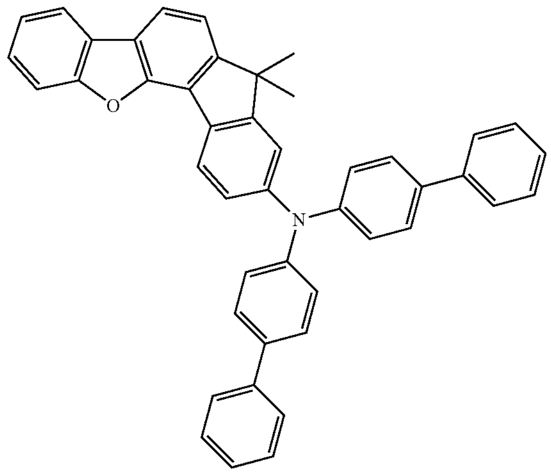

5.0 g (15.68 mmol) of the intermediate M-3, 5.04 g (15.68 mmol) of the intermediate A, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-1 as 7.8 g of a white solid (yield 82.3%).

Calculated value: C, 89.52; H, 5.51; N, 2.32; O, 2.65

Analyzed value: C, 89.51; H, 5.52; N, 2.32; O, 2.65

Example 2

Preparation of Compound C-31

[Reaction Scheme 44]

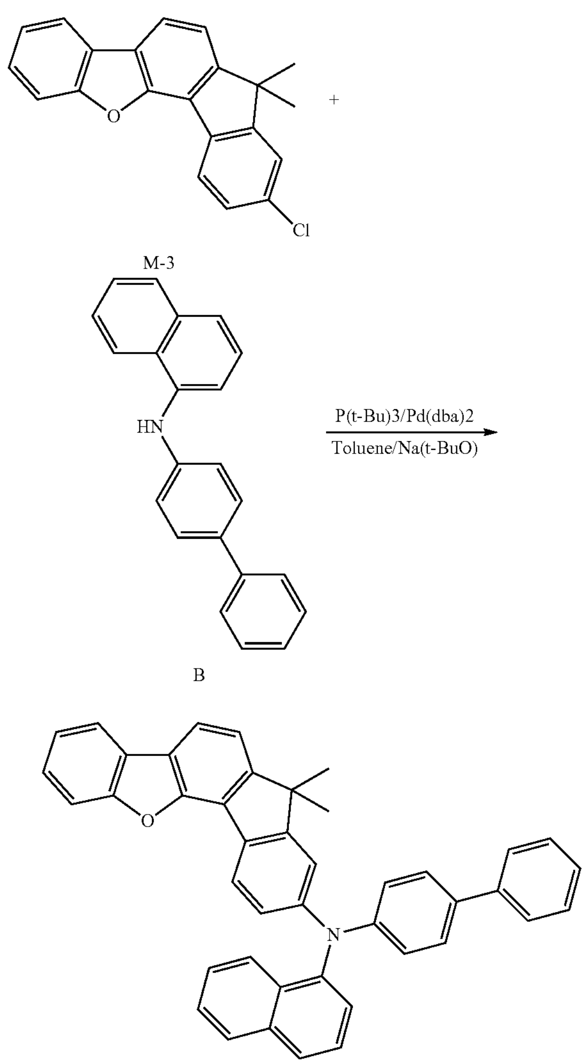

5.0 g (15.68 mmol) of the intermediate M-3, 4.63 g (15.68 mmol) of the intermediate B, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-31 as 7.3 g of a white solid (yield: 80.5%).

Calculated value: C, 89.40; H, 5.41; N, 2.42; O, 2.77

Analyzed value: C, 89.42; H, 5.39; N, 2.42; O, 2.77

Example 3

Preparation of Compound C-32

[Reaction Scheme 45]

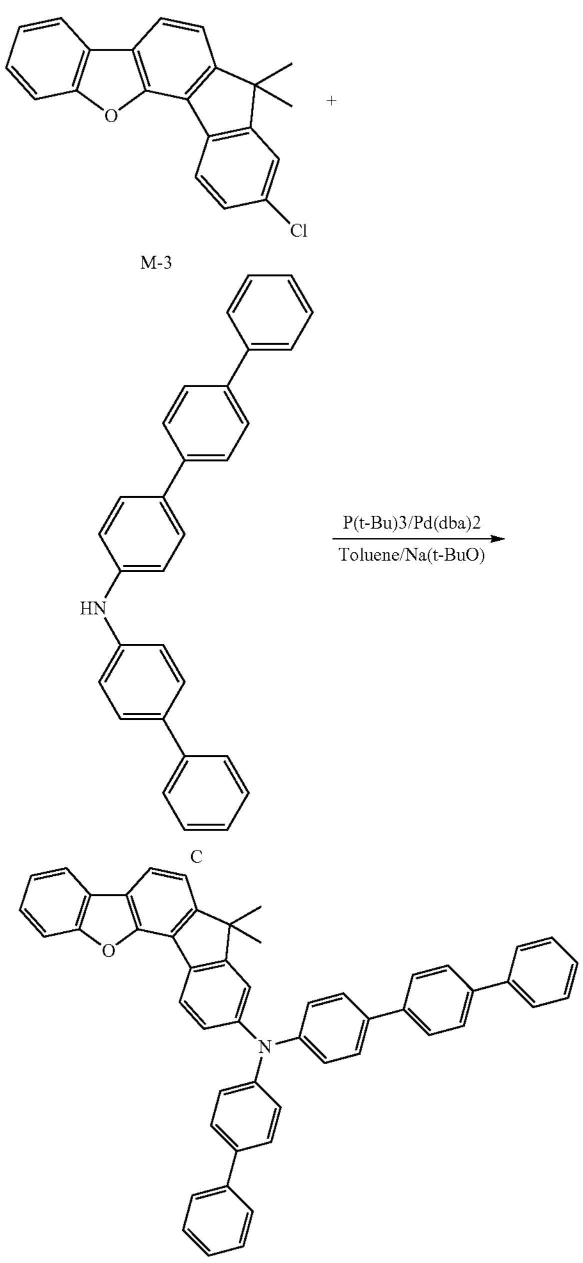

5.0 g (15.68 mmol) of the intermediate M-3, 6.23 g (15.68 mmol) of the intermediate C, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/ dichloromethane mixed in a volume ratio of 2:1, obtaining a desired compound C-32 as 9.2 g of a white solid (yield: 86.2%).

Calculated value: C, 90.10; H, 5.49; N, 2.06; O, 2.35

Analyzed value: C, 90.12; H, 5.47; N, 2.06; O, 2.35

Example 4

Preparation of Compound C-5

[Reaction Scheme 46]

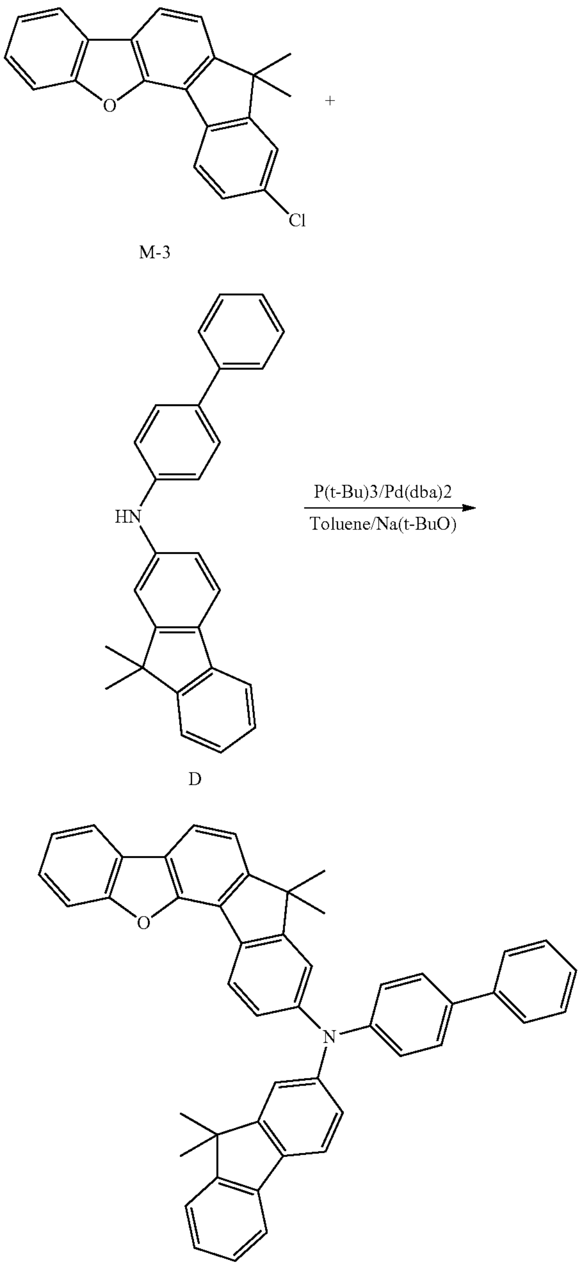

M-3

D 5.0 g (15.68 mmol) of the intermediate M-3, 5.67 g (15.68 mmol) of the intermediate D, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under reduced pressure. The resulting product was purified through silica gel column chromatography using n-hexane/dichloromethane mixed in a volume ratio of 2:1, obtaining a desired compound C-5 as 8.6 g of a white solid (yield 85.1%).

Calculated value: C, 89.55; H, 5.79; N, 2.18; O, 2.49

Analyzed value: C, 89.56; H, 5.78; N, 2.18; O, 2.49

Example 5

Preparation of Compound C-19

[Reaction Scheme 47]

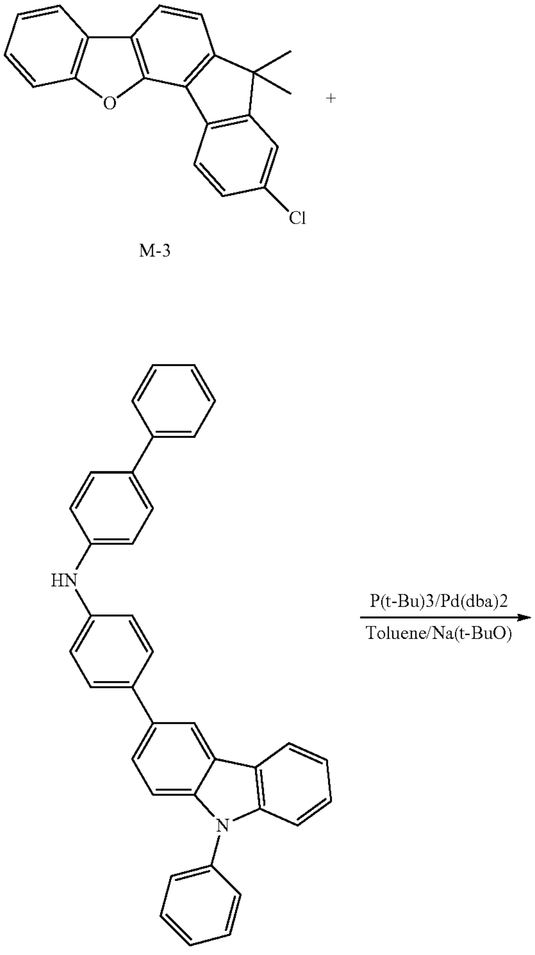

M-3

E

-continued

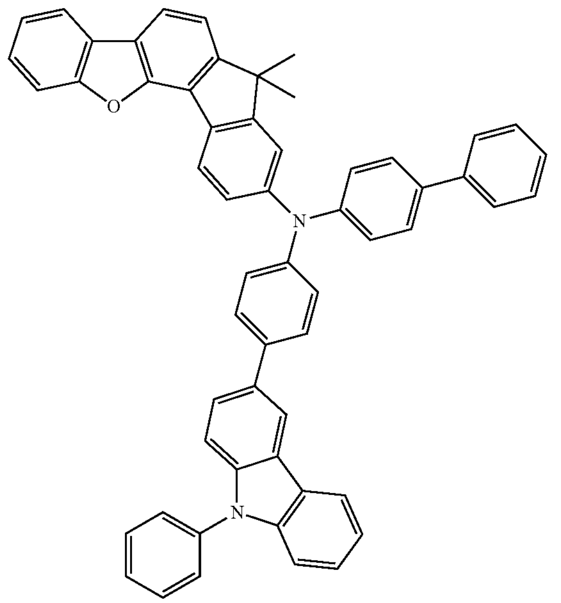

5.0 g (15.68 mmol) of the intermediate M-3, 7.63 g (15.68 mmol) of the intermediate E, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ were added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-19 as 10.5 g of a white solid (yield: 87%).

Calculated value: C, 89.03; H, 5.24; N, 3.64; O, 2.08

Analyzed value: C, 89.01; H, 5.26; N, 3.64; O, 2.08

Example 6

Preparation of Compound C-25

[Reaction Scheme 48]

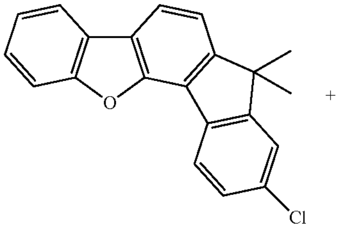

M-3

-continued

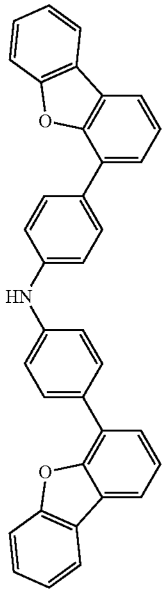

F

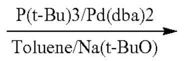

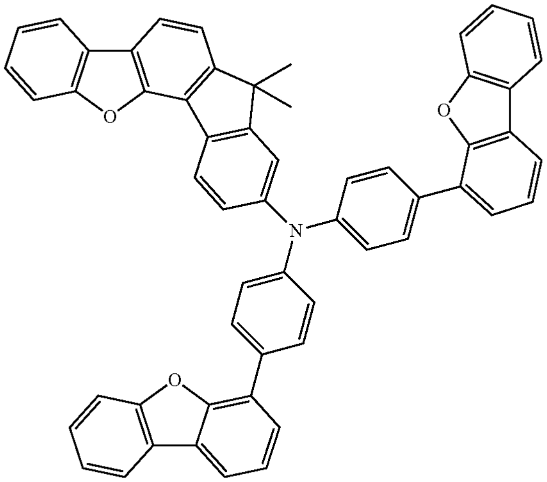

5.0 g (15.68 mmol) of the intermediate M-3, 7.87 g (15.68 mmol) of the intermediate F, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through a silica gel column chromatography using n-hexane/dichloromethane mixed in a volume ratio of 2:1, obtaining a desired compound C-25 as 10.7 g of a white solid (yield: 87%).

Calculated value: C, 87.33; H, 4.76; N, 1.79; O, 6.12

Analyzed value: C, 87.31; H, 4.78; N, 1.79; O, 6.12

Example 7

Preparation of Compound C-27

[Reaction Scheme 49]

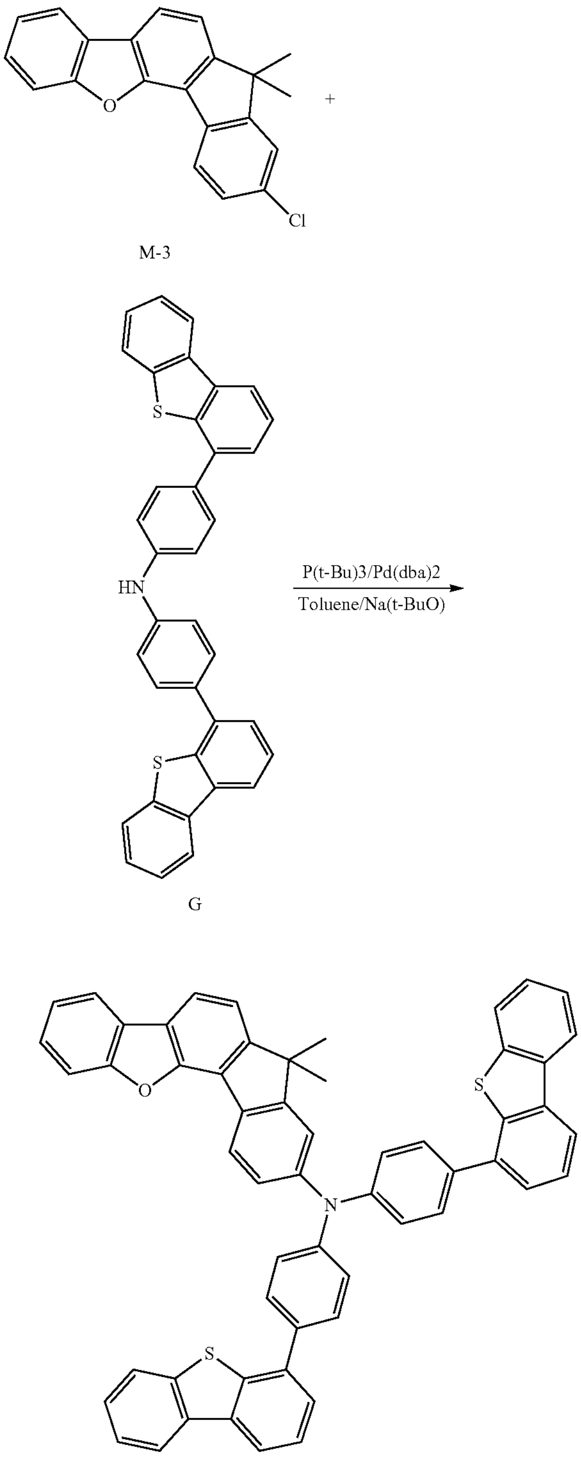

5.0 g (15.68 mmol) of the intermediate M-3, 8.37 g (15.68 mmol) of the intermediate G, 4.52 g (47.95 mmol) of sodium t-butoxide, and 0.1 g (0.47 mmol) of tri tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-27 as 10.4 g of a white solid (yield: 81.2%).

Calculated value: C, 83.89; H, 4.57; N, 1.72; O, 1.96; S, 7.86

Analyzed value: C, 83.86; H, 4.59; N, 1.72; O, 1.96; S, 7.86

Example 8

Preparation of Compound C-29

[Reaction Scheme 50]

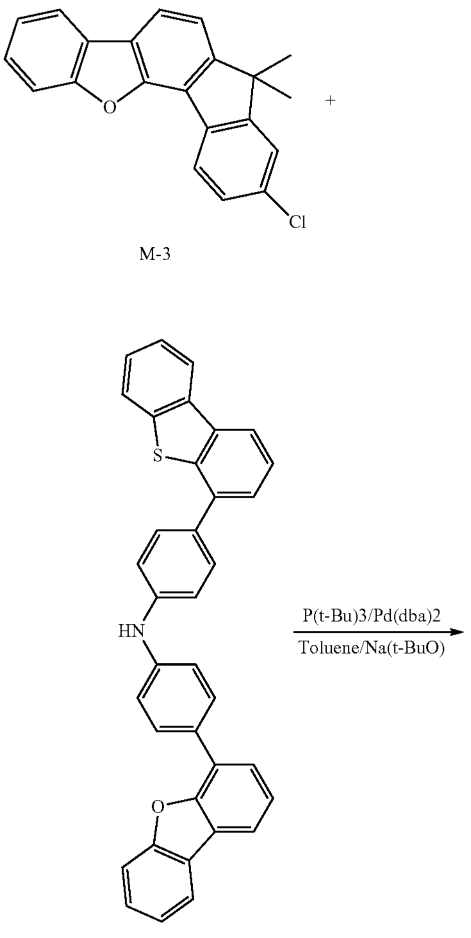

-continued

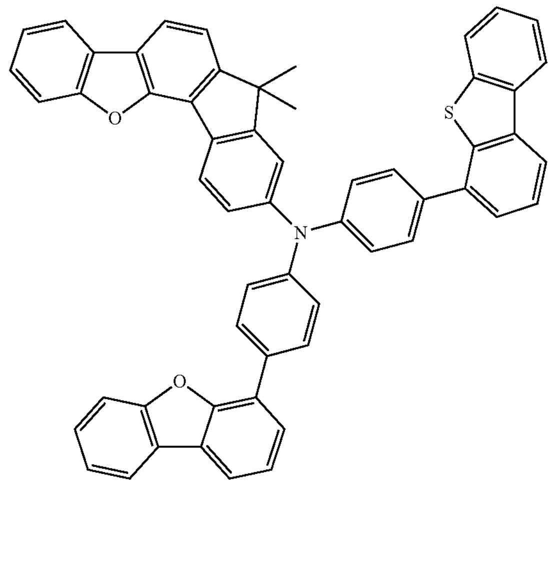

5.0 g (15.68 mmol) of the intermediate M-3, 8.12 g (15.68 mmol) of the intermediate H, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-29 as 10.8 g of a white solid (yield: 86%).

Calculated value: C, 85.58; H, 4.66; N, 1.75; O, 4.00; S, 4.01

Analyzed value: C, 85.59; H, 4.67; N, 1.75; O, 4.00; S, 4.01

Example 9

Preparation of Compound C-33

[Reaction Scheme 51]

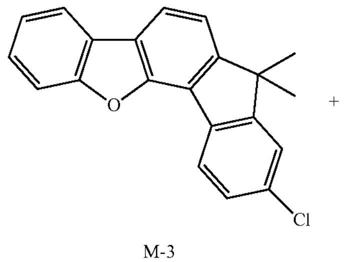

M-3

-continued

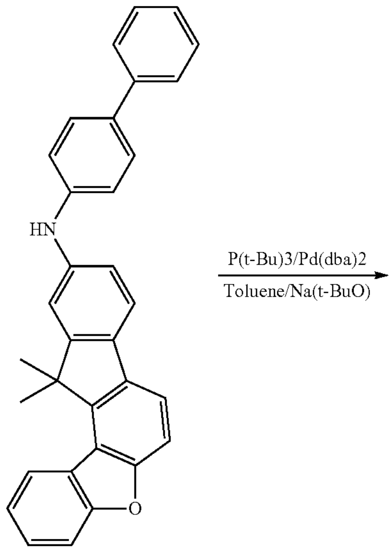

I

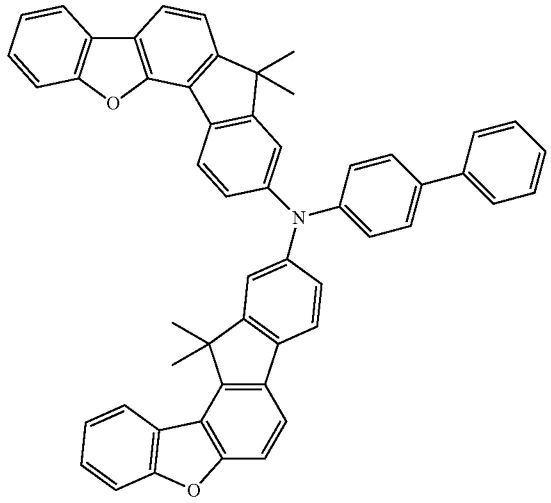

5.0 g (15.68 mmol) of the intermediate M-3, 7.08 g (15.68 mmol) of the intermediate I, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-33 as 9.4 g of a white solid (yield: 81.6%).

Calculated value: C, 88.37; H, 5.36; N, 1.91; O, 4.36

Analyzed value: C, 88.35; H, 5.38; N, 1.91; O, 4.36

Example 10

Preparation of Compound C-34

[Reaction Scheme 52]

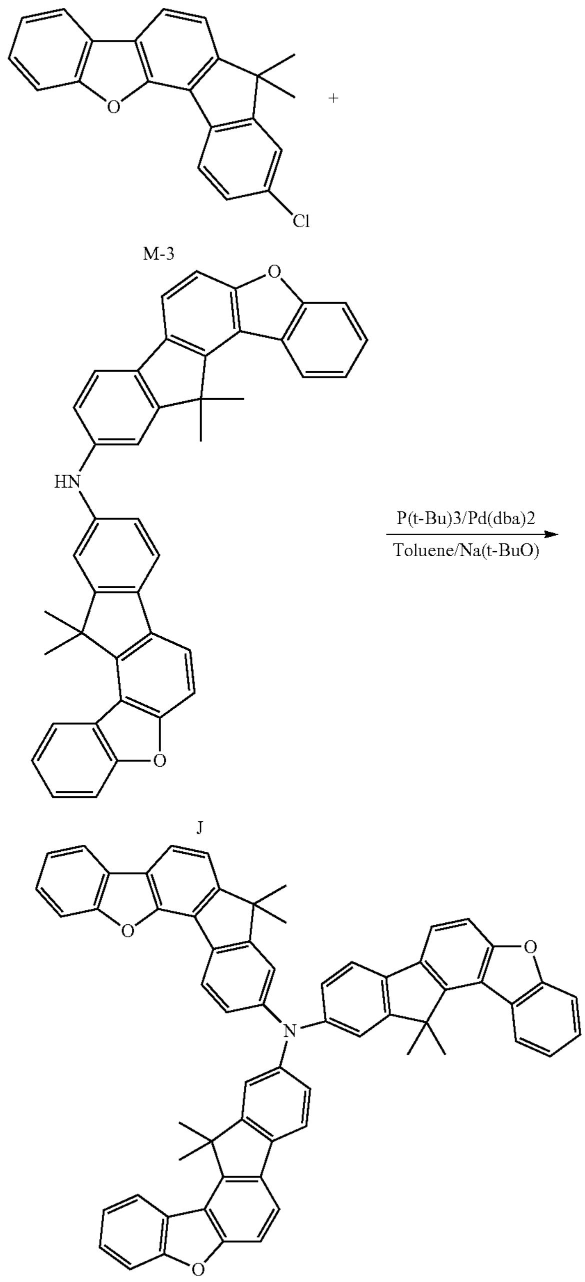

M-3

J 5.0 g (15.68 mmol) of the intermediate M-3, 9.12 g (15.68 mmol) of the intermediate J, 4.52 g (47.95 mmol) of sodium t-butoxide, and 0.1 g (0.47 mmol) of tris(tert-butyl)phosphine were dissolved in 200 ml of toluene, and 0.27 g (0.47 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-34 as 10.4 g of a white solid (yield: 76.7%).

Calculated value: C, 87.57; H, 5.25; N, 1.62; O, 5.56

Analyzed value: C, 87.59; H, 5.23; N, 1.62; O, 5.56

Example 11

Preparation of Compound C-2

[Reaction Scheme 53]

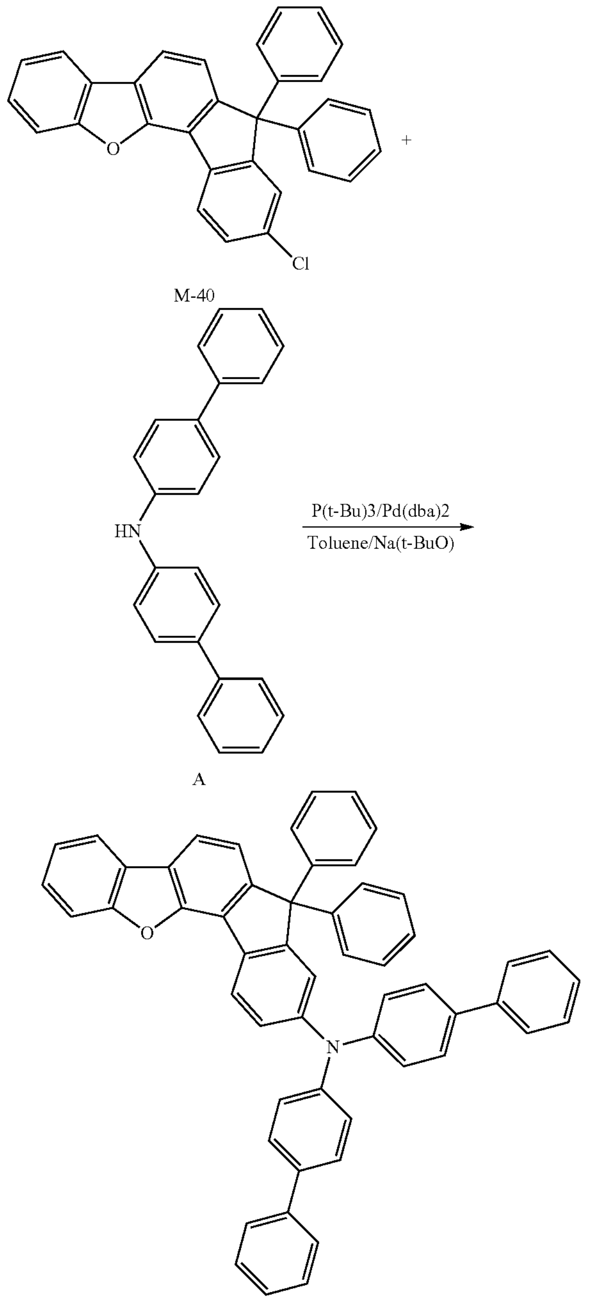

M-40

A 5.0 g (11.29 mmol) of the intermediate M-40, 3.63 g (11.29 mmol) of the intermediate A, 3.25 g (33.87 mmol) of sodium t-butoxide, and 0.07 g (0.34 mmol) of tris(tert-butyl)phosphine were dissolved in 200 ml of toluene, and 0.19 g (0.34 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-2 as 7.3 g of a white solid (yield: 88.8%).

Calculated value: C, 90.75; H, 5.12; N, 1.92; O, 2.20

Analyzed value: C, 90.73; H, 5.14; N, 1.92; O, 2.20

Example 12

Preparation of Compound C-35

[Reaction Scheme 54]

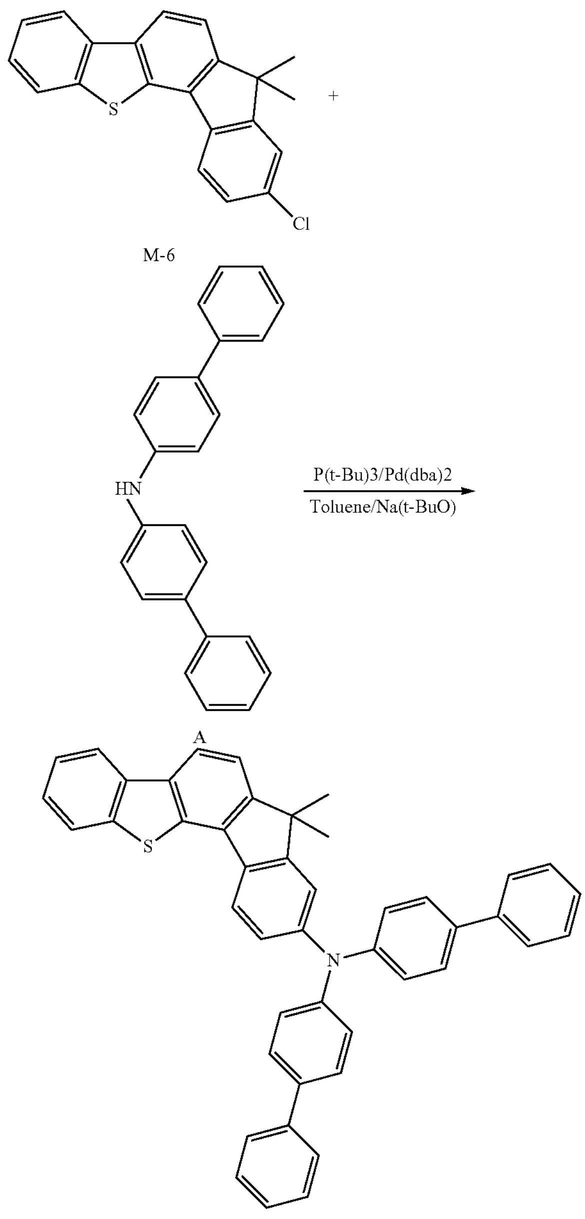

5.0 g (14.93 mmol) of the intermediate M-6, 4.8 g (14.93 mmol) of the intermediate A, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-35 as 7.5 g of a white solid (yield: 81%).

Calculated value: C, 87.20; H, 5.37; N, 2.26; S, 5.17

Analyzed value: C, 87.22; H, 5.35; N, 2.26; S, 5.17

Example 13

Preparation of Compound C-36

[Reaction Scheme 55]

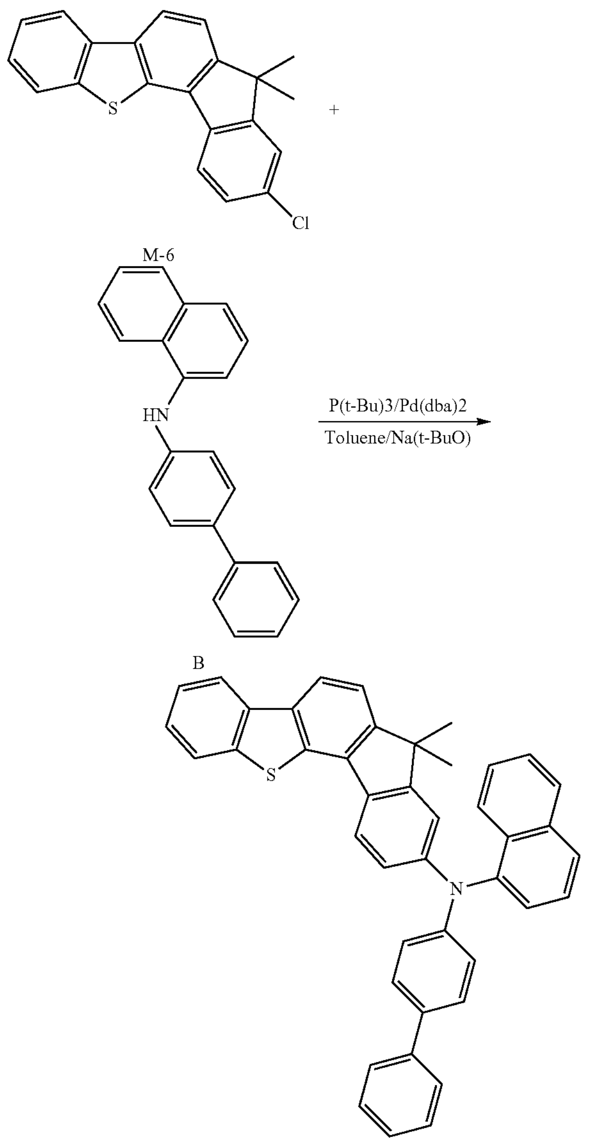

5.0 g (14.93 mmol) of the intermediate M-6, 4.41 g (14.93 mmol) of the intermediate B, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-36, as 7.6 g of a white solid (yield: 85.7%).

Calculated value: C, 86.98; H, 5.26; N, 2.36; S, 5.40

Analyzed value: C, 86.99; H, 5.25; N, 2.36; S, 5.40

Example 14

Preparation of Compound C-37

[Reaction Scheme 56]

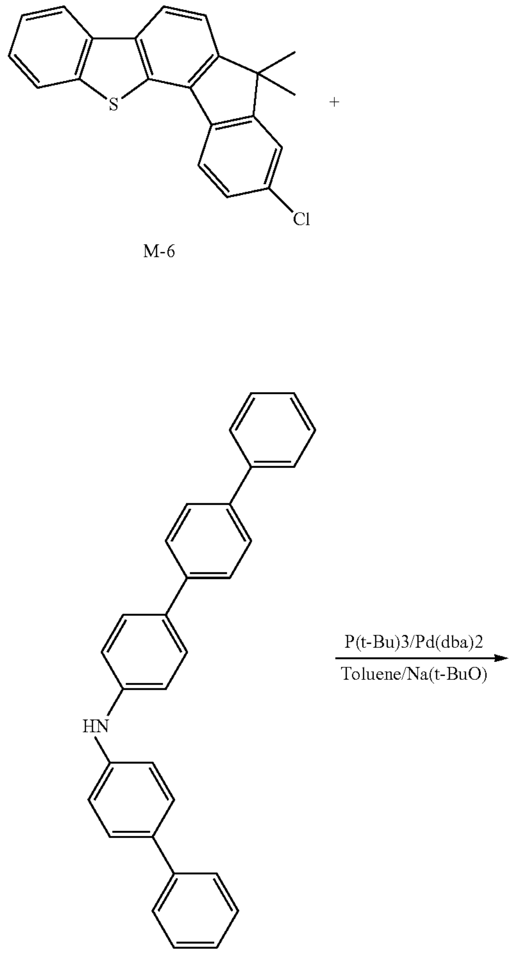

M-6

C

-continued

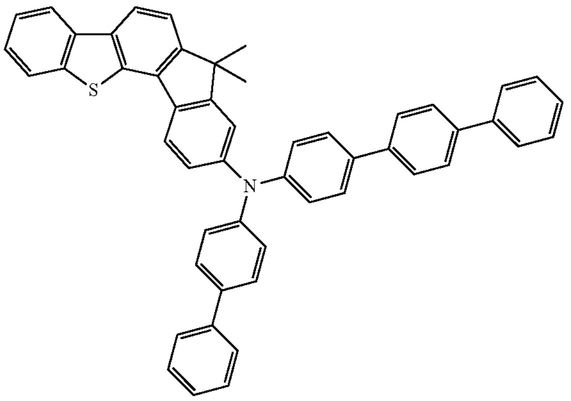

5.0 g (14.93 mmol) of the intermediate M-6, 5.94 g (14.93 mmol) of the intermediate C, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The extracted organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-37 as 8.2 g of a white solid (yield: 78.9%).

Calculated value: C, 88.02; H, 5.36; N, 2.01; S, 4.61

Analyzed value: C, 88.00; H, 5.38; N, 2.01; S, 4.61

Example 15

Preparation of Compound C-8

[Reaction Scheme 57]

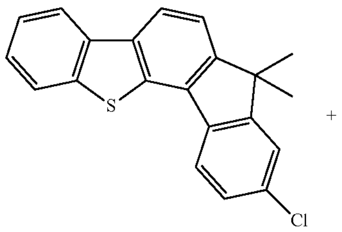

M-6

-continued

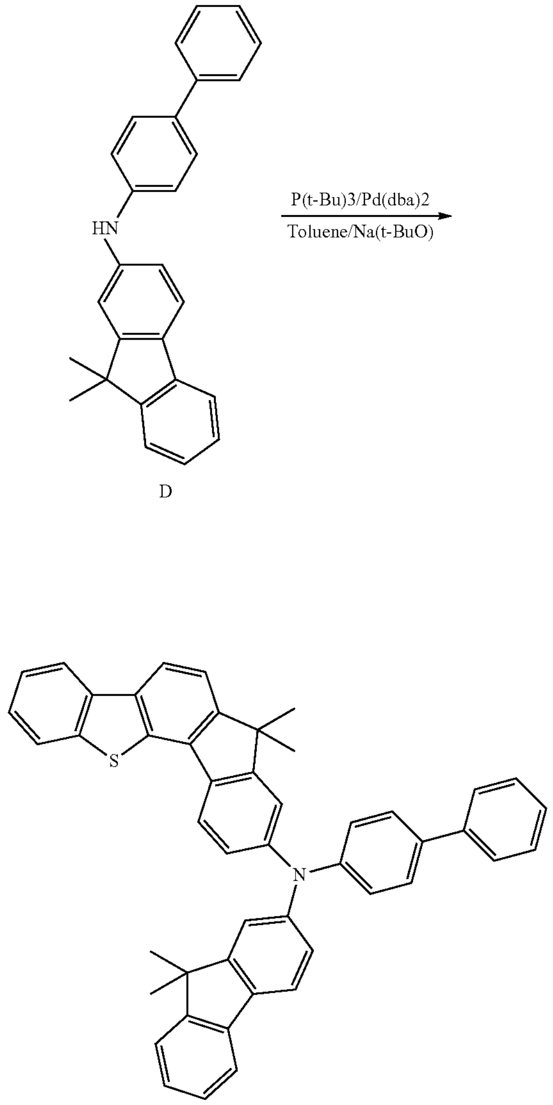

D 5.0 g (14.93 mmol) of the intermediate M-6, 5.4 g (14.93 mmol) of the intermediate D, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-36, as 8.4 g of a white solid (yield: 85.2%).

Calculated value: C, 87.37; H, 5.65; N, 2.12; S, 4.86

Analyzed value: C, 87.35; H, 5.67; N, 2.12; S, 4.86

Example 16

Preparation of Compound C-20

[Reaction Scheme 58]

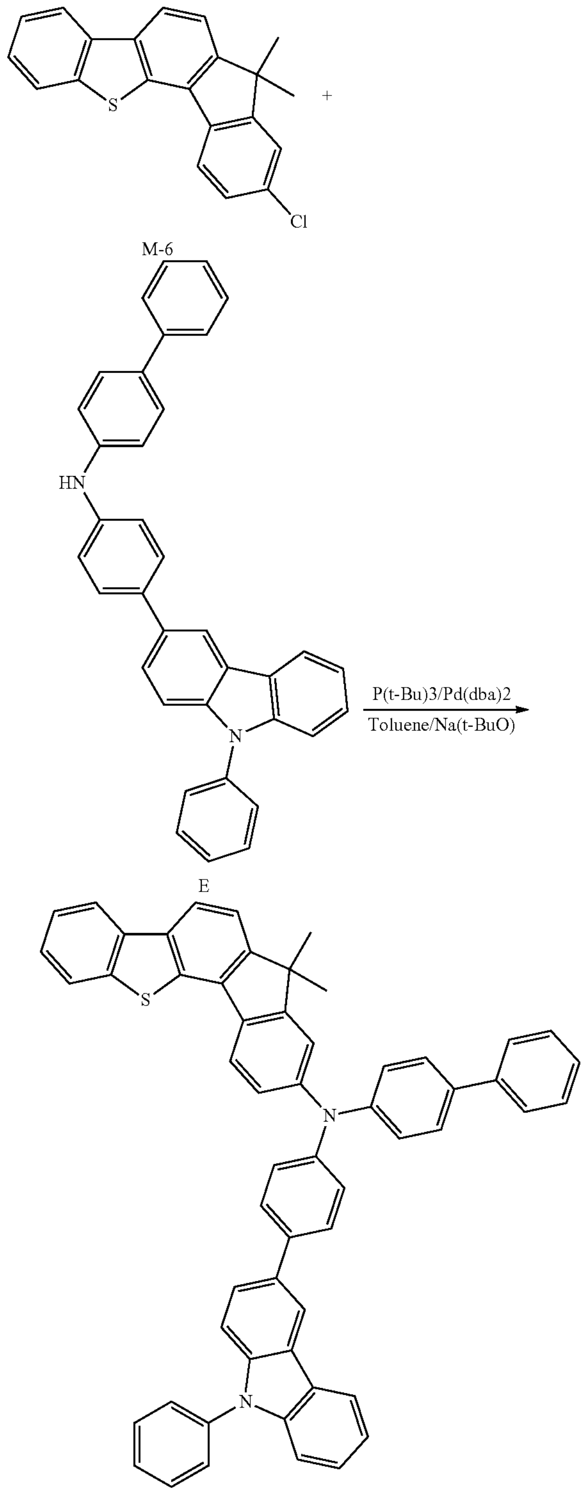

M-6

E 5.0 g (14.93 mmol) of the intermediate M-6, 7.27 g (14.93 mmol) of the intermediate E, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The extracted organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-20 as 9.4 g of a white solid (yield: 80.2%).

Calculated value: C, 87.21; H, 5.14; N, 3.57; S, 4.08

Analyzed value: C, 87.23; H, 5.12; N, 3.57; S, 4.08

Example 17

Preparation of Compound C-26

[Reaction Scheme 59]

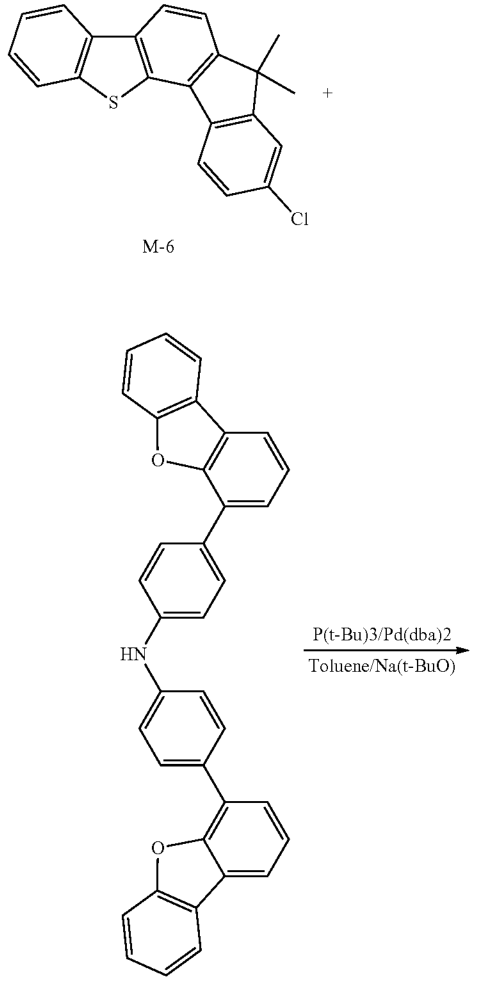

M-6

F

-continued

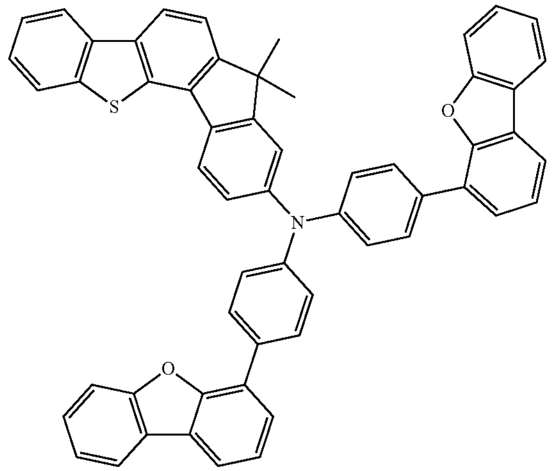

5.0 g (14.93 mmol) of the intermediate M-6, 4.41 g (14.93 mmol) of the intermediate F, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-26, as 9.7 g of a white solid (yield: 81.2%).

Calculated value: C, 85.58; H, 4.66; N, 1.75; O, 4.00; S, 4.01

Analyzed value: C, 85.59; H, 4.65; N, 1.75; O, 4.00; S, 4.01

Example 18

Preparation of Compound C-28

[Reaction Scheme 60]

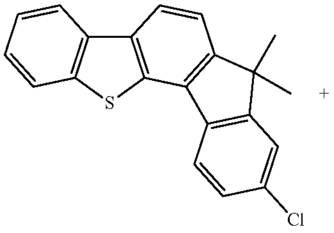

M-6

-continued

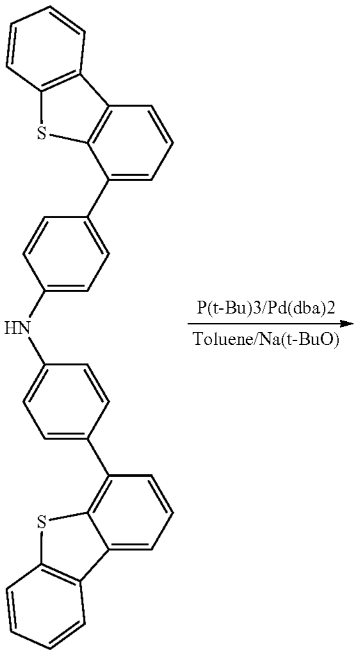

G

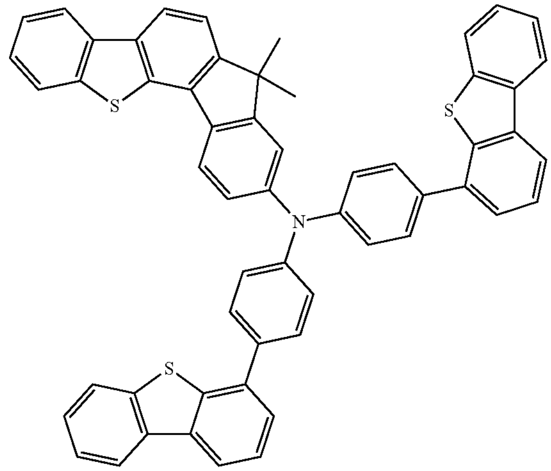

5.0 g (14.93 mmol) of the intermediate M-6, 7.97 g (14.93 mmol) of the intermediate G, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-28, as 10.3 g of a white solid (yield 82.9%).

Calculated value: C, 82.27; H, 4.48; N, 1.68; S, 11.56

Analyzed value: C, 82.25; H, 4.49; N, 1.68; S, 11.56

Example 19

Preparation of Compound C-30

[Reaction Scheme 61]

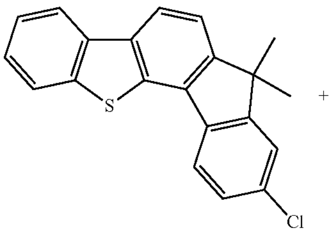

M-6

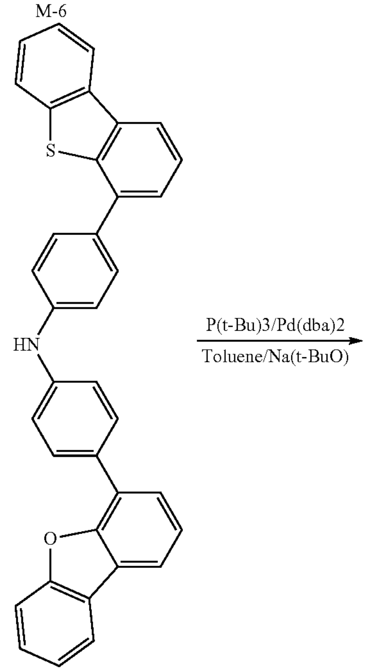

H

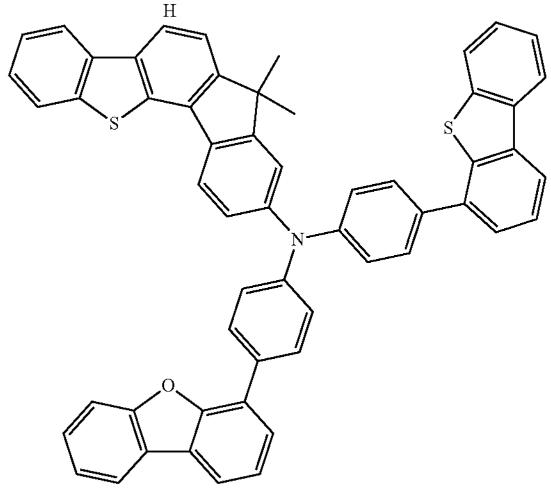

5.0 g (14.93 mmol) of the intermediate M-6, 7.73 g (14.93 mmol) of the intermediate B, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-30, as 10.3 g of a white solid (yield 84.5%).

Calculated value: C, 83.89; H, 4.57; N, 1.72; O, 1.96; S, 7.86

Analyzed value: C, 83.86; H, 4.60; N, 1.72; O, 1.96; S, 7.86

Example 20

Preparation of Compound C-38

[Reaction Scheme 62]

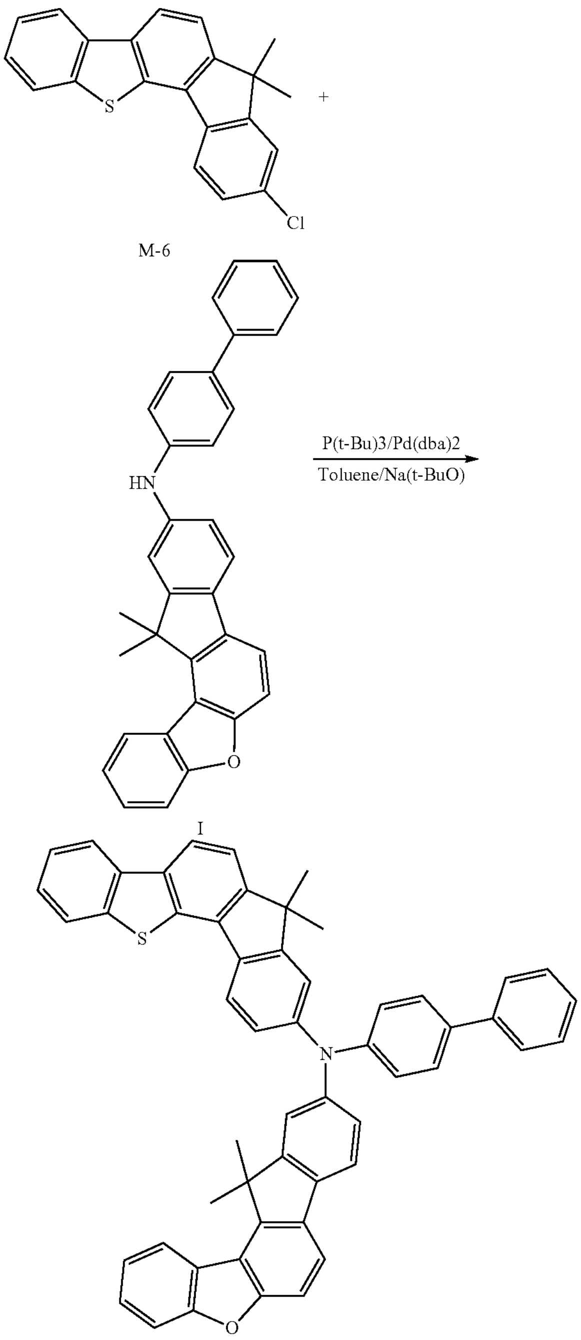

M-6

I 5.0 g (14.93 mmol) of the intermediate M-6, 6.74 g (14.93 mmol) of the intermediate I, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-38, as 9.4 g of a white solid (yield 83.9%).

Calculated value: C, 86.48; H, 5.24; N, 1.87; O, 2.13; S, 4.28

Analyzed value: C, 86.45; H, 5.27; N, 1.87; O, 2.13; S, 4.28

Example 21

Preparation of Compound C-39

[Reaction Scheme 63]

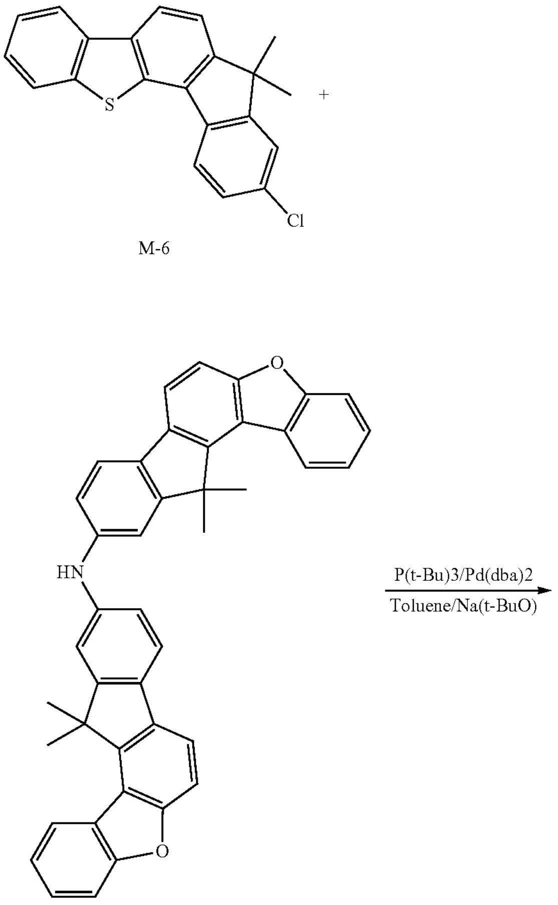

M-6

J

-continued

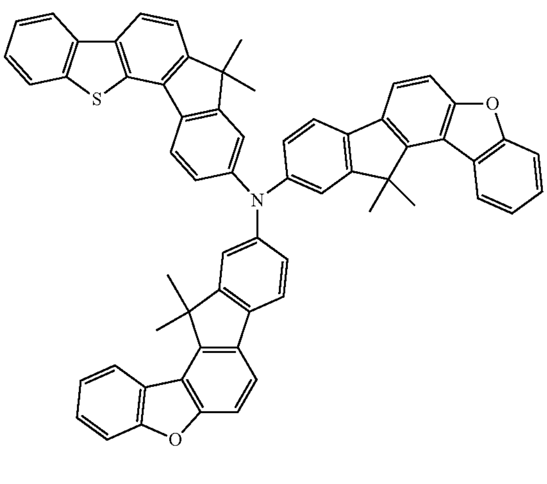

5.0 g (14.93 mmol) of the intermediate M-6, 8.69 g (14.93 mmol) of the intermediate J, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The extracted organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-38 as 10.4 g of a white solid (yield: 79.1%).

Calculated value: C, 85.98; H, 5.15; N, 1.59; O, 3.64; S, 3.64

Analyzed value: C, 85.97; H, 5.17; N, 1.59; O, 3.64; S, 3.64

Example 22

Preparation of Compound C-40

[Reaction Scheme 64]

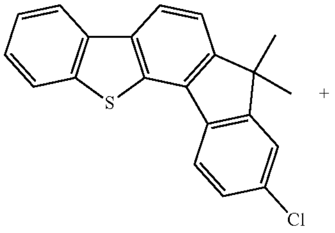

M-6

-continued

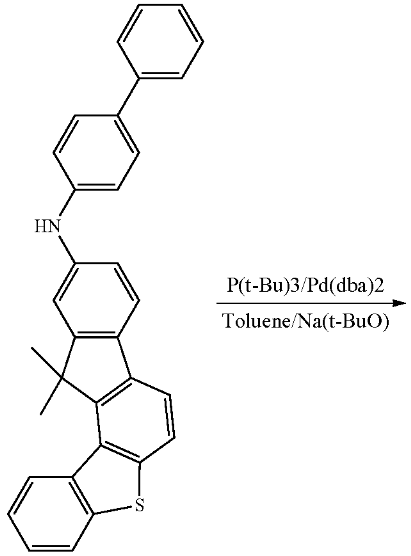

K

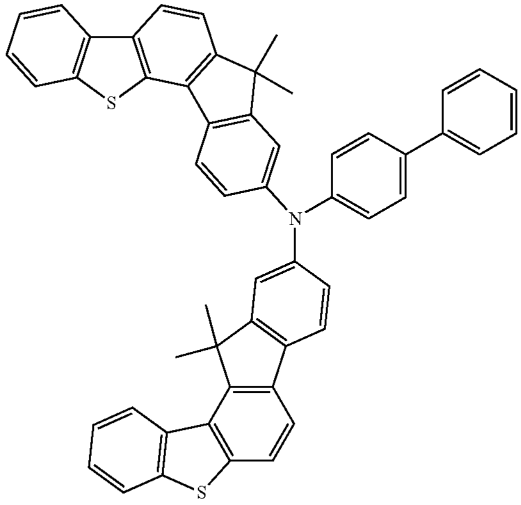

5.0 g (14.93 mmol) of the intermediate M-6, 6.98 g (14.93 mmol) of the intermediate K, 4.31 g (44.79 mmol) of sodium t-butoxide, and 0.09 g (0.45 mmol) of tris(tert-butyl)phosphine were dissolved in 200 ml of toluene, and 0.26 g (0.45 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-40, as 8.7 g of a white solid (yield 80.2%).

Calculated value: C, 84.38; H, 4.86; N, 1.93; S, 8.83

Analyzed value: C, 84.37; H, 4.87; N, 1.93; S, 8.83

Example 23

Preparation of Compound C-9

[Reaction Scheme 65]

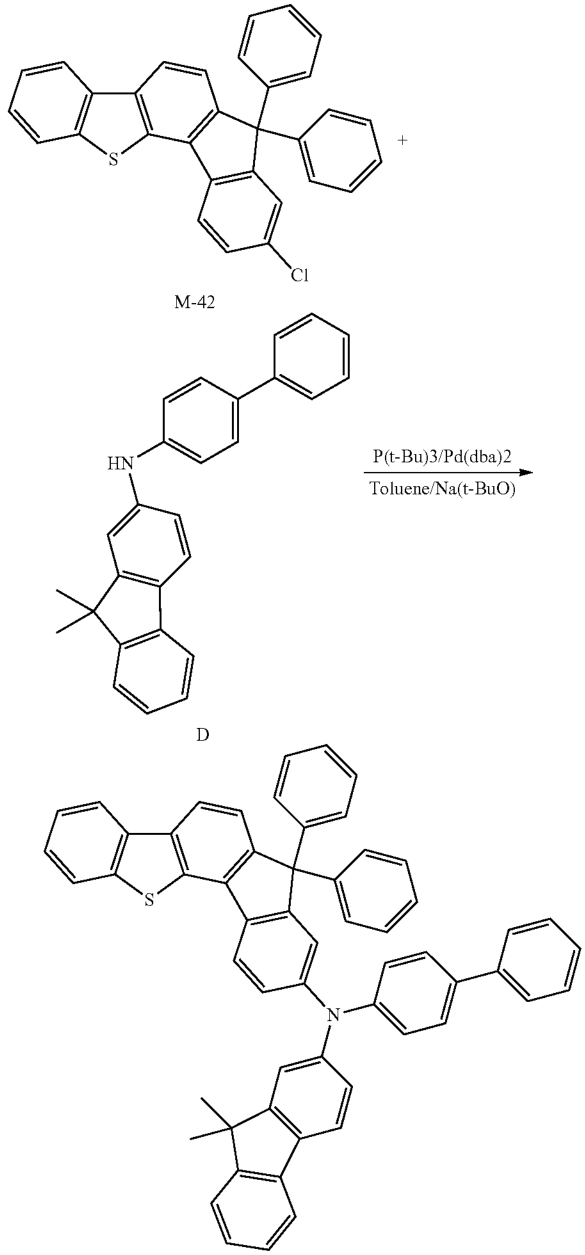

5.0 g (10.86 mmol) of the intermediate M-42, 3.94 g (10.86 mmol) of the intermediate D, 3.14 g (32.68 mmol) of sodium t-butoxide, and 0.07 g (0.33 mmol) of tris(tert-butyl)phosphine were dissolved in 200 ml of toluene, and 0.19 g (0.33 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-9, as 7.4 g of a white solid (yield 86.6%).

Calculated value: C, 88.85; H, 5.27; N, 1.79; S, 4.09

Analyzed value: C, 88.83; H, 5.29; N, 1.79; S, 4.09

Example 24

Preparation of Compound C-41

[Reaction Scheme 66]

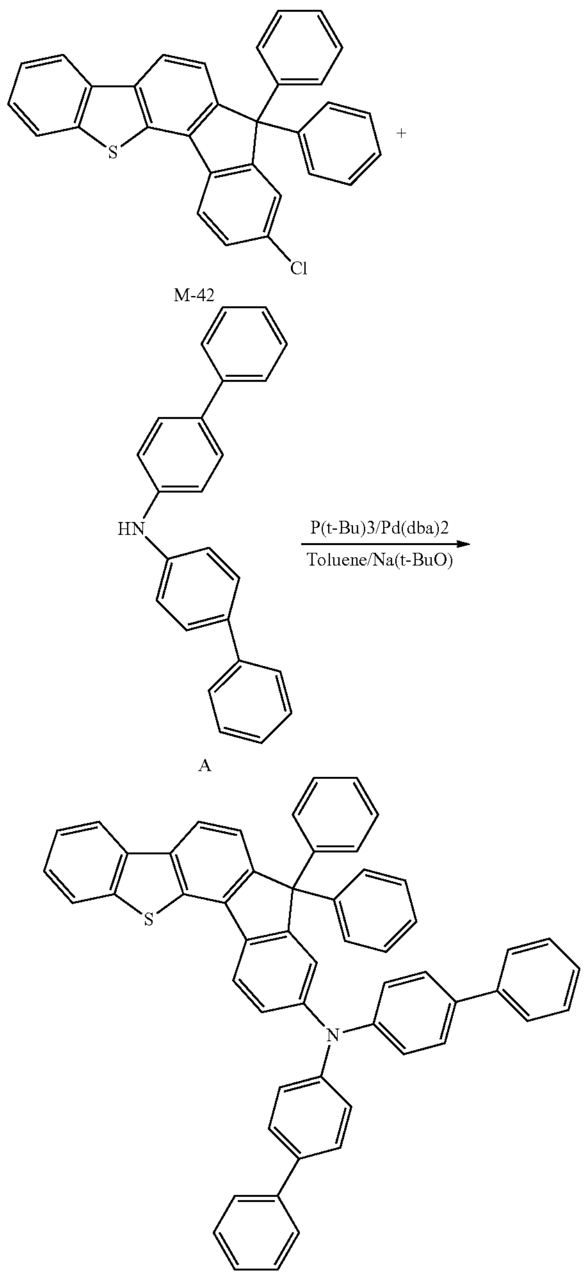

5.0 g (10.86 mmol) of the intermediate M-42, 3.5 g (10.86 mmol) of the intermediate A, 3.14 g (32.68 mmol) of sodium t-butoxide, and 0.07 g (0.33 mmol) of tris(tert-butyl)phosphine were dissolved in 200 ml of toluene, and 0.19 g (0.33 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound C-41, as 6.9 g of a white solid (yield: 85.1%).

Calculated value: C, 88.79; H, 5.01; N, 1.88; S, 4.31

Analyzed value: C, 88.77; H, 5.03; N, 1.88; S, 4.31

Example 25

Preparation of Compound A-28

[Reaction Scheme 67]

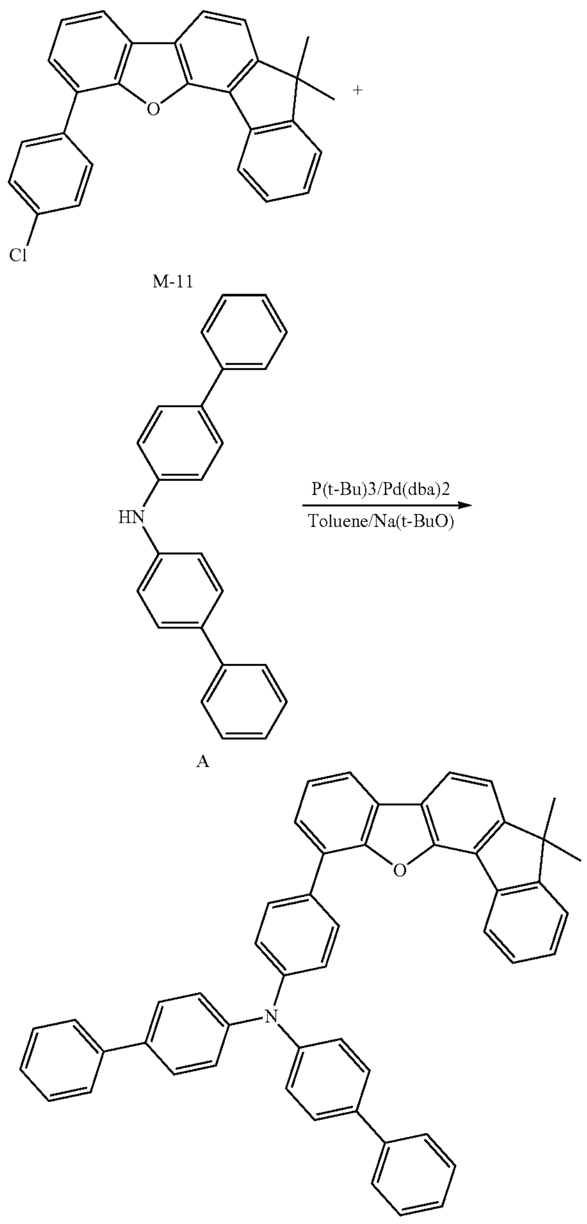

M-11

A 5.0 g (12.66 mmol) of the intermediate M-11, 4.07 g (12.66 mmol) of the intermediate A, 3.65 g (37.99 mmol) of sodium t-butoxide, and 0.08 g (0.38 mmol) of tris(tert-butyl)phosphine were dissolved in 200 ml of toluene, and 0.22 g (0.38 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound A-28, as 7.3 g of a white solid (yield: 84.8%).

Calculated value: C, 90.10; H, 5.49; N, 2.06; O, 2.35

Analyzed value: C, 90.12; H, 5.47; N, 2.06; O, 2.35

Example 26

Preparation of Compound A-30

[Reaction Scheme 68]

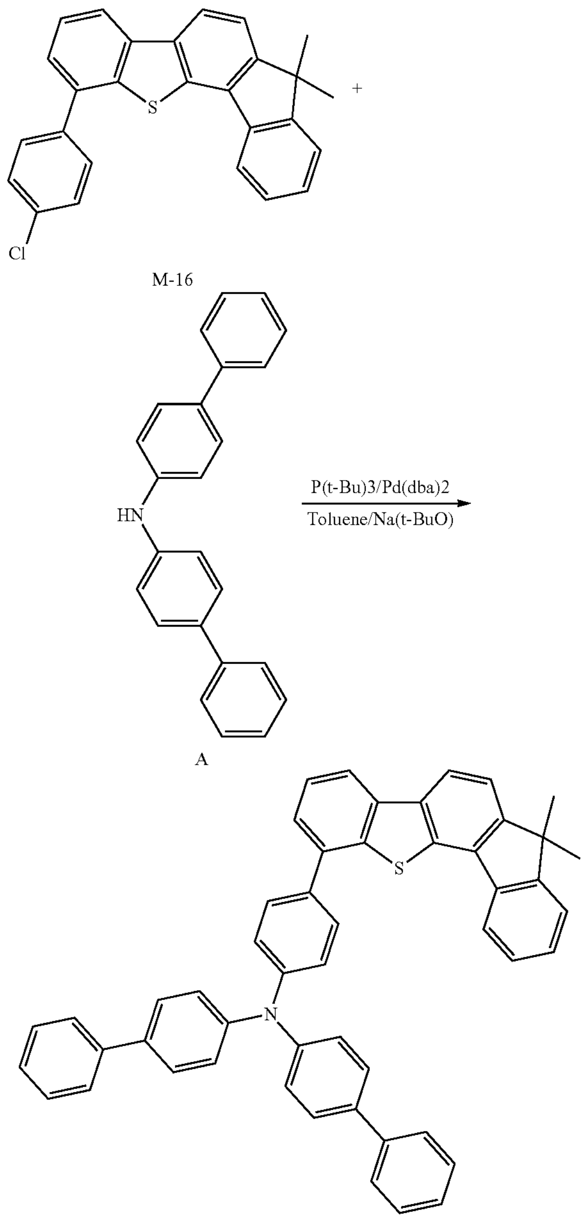

M-16

A 5.0 g (12.17 mmol) of the intermediate M-16, 3.91 g (12.17 mmol) of the intermediate A, 3.65 g (37.99 mmol) of sodium t-butoxide, and 0.07 g (0.36 mmol) of tris(tert-butyl)phosphine were dissolved in 200 ml of toluene, and 0.22 g (0.38 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound A-30, as 7.1 g of a white solid (yield: 83.8%).

Calculated value: C, 88.02; H, 5.36; N, 2.01; S, 4.61

Analyzed value: C, 88.04; H, 5.34; N, 2.01; S, 4.61

Example 27

Preparation of Compound B-19

[Reaction Scheme 69]

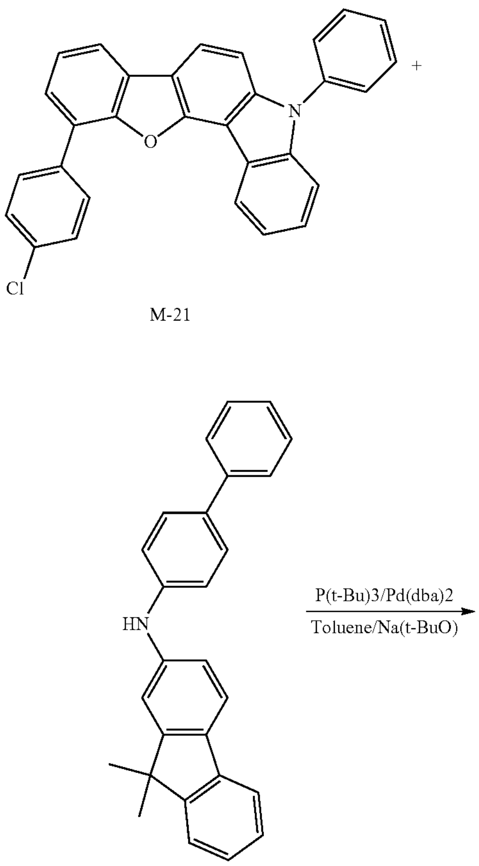

M-21

D

-continued

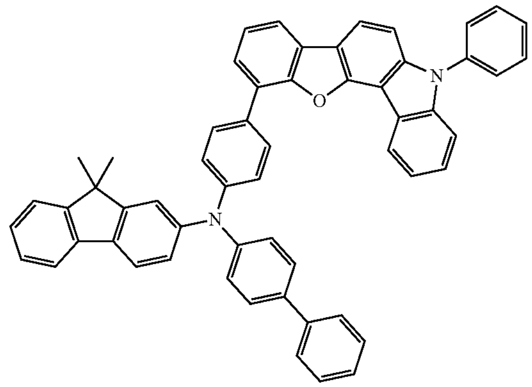

5.0 g (11.26 mmol) of the intermediate M-21, 4.07 g (11.26 mmol) of the intermediate D, 3.25 g (33.79 mmol) of sodium t-butoxide, and 0.07 g (0.34 mmol) of tris(tert-butyl)phosphine were dissolved in 200 ml of toluene, and 0.19 g (0.34 mmol) of $Pd(dba)_2$ was added thereto. The mixture was refluxed and agitated under a nitrogen atmosphere for 12 hours. When the reaction was complete, the reactant was extracted with toluene and distilled water. The extracted organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound B-19 as 7.2 g of a white solid (yield: 83.1%).

Calculated value: C, 89.03; H, 5.24; N, 3.64; O, 2.08

Analyzed value: C, 89.05; H, 5.22; N, 3.64; O, 2.08

Example 28

Preparation of Compound B-20

[Reaction Scheme 70]

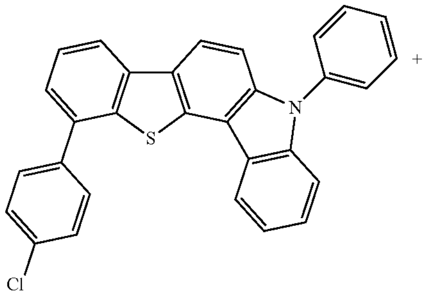

M-26

-continued

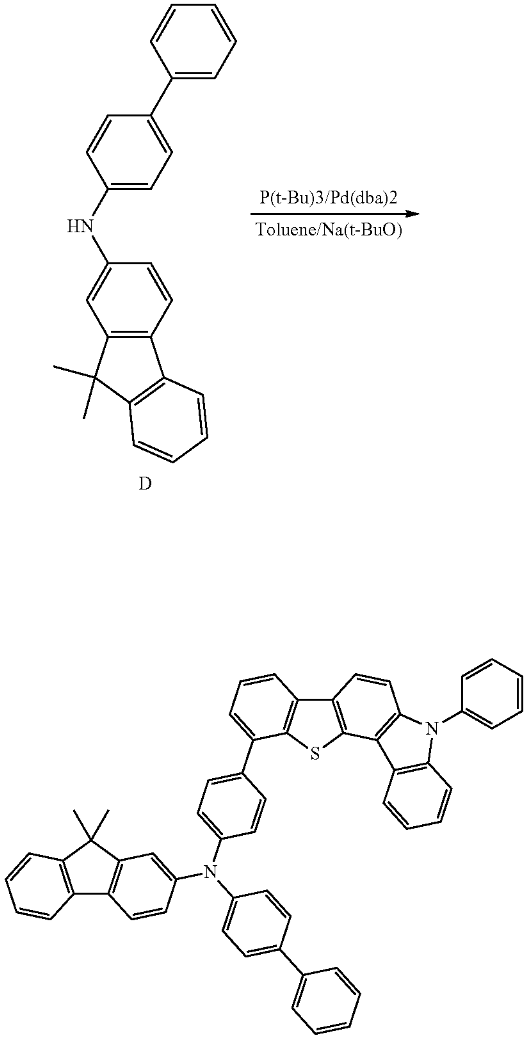

D 5.0 g (10.87 mmol) of the intermediate M-26, 3.93 g (10.87 mmol) of the intermediate D, 3.25 g (33.79 mmol) of sodium t-butoxide, and 0.07 g (0.34 mmol) of tris(tert-butyl)phosphine were dissolved in 200 ml of toluene, and 0.19 g (0.34 mmol) of $Pd(dba)_2$ was added thereto. The mixture was refluxed and agitated under a nitrogen atmosphere for 12 hours. When the reaction was complete, the reactant was extracted with toluene and distilled water. The obtained organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound B-20, as 7.3 g of a white solid (yield 85.5%).

Calculated value: C, 87.21; H, 5.14; N, 3.57; S, 4.08

Analyzed value: C, 87.24; H, 5.11; N, 3.57; S, 4.08

Example 29

Preparation of Compound D-09

[Reaction Scheme 71]

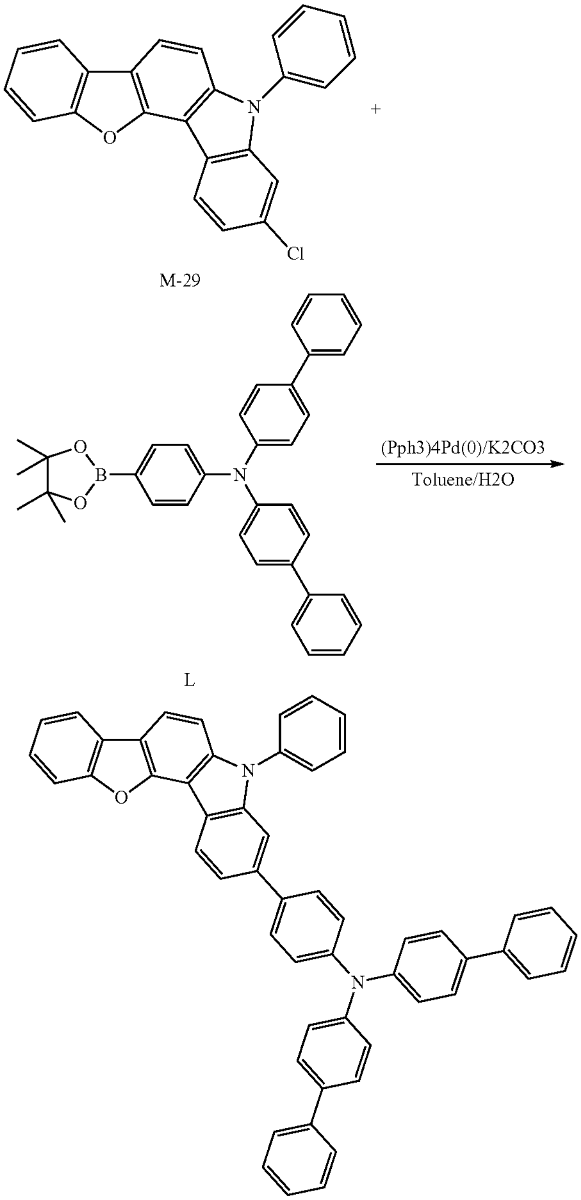

M-29

L 3.86 g (10.51 mmol) of the intermediate M-29, 5 g (9.55 mmol) of the intermediate L, and 0.33 g (0.29 mmol) of tetrakis(triphenylphosphine)palladium were dissolved in 200 ml of toluene in a 500 mL round-bottomed flask under a nitrogen atmosphere, and 2.64 g (19.1 mmol) of potassium acetate and 100 mL of water were added thereto. The mixture was refluxed at 90° C. for 24 hours. When the reaction was complete, the reactant was extracted with toluene and distilled water. The extracted organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound D-09 as 5.4 g of a white solid (yield: 77.5%).

Calculated value: C, 88.98; H, 4.98; N, 3.84; O, 2.20

Analyzed value: C, 88.99; H, 4.97; N, 3.84; O, 2.20

Example 30

Preparation of Compound D-10

[Reaction Scheme 72]

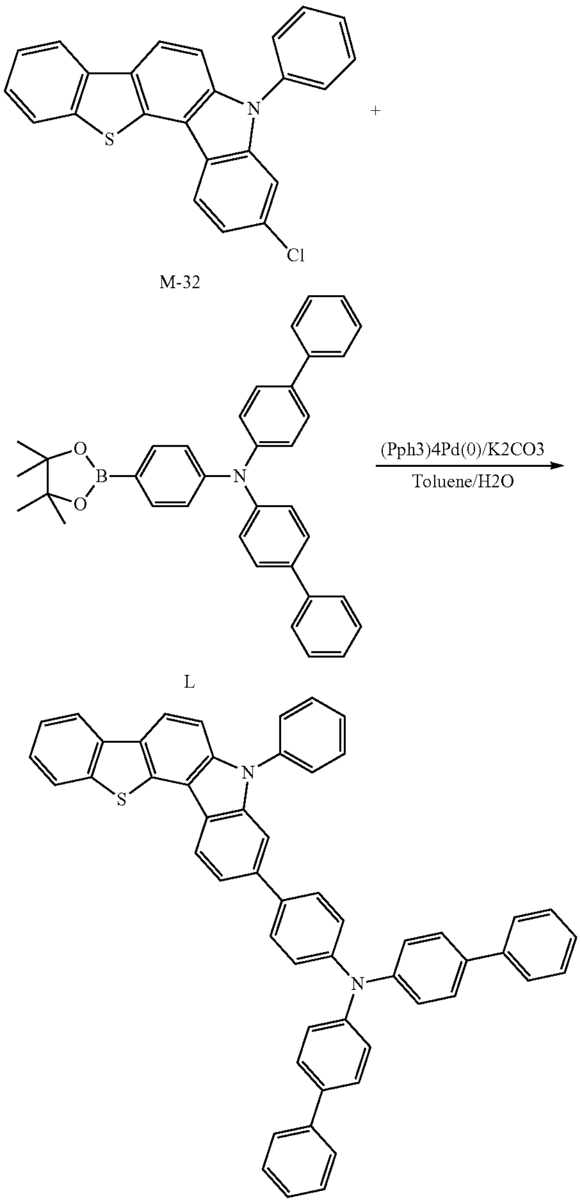

4.03 g (10.51 mmol) of the intermediate M-32, 5 g (9.55 mmol) of the intermediate L, and 0.33 g (0.29 mmol) of tetrakis(triphenylphosphine)palladium were dissolved in 200 ml of toluene in a 500 mL round-bottomed flask under a nitrogen atmosphere, and 2.64 g (19.1 mmol) of potassium acetate and 100 mL of water were added thereto. The mixture was refluxed at 90° C. for 24 hours. When the reaction was complete, the reactant was extracted with toluene and distilled water. The extracted organic layer was dried with anhydrous magnesium sulfate, filtered, and concentrated under a reduced pressure. The resulting product was purified through silica gel column chromatography using n-hexane/dichloromethane mixed in a volume ratio of 2:1, obtaining a desired compound D-10 as 5.5 g of a white solid (yield: 77.3%).

Calculated value: C, 87.06; H, 4.87; N, 3.76; S, 4.30

Analyzed value: C, 87.04; H, 4.89; N, 3.76; S, 4.30

Fabrication of Organic Light-Emitting Diode

Example 31

Fabrication of Organic Photoelectric Device

A glass substrate coated with ITO (Indium tin oxide) as a 1,500 Å-thick thin film was cleaned with distilled water and ultrasonic wave. Next, the glass substrate was cleaned with ultrasonic wave using a solvent including one of isopropyl alcohol, acetone, methanol, and the like, and dried. The dried substrate was moved in a plasma cleaner and cleaned with oxygen plasma for 5 minutes and then, moved in a vacuum depositor. This ITO transparent electrode was used as a positive electrode, and 4,4'-bis[N-[4-{N,N-bis(3-methylphenyl)amino}-phenyl]-N-phenylamino]biphenyl (DNTPD) was vacuum deposited to form a 600 Å-thick hole injection layer (HIL) thereon. Then, the compound according to Example 1 was vacuum-deposited to form a 300 Å-thick hole transport layer (HTL). On the hole transport layer (HTL), a 250 Å-thick emission layer was vacuum-deposited with 9,10-di-(2-naphthyl)anthracene (ADN) as a host and doped with 3 wt % of 2,5,8,11-tetra(tert-butyl)perylene (TBPe) as a dopant.

On the emission layer, Alq3 was vacuum deposited to form a 250 Å-thick electron transport layer (ETL). On the electron transport layer (ETL), a 10 Å-thick LiF layer and a 1,000 Å-thick Al layer were sequentially vacuum deposited to fabricate a cathode and thus fabricate an organic light emitting diode.

The organic light emitting diode had a structure of five thin organic layers, in particular, 1,000 Å Al/10 Å LiF/250 Å Alq3/250 Å EML[ADN:TBPe=97:3]/300 Å C-1/600 Å DNTPD/1,500 Å ITO.

Example 32

An organic light emitting diode was fabricated according to the same method as Example 31 by using the compound C-32 of Example 3 instead of the compound C-1 of Example 1.

Example 33

An organic light emitting diode was fabricated according to the same method as Example 31 by using the compound C-5 of Example 4 instead of the compound C-1 of Example 1.

Example 34

An organic light emitting diode was fabricated according to the same method as Example 31 by using the compound C-19 of Example 5 instead of the compound C-1 of Example 1.

Example 35

An organic light emitting diode was fabricated according to the same method as Example 31 by using the compound C-2 of Example 11 instead of the compound C-1 of Example 1.

Example 36

An organic light emitting diode was fabricated according to the same method as Example 31 by using the compound C-35 of Example 12 instead of the compound C-1 of Example 1.

Example 37

An organic light emitting diode was fabricated according to the same method as Example 31 by using the compound C-37 of Example 14 instead of the compound C-1 of Example 1.

Example 38

An organic light emitting diode was fabricated according to the same method as Example 31 by using the compound C-8 of Example 15 instead of the compound C-1 of Example 1.

Example 39

An organic light emitting diode was fabricated according to the same method as Example 31 by using the compound C-20 of Example 16 instead of the compound C-1 of Example 1.

Example 40

An organic light emitting diode was fabricated according to the same method as Example 31 by using the compound C-9 of Example 23 instead of the compound C-1 of Example 1.

Example 41

An organic light emitting diode was fabricated according to the same method as Example 31 by using the compound C-41 of Example 24 instead of the compound C-1 of Example 1.

Comparative Example 1

An organic light emitting diode was fabricated according to the same method as Example 31 except for using NPB instead of the compound C-1 of Example 1. The NPB structure is shown below.

Comparative Example 2

An organic light emitting diode was fabricated according to the same method as Example 31 except for using HT1 instead of the compound C-1 of Example 1. The HT1 structure is shown below.

The DNTPD, ADN, TBPe, NPB, and HT1 structures used to fabricate an organic light emitting diode are shown below.

[DNTPD]

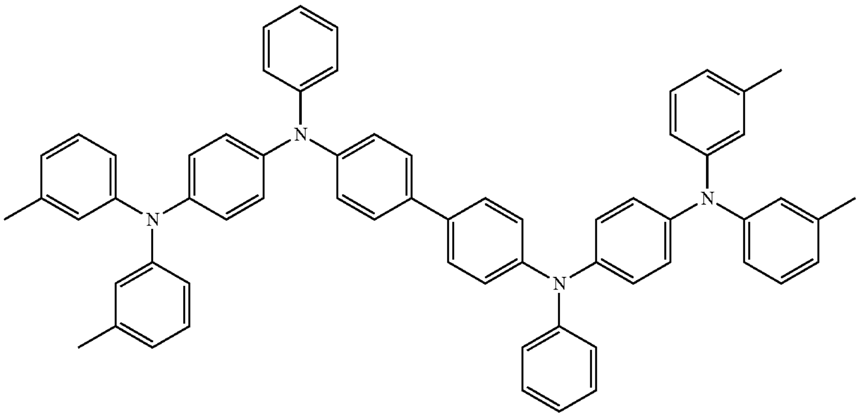

[ADN]

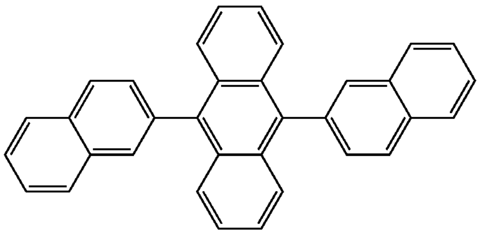

[TBPe]

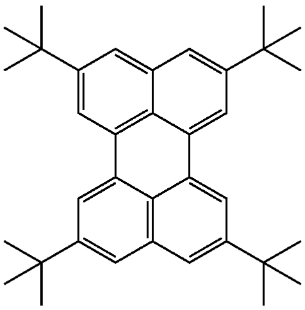

-continued

[NPB]

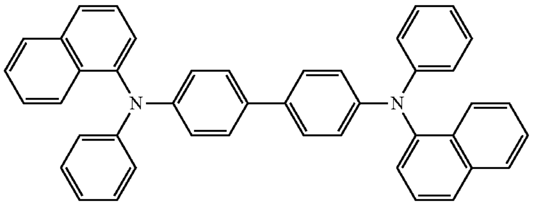

[HT1]

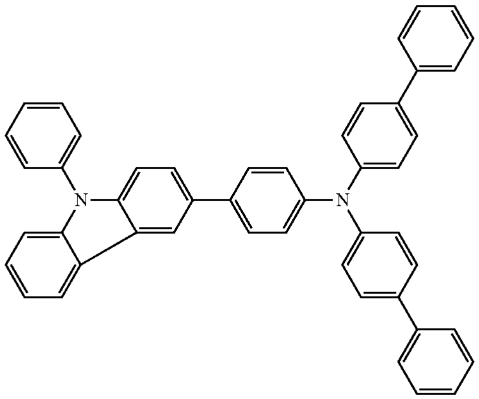

(Performance Evaluation of Organic Light Emitting Diode)

Each organic light emitting diode according to Examples 31 to 41 and Comparative Examples 1 and 2 was measured regarding current density change, luminance change, and luminous efficiency depending on voltage. A method of measuring the above values is as follows. The results are provided in the following Table 1.

(1) Current Density Change Depending on Voltage Change

The organic light emitting diodes were measured regarding current flowing in a unit device by using a current-voltage meter (Keithley 2400) while their voltages were increased from 0 V to 10 V. The current value was divided by an area to obtain a current density.

(2) Luminance Change Depending on Voltage Change

The organic light emitting diodes were measured regarding luminance by using a luminance meter (Minolta Cs-1000A), while their voltage were increased from 0 V to 10 V.

(3) Luminous Efficiency

The luminance and current density obtained from the above (1) and (2) and voltage were used to calculate current efficiency (cd/A) at the same current density (10 mA/$cm^2$).

TABLE 1

| Devices | Compound of hole transport layer (HTL) | Driving voltage (V) | Color (EL color) | Efficiency (cd/A) |
|---|---|---|---|---|
| Example 31 | C-1 | 6.3 | Blue | 6.3 |
| Example 32 | C-32 | 6.3 | Blue | 6.2 |
| Example 33 | C-5 | 6.2 | Blue | 6.0 |
| Example 34 | C-19 | 6.2 | Blue | 6.0 |
| Example 35 | C-2 | 6.4 | Blue | 6.1 |
| Example 36 | C-35 | 6.2 | Blue | 6.2 |
| Example 37 | C-37 | 6.3 | Blue | 6.3 |
| Example 38 | C-8 | 6.4 | Blue | 6.3 |
| Example 39 | C-20 | 6.5 | Blue | 6.2 |
| Example 40 | C-9 | 6.3 | Blue | 6.3 |
| Example 41 | C-41 | 6.4 | Blue | 6.2 |
| Comparative Example 1 | NPB | 7.1 | Blue | 4.9 |
| Comparative Example 2 | HT1 | 6.6 | Blue | 5.7 |

Current density: 10 mA/$cm^2$

As may be seen in Table 1, the organic light emitting diodes of the Examples had low driving voltage and excellent efficiency, compared with the organic light emitting diodes according to Comparative Examples 1 and 2.

By way of summation and review, the organic light emitting diode transforms electrical energy into light by applying a current to an organic light emitting material. The OLED may have a structure in which a functional organic material layer is interposed between an anode and a cathode. The organic material layer may include a multi-layer including different materials, for example, a hole injection layer (HIL), a hole transport layer (HTL), an emission layer, an electron transport layer (ETL), and an electron injection layer (EIL), in order to improve efficiency and stability of an organic light emitting diode.

In such an organic light emitting diode, when a voltage is applied between an anode and a cathode, holes from the anode and electrons from the cathode are injected to an organic material layer. The holes and electrons are recombined to generate excitons having high energy. The generated excitons generate light of a certain wavelength while shifting to a ground state.

A phosphorescent light emitting material, as well as a fluorescent light emitting material, may be used as a light emitting material for an organic light emitting diode. Such a phosphorescent material emits light by transiting the electrons from a ground state to an exited state, transiting a singlet exciton to a triplet exciton without radiance through intersystem crossing, and transiting the triplet exciton to a ground state.

As described above, an organic material layer for an organic light emitting diode may include a light emitting material and a charge transport material, e.g., a hole injection material, a hole transport material, an electron transport material, an electron injection material, or the like.

The light emitting material may be classified as blue, green, and red light emitting materials according to emitted colors, and yellow and orange light emitting materials to emit colors near to natural colors.

When one material is used as a light emitting material, a device may exhibit deteriorated efficiency because interactions among molecules may shift a maximum light emitting wavelength to a long wavelength, may decrease color purity, or may quench light emitting effects. Therefore, a host/dopant system may be used as a light emitting material in order to improve color purity and increase luminous efficiency and stability through energy transfer.

In order to implement excellent performance of an organic light emitting diode, a material forming an organic material layer, e.g., a hole injection material, a hole transport material, a light emitting material, an electron transport material, an electron injection material, and a light emitting material such as a host and/or a dopant should be stable and have good efficiency.

In general, an organic light emitting diode may be classified into a low molecular weight organic light emitting diode and a polymer organic light emitting diode. The low molecular weight organic light emitting diode may be fabricated in a form of a thin film using a vacuum deposit method and thus, may have excellent efficiency and life-span performance. On the other hand, the polymer organic light emitting diode may be fabricated using an inkjet method or a spin coating method and thus, may have a low cost in the initial step while having a large area.

Both the low molecular weight organic light emitting diode and the polymer organic light emitting diode exhibit self-light emission, fast response speed, wide photviewing angle, ultra thin film, high image quality, durability, broad operation temperature range, and the like, and thus, draw attention as a next generation display. In particular, the low molecular weight organic light emitting diode and the polymer organic light emitting diode self-emit light and thus, have good visibility in a dark place or against an external light, with no need of a backlight. Accordingly, they may be fabricated to have about ⅓ less thickness and weight than a conventional liquid crystal display (LCD).

In addition, the low molecular weight organic light emitting diode and the polymer organic light emitting diode may have more than 1,000 times faster response speed than LCD (by a micro second) and thus, may realize a perfect motion picture without an after-image. Accordingly, the low molecular weight organic light emitting diode and the polymer organic light emitting diode may be an optimum display in a multimedia era, since they have 80 times improved efficiency and more than 100 times improved life-span due to remarkable technological development since the first model was developed in the late 1980s. Organic light emitting diodes are finding bigger applications, e.g., a 40 inch organic light emitting diode panel and the like have been developed.

Improved luminous efficiency and improved life-span are desirable. Luminous efficiency of a device may require smooth combination of a hole with an electron in an emission layer. However, an organic material may exhibit slower electron mobility than hole mobility. Thus, an electron transport layer (ETL) may be used to increase electron injection and mobility from a cathode and simultaneously block hole mobility, so that a hole may be efficiently combined with an electron in an emission layer.

In addition, to improve life-span of a device, crystallization of the organic material due to Joule heat generated during operation should be prevented. Therefore, an organic compound with excellent electron injection and mobility and high electrochemical stability is desired.

The embodiments provide a compound for an organic optoelectronic device that helps ensure good life span, efficiency, electrochemical stability, and thermal stability of a device.

The embodiments provide a compound for an organic optoelectronic device that may act as a hole injection and hole transport material, or an electron injection and transport material, and also act as a light emitting host along with an appropriate dopant.

The embodiments also provide an organic optoelectronic device having excellent life span, efficiency, driving voltage, electrochemical stability, and thermal stability.

The compound may exhibit excellent hole or electron transporting properties, film stability, and thermal stability as well as high triplet excitation energy.

The compound may be used in an emission layer as a hole injection/transport material, a host material, or an electron injection/transport material. The organic photoelectric device including the compound may exhibit excellent life-span and luminous efficiency while having low driving voltages due to excellent electrochemical and thermal stability.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound including a moiety represented by the following Chemical Formula 4 and a moiety represented by the following Chemical Formula 5:

[Chemical Formula 4]

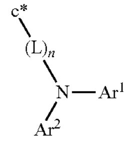

[Chemical Formula 5]

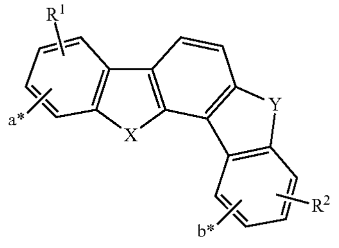

wherein in Chemical Formulae 4 and 5, $Ar^1$ and $Ar^2$ are each independently a substituted or unsubstituted C6 to C30 aryl group or a substituted or unsubstituted C2 to C30 heteroaryl group, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof, n is 0 or 1, X is O, S, (O═S═O), (P═O), or (C═O), Y is CR'R" or NR', R', R", $R^1$, and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and one of a* and b* of the above Chemical Formula 5 forms a sigma bond with the c* of the above Chemical Formula 4, and the other of a* and b*, not linked to c *, is hydrogen.

2. The compound as claimed in claim 1, wherein the compound is represented by the following Chemical Formula 6:

[Chemical Formula 6]

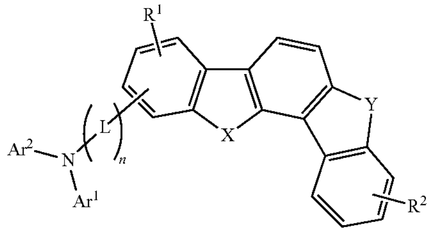

wherein, in Chemical Formula 6,

X is O, S, (O═S═O), (P═O), or (C═O),

Y is CR'R" or NR',

R', R", $R^1$ and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof, $Ar^1$ and $Ar^2$ are each independently a substituted or unsubstituted C6 to C30 aryl group or a substituted or unsubstituted C2 to C30 heteroaryl group, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof, and n is 0 or 1.

3. The compound as claimed in claim 2, wherein:

Y is CR'R", and

R' and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

4. The compound as claimed in claim 2, wherein:

Y is NR', and

R' is hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

5. The compound as claimed in claim 1, wherein the compound is represented by the following Chemical Formula 7:

[Chemical Formula 7]

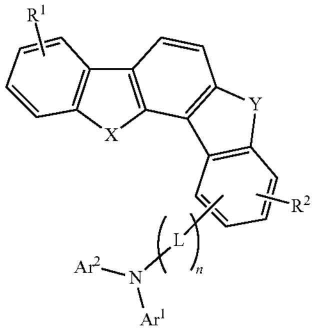

wherein, in Chemical Formula 7,

X is O, S, $SO_2$(O═S═O), PO(P═O), or CO(C═O),

Y is CR'R" or NR',

R', R", $R^1$, and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof, $Ar^1$ and $Ar^2$ are each independently a substituted or unsubstituted C6 to C30 aryl group or a substituted or unsubstituted C2 to C30 heteroaryl group, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof, and n is 0 or 1.

6. The compound as claimed in claim 5, wherein:

Y is CR'R", and

R' and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

7. The compound as claimed in claim 5, wherein:

Y is NR', and

R' is hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 an alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

8. The compound as claimed in claim 1, wherein the compound is represented by one of the following Chemical Formulae A-1 to A-7 and A-9 to A-51:

[A-1]

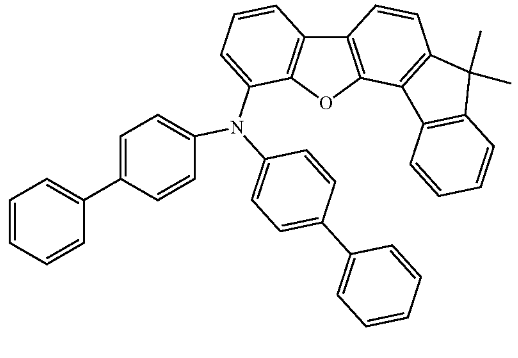

-continued
[A-2]
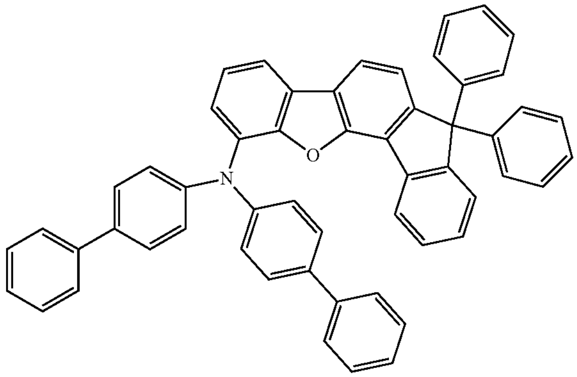
[A-3]
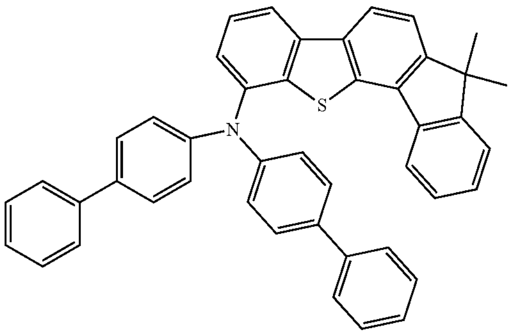
[A-4]
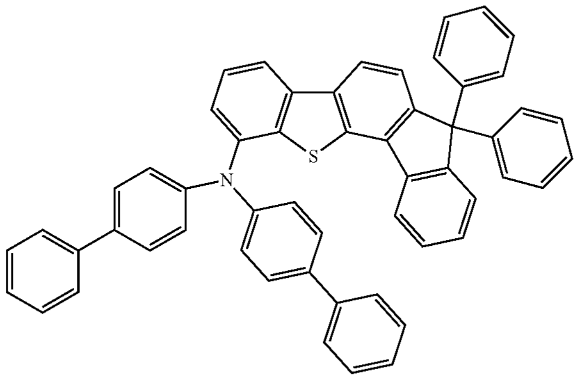
[A-5]
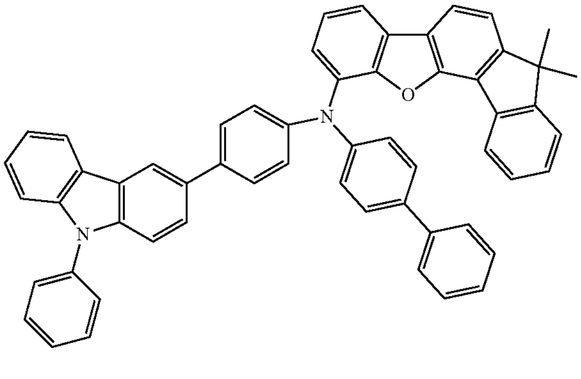
-continued
[A-6]
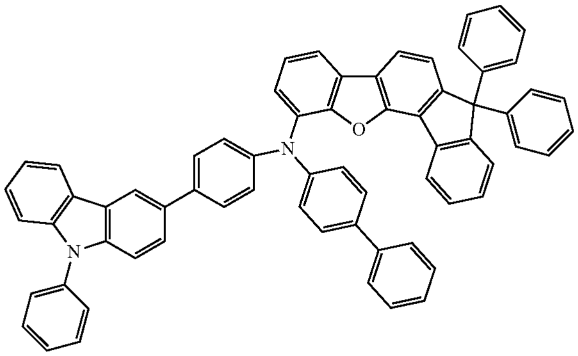
[A-7]
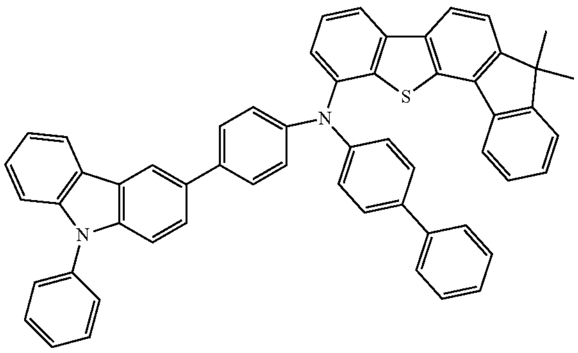
[A-9]
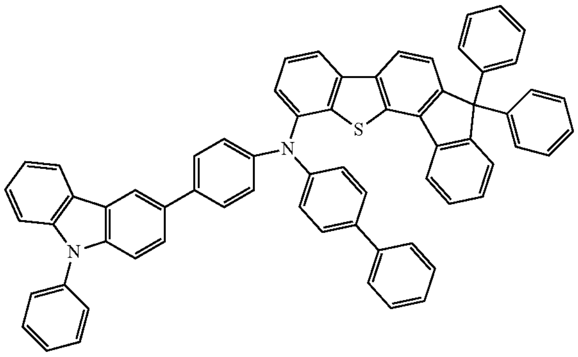
[A-10]
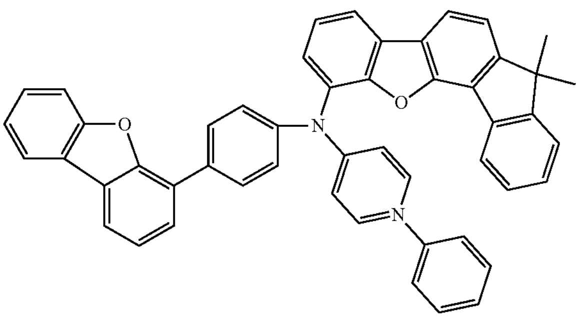

-continued
[A-11]
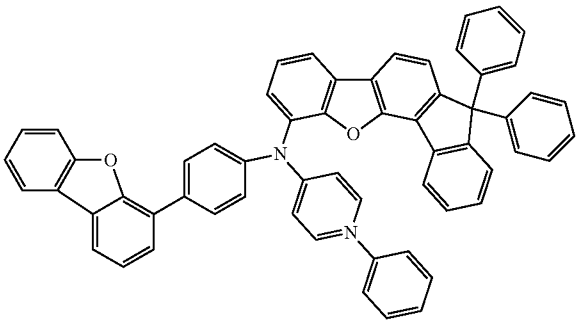
[A-12]
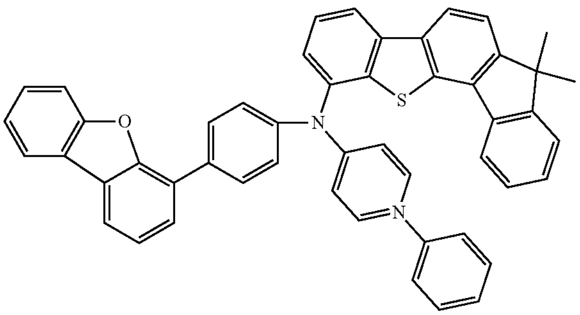
[A-13]
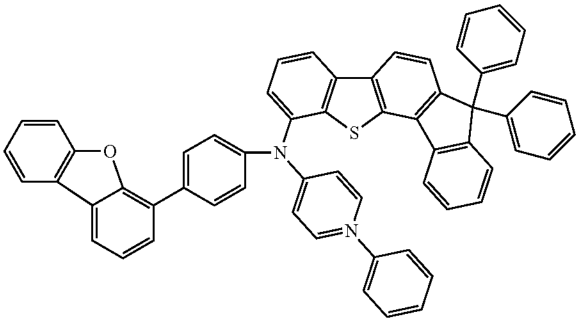
[A-14]
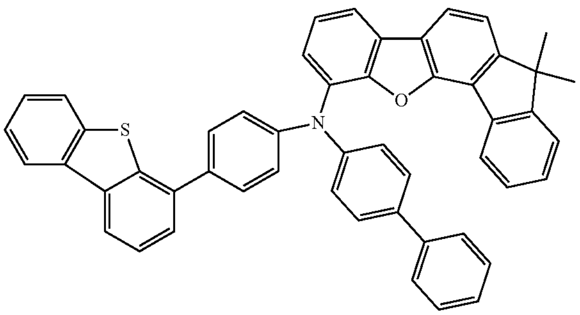
-continued
[A-15]
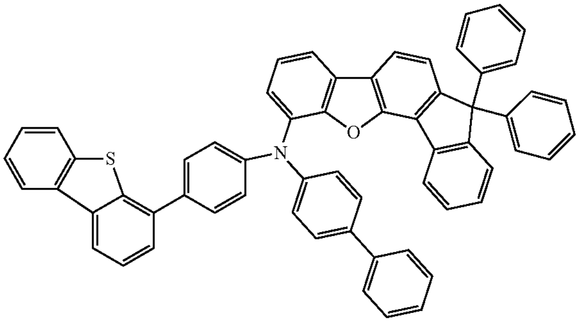
[A-16]
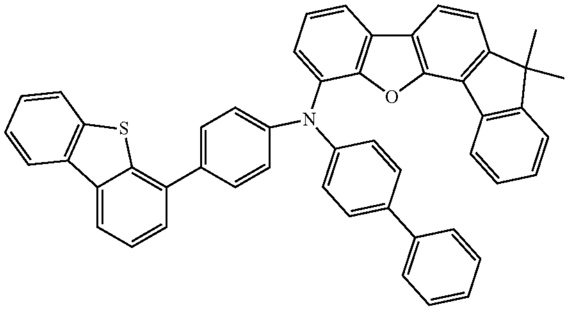
[A-17]
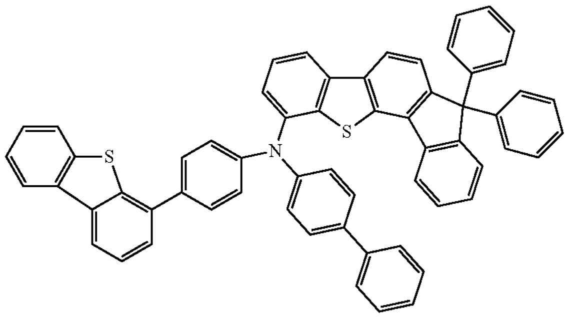
[A-18]
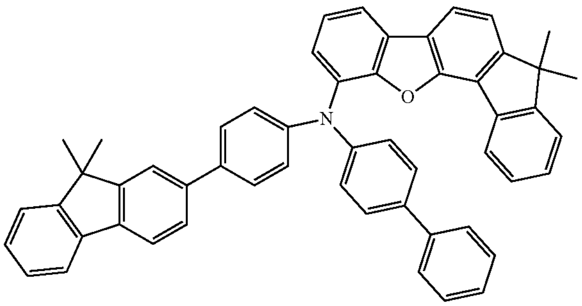

-continued
[A-19]
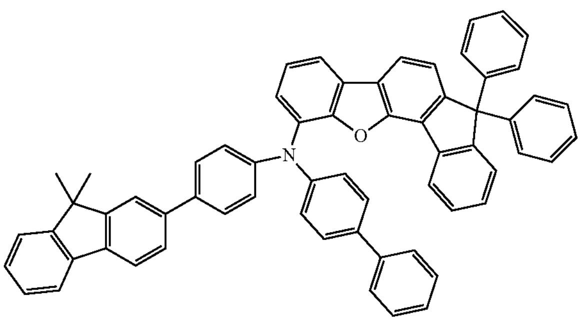
[A-20]
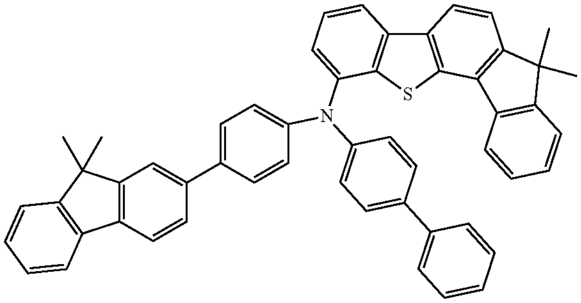
[A-21]
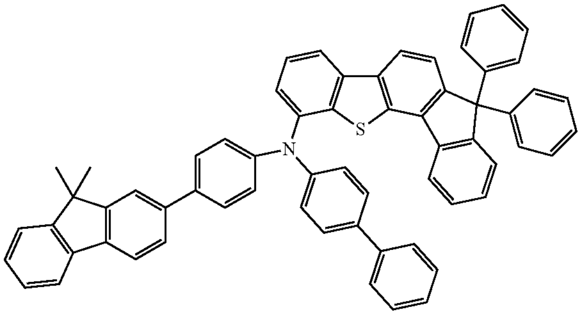
[A-22]
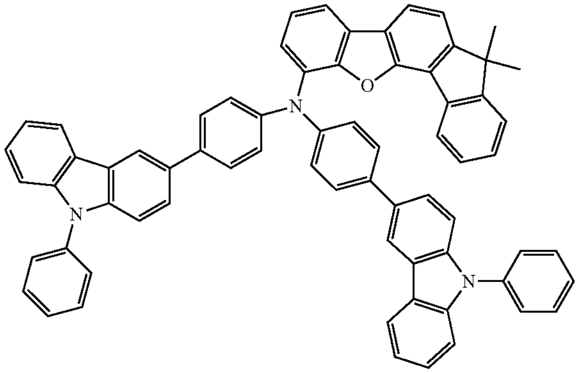
-continued
[A-23]
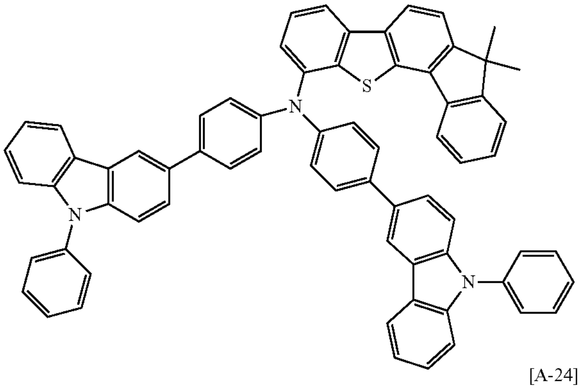
[A-24]
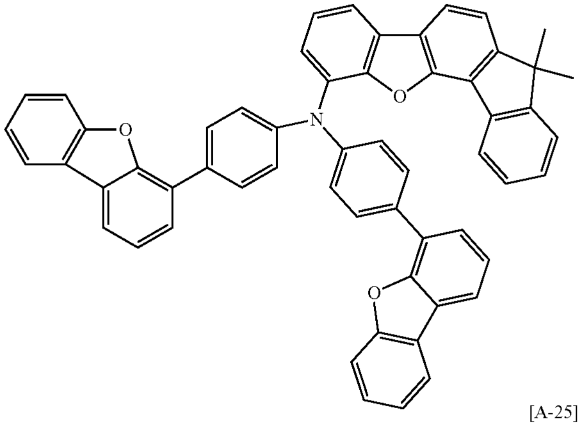
[A-25]
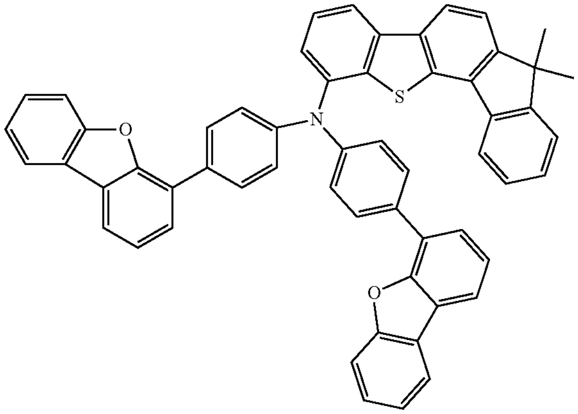
[A-26]
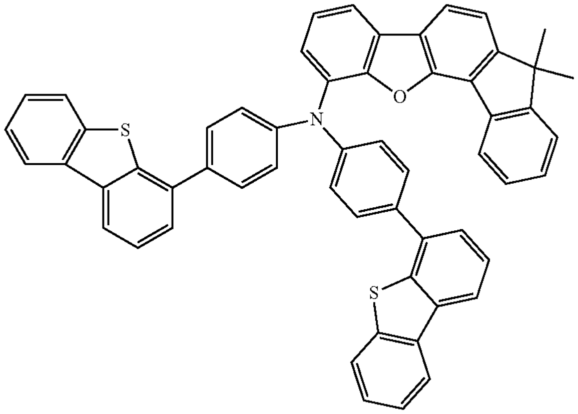

-continued
[A-27]
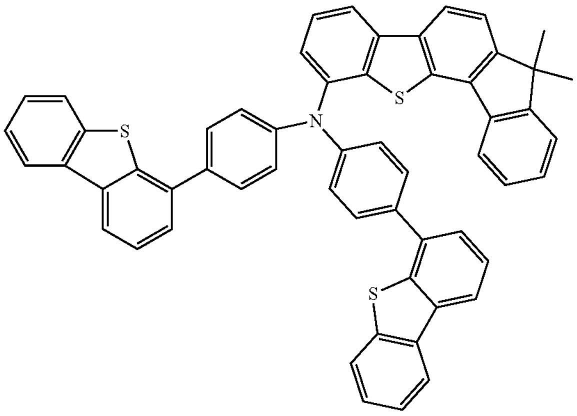
[A-28]
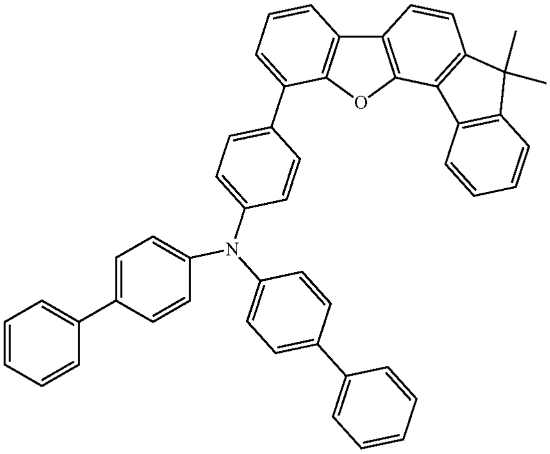
[A-29]
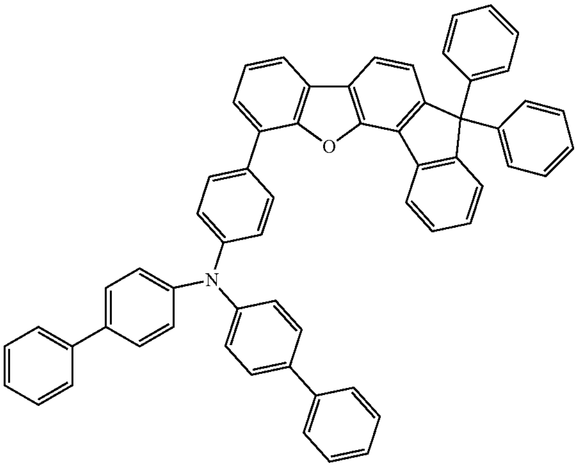
-continued
[A-30]
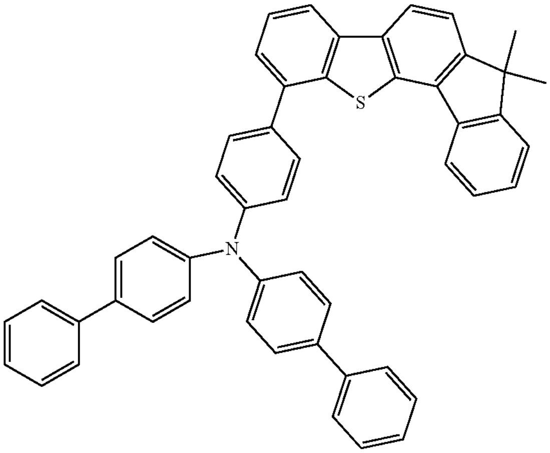
[A-31]
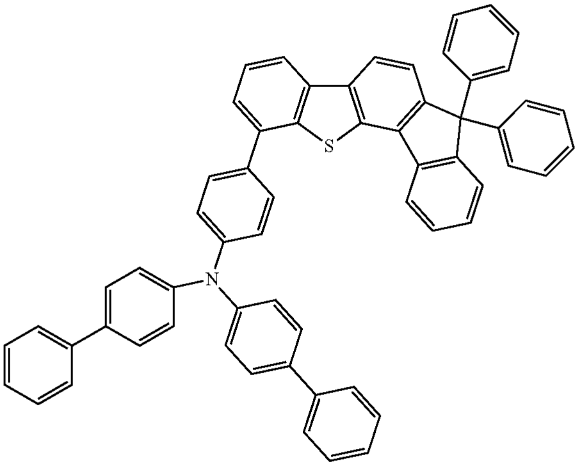
[A-32]
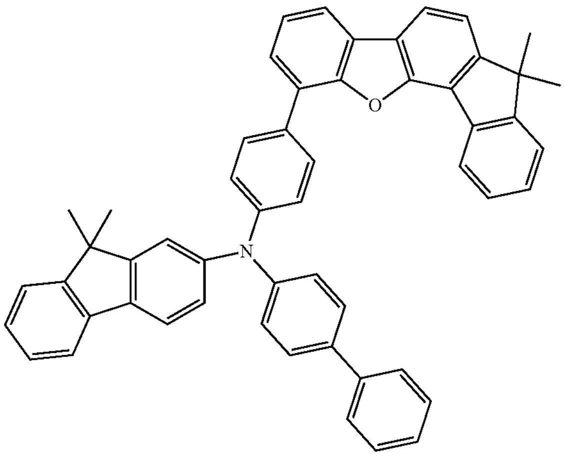

-continued
[A-33]
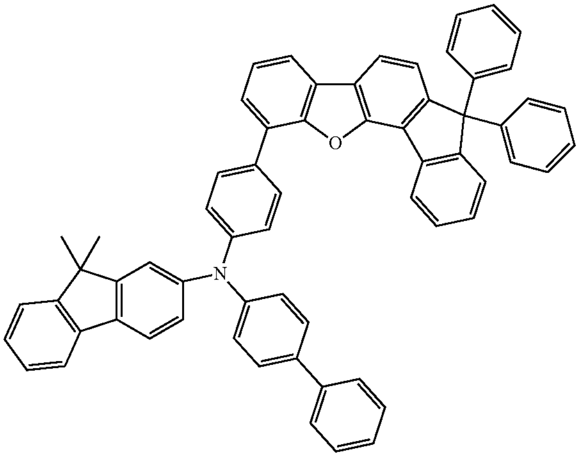
[A-34]
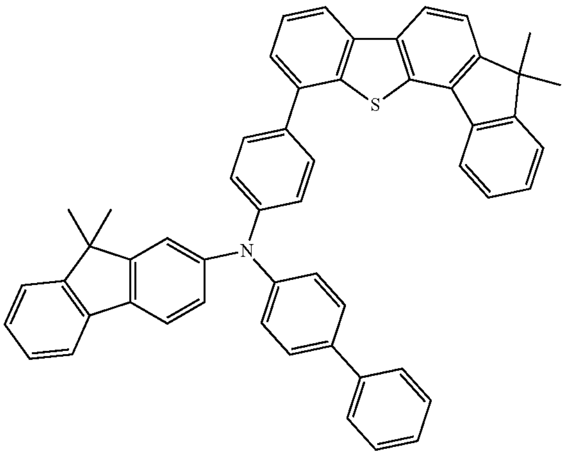
[A-35]
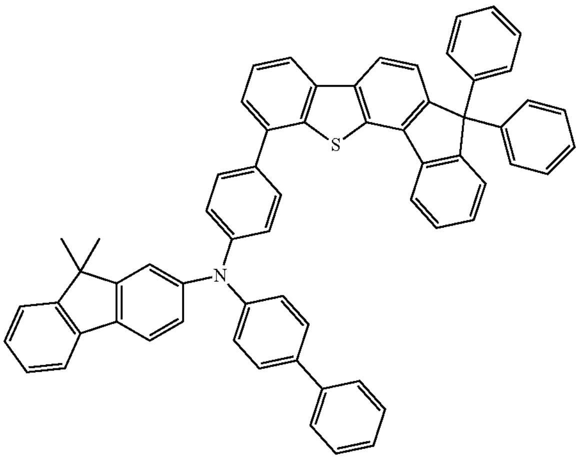
-continued
[A-36]
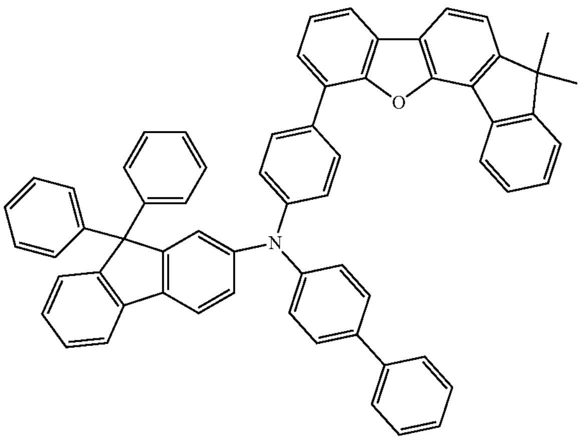
[A-37]
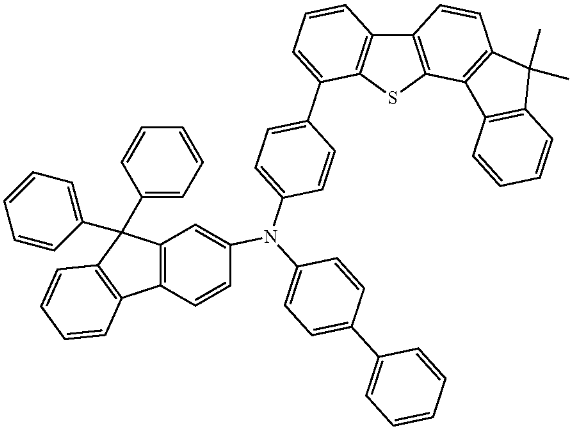
[A-38]
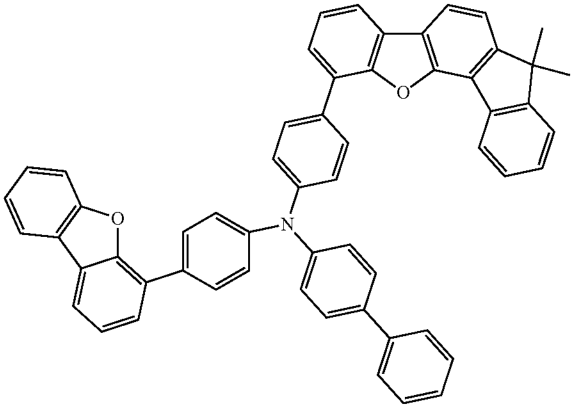

-continued
[A-39]
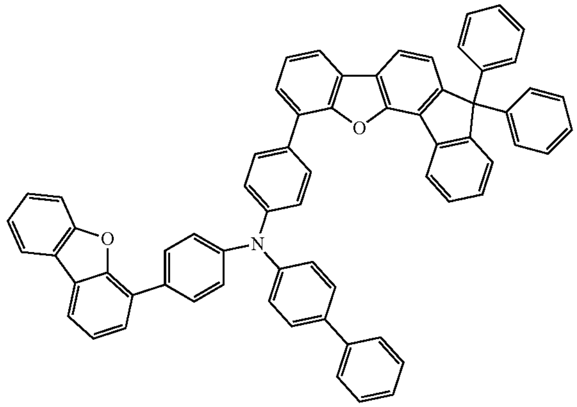
[A-40]
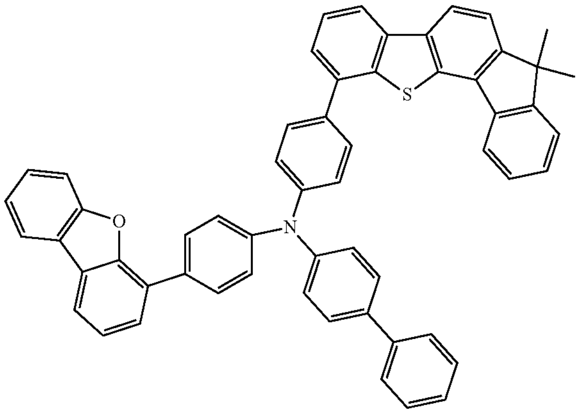
[A-41]
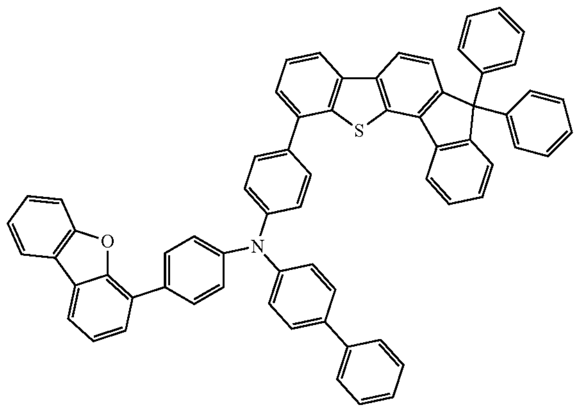
-continued
[A-42]
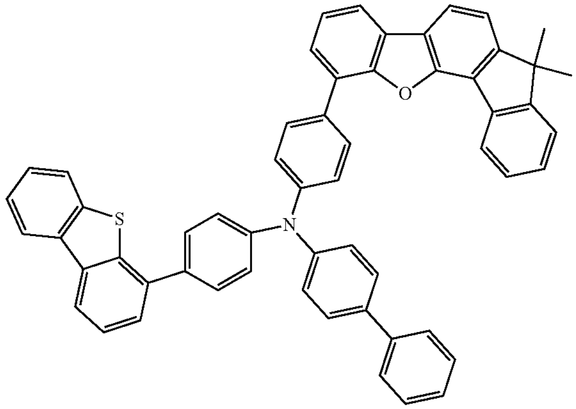
[A-43]
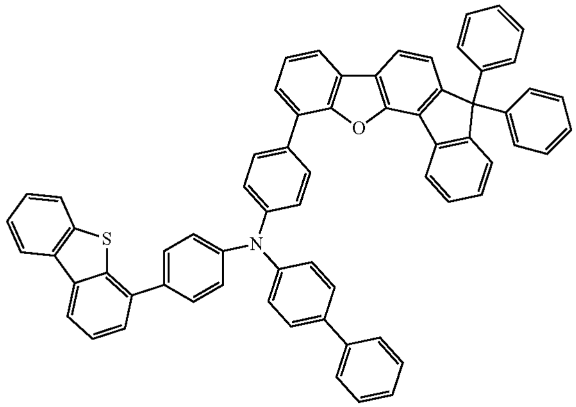
[A-44]
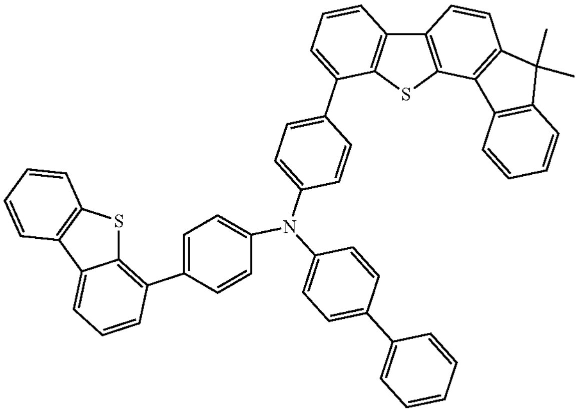

-continued
[A-45]
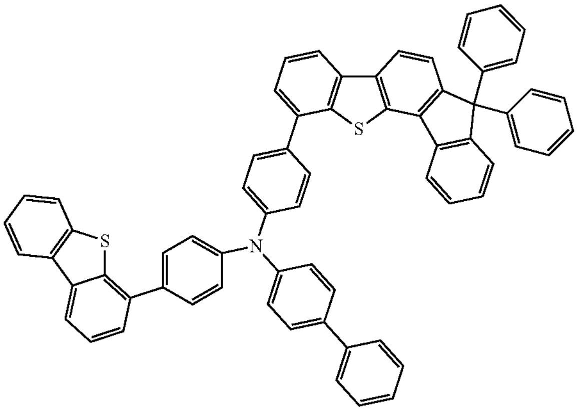
[A-46]
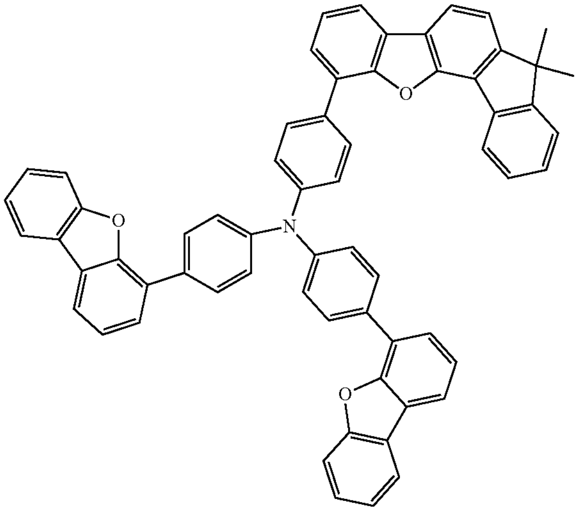
[A-47]
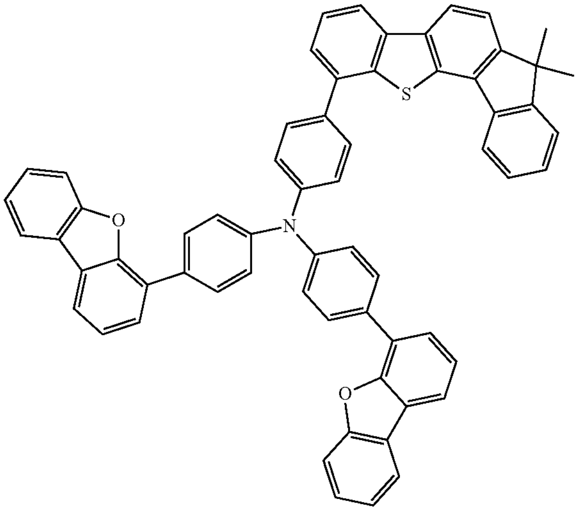
-continued
[A-48]
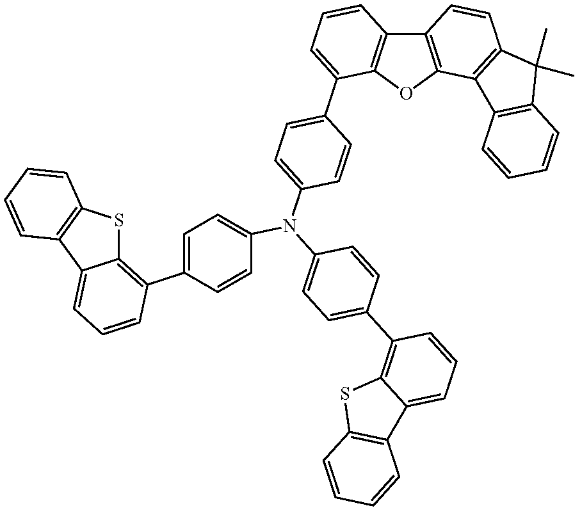
[A-49]
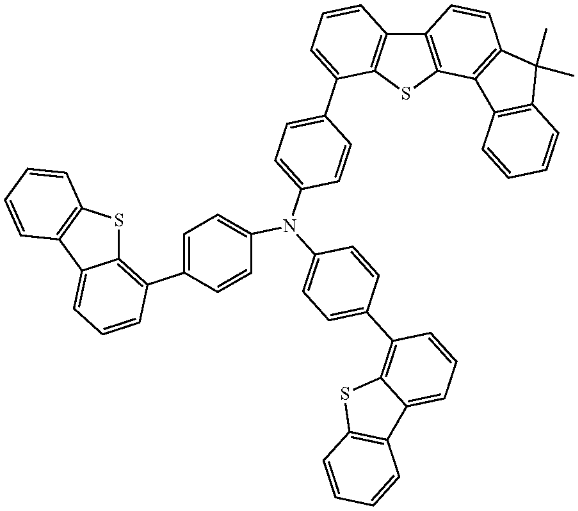
[A-50]
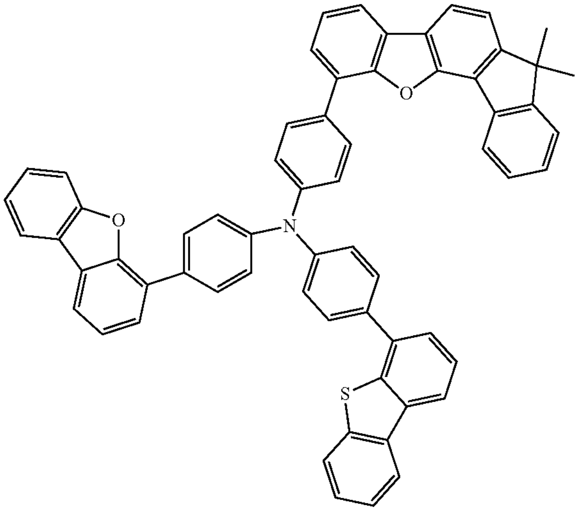

-continued
[A-51]
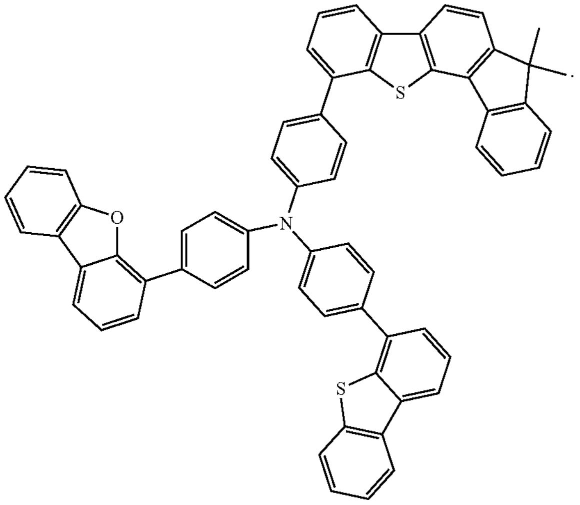
9. The compound as claimed in claim 1, wherein the compound is represented by one of the following Chemical Formulae B-1 to B-32:
[B-1]
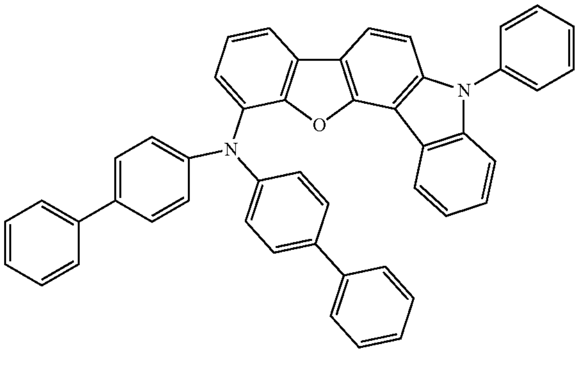
[B-2]
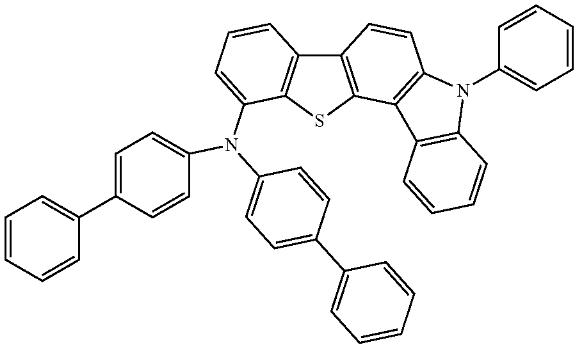
-continued
[B-3]
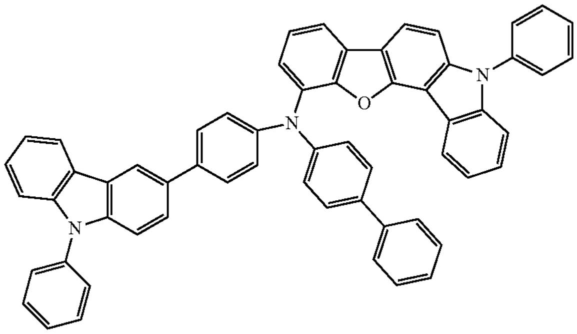
[B-4]
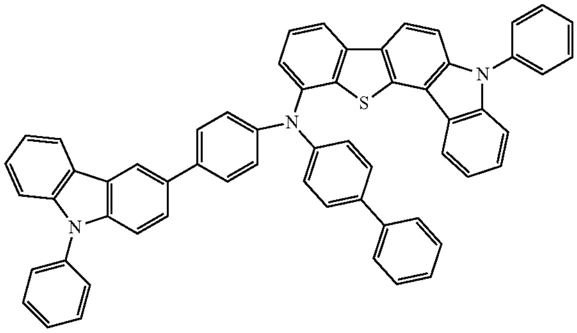
[B-5]
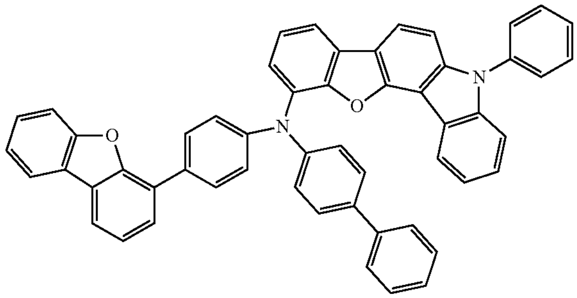
[B-6]
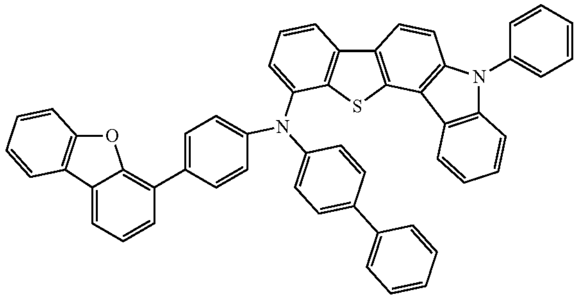

-continued
[B-7]
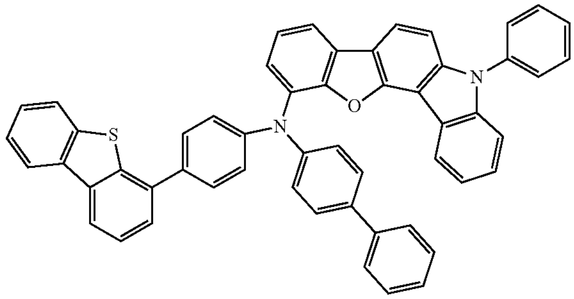
[B-8]
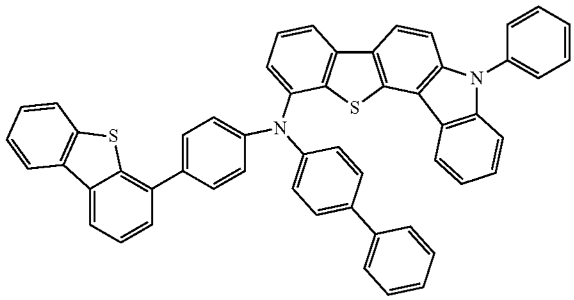
[B-9]
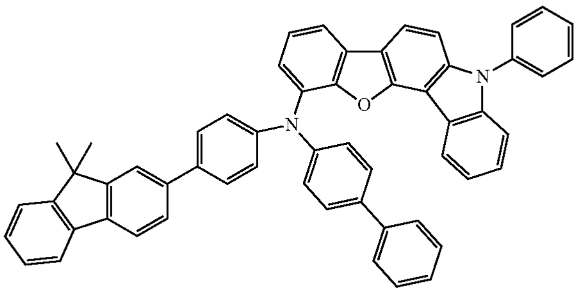
[B-10]
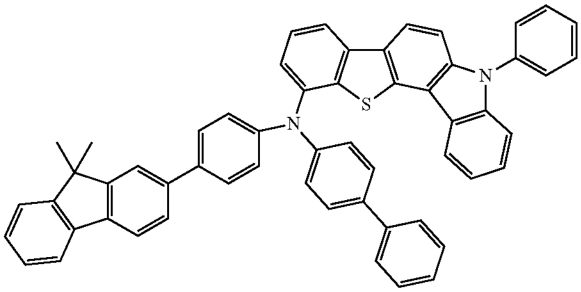
-continued
[B-11]
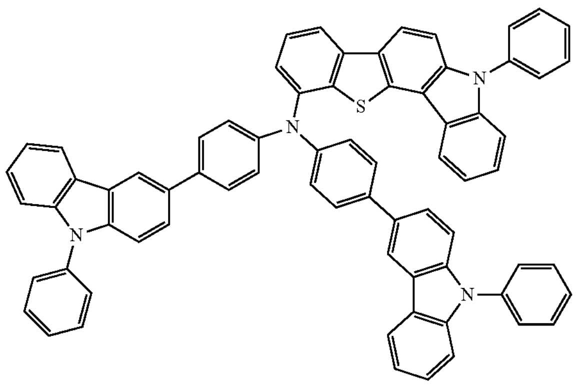
[B-12]
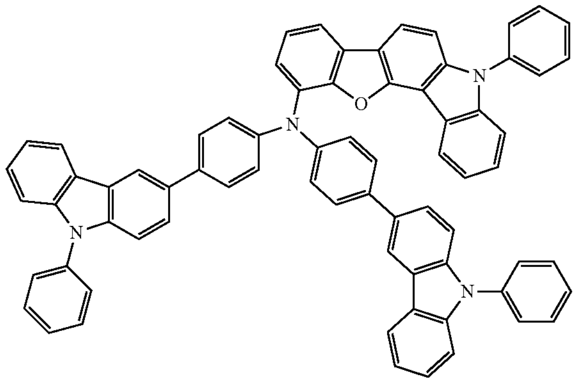
[B-13]
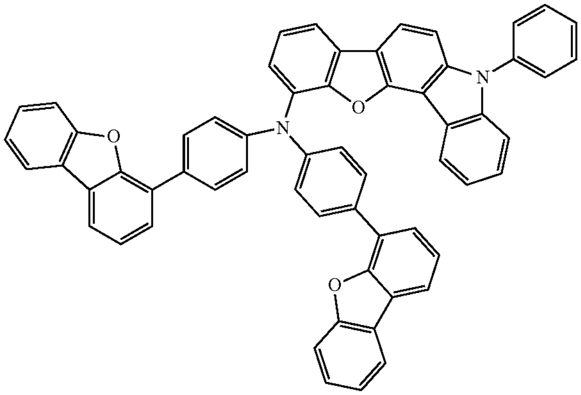
[B-14]
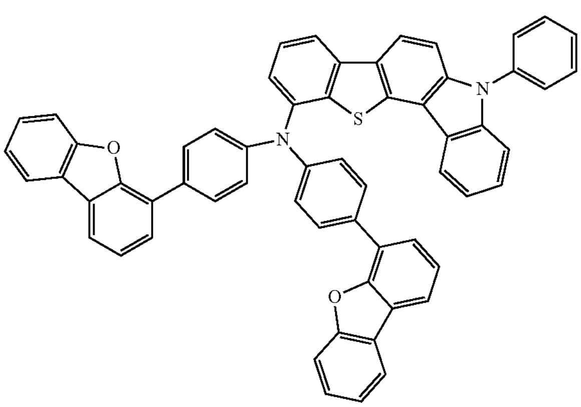

-continued
[B-15]
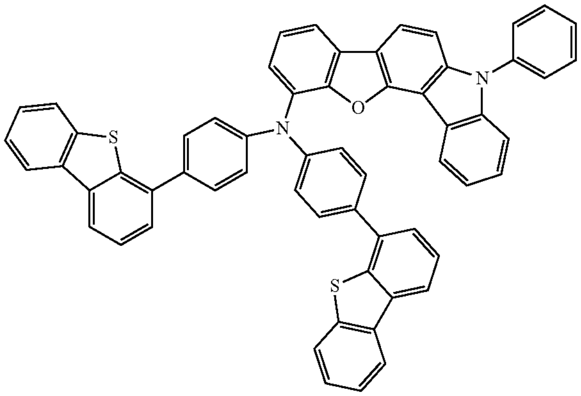
[B-16]
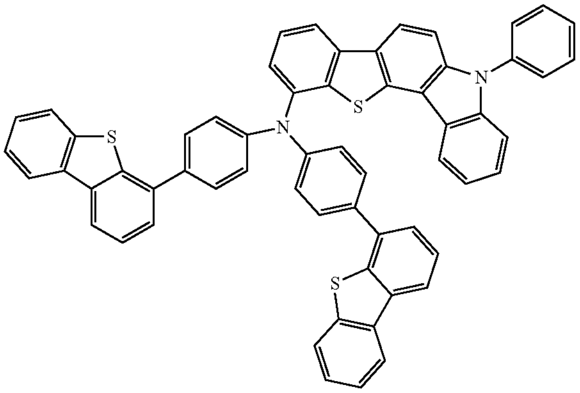
[B-17]
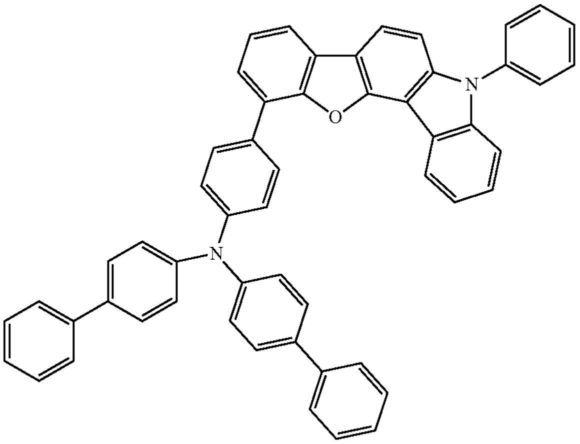
-continued
[B-18]
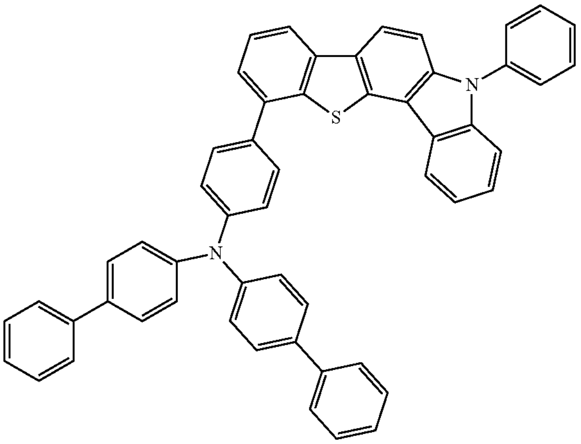
[B-19]
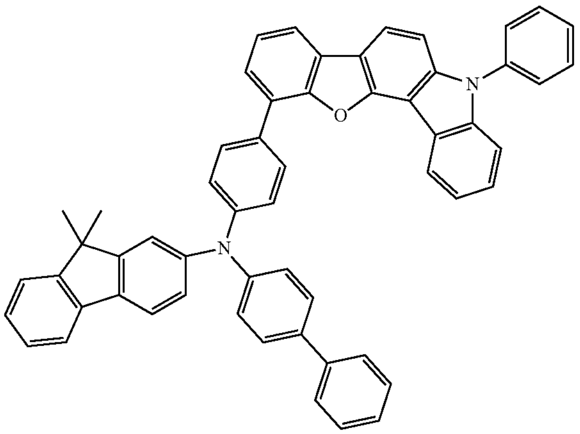
[B-20]
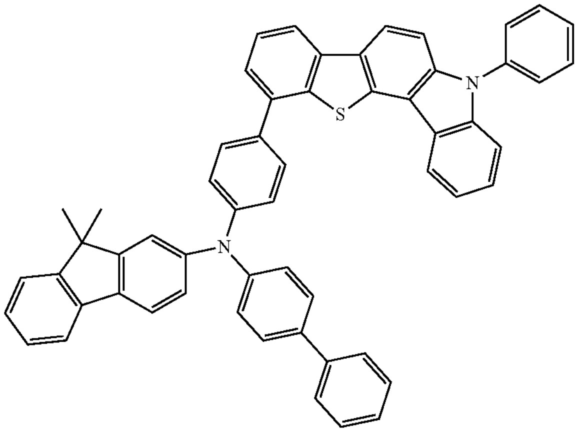

-continued
[B-21]
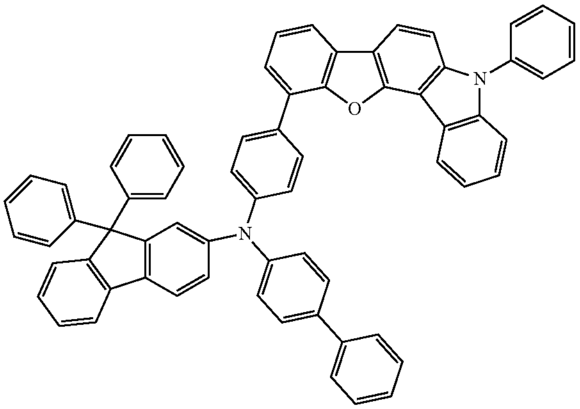
[B-22]
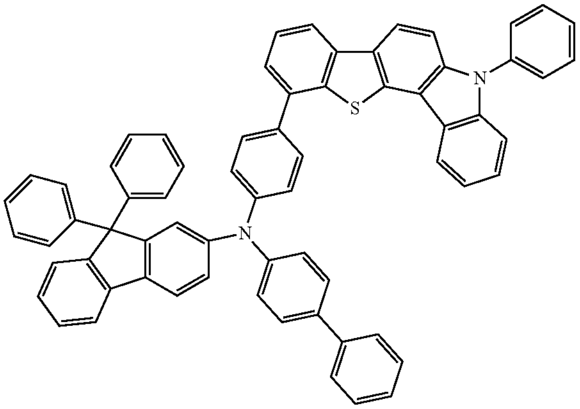
[B-23]
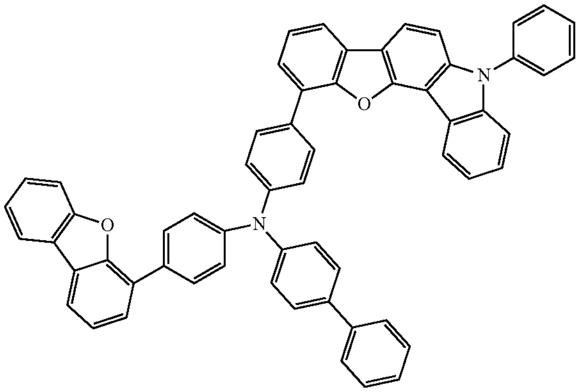
-continued
[B-24]
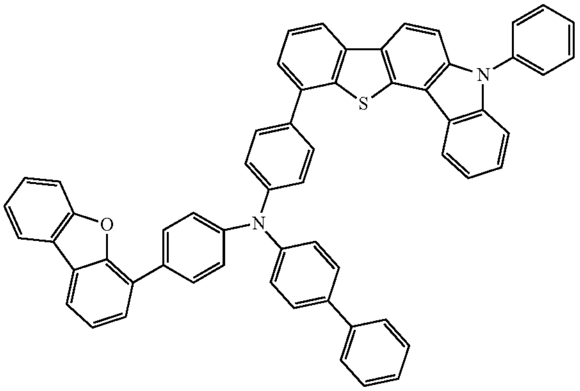
[B-25]
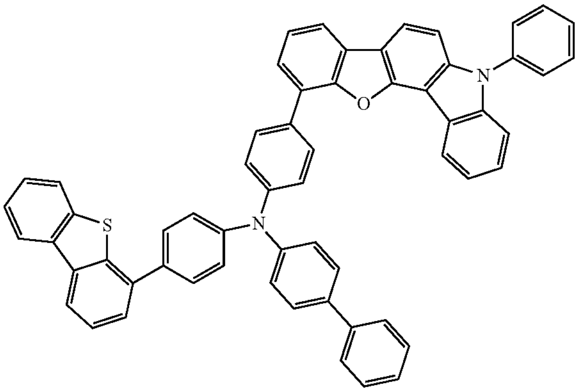
[B-26]
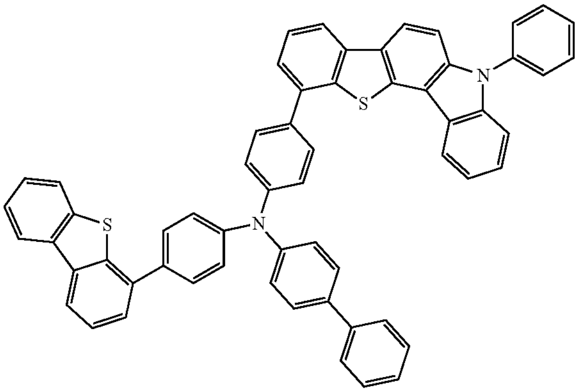

-continued
[B-27]
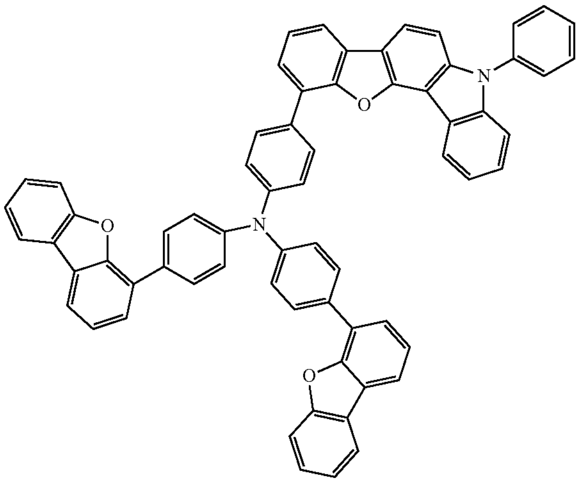
[B-28]
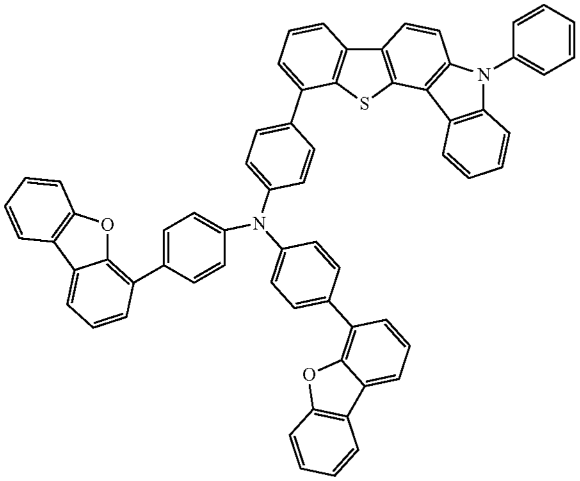
[B-29]
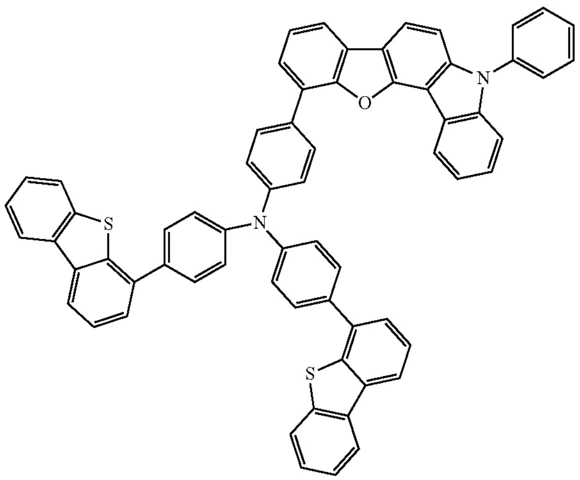
-continued
[B-30]
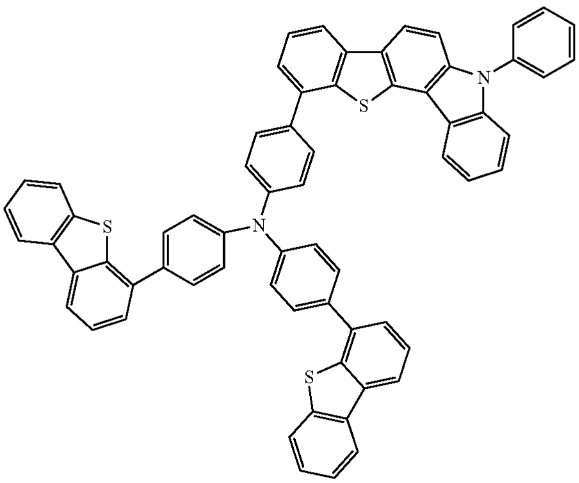
[B-31]
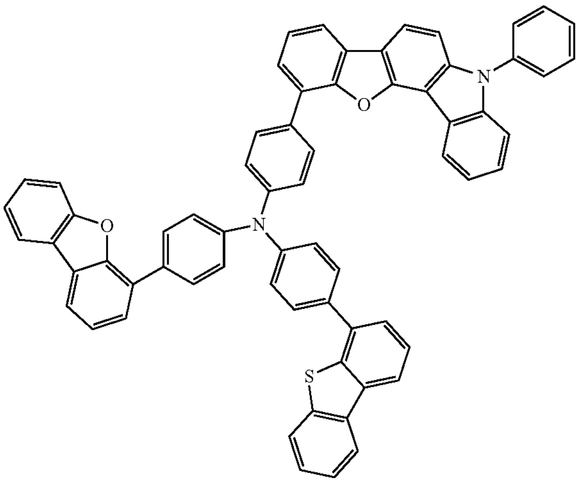
[B-32]
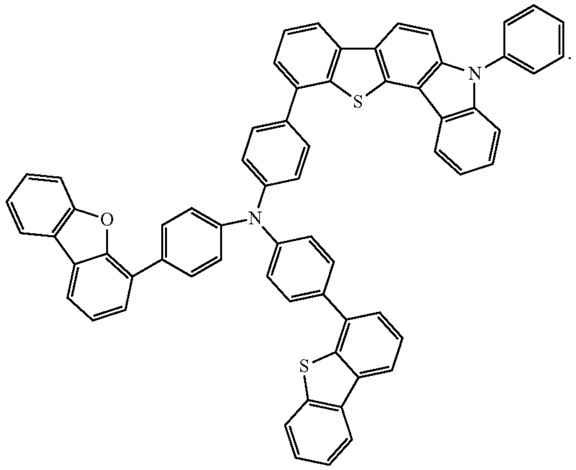
10. The compound as claimed in claim 1, wherein the compound is represented by one of the following Chemical Formulae C-1 to C-40:

-continued
[C-1]
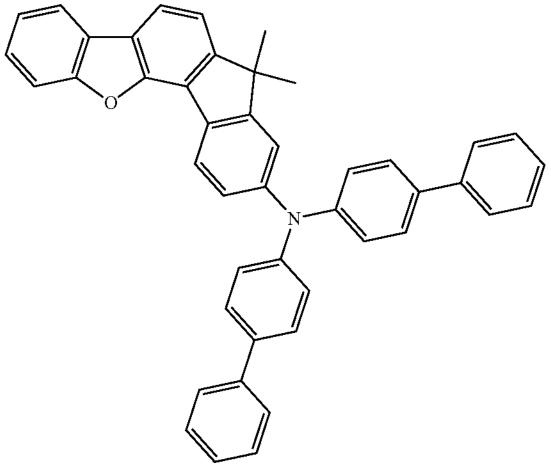
[C-2]
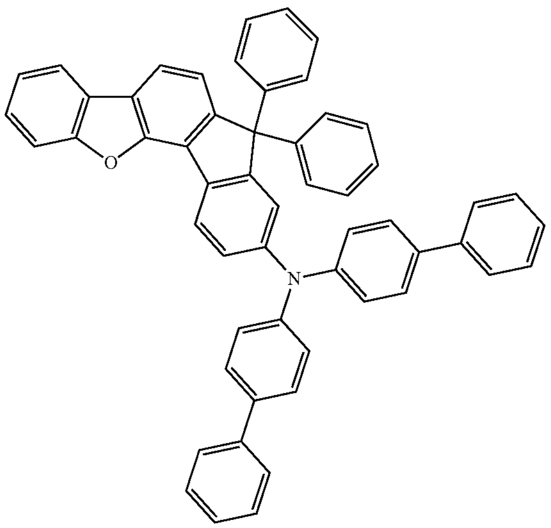
[C-3]
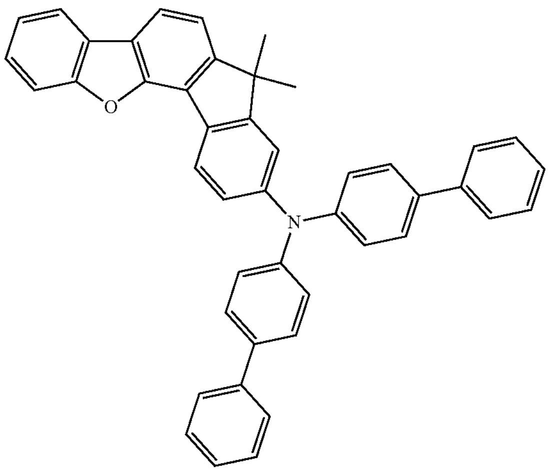
[C-4]
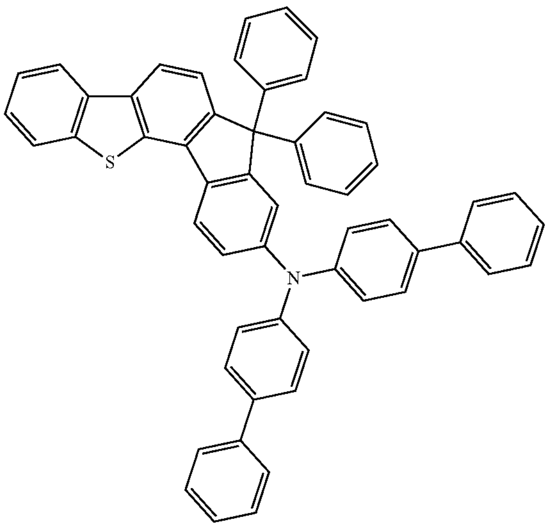
[C-5]
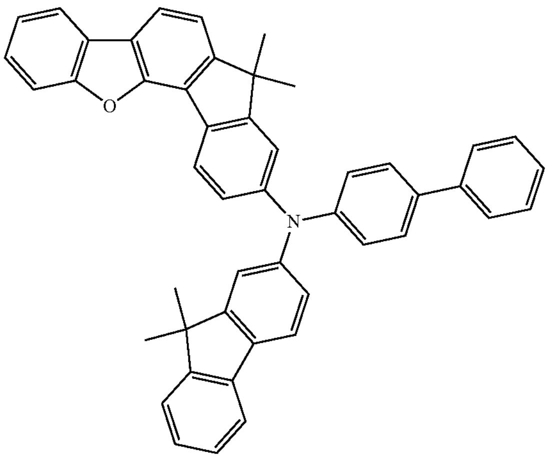
[C-6]
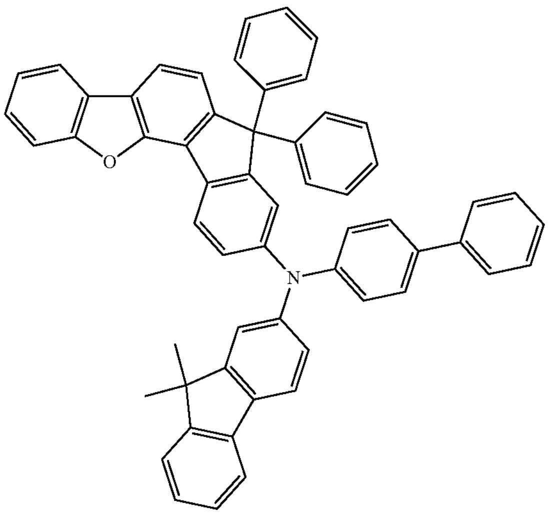

-continued
[C-7]
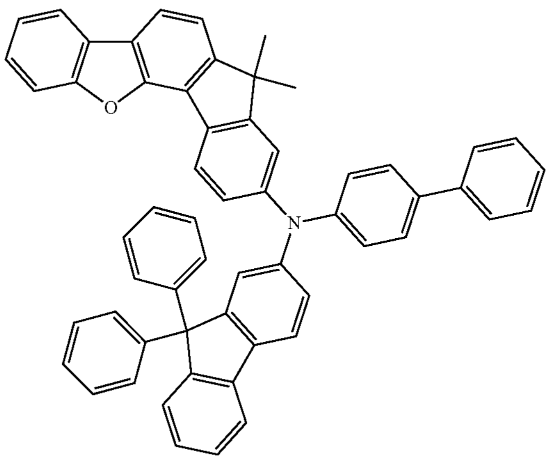
[C-8]
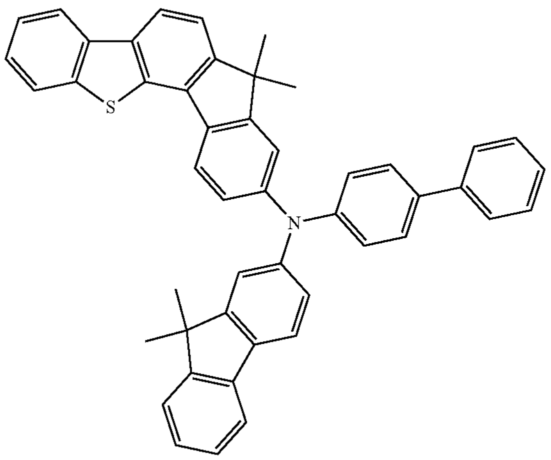
[C-9]
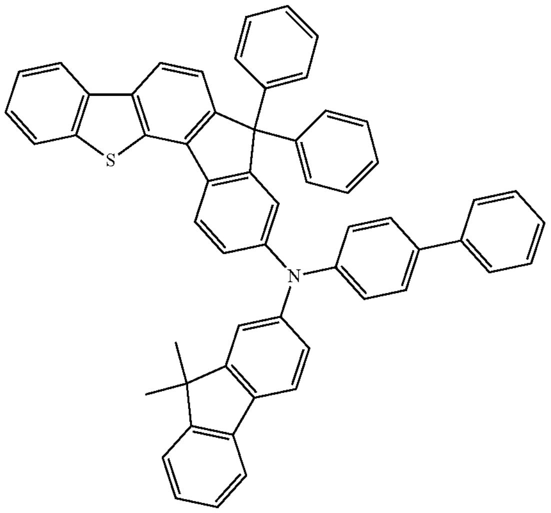
-continued
[C-10]
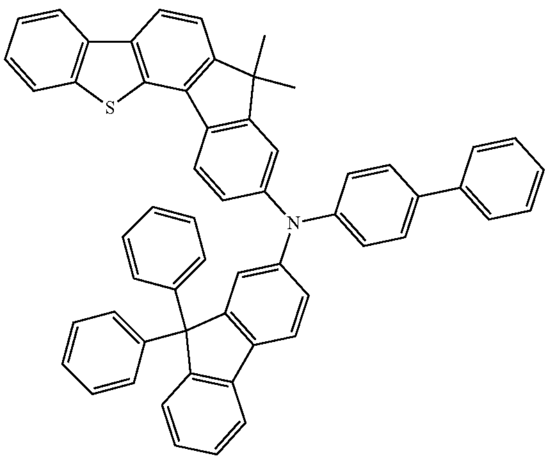
[C-11]
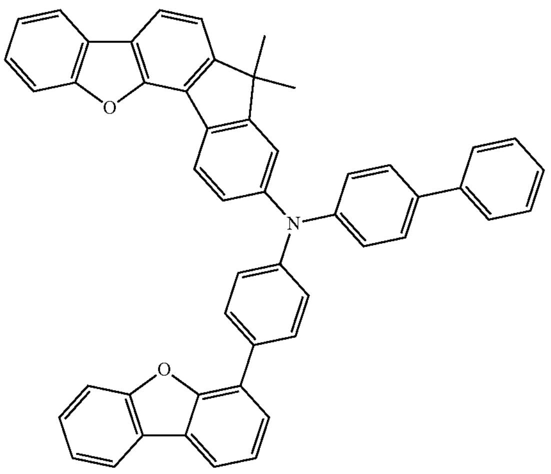
[C-12]
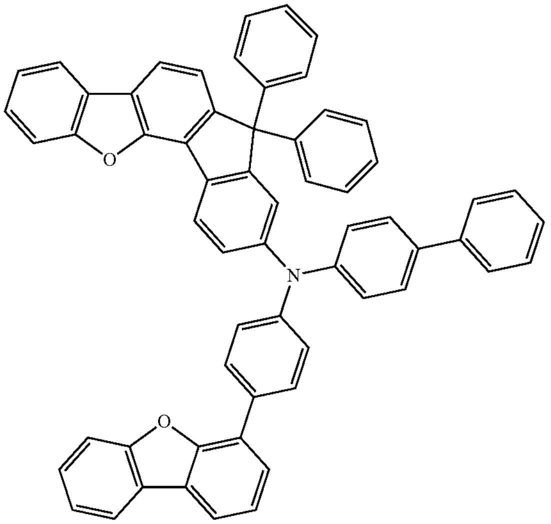

-continued
[C-13]
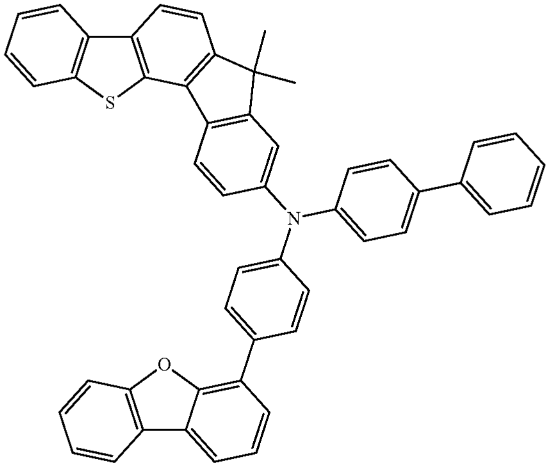
[C-14]
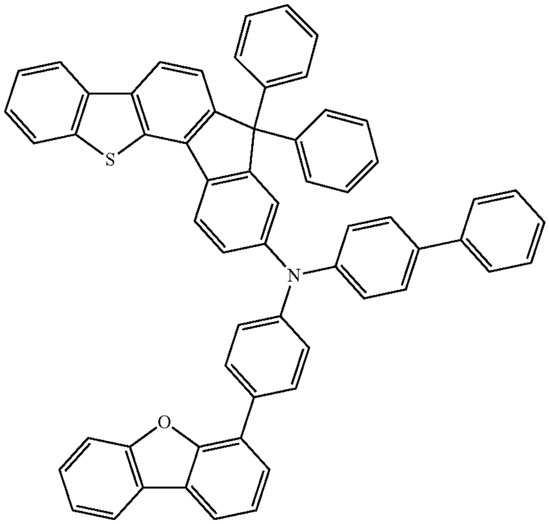
[C-15]
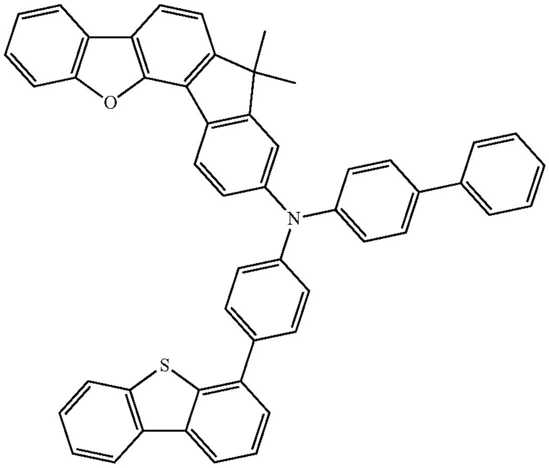
-continued
[C-16]
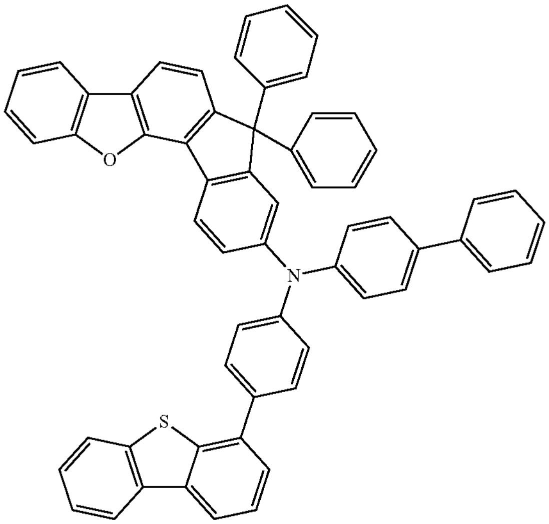
[C-17]
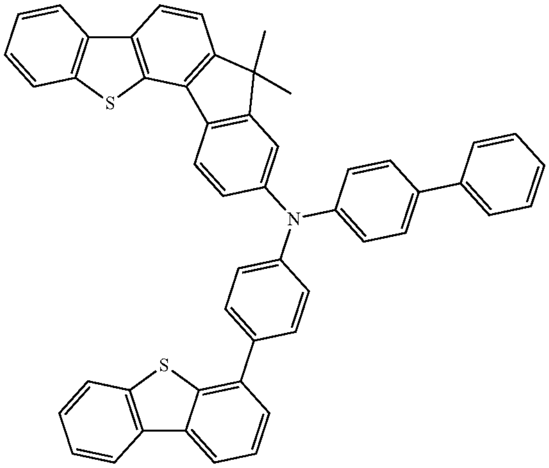
[C-18]
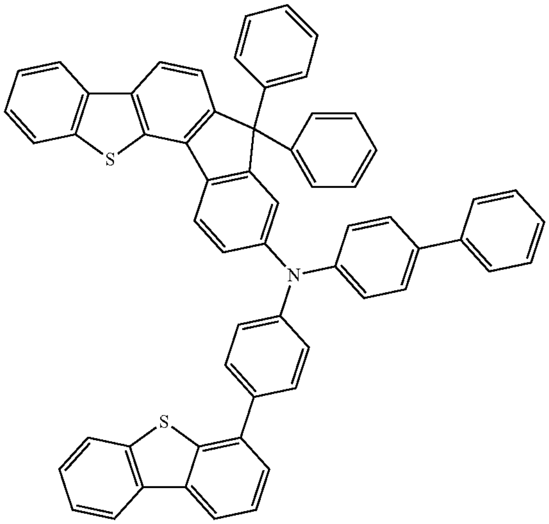

-continued
[C-19]
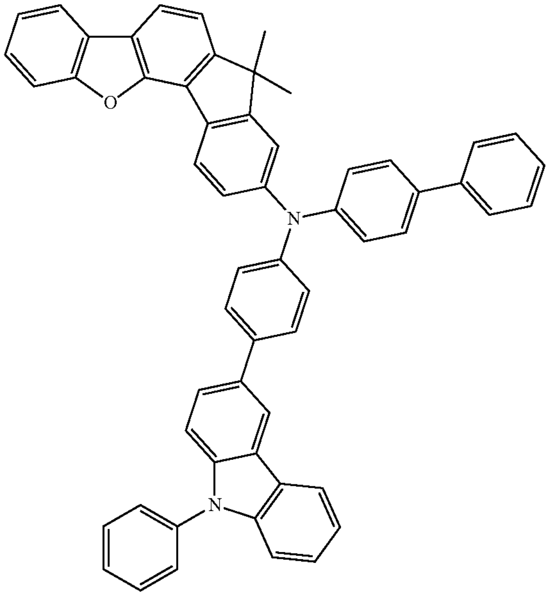
[C-20]
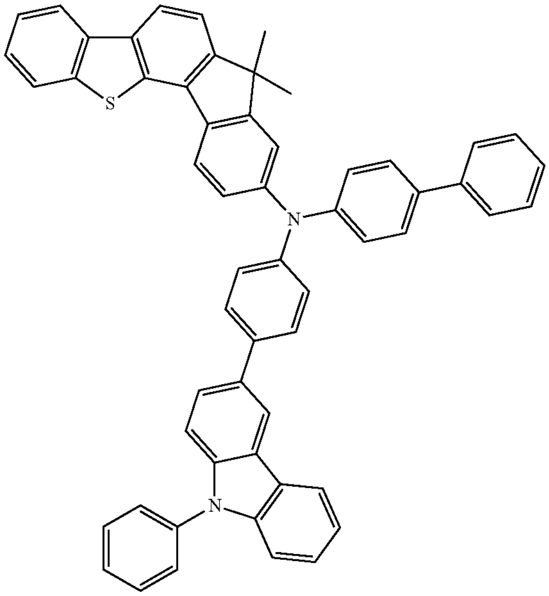
-continued
[C-21]
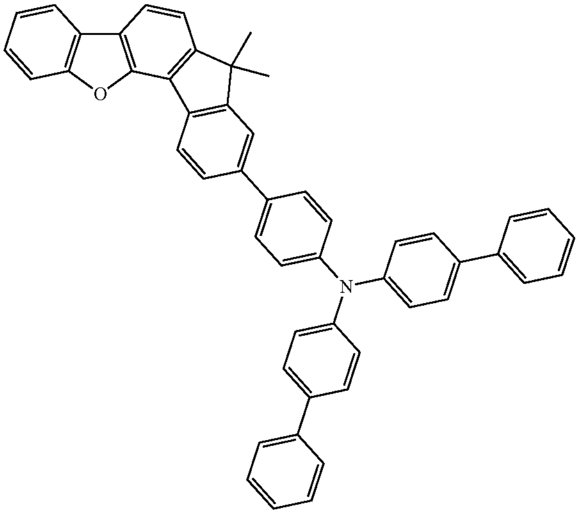
[C-22]
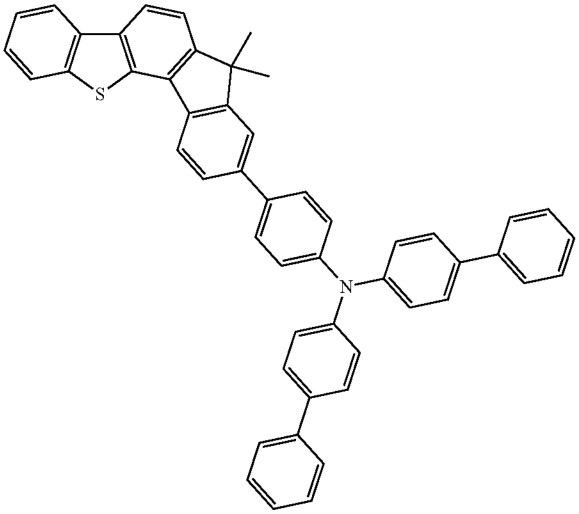
[C-23]
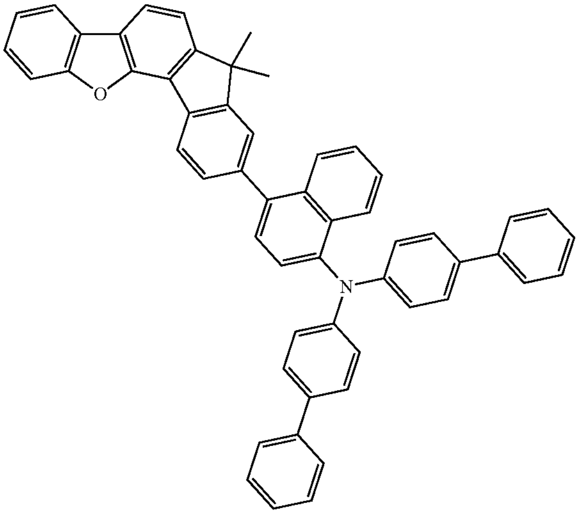

[C-24]
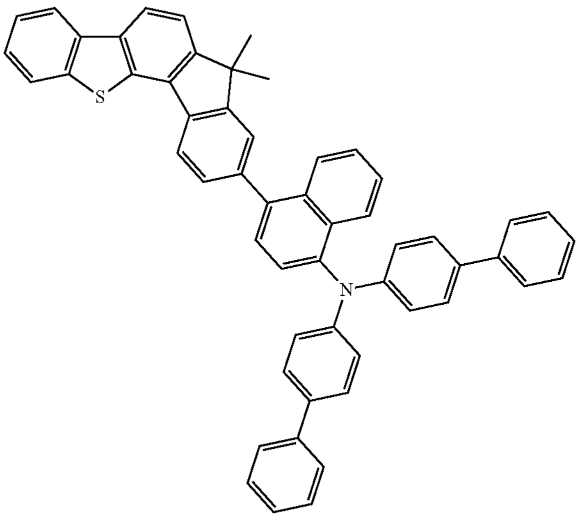
[C-25]
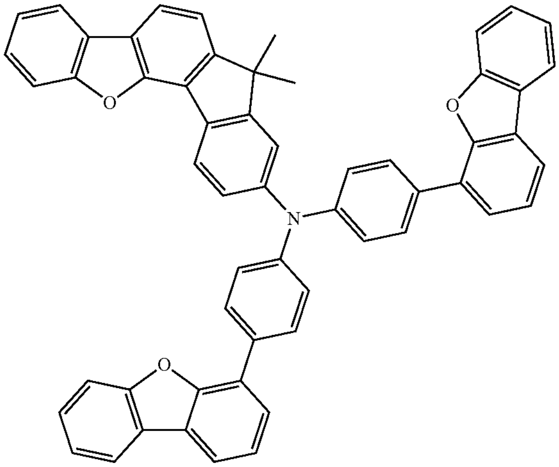
[C-26]
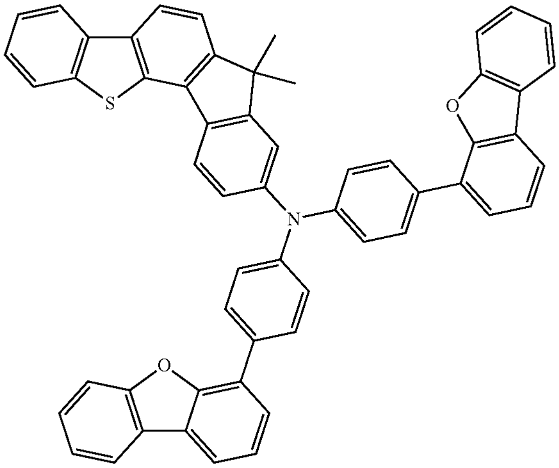
[C-27]
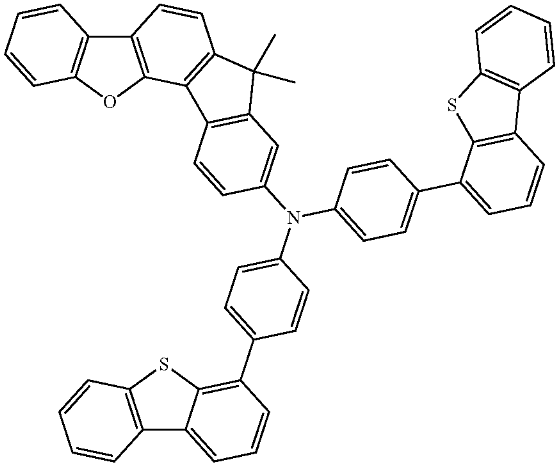
[C-28]
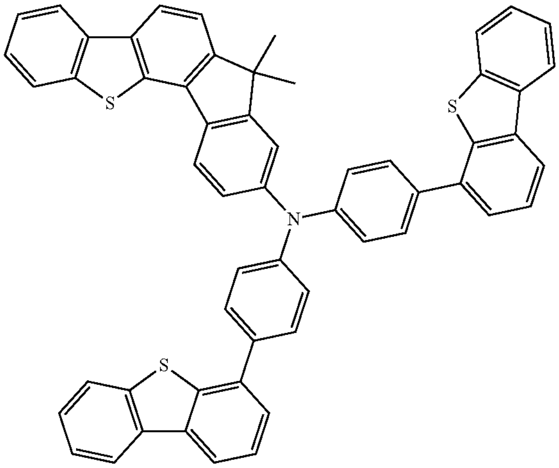
[C-29]
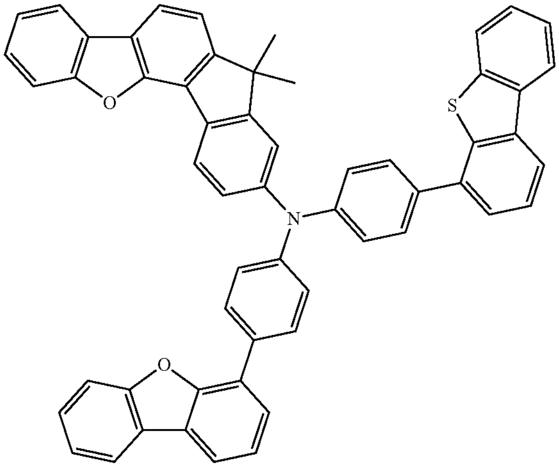

-continued
[C-30]
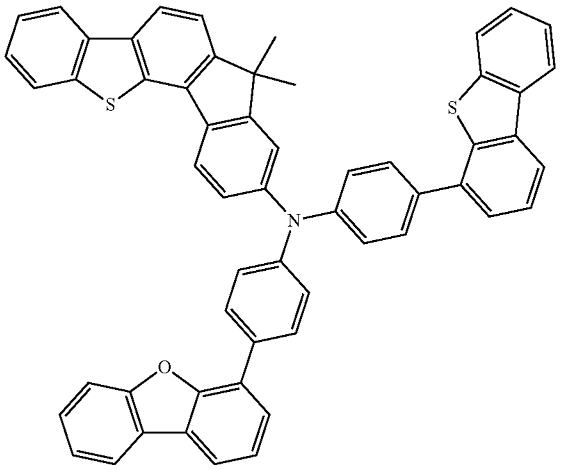
[C-31]
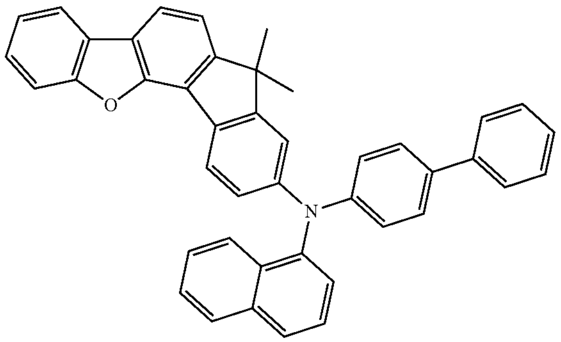
[C-32]
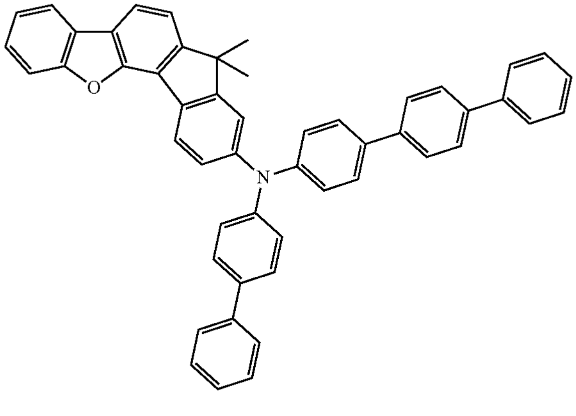
-continued
[C-33]
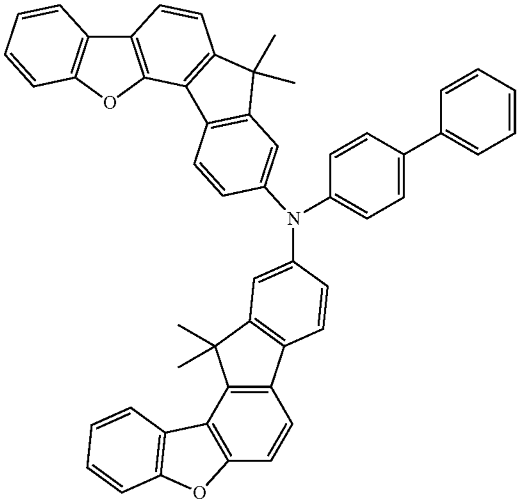
[C-34]
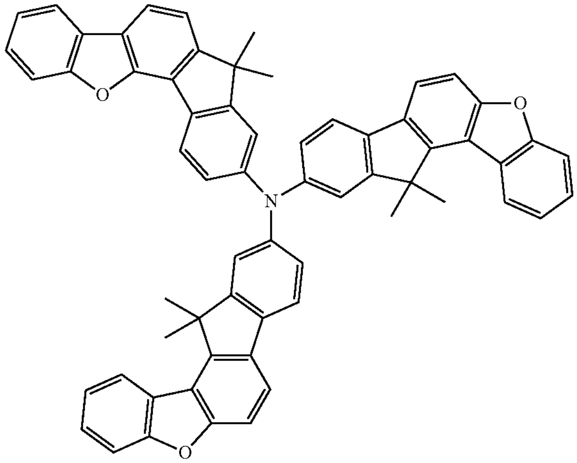
[C-35]
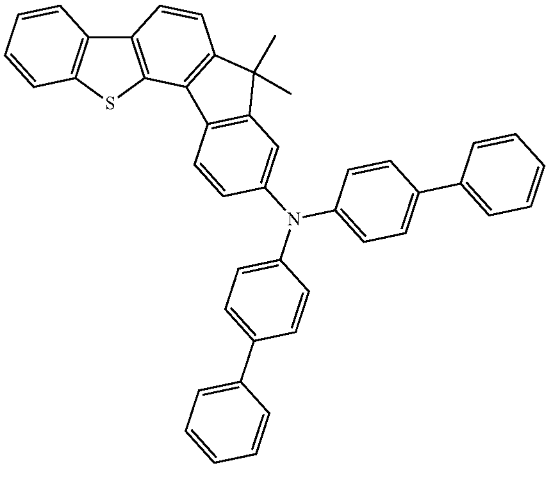

-continued
[C-36]
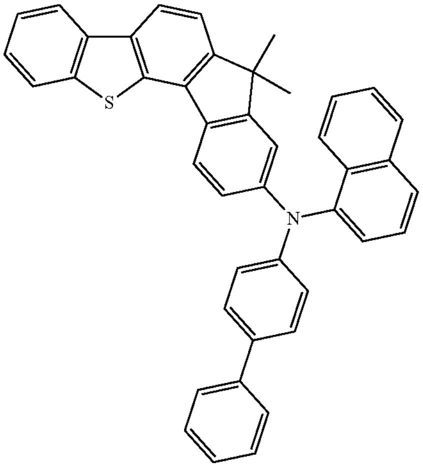
[C-37]
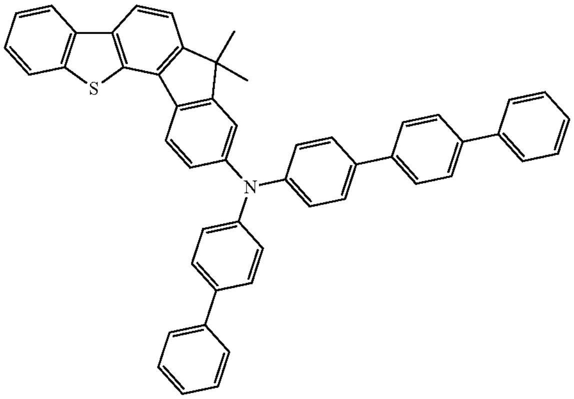
[C-38]
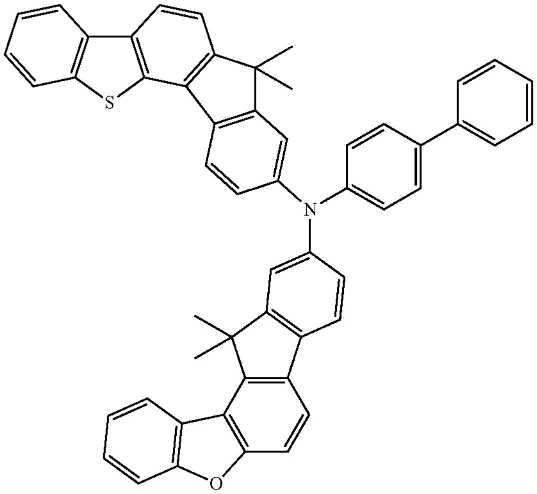
-continued
[C-39]
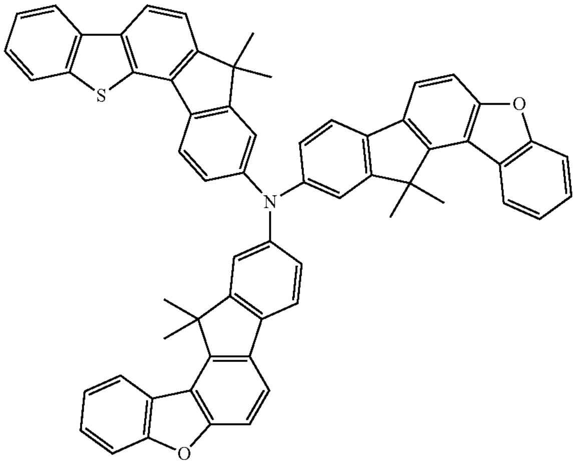
[C-40]
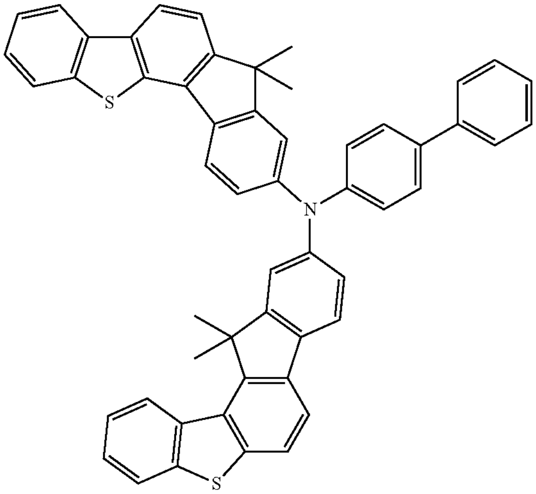
[C-41]
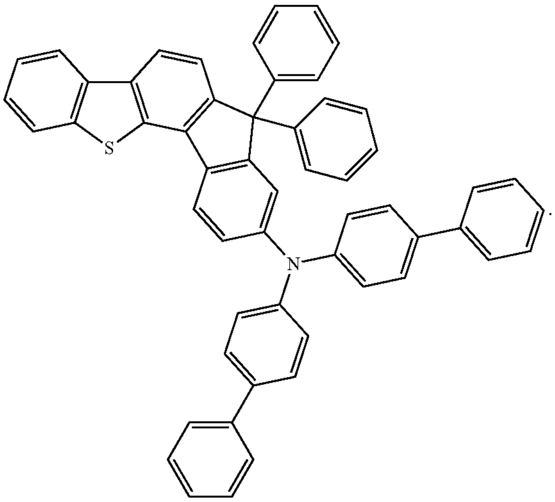
11. The compound as claimed in claim 1, wherein the compound is represented by one of the following Chemical Formulae D-1 to D-20:

[D-1]
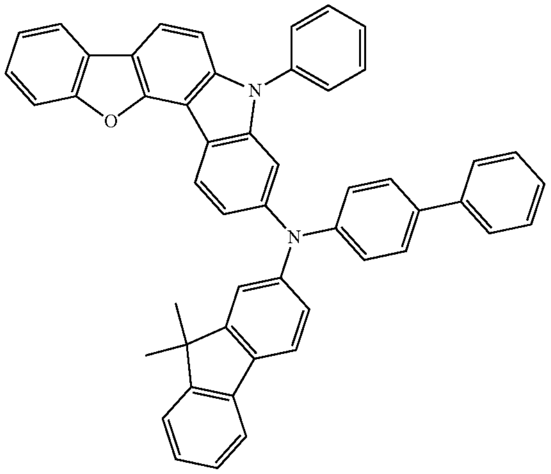
[D-2]
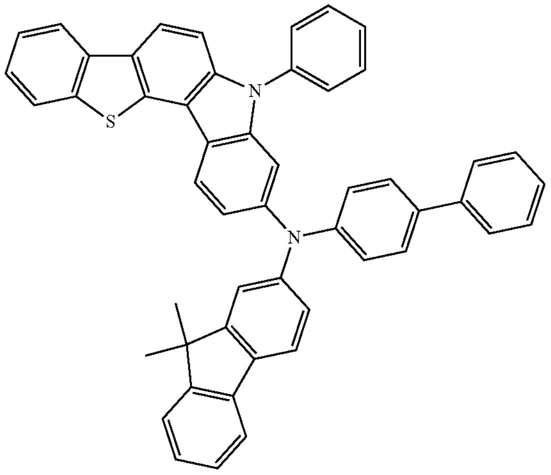
[D-3]
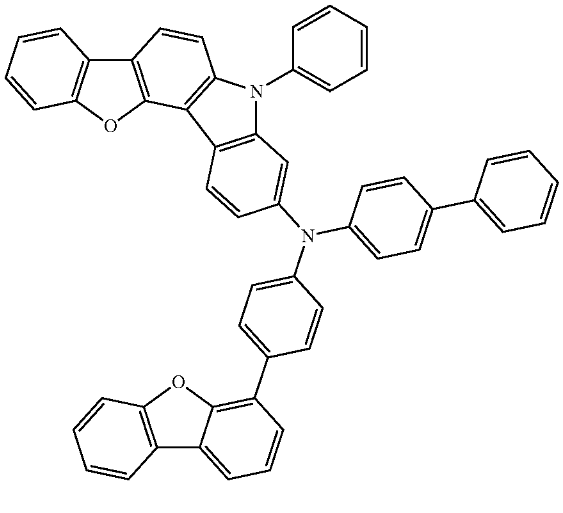
-continued
[D-4]
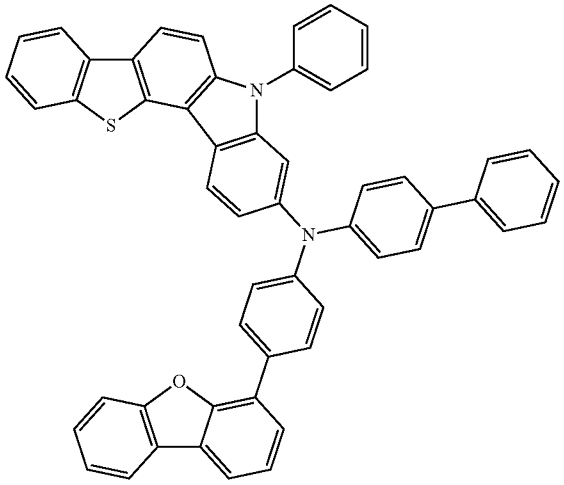
[D-5]
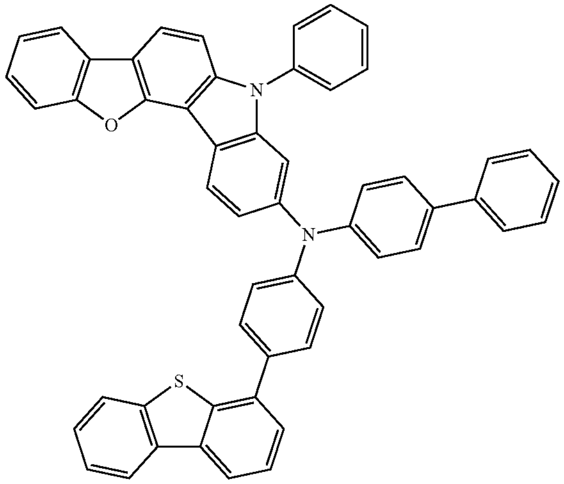
[D-6]
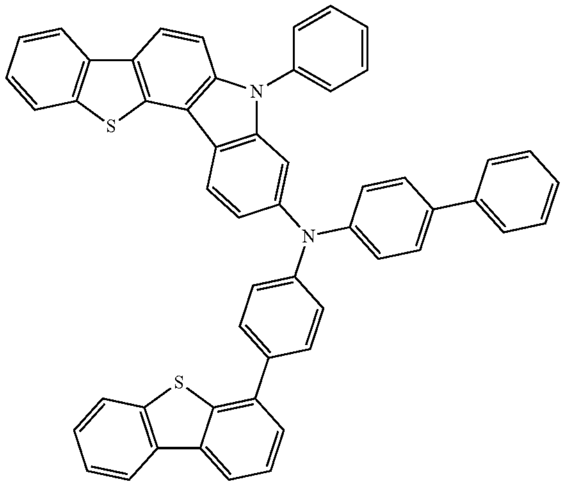

-continued
[D-7]
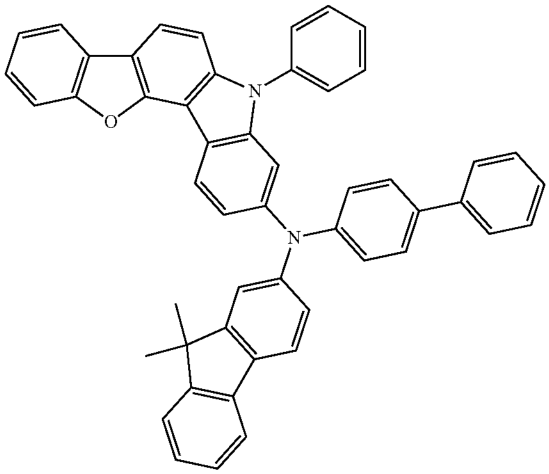
[D-8]
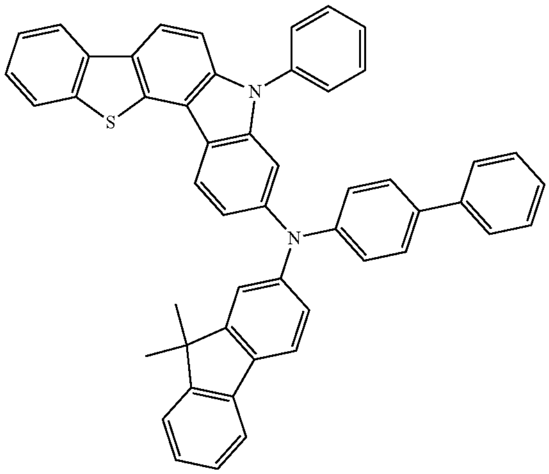
[D-9]
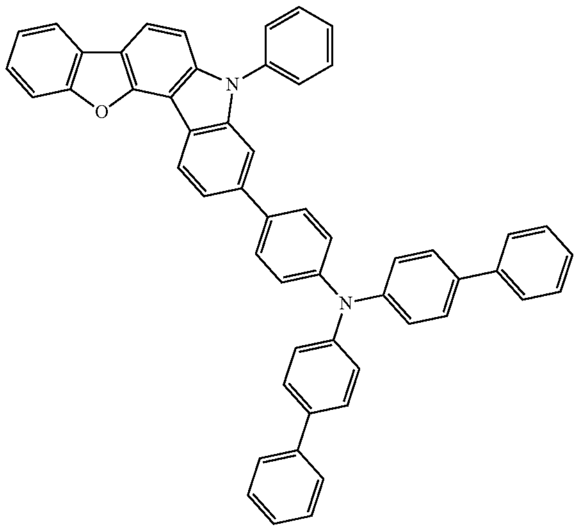
-continued
[D-10]
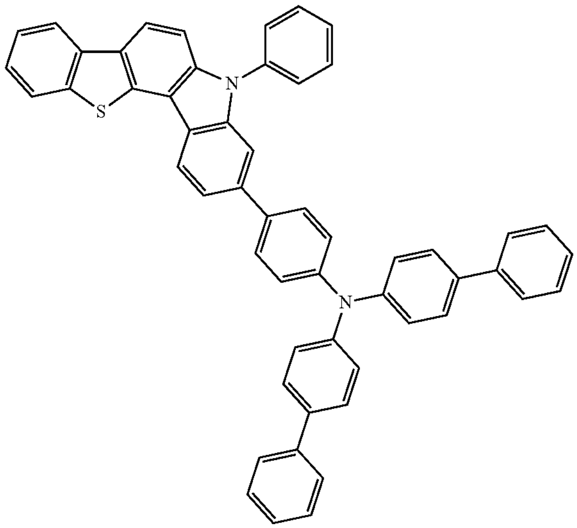
[D-11]
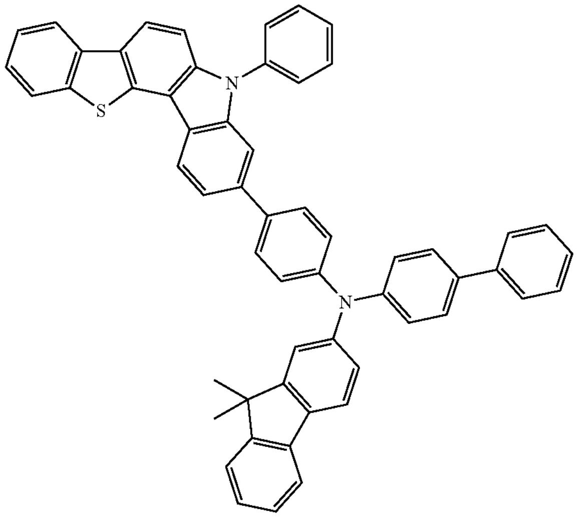
[D-12]
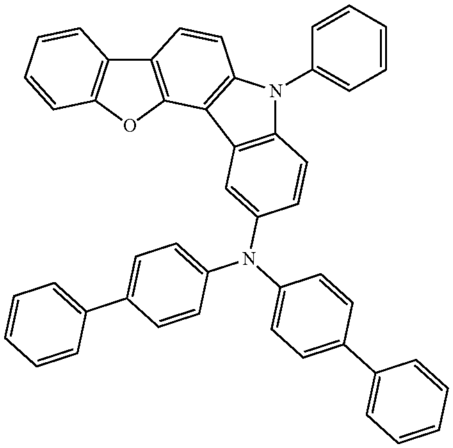

-continued
[D-13]
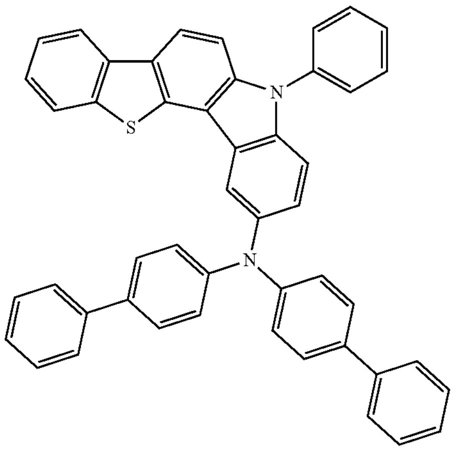
[D-14]
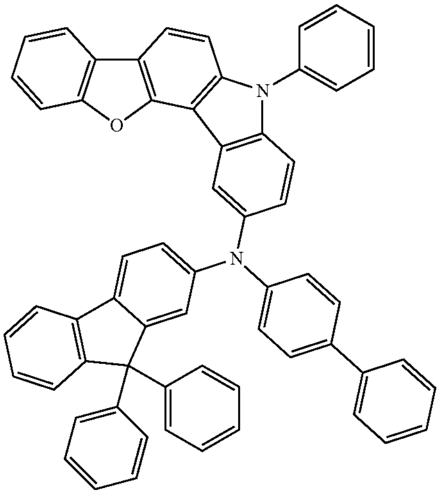
[D-15]
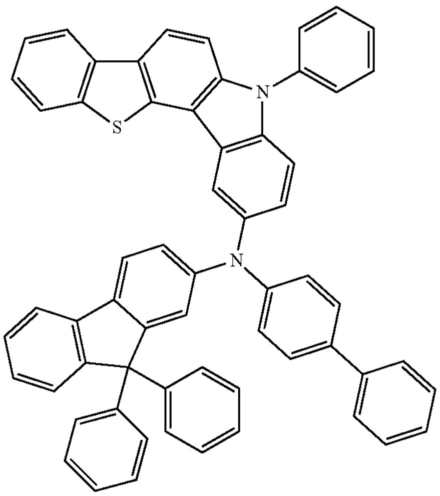
-continued
[D-16]
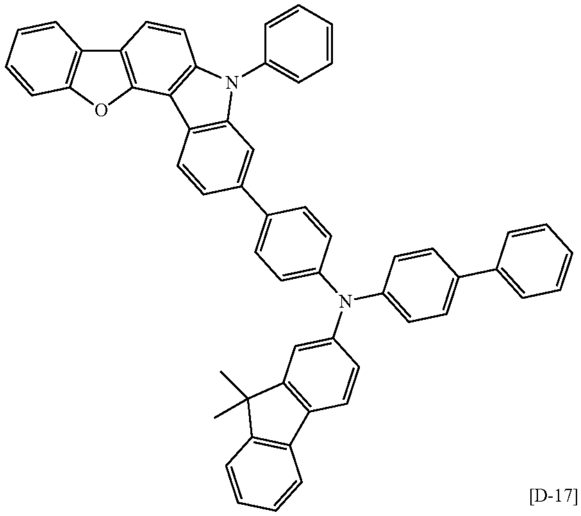
[D-17]
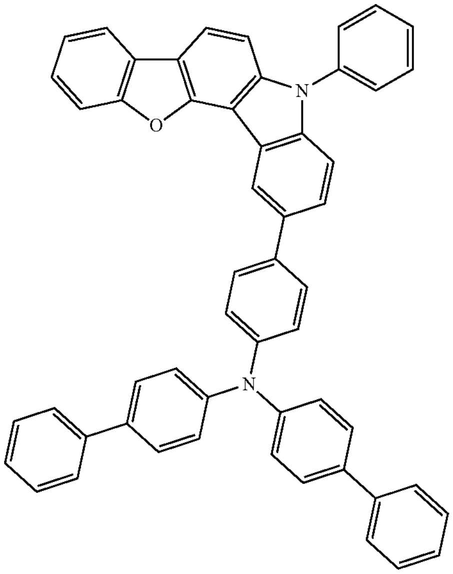
[D-18]
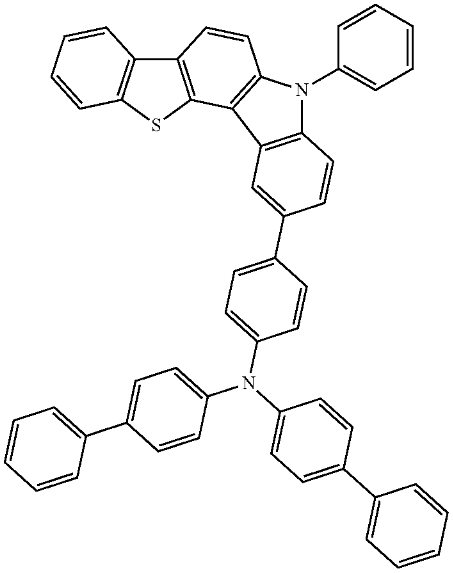

-continued

[D-19]

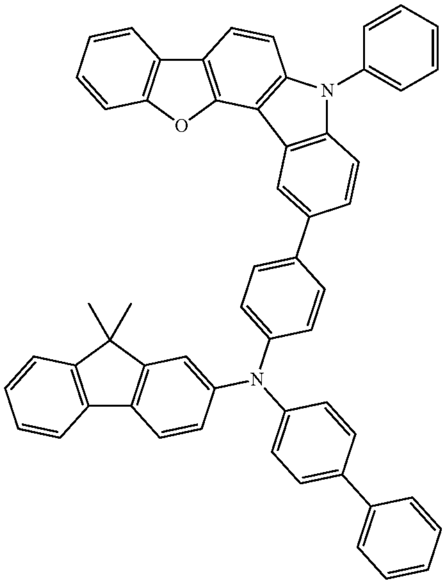

[D-20]

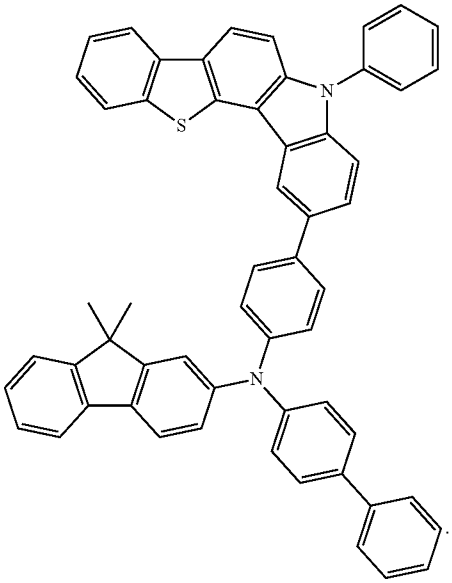

12. The compound as claimed in claim 1, wherein the compound is a hole transport material or a hole injection material for an organic light emitting diode.

13. The compound as claimed in claim 1, wherein the compound has a triplet excitation energy (T1) of about 2.0 eV or greater.

14. The compound as claimed in claim 1, wherein the organic optoelectronic device is selected from the group of an organic photoelectronic device, an organic light emitting diode, an organic solar cell, an organic transistor, an organic photoconductor drum, and an organic memory device.

15. An organic light emitting diode, comprising:

an anode;

a cathode; and at least one organic thin layer between the anode and the cathode, wherein the at least one organic thin layer includes the compound for an organic optoelectronic device as claimed in claim 1.

16. The organic light emitting diode as claimed in claim 15, wherein the at least one organic thin layer is selected from the group of an emission layer, a hole transport layer (HTL), a hole injection layer (HIL), an electron transport layer (ETL), an electron injection layer (EIL), a hole blocking film, and a combination thereof.

17. The organic light emitting diode as claimed in claim 15, wherein the at least one organic thin layer includes a hole transport layer (HTL) or a hole injection layer (HIL), and the compound for an organic optoelectronic device is included in the hole transport (HTL) or the hole injection layer (HIL).

18. The organic light emitting diode as claimed in claim 15, wherein the at least one organic thin layer includes an emission layer, and the compound for an organic optoelectronic device is included in the emission layer.

19. The organic light emitting diode as claimed in claim 15, wherein the at least one organic thin layer includes an emission layer, and the compound for an organic optoelectronic device is a phosphorescent host material or fluorescent host material in the emission layer.

20. A display device comprising the organic light emitting diode as claimed in claim 15.

21. The compound as claimed in claim 1, wherein the compound including the moiety represented by Chemical Formula 4 and the moiety represented by Chemical Formula 5 is represented by the following Chemical Formula C-1:

[C-1]

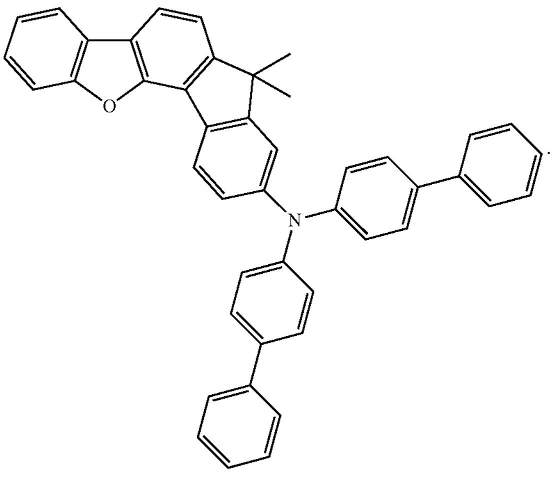

* * * * *